(12) United States Patent
Foung et al.

(10) Patent No.: US 8,858,947 B2
(45) Date of Patent: Oct. 14, 2014

(54) HEPATITIS C ANTIBODIES AND USES THEREOF

(75) Inventors: Steven Foung, Stanford, CA (US); Zhen-yong Keck, Redwood City, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 227 days.

(21) Appl. No.: 13/122,598

(22) PCT Filed: Oct. 5, 2008

(86) PCT No.: PCT/US2008/078884
§ 371 (c)(1),
(2), (4) Date: Jul. 26, 2011

(87) PCT Pub. No.: WO2010/039154
PCT Pub. Date: Apr. 8, 2010

(65) Prior Publication Data
US 2012/0039846 A1    Feb. 16, 2012

(51) Int. Cl.
*C07K 16/00* (2006.01)
*C07K 16/08* (2006.01)
*C07K 16/10* (2006.01)
*A61K 39/42* (2006.01)

(52) U.S. Cl.
USPC ............ 424/149.1; 424/161.1; 435/339; 530/388.1; 530/388.3

(58) Field of Classification Search
None
See application file for complete search history.

(56) References Cited

U.S. PATENT DOCUMENTS

2006/0104980 A1   5/2006  Foung et al.
2006/0257852 A1  11/2006  Rappuoli et al.

FOREIGN PATENT DOCUMENTS

WO   WO-00/26418 A1   5/2000

OTHER PUBLICATIONS

Hadlock et al. Human Monoclonal Antibodies That Inhibit Binding of Hepatitis C Virus E2 Protein to CD81 and Recognize Conserved Conformational Epitopes. Journal of Virology 2000, vol. 74, No. 22, p. 10407-10416.*
Keck et al. Definition of a Conserved Immunodominant Domain on Hepatits C Virus E2 Glycoprotein by Neutralizing Human Monoclonal Antibodies. Journal of Virology Apr. 4, 2008 epub, vol. 82, No. 12, pp. 6061-6066.*
Riechmann et al. Reshaping human antibodies for therapy. Nature 1988, vol. 332, pp. 323-327.*
Greenspan et al. Defining epitopes: Its not as easy as it seems. Nature Biotechnology 1999, vol. 17, pp. 936-937.*
Mateu et al. Non-additive effects of multiple amino acid substitutions on antigen-antibody recognition. European Journal of Immunology 1992, vol. 22, pp. 1385-1389.*
Keck, Z. et al., Analysis of a Highly Flexible Conformational Immunogenic Domain A in Hepatitis C Virus E2, Journal of Virology, 79(21): 13199-13208 (2005).
International Search Report for PCT/US08/78884, 2 pages (Jan. 30, 2009).

\* cited by examiner

*Primary Examiner* — Louise Humphrey
(74) *Attorney, Agent, or Firm* — Brenda Herschbach Jarrell; Nathan A. Billings; Choate, Hall & Stewart LLP

(57) ABSTRACT

The present invention provides identification and characterization of conformational epitopes of the envelope protein E2 of the Hepatitis C virus (HCV). The present invention provides a panel of human monoclonal antibodies that recognize conformational epitopes of E2. The antibodies are derived from patients infected with HCV. The present invention provides methods for utilizing HCV antibodies as therapeutic, diagnostic, and/or prophylactic agents. The present invention provides mimotopes with conformational epitopes intact and methods of using mimotopes. The present invention provides methods of stratifying patients based on their response to HCV. The present invention provides pharmaceutical compositions for prevention and treatment of HCV comprising one or more HCV antibodies.

26 Claims, 11 Drawing Sheets
(5 of 11 Drawing Sheet(s) Filed in Color)

Figure 1

| HMAbs | HCVpp | | | | | | | | |
|---|---|---|---|---|---|---|---|---|---|
| | 1a | 1b | 2A | 2B | 3A | 4 | 5 | 6 |
| HC-1 | + | + | + | + | + | + | + | + |
| HC-3 | + | + | + | + | + | + | + | + |
| HC-11 | + | + | + | + | + | + | + | + |
| CBH-23 | + | + | + | + | + | + | + | + |
| RO4 | -- | -- | -- | -- | -- | -- | -- | -- | a: Indirect immunofluorescent assay against E1E2 transfected 293T cells

Figure 2

HC-1: CDR1 (SEQ ID NO: 10); CDR2 (SEQ ID: 11); CDR3 (SEQ ID NO: 12)
HC-3: CDR1 (SEQ ID NO: 13); CDR2 (SEQ ID: 14); CDR3 (SEQ ID NO: 15)
HC-11: CDR1 (SEQ ID NO: 16); CDR2 (SEQ ID: 17); CDR3 (SEQ ID NO: 18)
CBH-23: CDR1 (SEQ ID NO: 19); CDR2 (SEQ ID: 20); CDR3 (SEQ ID NO: 22)

Heavy Chain

| | CDR1 | CDR2 | CDR3 |
|---|---|---|---|
| HC-1 | GGTYNSEV | FIPMFGTA | AKVLQVGGNLVVRPL |
| HC-3 | GFSLSTTGVG | IYWDDDK | ALNSYRSGTILYRELELRGLFYI |
| HC-11 | GATESSFI | IIPMFGTA | AMEVPGFCRGGSCSGYMDV |
| CBH-23 | GGTFSSYA | IVPMFGTE | ARHENIYGTPFDY |

HC-1: CDR1 (SEQ ID NO: 22); CDR3 (SEQ ID NO: 23)
HC-3: CDR1 (SEQ ID NO: 24); CDR3 (SEQ ID NO: 25)
HC-11: CDR1 (SEQ ID NO: 26); CDR3 (SEQ ID NO: 27)
CBH-23: CDR1 (SEQ ID NO: 28); CDR3 (SEQ ID NO: 29)

Light Chain

| | CDR1 | CDR2 | CDR3 |
|---|---|---|---|
| HC-1 | QTISSTH | GVS | HQYGNSPQT |
| HC-3 | QSISSW | ESS | QQYESSSWT |
| HC-11 | HSVSSSN | GAS | QQYGSSPIT |
| CBH-23 | HSITRY | AAS | QQSYSTLLT |

Figure 3

| | IgG1 | IgG2 | IgG3 | IgG4 |
|---|---|---|---|---|
| HC-1 | - | +++ | - | - |
| HC-3 | +++ | - | - | - |
| HC-11 | +++ | - | - | - |
| CBH-23 | +++ | - | - | - |

Figure 4

| HMAb | HCVpp[a] | | | | | | | | HCVcc[b] | |
|---|---|---|---|---|---|---|---|---|---|---|
| | 1a | 1b | 2a | 2b | 3a | 4 | 5 | 6 | 1a | 2a |
| HC-1 | 86[c] | 78 | 38 | 41 | 39 | 29 | 58 | 48 | 95 | 100 |
| HC-3 | 70 | 18 | NA[d] | NA | NA | NA | NA | NA | NA | 100 |
| HC-11 | 90 | 87 | 58 | 52 | 37 | 52 | 11 | 45 | 90 | 100 |
| CBH-23 | 82 | 40 | 42 | 25 | 21 | 20 | 7 | -10 | NA | 85 |
| RO4 | 5 | 5 | 0 | 4 | 2 | 0 | 0 | 0 | 0 | 0 |

[a]: HCVpp is HCV pseudoparticles
[b]: HCVcc is cell cultured infectious HCV virions
[c]: Number is percent neutralization
[d]: Not available

US 8,858,947 B2

HEPATITIS C ANTIBODIES AND USES THEREOF

GOVERNMENT SUPPORT

This invention was made with government support under grant number HL079381 awarded by the United States National Institutes of Health. The government has certain rights in the invention.

CROSS-REFERENCE TO RELATED APPLICATIONS

This application is a National Phase Entry of International Application Number PCT/US08/78884, filed Oct. 5, 2008 (published on Apr. 8, 2010, as WO/2010/039154), which is incorporated herein by reference in its entirety.

SEQUENCE LISTING

In accordance with 37 C.F.R. §1.52(e)(5), a Sequence Listing in the form of a text file (entitled "Sequence Listing," created on Oct. 5, 2008 and 162 kilobytes) is incorporated herein by reference in its entirety.

BACKGROUND

Over 170 million people worldwide are infected with hepatitis C virus (HCV). Acute infection is usually silent, but the majority of infected individuals develop persistent infections (Major et al., 2001, "Hepatitis C viruses," *Fields Virology*, 1127-1162; incorporated herein by reference). A small percentage of acute infections however resolve viremia with disease resolution. Cellular immunity is necessary, as a robust and sustained $CD4^+$ T cell response is temporally associated with virus clearance leading to disease resolution (reviewed in Shoukry et al., 2004, *Annu. Rev. Microbiol.*, 58:391; incorporated herein by reference).

Antiviral drugs (e.g., interferon or PEGylated interferon) taken alone or in combination with ribavirin (i.e., nucleoside analog which interferes with viral genome replication) can be used for the treatment of persons with chronic hepatitis C, but the cost of treatment is very high. Treatment with interferon alone is effective in about 10% to 20% of patients, while interferon combined with ribavirin is effective in about 30% to 50% of patients.

The present invention encompasses the recognition that antibodies may be developed that can be useful for prophylaxis, treatment, and/or diagnosis of HCV. A significant challenge for antibody-based vaccine development is defining conserved protective epitopes and generating antibodies that specifically recognize these epitopes.

SUMMARY OF THE INVENTION

The present invention provides monoclonal antibodies, including human monoclonal antibodies, which bind to multiple hepatitis C virus (HCV) genotypes and/or subtypes. Such antibodies are useful in the prophylaxis, treatment, diagnosis, and/or study of HCV. In particular, the present invention provides monoclonal antibodies binding to conserved conformational epitopes of HCV envelope glycoprotein E2. In some embodiments, HCV antibodies in accordance with the present invention are able to bind to many, most, or all cases of HCV. In some embodiments, monoclonal antibodies find use in a variety of diagnostic assays. HCV antibodies in accordance with the invention find use in passive immunotherapy for reducing viral load of infected individuals. Use of HCV antibodies in accordance with the invention may also interfere with the infection of target cells. Antibodies recognizing conserved epitopes can be used to provide a template for the rational design of peptide and conformationally defined epitope mimetics (e.g., organic compounds, organometallic compounds, inorganic compounds, small molecules, etc.). In some embodiments, conserved regions of HCV E2 protein and fragments thereof are provided for use in therapeutics, prophylaxis, diagnostics, and/or other purposes.

In some embodiments, antibodies in accordance with the invention are directed to conformational epitopes of the E2 protein of HCV. Conformational and linear epitopes of E2 have been identified using a panel of monoclonal antibodies and a series of deletion constructs of E2. Previous studies (see, e.g. U.S. Pat. No. 6,692,908; and U.S. Patent Publications 2006/0104980 and 2006/0188571; all of which are incorporated herein by reference) have reported a class of antibodies that bind to conformational epitopes between E2 amino acids 411-644 from HCV 1b. Antibodies of this class have been found to inhibit the interaction of E2 with CD81. Another class of antibodies has been found to bind to conformational epitopes between HCV 1b E2 amino acids 470-644. A third class of antibodies binds to conformational epitopes between HCV 1b E2 amino acids 470-644 but fails to inhibit the binding of E2 to CD81. A fourth class binds to conformational epitopes between HCV 1b E2 amino acids 644-661. A fifth class binds to conformational epitopes between HCV 1b E1 amino acids 230-313. A sixth class binds to a linear HCV E1 epitopes derived from multiple genotypes. A seventh class binds to conformational epitopes that include in part HCV 1a E2 amino acids 657-698.

In some embodiments, conformational epitopes to which HCV antibodies are directed are conserved among HCV genotypes (e.g., genotypes 1, 2, 3, 4, 5, 6, 7, 8, 9, 10, 11, and/or combinations thereof). In some embodiments, conformational epitopes to which HCV antibodies are directed are conserved among HCV subtypes (e.g., subtypes 1a, 1b, 1c, 2a, 2b, 2c, 3a, 3b, 4a, 4b, 4c, 4d, 4e, 5a, 6a, 7a, 7b, 8a, 8b, 9a, 10a, 11a, and/or combinations thereof). In some embodiments, conformational epitopes to which HCV antibodies are directed are conserved among HCV strains. It is estimated that over 100 strains of HCV exist, which are given numerical designations (e.g., 1, 2, 3, etc.) after the genotype and subtype indication.

The present invention provides monoclonal antibodies that recognize HCV E2 epitopes that are more precisely defined than any of the epitopes described above. Antibodies in accordance with the invention cross-compete with some of the previously-described antibodies. However, some antibodies in accordance with the invention neutralize HCV in respected model systems with greater potency than previously-described antibodies. Thus, the present invention encompasses the recognition that the newly-identified antibodies, described herein, may provide greater therapeutic and/or prophylactic benefit than previously-described antibodies.

In some embodiments, anti-HCV E2 antibodies are selected from the group consisting of human monoclonal antibody HC-1 which is secreted by the hybridoma cell line deposited in the American Type Culture Collection (ATCC) under Accession number PTA-9416; human monoclonal antibody HC-3 secreted by the hybridoma cell line deposited in the ATCC under Accession number PTA-9417; human monoclonal antibody HC-11 secreted by the hybridoma cell line deposited in the ATCC under Accession number PTA-9418;

and human monoclonal antibody CBH-23 secreted by the hybridoma cell line deposited in the ATCC under Accession number PTA-9419.

Antibodies in accordance with the present invention may be combined with pharmaceutically acceptable excipients to provide pharmaceutical formulations. The present invention provides pharmaceutical compositions for treatment, prevention, and/or diagnosis of hepatitis C infection. In some embodiments, pharmaceutical compositions in accordance with the invention comprise human antibodies capable of binding to the HCV envelope glycoprotein E2 and capable of neutralizing HCV infection in vitro and in vivo.

In some embodiments, pharmaceutical compositions in accordance with the invention may comprise fragments of HCV antibodies (e.g., HC-1, HC-3, HC-11, and/or CBH-23) that substantially retain the antigen binding characteristics of the whole antibody. In some embodiments, pharmaceutical compositions may comprise HCV antibodies produced by recombinant methods that are well known in the art.

The present invention provides various therapeutic, prophylactic, and/or diagnostic uses of HCV antibodies in accordance with the invention. In some embodiments, pharmaceutical compositions comprising HC-1, HC-3, HC-11, and CBH-23 antibodies may be used for the treatment of chronic and/or acute hepatitis C infection by administering to patients a therapeutically effective amount of the antibodies, or fragments thereof, capable of binding to HCV E2. A therapeutically effective amount is an amount sufficient to achieve one or more particular biological effects. A therapeutically effective amount may be administered in a single dose at a single time, or may be distributed over time in multiple individual doses (of the same or different sizes), or in continuous delivery (at a constant or variable rate). In certain embodiments, a therapeutically effective amount is an amount effective to achieve one or more desired biological results including, but not limited to: (i) alleviating one or more symptoms of HCV infection; (ii) reducing the number of circulating viral particles in an individual and/or in any one of an individual's organs (e.g., liver); (iii) preventing reemergence, reducing the likelihood of reemergence, and/or delaying the reemergence of one or more symptoms of HCV infection; and/or (iv) preventing, reducing the likelihood of, and/or delaying the onset of an increase in the number of circulating viral particles in an HCV-infected individual and/or in any one of an individual's organs (e.g., liver). Pharmaceutical compositions in accordance with the invention may be used to prevent, reduce the recurrence of, and/or delay the onset of HCV infection. They may be used, for example, for passive immunization of individuals recently exposed to HCV or at risk of being exposed to HCV, newborn babies born to HCV-positive mothers, and/or liver transplantation patients (e.g., to prevent possible recurrent HCV infections in such patients).

The invention also provides pharmaceutical compositions comprising therapeutically effective amounts of antibodies in accordance with the invention combined with at least one other anti-viral agent as an additional active ingredient. Such agents may include, but are not limited to, interferons (e.g., interferon α-2b, interferon-γ, etc.), anti-HCV monoclonal antibodies, anti-HCV polyclonal antibodies, RNA polymerase inhibitors, protease inhibitors, ribavirin, IRES inhibitors, helicase inhibitors, immunomodulators, antisense compounds, short interfering RNAs, short hairpin RNAs, micro RNAs, RNA aptamers, ribozymes, and combinations thereof.

Antibodies in accordance with the present invention define conformational epitopes in the HCV E2 protein, and compositions and compounds containing such epitopes are provided. For example, the present invention provides proteins, peptides, and small molecules comprising conformational epitopes of HCV E2 protein. Peptides may contain one or more epitopes recognized by antibodies in accordance with the present invention. In certain embodiments, proteins are strings of concatenated peptides with optional linking sequences, at least one of which contains at least one conformational epitope of HCV. Peptides of the string may contain different conformational epitopes of HCV E2 protein. Alternatively, peptides of the string may all contain the same epitope. In general, it is desirable that the peptides of the string fold properly in order to display the conformational epitope(s) substantially as it appears in nature. Such proteins and peptides may be used in formulating vaccines or used in diagnostic tests.

The present invention also provides methods for stratifying patients based on their immunological response to HCV and for identifying those patients likely to respond well to HCV immunotherapy. For example, a patient's serum may be used to test for the presence of antibodies directed against a particular epitope of HCV. If the patient does not have adequate levels of antibodies directed to such an epitope, specifically a conformational epitope of HCV E2 protein, human monoclonal antibodies directed against the epitope may be administered to the patient. The patient's own immune response may be supplemented with antibodies in accordance with the invention or compositions thereof. In certain embodiments, immunotherapy aids in clearance of HCV virus and/or resolution of HCV infection. In certain embodiments, immunotherapy in accordance with the present invention treats and/or prevents chronic HCV infection.

Definitions

Amino acid: As used herein, term "amino acid," in its broadest sense, refers to any compound and/or substance that can be incorporated into a polypeptide chain. In some embodiments, an amino acid has the general structure $H_2N$—$C(H)(R)$—$COOH$. In some embodiments, an amino acid is a naturally occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In certain embodiments, the animal is susceptible to infection by HCV. In some embodiments, an animal may be a transgenic animal, genetically engineered animal, and/or a clone.

Antibody: As used herein, the term "antibody" refers to any immunoglobulin, whether natural or wholly or partially synthetically produced. All derivatives thereof which maintain specific binding ability are also included in the term. The term also covers any protein having a binding domain which is homologous or largely homologous to an immunoglobulin-binding domain. Such proteins may be derived from natural sources, or partly or wholly synthetically produced. An antibody may be monoclonal or polyclonal. An antibody may be a member of any immunoglobulin class, including any of the human classes: IgG, IgM, IgA, IgD, and IgE. In certain embodiments, an antibody may be a member of the IgG immunoglobulin class. As used herein, the terms "antibody fragment" or "characteristic portion of an antibody" are used interchangeably and refer to any derivative of an antibody which is less than full-length. In general, an antibody fragment retains at least a significant portion of the full-length antibody's specific binding ability. Examples of antibody fragments include, but are not limited to, Fab, Fab', F(ab')2, scFv, Fv, dsFv diabody, and Fd fragments. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains which are linked together, for example, by disulfide linkages. An antibody fragment may optionally comprise a multimolecular complex. A functional antibody fragment typically comprises at least about 50 amino acids and more typically comprises at least about 200 amino acids. In some embodiments, an antibody may be a human antibody. In some embodiments, an antibody may be a humanized antibody.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any substance that has activity in a biological system (e.g., cell culture, organism, etc.). For instance, a substance that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Characteristic portion: As used herein, the term a "characteristic portion" of a substance, in the broadest sense, is one that shares some degree of sequence or structural identity with respect to the whole substance. In certain embodiments, a characteristic portion shares at least one functional characteristic with the intact substance. For example, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally contains at least 2, 5, 10, 15, 20, 50, or more amino acids. In general, a characteristic portion of a substance (e.g., of a protein, antibody, etc.) is one that, in addition to the sequence and/or structural identity specified above, shares at least one functional characteristic with the relevant intact substance. In some embodiments, a characteristic portion may be biologically active.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Functional: As used herein, a "functional" biological molecule is a biological molecule in a form in which it exhibits a property and/or activity by which it is characterized.

Gene: As used herein, the term "gene" has its meaning as understood in the art. It will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as tRNAs, RNAi-inducing agents, etc. For the purpose of clarity we note that, as used in the present application, the term "gene" generally refers to a portion of a nucleic acid that encodes a protein; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a protein-coding nucleic acid.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM 120 weight residue table, a gap length penalty of 12 and a gap penalty of 4. The percent identity between two nucleotide sequences can, alternatively, be determined using the GAP program in the GCG software package using an NWSgapdna.CMP matrix.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.)

Mimotope: As used herein, the term "mimotope" refers to a macromolecule which mimics the structure of an epitope. In some embodiments, a mimotope elicits an antibody response identical or similar to that elicited by its corresponding epitope. In some embodiments, an antibody that recognizes an epitope also recognizes a mimotope which mimics that epitope. In some embodiments, a mimotope is a peptide. In some embodiments, a mimotope is a small molecule, carbohydrate, lipid, or nucleic acid. In some embodiments, mimotopes are peptide or non-peptide mimotopes of conformationally-conserved HCV epitopes. In some embodiments, by mimicking the structure of the conformationally defined viral epitope, a mimotope interferes with the ability of HCV virus particles to bind to its natural binding partners (e.g., HCV target receptor, E1 protein, etc.), e.g., by binding to the natural binding partner itself.

Nucleic acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, 4, 5, 6, 7, 8, 9, 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Recurrent HCV infection: As used herein, a "recurrent HCV infection" refers to reemergence of clinical and/or laboratory evidence of infection, e.g., one or more symptoms of infection or the presence of circulating HCV particles and/or HCV particles in the subject's liver. In some embodiments, a recurrent HCV infection refers to such a condition in a subject who has been previously infected with HCV but who has received a liver transplant.

Small Molecule: In general, a "small molecule" is understood in the art to be an organic molecule that is less than about 2000 g/mol, less than about 1500 g/mol, less than about 1000 g/mol, less than about 800 g/mol, or less than about 500 g/mol. In some embodiments, small molecules are non-polymeric. In some embodiments, small molecules are not proteins, peptides, or amino acids. In some embodiments, small molecules are not nucleic acids or nucleotides. In some embodiments, small molecules are not saccharides or polysaccharides.

Subject: As used herein, the term "subject" or "patient" refers to any organism to which a composition of this invention may be administered, e.g., for experimental, diagnostic, prophylactic, and/or therapeutic purposes. Typical subjects include animals (e.g., mammals such as mice, rats, rabbits, non-human primates, and humans; insects; worms; etc.). In some embodiments, a subject may be infected with, suffering from, and/or susceptible to HCV.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition (e.g., HCV infection) has been diagnosed with and/or displays one or more symptoms of a disease, disorder, and/or condition.

Susceptible to: An individual who is "susceptible to" a disease, disorder, and/or condition (e.g., HCV infection) has not been diagnosed with a disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Therapeutically effective amount: As used herein, the term "therapeutically effective amount" means an amount of inventive composition that is sufficient, when administered to a subject suffering from or susceptible to a disease, disorder, and/or condition (e.g., HCV infection), to treat, diagnose, prevent, and/or delay the onset of the disease, disorder, and/or condition.

Therapeutic agent: As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of and/or reduce incidence of one or more symptoms or features of HCV infection.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a disease, disorder, and/or condition (e.g., HCV infection). Treatment may be administered to a subject who does not exhibit signs of a disease, disorder, and/or condition. In some embodiments, treatment may be administered to a subject who exhibits only early signs of the disease, disorder, and/or condition for the purpose of decreasing the risk of developing pathology associated with the disease, disorder, and/or condition.

Vector: As used herein, "vector" refers to a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

HCV Nomenclature

It is well known by those skilled in the art that HCV nomenclature typically utilizes an Arabic numeral (e.g., "1," "2," "3," "4," etc.) that represents HCV genotype and a lowercase letter (e.g., "a," "b," etc.) that represents HCV subtype. Although the rules of nomenclature are generally accepted in the art, those of ordinary skill in the art recognize that the rules of nomenclature are not always strictly followed by those of skill in the art in publications, presentations, conversation, etc. Thus, those skilled in the art would recognize that, for example, it is implicit that "HCV 1a," "HCV genotype 1a," and "HCV subtype 1a" could be used interchangeably by one of skill in the art, and that all three terms are intended to refer to HCV genotype 1, subtype a.

As used herein, Arabic numerals (e.g., "1," "2," "3," "4," etc.) are used to refer to HCV genotype, and lowercase letters (e.g., "a," "b," etc.) are used to refer to HCV subtypes. It will also be understood that, when HCV of a particular genotype is referred to herein, it is meant to encompass all subtypes of the named genotype. To give but one example, "genotype 1" is used herein to refer to all subtypes of genotype 1 (e.g., genotype 1, subtype a; genotype 1, subtype b; etc.).

As used herein, any Arabic numerals (e.g., "1," "2," "3," "4," etc.) that are present after the genotype and subtype designations will be understood to refer to the HCV strain.

BRIEF DESCRIPTION OF THE DRAWING

The patent or application file contains at least one drawing executed in color. Copies of this patent or patent application publication with color drawing(s) will be provided by the Office upon request and payment of the necessary fee.

FIG. 1: Binding to different HCV genotypes by indirect immunofluorescent assay. 293T cells were transfected with the constructs bearing E1E2 sequences of genotypes 1 to 6. Twenty-four hours post-transfection, cells were fixed onto slides, and antibody binding to fixed cells was detected by fluorescence microscopy. HC-1, HC-3, HC-11, and CBH-23 bound to genotypes 1a, 1b, 2a, 2b, 3a, 4, 5, and 6.

FIG. 2: Human monoclonal antibodies $V_L$ and $V_H$ domain CDR sequences translated from cDNA sequences. Analysis revealed that each antibody contains distinct $V_L$ and $V_H$ CDR sequences. Heavy chain sequence identifiers are as follows: HC-1 CDR1 (SEQ ID NO: 10), HC-1 CDR2 (SEQ ID NO: 11), HC-1 CDR3 (SEQ ID NO: 12), HC-3 CDR1 (SEQ ID NO: 13), HC-3 CDR2 (SEQ ID NO: 14), HC-3 CDR 3 (SEQ ID NO: 15), HC-11 CDR1 (SEQ ID NO: 16), HC-11 CDR2 (SEQ ID NO: 17), HC-11 CDR3 (SEQ ID NO: 18), CBH-23 CDR1 (SEQ ID NO: 19), CBH-23 CDR2 (SEQ ID NO: 20), and CBH-23 CDR3 (SEQ ID NO: 21). Light chain sequence identifiers are as follows: HC-1 CDR1 (SEQ ID NO: 22), HC-1 CDR3 (SEQ ID NO: 23), HC-3 CDR1 (SEQ ID NO: 24), HC-3 CDR3 (SEQ ID NO: 25), HC-11 CDR1 (SEQ ID NO: 26), HC-11 CDR3 (SEQ ID NO: 27), CBH-23 CDR1 (SEQ ID NO: 28) and CBH-23 CDR3 (SEQ ID NO: 29).

FIG. 3: IgG subclass typing. HC-1 is IgG2, whereas HC-3, HC-11, and CBH-23 are IgG1.

FIG. 4: Neutralization with different HCV genotypes. Each antibody was tested at 20 μg/ml for its ability to neutralize different HCV genotypes. The numbers are percent neutralization compared to no antibody control. RO4 is an isotype-matched human monoclonal antibody to HCMV and serves as a negative control.

DESCRIPTION OF CERTAIN EMBODIMENTS OF THE INVENTION

The present invention provides antibodies which recognize hepatitis C virus (HCV) envelope glycoprotein 2 (E2). In some embodiments, HCV E2 antibodies are monoclonal antibodies, such as human monoclonal antibodies. In some embodiments, HCV E2 antibodies bind to E2 associated with one or more hepatitis C virus (HCV) genotypes and/or subtypes. In some embodiments, HCV E2 antibodies are useful for therapeutic, diagnostic, and/or prophylactic applications. The present invention provides pharmaceutical compositions comprising HCV E2 antibodies and methods for treating patients using HCV E2 antibodies.

Figure 6:
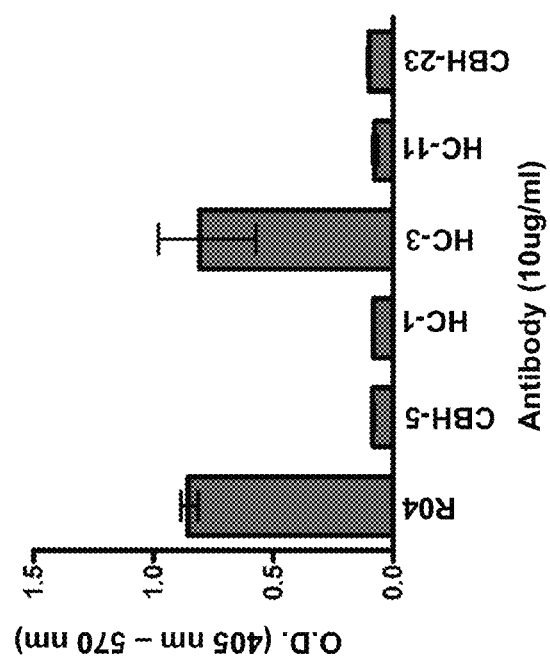
FIG. 6: Inhibition of E2 binding to CD81 by human monoclonal antibodies. Genotype 1b E1E2 expressed in 293T containing 1 μg/ml E2 was incubated with each test antibody at 10 μg/ml and the antibody-antigen complex was then added onto CD81 pre-coated wells. Detection of bound E2 to CD81 was measured with biotinylated CBH-4D. CBH-5 was used as a positive control and RO4 as a negative control. Preincubation of E2 glycoproteins with HC-1, HC-11, CBH-23, or CBH-5 reduced by over 90% E2 binding to CD81 compared to the RO4 negative control. Similar to other domain B or C HCV antibodies, these HCV antibodies neutralize HCV by blocking E2 binding to CD81. In contrast, preincubation of E2 glycoproteins in the presence of HC-3 did not reduce E2 binding to CD81. Experiments were performed twice in triplicate. Error bars indicate one standard deviation from the mean.

In some embodiments, HCV E2 antibodies are identified and isolated from serum from infected patients. As described in the examples, a group of human monoclonal antibodies from peripheral B-cells of three HCV-infected individuals having high serum neutralization of binding titers were produced and characterized. Four human monoclonal antibodies to HCV E2 were produced and isolated, HC-1, HC-3, HC-11, and CBH-23. All four antibodies bind to genotypes 1a, 1b, 2a, 2b, 3a, 4, 5, and 6 of HCV (FIG. 1). These antibodies bind to conformational epitopes, which are conserved across virus types and genotypes. HC-1, HC-11 and CBH-23 inhibit the interaction of E2 protein with human CD81 (FIG. 6). HC-3 does not inhibit E2 binding to CD81 (FIG. 6).

In some embodiments, HCV E2 antibodies in accordance with the invention provide for neutralization of a broad spectrum of HCV genotypes and/or subtypes. Both breadth of reactivity to multiple HCV genotypes and/or subtypes and the ability to interfere with the binding of HCV virions to susceptible cells are desirable for a therapeutically useful neutralizing antibody. The present invention also provides for design of peptide and non-peptide structural mimetics of HCV envelope proteins.

Hepatitis C Virus (HCV)

Hepatitis C virus (HCV) is an enveloped virus the genetic information for which is encoded in a 9.5 kb positive strand RNA genome. A highly conserved noncoding region of 341 bp is localized at the 5'-end of this viral genome, which is followed by a long open-reading frame coding for a polyprotein of approximately 3,010 amino acids. Two putative envelope glycoproteins E1 (gp35) and E2 (gp72) have been identified with 5 or 6 and 11 N-linked glycosylation sites, respectively. A high level of genetic variability is associated with the envelope genes. This variability is highly accentuated at the 5'-end of the E2 gene, where two hypervariable regions termed HVR1 and HVR2, have been described. Antibodies to HVR1 appear to mediate virus neutralization in cell culture and chimpanzee protection studies (Farci et al., 1996, *Proc. Natl. Acad. Sci., USA*, 93:15394-15399; and Shimizu et al., 1994, *J. Virol.*, 68:1494-1500; both of which are incorporated herein by reference). Although progress has been made at inducing a broader immune response to HVR1 related sequences (Puntoriero et al., 1998, *EMBO J.*, 17:3521-3533; incorporated herein by reference), unfortunately, antibodies to HVR1 tend to be isolate-specific and over time drive the replication of new viral variants that the existing immune response does not recognize (Farci et al., 1994, *Proc. Natl. Acad. Sci., USA*, 91:7792-7796; Weiner et al., 1992, *Proc. Natl. Acad. Sci., USA*, 89:3468-3472; and Kato et al., 1993, *J. Virol.*, 67:3923-3930; all of which are incorporated herein by reference). HCV envelope antigens appear to be highly immunogenic when expressed in glycosylated forms (da Silva Cardoso et al., 1997, *Ann. Hematol.*, 74:135-7; incorporated herein by reference). Preliminary data suggest the existence of conserved epitopes within the E2 protein (Lesniewski et al., 1995, *J. Med. Virol.*, 45:415-22; incorporated herein by reference). The existence of neutralizing antibodies in serum from infected patients has been proposed.

Studies using HCV E1-E2 proteins expressed in mammalian cells have shown that infected individuals have an antibody response to HCV E2 composed in part to epitopes that are both conformational and linear in nature (Harada et al., 1994, *J. Gen. Virol.*, 76:1223-1231; incorporated herein by reference). Studies involving the isolation of human monoclonal or recombinant antibodies to HCV E2 protein showed that a substantial fraction of these antibodies recognize conformational epitopes (da Silva Cordoso et al., 1998, *J. Med. Virol.*, 55:28-34; incorporated herein by reference). As to biological function of these domains, investigators have employed surrogate assays to provide insights into virus neutralization since the virus cannot be grown in vitro (Houghton, "Hepatitis C viruses," In Fields, Knipe, Howley (eds.) *Virology*, Lippincott-Raven, Philadelphia, 1035-1058; incorporated herein by reference). One surrogate assay, the neutralization of binding (NOB) assay, evaluates the ability of a given antibody or serum to prevent the association of HCV E2 protein with a human T-cell line (Rosa et al., 1996 *Proc. Natl. Acad. Sci., USA*, 93:1759-1763; incorporated herein by reference). The finding that serum antibodies obtained from chimpanzees protected by vaccination were strongly positive in the NOB assay provides support for the relevance of the assay as a measure of virus neutralization activity (Rosa et al., supra; and Ishii et al., 1998, *Hepatology*, 28:1117-1120; both of which are incorporated herein by reference).

The human tetraspannin cell surface protein CD81 (also known as TAPA-1; for review see Levy et al., 1998, *Ann. Rev. Immunol.*, 16:89-109; incorporated herein by reference) is the target protein bound by HCV E2 in the NOB assay (Pileri et al., 1998, *Science*, 282:938-941; incorporated herein by reference). Furthermore, human CD81 binds to free virions, and subsequently is a possible receptor for HCV (Pileri et al., supra). However, little is known about the conservation of the epitopes recognized by the previously identified NOB positive antibodies in HCV E2 proteins of different genotypes and/or subtypes.

Other approaches to detection of and protection against HCV include the development of peptide mimetics. As an example, peptide mimetics of Hepatitis type A and C viral proteins have been created through production of randomly generated synthetic and phage-display peptide libraries for use in detection assays and vaccination therapies (Mattioli et al., 1995, *J. Virol.*, 69:5294-5299; and Prezzi et al., 1996, *J. Immunol.*, 156:4504-4513; both of which are incorporated herein by reference). However, effective antibody binding of these mimotopes has only been compared to linearly defined viral epitopes. The sequential recombinant fusing of several linearly defined immunodominant HCV epitopes has been described for use in diagnostic assays (Chein et al., 1999, *J. Clin. Microbiol.*, 37:1393-1397; incorporated herein by reference). However, this multiple-epitope fusion antigen designed from linear epitopes was not created to function in the same capacity as a conformational mimetic. It was not designed to interfere with binding to a target receptor.

References providing background information concerning HCV include Abrignani, 1997, *Springer Semin. Immunopathology*, 19:47-55; Simmonds, 1995, *Hepatology*, 21:570:583; and Mahaney et al., 1994, *Hepatology*, 20:1405-1411; all of which are incorporated herein by reference. Vaccinia virus or baculovirus constructs having a portion of the HCV genome are described by Ralston et al. (1993, *J. Virology*, 67:6733-6761; incorporated herein by reference) and Lanford et al. (1993, *Virology*, 197:225-235; incorporated herein by reference).

HCV Antibodies

HCV envelope glycoprotein genes display some of the highest levels of genetic heterogeneity across genotypes and subtypes, with E2 displaying greater variability than E1. A hypervariable region (HVR1) found at the N-terminus of E2 is highly immunogenic and is the major determinant for isolate-specific neutralizing antibody responses (Farci et al., 1996, *Proc. Natl. Acad. Sci., USA*, 93:15394; and Shimizu et al., 1994, *J. Virol.*, 68:1494; both of which are incorporated herein by reference). A study of sequential HCV isolates obtained from serum samples collected over a 26-year period from a specific patient showed that the serum antibodies fail to neutralize the concurrent dominant E1E2 species present at the same time point (von Hahn et al., 2007, *Gastroenterology*, 132:667; incorporated herein by reference). Escape is associated with mutations in HVR1 leading to decreased binding and neutralization by monoclonal antibodies to HVR1 that were produced to the earliest isolate obtained from this patient. More broadly neutralizing antibodies are usually directed against conformational epitopes within E2 (Allander et al., 2000, *J. Gen. Virol.*, 81:2451; Bugli et al., 2001, *J. Virol.*, 75:9986; Habersetzer et al., 1998, *Virology*, 249:32; Hadlock et al., 2000, *J. Virol.*, 74:10407; and Ishii et al., 1998, *Hepatology*, 28:1117; all of which are incorporated herein by reference).

The present inventors previously described a panel of neutralizing and nonneutralizing human monoclonal antibodies to conformational epitopes on HCV E2 derived from peripheral B cells of an individual infected with genotype 1b HCV. By cross-competition analysis three immunogenic clusters of overlapping epitopes with distinct functions and properties were identified (Keck et al., 2005, *J. Virol.*, 79:13199; and Keck et al., 2004, *J. Virol.*, 78:9224; both of which are incorporated herein by reference). All nonneutralizing antibodies fell within one cluster designated as domain A (Keck et al., 2005, *J. Virol.*, 79:13199; incorporated herein by reference). Neutralizing antibodies segregated into two clusters, designated as domains B and C, with domain B antibodies having greater potency than domain C antibodies in blocking genotype 2a infectious cell culture virus (HCVcc) infection (Keck et al., 2007, *J. Virol.*, 81:1043; incorporated herein by reference). All domain B antibodies as well as domain C antibodies were shown to inhibit E2 binding to CD81, a receptor for HCV shown to be essential for HCVpp and HCVcc entry into host cells (Hsu et al., 2003, *Proc. Natl. Acad. Sci., USA*, 100:7271; and Tscherne et al., 2006, *J. Virol.*, 80:1734; both of which are incorporated herein by reference).

Although four antibodies to overlapping epitopes within domain B were previously isolated from one HCV infected individual, it remains unclear to the extent that domain B epitopes on E2 are dominant targets of the immune response. Example 1 describes the isolation of two new human monoclonal antibodies, HC-1 and HC-11, from a genotype 1a HCV infected individual that cross-compete with domain B antibodies from the earlier panel, thus, expanding the number of overlapping epitopes within this domain. These antibodies are directed at conformational epitopes conserved among all genotypes and/or subtypes; neutralize HCVpp and HCVcc, with some having greater potency than previously noted with other antibodies to this domain. The mechanism of neutralization with these antibodies is by inhibiting E2 binding to CD81. In addition, alanine substitution studies on E2 in a region that has been defined to engage CD81 (Owsianka et al., 2006, *J. Virol.*, 80:8695; incorporated herein by reference) show that some contact residues within these HCV antibody epitopes are the same contact residues needed for E2 binding to CD81. A third human monoclonal antibody, CBH-23, was isolated from a genotype 1b HCV infected individual. CBH-23 cross-competes with a representative antibody to domain C and mediates neutralization by inhibiting E2 binding to CD81. A fourth human monoclonal antibody, HC-3, was isolated from a genotype 1b HCV infected individual. HC-3 does not cross-compete with representative domain A, B, and C antibodies from the earlier panel, thus indicating a new domain, designated D. HC-3 does not inhibit E2 binding to CD81 (FIG. 6). The present invention encompasses the recognition that mechanisms by which HC-3 mediates virus neutralization occur at approximately the same time during virus entry as the virus interacts with CD81. While not wishing to be bound by any one particular theory, HC-3 may mediate virus neutralization by blocking virus attachment, which occurs prior to E2 binding to CD81; blocking virus interaction with a different co-receptor just before or after E2 binds to CD81; and/or blocking a conformational change in one or more viral envelope glycoproteins involved in successful virus entry.

By virtue of the variety of binding profiles of the antibodies, diagnostic assays may be employed which will detect a plurality of types and genotypes and/or subtypes, so as to provide a pan-anti-HCV antibody. In some embodiments, antibodies may be used for passive immunization, as protective therapy for individuals at risk for HCV or as a therapy for people who are seropositive for HCV.

References relating to the use of antibodies to HCV include Akatsuka et al., 1993, *Hepatology*, 18:503-510; DeLalla et al., 1993, *J. Hepatol.*, 18:163-167; Mondelli et al., 1994, *J. Virol.*, 68:4829-4836; Siemoneit et al., 1994, *Hybridoma*, 13:9-13; and Moradpour et al., 1996, *J. Med. Virol.*, 48:234-241; all of which are incorporated herein by reference.

HCV antibodies in accordance with the invention offer several advantages over existing antibodies against HCV. Because non-homologous primary amino acid sequences may still define immunologically identical three-dimensional protein structures, antibodies binding to structurally conserved epitopes can recognize multiple, sequentially divergent HCV genotypes and/or subtypes in native conformation, whereas antibodies recognizing only linear or denatured epitopes may not. In particular, antibodies that recognize conformationally dependent epitopes of E2 may effectively interfere with the interaction of HCV virus with its cellular target receptor. Using antibodies that recognize conformationally dependent epitopes to actively interfere with the ability of native HCV virus to bind to target cell receptors (e.g., CD81) has specific therapeutic application for reducing viral load in infected individuals, and/or preventing infection or re-infection of organs in non-infected individuals (for example, by (i) recognizing HCV E2 proteins encoded by different HCV genotypes and/or subtypes; (ii) binding HCV particles; and/or (iii) preventing attachment and entry of HCV viral particles to their target cells), particularly in recent organ transplant recipients, individuals undergoing renal dialysis, babies born to HCV-infected mothers, and/or individuals undergoing treatment for hemophilia or other blood clotting disorders. In some embodiments, other recipients include individuals recently exposed to HCV (e.g., via exposure to HCV-containing bodily fluids). In some embodiments, HCV antibodies may be useful for treatment of patients with strains of HCV that are identical to the strain of HCV to which the antibodies were raised. In some embodiments, HCV antibodies may be useful for treatment of patients with strains of HCV that are different from the strain of HCV to which the antibodies were raised. Both individual HCV antibodies and a cocktail of several HCV antibodies recognizing several epitopes may be employed.

In some embodiments, HCV antibodies may interfere with E2-associated viral infection by mechanisms other than preventing direct interaction with CD81. In some embodiments, HCV antibodies may interfere with viral infectivity by a number of possible mechanisms, including preventing E2 binding to co-receptor proteins, disrupting conformational changes in E2 proteins necessary for target cell binding, inhibiting E2-mediated viral fusion to target cells, and/or inhibiting uncoating of HCV virions. In some embodiments, HCV antibodies that directly interfere with E2 binding to CD81 may effectively complement HCV antibodies that interfere with infectivity by other mechanisms.

HCV antibodies in accordance with the invention which recognize viral epitopes and interfere with virus/target receptor interaction and viral epitopes which bind to such antibodies may also serve as templates for rationally designing peptide and other structural mimics of the viral epitopes. Structural molecular mimics defined by these HCV antibodies find use in their ability to block binding of the native virus to target receptors by binding to the target receptor themselves.

By producing human or humanized monoclonal antibodies, it is possible to directly analyze the human immune response to HCV. In some cases, it is desirable to use human or humanized monoclonal antibodies. By using human monoclonal antibodies, immune responses against the antibodies themselves as foreign antigens can be minimized, whereas vigorous immune responses are typically generated against monoclonal antibodies produced from non-human sources, because they are recognized as foreign antigens. Selecting for HCV antibodies that recognize conserved viral conformational epitopes affords broader and more effective therapeutic application of these reagents for ameliorating or preventing HCV infection than antibodies able to bind only linear or denatured epitopes. Antibodies described herein recognize conformational epitopes, which are highly conserved HCV E2 proteins of multiple different genotypes and/or subtypes. Thus, antibodies described herein have the advantage that they are more potent against a wide range of HCV isolates than many previously described neutralizing antibodies. An additional advantage is that the high conservation of the epitopes recognized by the antibodies described herein indicates that these antibodies recognize sequences with functional and/or structural significance within the HCV E2 protein. Thus peptides or small molecules isolated with these antibodies have a high probability of being functional regions within HCV E2.

Production and Characterization of HCV Antibodies

The overall strategy employed for the development of the subject HCV antibodies is described in Example 1. Briefly, (1) individuals with evidence of exposure to HCV were identified; (2) antigen specific B-cells from their peripheral blood were expanded and activated in vitro; (3) these cells were immortalized by electrofusion with a suitable mouse-human heteromyeloma; (4) relevant human antibody secreting hybridomas were identified; and (5) the relevant hybridomas were stabilized by cloning. This strategy resulted in the identification of HCV antibodies that are specific to the HCV E2 protein and which bound to conformational epitopes of E2 of HCV genotypes 1a, 1b, 2a, 2b, 3a, 4, 5, and 6 (FIG. 1).

As described in Example 1, peripheral B cells from individuals with either HCV 1a or 1b infection and high serum antibody neutralization activities were used to produce and characterize a panel of human monoclonal antibodies. The initial screening made use of a genotype 1b E2 protein to screen for antibodies derived from a 1a infected donor, or 1a E2 protein to screen for antibodies derived from a 1b infected donor. This step biased the screening approach used to the selection of antibodies to epitopes conserved between genotypes 1a and 1b since the donor was infected with either a genotype 1a or 1b isolate. Antibodies identified by such screening (i.e., HC-1, HC-3, HC-11, and CBH-23) did not recognize E2 protein by western blot, but did recognize E2 protein by immunoprecipitation. These results suggest that these HCV antibodies recognize conformational epitopes.

HCV antibodies HC-1, HC-3, HC-11, and CBH-23 were all able to bind to E1E2 of HCV genotypes 1a, 1b, 2a, 2b, 3a, 4, 5, and 6 (FIG. 1). HC-1 and HC-11 neutralize the majority of HCV genotypes 1a, 1b, 2a, 2b, 3a, 4, 5, and 6 HCVpp 1a (FIG. 4) and 1b infection, as well as HCVcc 1a and 2a infection (FIG. 4). HC-3 was able to neutralize HCVpp 1a and HCVcc 2a. HC-3 neutralizes 1a HCVpp and 2a HCVcc (FIG. 4), and CBH-23 neutralizes genotype 1a, 1b, 2a HCVpp, and 2a HCVcc (FIG. 4). These data indicate that all four HCV antibodies are able to recognize and neutralize multiple HCV genotypes. CD81 capture assays show that three of these four antibodies (i.e., HC-1, HC-11, and CBH-23) are capable of blocking the interaction of E2 and CD81 (FIG. 6). The present invention shows that epitopes that partially or fully overlap the CD81 binding site within HCV E2 are both conformational in nature and highly conserved. A high degree of sequence conservation in the CD81 binding site is consistent with the proposition that the interaction between HCV E2 and CD81 is biologically relevant. The present invention encompasses the recognition that, since HC-3 neutralizes HCV 1a and 2a but does not inhibit E2 binding to CD81, HC-3 might utilize alternative mechanisms of virus neutralization.

Competition analysis has been employed to define antibodies with similar binding sites in HCV E2. Previously identified HCV antibodies that recognize one of HCV E2 domains A, B, or C were biotinylated, and the binding of the biotinylated antibodies to HCV E2 in the presence of increasing amounts of competing HCV antibodies (i.e., HC-1, HC-3, HC-11, and CBH-23) was determined. HCV antibodies HC-1 and HC-11 effectively competed with antibodies that recognize domain B, but not domains A or C. CBH-23 effectively competed with an antibody recognizing domain C and not domains A or B. HC-3 did not compete with any domain A, B, or C antibodies.

These results indicate that conformational epitopes within HCV E2 glycoprotein are highly conserved among divergent HCV genotypes and/or subtypes. The antibodies that recognize these epitopes are useful as reagents to better define the structure of HCV E2. Furthermore, the antibodies that inhibited binding of HCV virions to human CD81 were shown to mediate virus neutralization of HCVpp and HCVcc models, which are well-accepted HCV models in the art. Indeed, one of ordinary skill in the art recognizes that successful neutralization of HCVpp and/or HCVcc is predictive of in vivo therapeutic activity (see, e.g., Lavie et al., 2007, *Curr. Issues Mol. Biol.*, 9:71-86; Bartosch et al., 2003, *J. Exp. Med.*, 197: 633-642; and Law et al., 2008, *Nat. Med.*, 14:25-27; all of which are incorporated herein by reference).

Thus, the present invention provides HCV E2 antibodies HC-1, HC-3, HC-11, and/or CBH-23. The present invention provides antibodies that recognize the same or similar epitopes as HC-1, HC-3, HC-11, and/or CBH-23. In some embodiments, the invention provides antibodies that compete with HC-1, HC-3, HC-11, and/or CBH-23 for binding to E2 protein. In some embodiments, the invention provides antibodies that decrease HC-1, HC-3, HC-11, and/or CBH-23 binding to E2 protein by about 30%, about 40%, about 50%, about 60%, about 70%, about 80%, about 90%, about 95%, or more than about 95%.

In some embodiments, the invention provides agents (e.g., small molecules, peptides, nucleic acids, lipids, nanoparticles, etc.) that compete with HC-1, HC-3, HC-11, and/or CBH-23 for binding to E2 protein. In some embodiments, the invention provides (e.g., small molecules, peptides, nucleic acids, lipids, nanoparticles, etc.) that decrease HC-1, HC-3, HC-11, and/or CBH-23 binding to E2 protein by about 30%, about 40%, about 50%, about 60%, about 70%, about 80%, about 90%, about 95%, or more than about 95%.

The HCVpp (HCV pseudotyped particle) model comprises infectious retroviral particles pseudotyped with unmodified HCV E1 and E2 proteins (see, e.g., Bartosch et al., 2003, *J. Exp. Med.*, 197:633-642; Drummer et al., 2003; *FEBS Lett.*, 546:385-390; Op De Beeck et al., 2004, *J. Virol.*, 78:2994-3002; and Hsu et al., 2003, *Proc. Natl. Acad. Sci., USA*, 100:7271-7276; all of which are incorporated herein by reference). HCVpp preferentially infect human hepatic cells, are neutralized by anti-E2 antibodies, are neutralized by HCV-infected patient serum, and mimic the early stages of HCV infection, including viral entry (Bartosch et al., 2003, supra; and Lavie et al., 2007, *Curr. Issues Mol. Biol.*, 9:71-86; both of which are incorporated herein by reference). HCVpp-based assays are useful to observe virus entry and correlate with physiological conditions in vivo, and are suitable for development of new antiviral therapies (Bartosch et al., 2003, supra).

The HCVcc (cell cultured HCV virion) model provides a cell-culture system that allows production of infectious, fully replicative HCV virions (Lindenbach et al., 2005, *Science*, 309:623-626; Wakita et al., 2005, *Nat. Med.*, 11:791-796; and Zhong et al., 2005, *Proc. Natl. Acad. Sci., USA*, 102:9294-9299; all of which are incorporated herein by reference). The HCVcc system is based on the transfection of the human hepatoma cell line Huh-7 with genomic HCV RNA of the genotype 2a JFH1 strain cloned from an individual with fulminant hepatitis. In order to allow comparative studies between different HCV strains, chimeric genomes encoding structural proteins from different genotypes and non-structural proteins from the JFH1 isolate have also been made (Pietschmann et al., 2006). HCVcc models are able to replicate in vitro in cell culture and in vivo in chimpanzees (Wakita et al., 2005, supra). The HCVcc system allows for the study of the complete viral cycle life and confirms data generated with the HCVpp system.

It is well-established that the results of virtually all experiments performed using HCVcc virions are consistent with the results of similar experiments performed using HCVpp virions. See Lindenbach et al., 2005, *Science*, 309:623-626; Lavie et al., 2007, *Curr. Issues Mol. Biol.*, 9:71-86; Chapel et al., 2007, *J. Gen. Virol.*, 88:1133-1143; Regeard et al., 2007, *FEBS J.*, 274:4705-4718; Pietschmann et al., 2006, *Proc. Natl. Acad. Sci., USA*, 103:7408-7413; Wakita et al., 2005, *Nature Medicine*, 11:791-796; Yi et al., 2006, *Proc. Natl. Acad. Sci., USA*, 103:2310-2315; Zhong et al., 2005, *Proc. Natl. Acad. Sci., USA*, 102:9294-9299; all of which are incorporated herein by reference.

Another established model for studying HCV is the "HCV-Trimera" mouse model (Ilan et al., 2002, *J. Infect. Dis.*, 185: 153-61; incorporated herein by reference). The HCV-Trimera mouse model was developed by using lethally irradiated mice, reconstituted with Severe Combined Immunodeficiency (SCID) mouse bone marrow cells, in which human liver fragments infected ex vivo with HCV had been transplanted. HCV Trimera mice may be useful for assessing in vivo therapeutic efficacy of potential HCV therapeutic and/or diagnostic agents (Ilan et al., 2002, *J. Infect. Dis.*, 185:153-61; Eren et al., 2006, *J. Virol.*, 80:2654-2664; both of which are incorporated herein by reference).

It is well-established that the results of experiments performed using either HCVcc or HCVpp virions in culture systems are consistent with the results of animal experiments performed using human liver-mouse chimeric models (Eren et al., 2006, *J. Virol.*, 80:2654-2664; and Law et al., 2008, *Nat. Med.*, 14:25-27; both of which are incorporated herein by reference). Furthermore, it has been established that inhibition of HCV replication in both in vitro assays and, by extension, in vivo small animal human mouse chimera models, e.g., the Trimera mouse model, correlate with inhibition of HCV in non-human primates in vivo. For example, in a study that focused in part on the ability of selected polyclonal human IgG preparations in preventing infection in chimpanzees, preparations with high neutralization titers as defined by HCVpp assays were protective while preparations with low neutralization titers were not. See Yu et al., 2004, *Proc. Natl. Acad. Sci., USA*, 101:7705-7710; incorporated herein by reference.

Given the predictive value of these model systems, one of ordinary skill in the art will readily recognize that HC-1, HC-3, HC-11, and/or CBH-23 (or antibodies that recognize the same epitopes as HC-1, HC-3, HC-11, and/or CBH-23) may be successfully used for neutralization of HCV in vivo. Analogous to the success achieved with hepatitis B immunoglobulin in liver transplantation (Dickson, 1998, *Liver Transpl. Surg.*, 4(5 Suppl 1):S73-S78; and Markowitz et al., 1998, *Hepatology* 28:585-589; both of which are incorporated herein by reference), one possible application is to suppress HCV infection in liver transplant recipients with broadly reactive neutralizing human monoclonal antibodies.

While human monoclonal antibodies are provided, other antibodies from other sources may recognize the same epitopes recognized by the human antibodies described herein, and may also be employed. Generally antibodies from murine sources (e.g., mice, rats, lagomorpha, etc.) and domestic animals (e.g., rabbit, guinea pig, goat, sheep, pig, chicken, horse, hamster, etc.) find use. One may produce antibodies having the conserved regions of mammalian sources using genetic engineering and replacing the constant regions of the HCV antibodies provided herein or may use the proteins to be described below as immunogens for immunizing the animals and then immortalizing the resulting B cells and screening as described below for immortalized cells which produce monoclonal antibodies having analogous broad range binding specificity. By screening in competitive assays with the subject HCV antibodies, one can determine whether the non-human antibodies bind to the same epitope.

Instead of using hybridomas as a source of the antibodies, genes encoding an HCV antibody or portion thereof may be isolated and introduced into an appropriate mammalian host cell, e.g., CHO, CHO-K1, 293T, Huh7, Huh7.5, HeLa, CV1, or the like. Suitable expression plasmids include pcDNA3.1 Zeo, pIND(SP1), pREP8 (all available from Invitrogen, Carlsbad, Calif.) (see Example 1), and the like. Antibody genes may be expressed via viral or retroviral vectors, which may be exemplified by MLV based vectors, vaccinia virus based vectors, etc. Similarly, antibody genes may be expressed using the pCOMB series of vectors on the surface of M13 phage, as two independent chains, which may be renatured to form the intact antibody. Alternatively, antibodies may be expressed as a single chain, including at least the variable regions. Genes may be used for gene therapy by introducing the genes into appropriate cells, such as lymphocytes, muscle cells, fibroblasts, and the like, where antibodies may be expressed and secreted, either constitutively or inductively, to provide a continuous or intermittent source of antibody over a predetermined period of time, based on the lifetime of the host cell. Genes in conjunction with a marker gene (e.g., antibiotic resistance; fluorescent label; nutrient selection; etc.) may be introduced in cell cultures of cells taken from a subject, the modified cells selected by means of the marker and the marked cells returned to the host. DNA may be introduced into cells using various plasmid DNA, naked DNA, DNA virus constructs (e.g., adenovirus, adeno-associated virus, or vaccinia virus), and/or RNA viruses (e.g., Vesicular stomatitis virus, sindbis virus, and semiliki forest virus), to name but a few. In some embodiments, a DNA construct has a promoter for which transcription factors are present in the subject cells or can be induced or introduced and the genes under the transcriptional control of such promoter. Other regulatory sequences may also be present, such as leaders for secretion, enhancers, RNA stabilizing sequences, and the like.

Figure 3:
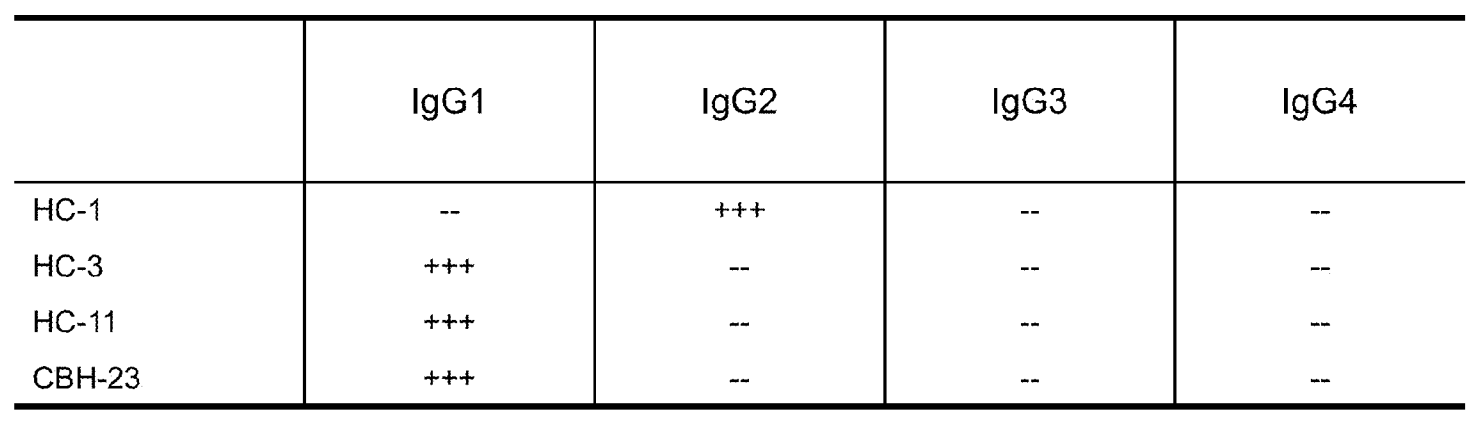

In some embodiments, antibodies are of the IgG class. In some embodiments, antibodies are of the IgG1 or IgG2 class (FIG. 3). In some embodiments, antibodies are of the $IgG_1$ class. In certain embodiments, antibodies are of the $IgG_{1\kappa}$ class. In some embodiments, antibodies are of the $IgG_{1\gamma}$, $IgG_{1\delta}$, or $IgG_{1\lambda}$ class. In some embodiments, antibodies are of the IgG$_2$, IgG$_3$, or IgG$_4$ class. In some embodiments, antibodies are of the IgA, IgD, IgE, or IgM class. In some embodiments, antibodies are of the IgA$_1$ or IgA$_2$ class.

Antibodies may be used in their native form or may be truncated to provide Fab or F(ab')$_2$ fragments. Genes encoding heavy and light chains may be isolated and modified in a number of different manners. Conveniently, using RT-PCR, cDNA may be obtained for the genes in a convenient construction for further manipulation. Nucleotide sequences of variable regions of heavy and light chains may be isolated and joined, either directly or indirectly or through a chain of 3n nucleotides, where n is at least 1 and not more than about 60, usually not more than about 40, to provide a linker of amino acids between the two variable regions. The length of the chain can be determined empirically to provide the optimum affinity and other properties, e.g., linkage through mercapto, carboxy, or amino groups, for chelation, bonding to a surface or other molecule, or the like.

Labels or tags may be attached to the gene encoding the antibody to provide for specific affinity isolation methods for the expressed antibody, attachment to a surface, labels or tags for identification, etc. Labels or tags may otherwise improve the utility of the isolated antibody gene. In some embodiments, labels or tags are associated with antibodies via linkers, such as cleavable arms, protease sites, etc. In some embodiments, labels or tags are directly associated (e.g., covalently or non-covalently) to an antibody, a gene encoding an antibody, or fragments thereof.

Labels may include enzymes, chelating groups, ligands for binding to ligand binding proteins, e.g., biotin/streptavidin, digoxigenin/antidigoxigenin, etc., green fluorescent protein, and the like. The biotinylation sequence of E. coli biotin carboxylase carrier protein (BCCP) can be used for in vivo biotinylation of proteins expressed in E. coli or introduced in a lysate of E. coli. A sequence of six histidines or a sequence of alternating histidines and aspartic acids that are suitable for allowing binding of the antibody to a column containing immobilized divalent cations can be used. Sequences encoding high affinity epitopes may be employed, such as the FLAG epitope DYKDDDDK (SEQ ID NO: 1), the T7 tag sequence MASMTGGQMG (SEQ ID NO: 2), the S-tag sequence KETAAAKFERQHMDS (SEQ ID NO: 3), or any other sequence that confers high affinity binding to its correlative binding member or a protein reagent. Fusion proteins, besides the ones indicated above, include glutathione-S-transferase, luciferase, ligands to cell surface receptors found on hepatocytes, T-cells or other desirable cellular target, and the like. Such fusions are usually joined via a linker sequence of 3-50 amino acids that promotes the bi-functionality of the protein.

In some embodiments, labels include fluorescent, radioactive, luminescent, and/or enzymatically detectable moieties. Alternatively, antibodies may be linked to chelated toxic heavy metals or radioactive isotopes (e.g., technetium, radioactive iodine, etc.). Antibodies may be chemically linked to fluorophores or chemiluminescent molecules. Chemical coupling may involve biotinylation using the activated carboxylic acid group or biotin-C11-hydroxysuccinimide ester, which will react with cysteines; coupling through the use of CNBr activation of various beads (sepharose, agarose, magnetic, polystyrene, etc.) or surfaces to link the antibodies, and the like; any number of other methods generally involving bridging the antibody to a useful chemical moiety, usually accomplished by modifying lysine or other basic residues or through use of reagents specific for free sulfhydryl groups.

In some embodiments, a label may provide cysteines for forming thioethers with maleimide groups, polyhistidine/cysteines or polyhistidines/aspartic acids for chelating metals, polylysines for reacting with aldehydes in reductive animation reactions, etc.

In some embodiments, a label may be a toxin, such as diphtheria toxin, ricin, abrin, ribosome inactivating proteins, apoptosis signaling proteins, pore forming proteins (e.g., perforin), etc.

Genes for antibody heavy and light chain variable regions (particularly the hypervariable regions of the variable regions) may be mutated in accordance with known ways to enhance antibody binding affinity or to broaden reactivity. One may use in vitro selection to identify the optimum binding antibodies using phage display methodologies, random or directed mutagenesis of sequences, or other similar methodologies. Alternatively, one may use an alanine or glycine walk of the hypervariable regions to identify essential amino acids and then vary the amino acids at those or other sites to identify improved binding of the epitope. Other techniques known in the art may be employed to provide the mutagenized antibodies. See, e.g., Gram et al., 1992, *Proc. Natl. Acad. Sci., USA*, 89:3576-80; Griffiths et al., 1993, *EMBO J.*, 12:725-34; de Kruif et al., 1995, *J. Mol. Biol.*, 248:97-105; Low et al., 1996, *J. Mol. Biol.*, 260:359-368; Hanes et al., 2000, *Nat. Biotechnol.*, 18:1287-1292; Boder et al., 2000, *Proc. Natl. Acad. Sci., USA*, 97:10701-10705; Graff et al., 2004, *Protein Eng. Des. Sel.*, 17:293-304; Cumbers et al., 2002, *Nat. Biotechnol.*, 20:1129-1134; Chowdhury and Pastan, 1999, *Nat. Biotechnol.*, 17:568-572; Neuberger and Milstein, 1995, *Curr. Opin. Immunol.*, 7:248-254; Jolly et al., 1996, *Semin. Immunol.*, 8:159-168; Neuberger et al., 1998, *Immunol. Rev.*, 162:107-116; Neuberger, 2002, *Biochem. Soc. Trans.*, 30:341-350; Beers et al., 2000, *Clin. Cancer Res.*, 6:2835-2843; and Salvatore et al., 2002, *Clin. Cancer Res.*, 8:995-1002; all of which are incorporated herein by reference.

References relating to production of human antibodies include Foung et al., 1990, *J. Immunol. Methods*, 70:83-90; and Zimmermann et al., 1990, *J. Immunol. Methods*, 134:43-50; both of which are incorporated herein by reference. References relating to production of modified antibodies using combinatorial libraries, Burton and Barbas, Dixon, F J (Ed.) *Advances in Immunology*, Vol. 57, Vi+391 p. Academic Press, Inc., San Diego, Calif., 191-280, 1994; Plaisant et al., 1997, *Res. Virol.*, 148-169; and Barbas and Burton, *Monoclonal Antibodies from Combinatorial Libraries. Cold Spring Harbor Laboratory Course Manual*, Cold Spring Harbor, N.Y., 1994; all of which are incorporated herein by reference. Modified antibodies can be produced by mutagenesis followed by in vitro selection for a desirable property, such as increased affinity to a target antigen or broader or narrower specificity. Antibodies can also be modified by a toxin or other bioactive molecule. An assay for antibodies binding to HCV E2 is described by Rosa et al. (1996, *Proc. Natl. Acad. Sci., USA*, 93:1759-1763; incorporated herein by reference).

Conformational Epitopes

Characterization of Epitopes

Antibodies may be used to identify the structural epitopes on E2 protein that they bind. Two basic approaches may be employed using the monoclonal antibodies for identifying conformational epitopes. In the first, natural variants or mutation analysis of HCV isolates may be used to identify regions, and ultimately individual amino acids that are involved in the epitopes recognized by the monoclonal antibodies (Schwartz et al., 1999, *J. Mol. Biol.*, 287:983-999; incorporated herein by reference). Antibodies are screened against a number of different HCV E2 isolates, identifying isolates that are selectively non-reactive with individual antibodies. "Chimeric" E2 envelope proteins are then constructed in which portions of the chimera are derived from E2 protein from one HCV genotype and other portions are derived from E2 protein of another HCV genotype. Chimeric E2 proteins are constructed by PCR amplifying overlapping fragments, and/or by using restriction sites common to both E2 proteins. An alternative method is DNA shuffling as pioneered by the biotechnology company MaxyGen (reviewed in Cohen, 2001, *Science*, 293: 237; Locher et al., 2005, *DNA Cell Biol.*, 24: 256-263; Locher et al., 2004, *Expert Opin. Biol. Ther.*, 4:589-597; Locher et al., 2004, *Curr. Opin. Mol. Ther.*, 6:34-39; Kurtzman et al., 2001, *Curr. Opin. Biotech.*, 12:361-370; and Minshull and Stemmer, 1999, *Curr. Opin. Chem. Biol.*, 3: 284-290; all of which are incorporated herein by reference). By surveying the observed binding reactivities of different chimeric E2 proteins with different monoclonal antibodies, amino acid regions in the E2 proteins involved in forming conformational epitopes are identified. Once the relevant regions are identified, individual amino acids that differ between the different genotypes are mutated to compose a reactive E2 sequence. Mutants that restore full reactivity identify amino acids that are involved in forming the epitope.

A second basic approach to defining a conformational epitope is to synthesize a series of overlapping peptides 10-15 residues in length that encode the desired sequence of HCV E2 (see, e.g., Petit et al., 2003, *J. Biol. Chem.*, 278:44385-44392; Moskalenko et al., 2000, *J. Virol.*, 74:1761-1766; Pettersson, 1992, *Mol. Biol. Rep.*, 16:149-53; Gerlofs-Nijland et al., 2003, *Nephron Exp. Nephrol.*, 94:e25-34; all of which are incorporated herein by reference). Peptides are then screened against the antibodies using high concentrations of antibody (often 100 µg/ml or higher). Individual regions that comprise the full conformational epitope often retain residual binding activity with the antibody that can be detected. Once these regions are identified, they can be confirmed using mutational studies involving the 10-15 residues of the peptide, either in the context of the peptide or by substituting into a conformationally intact HCV E2 protein. A variation of this methodology is described in Reineke et al. (1999, *Nat. Biotech.*, 17:271-275; incorporated herein by reference).

In some embodiments, the present invention provides definition of conformational epitopes in HCV E2 protein, and further provides compositions and compounds containing such epitopes. For example, the present invention provides mimicking agents (e.g., proteins, peptides, small molecules, carbohydrates, lipids, nanoparticles, nucleic acids, mimotope, organic compound, organometallic compound, inorganic compound, etc.) comprising conformational epitopes of HCV E2 protein. Peptide agents may contain one or more epitopes recognized by the antibodies of the present invention. In certain embodiments, proteins are strings of concatenated peptides at least one of which contains a conformational epitope of HCV E2. The peptides of the string may contain different conformational epitopes of HCV or the peptides may contain the same epitope. The peptides of the string should preferably fold properly in order to display the conformational epitope substantially as it appears in nature. Such proteins and peptides may be used in formulating vaccines or may be used in diagnostic tests.

The present invention provides a method for stratifying patients based on their immunological response to HCV and of identifying those patients likely to respond well to HCV immunotherapy. For example, a patient's serum may be used to test for the presence of antibodies directed against a particular epitope of HCV E2. If the patient does not have adequate levels of antibodies directed to such an epitope, human monoclonal antibodies directed against the epitope may be administered to the patient.

In formulating vaccines to HCV, any agent that mimics at least one conformational epitope of HCV E2 protein may be used. In some embodiments, epitopes represented in a vaccine include ones that are conserved among different genotypes of the virus or among different strains of the virus. In some embodiments, peptides or proteins that contain the conformationally-defined epitopes of E2 of HCV are used in the formulation of a vaccine to prevent an infection by HCV or to treat an HCV infection. In some embodiments, peptide or protein mimics may be less than 500, less than 200, less than 100, less than 50, less than 40, less than 30, or less than 20 amino acids in length. In some embodiments, peptides to be used in formulating a vaccine are peptide fragments of E2 protein of HCV. In some embodiments, a peptide folds in a manner similar to its fold in the native E2 protein thus preserving the three-dimensional structure of the conformational epitope.

A vaccine may also contain proteins that represent concatenated peptides that have the conformational epitope to which antibodies are desired. Several different peptides making up the multimer may be used so that each peptide contains a different epitope, or the same peptide may be used more than once in the multimer.

Peptides may be synthesized using any method known in the art including Merrifield solid phase chemistry. The peptides may also be obtained by cleavage of E1 or E2 protein and purification. The peptides may be made recombinantly and produced in *E. coli*, yeast (e.g., *S. cerevisiae*), insect cells (e.g., Sf9 cells), or mammalian cells (e.g., CHO cells) using any available techniques in the art (Sambrook et al.; Miller & Calos, eds., *Gene Transfer vectors for Mammalian Cells*, 1987; Ausubel et al., eds., *Current Protocols in Molecular Biology*, 1987; each of which is incorporated herein by reference). Peptides may be modified to increase their immunogenicity, solubility in aqueous solution, or to increase their propensity to fold correctly. For example, peptides may be glycosylated, farnesylated, hydroxylated, reduced, oxidized, etc.

In some embodiments, a peptide comprises amino acids 657-698 of the E2 protein of HCV. In some embodiments, a peptide comprises one or more of amino acids D658, F679, L692, I696, or D698 of the E2 protein of HCV. As would be appreciated by one of ordinary skill in this art, analogous amino acid sequences of E2 proteins from any genotype of HCV may be used. Analogous sequences may be determined by aligning multiple sequences of the E2 protein from different strains or genotypes of HCV. Homologous sequences that preserve the desired epitope may also be used in the formulation of vaccines. In some embodiments, sequences are at least 50%, at least 60%, at least 70%, at least 75%, at least 80%, at least 85%, at least 90%, at least 95%, at least 98%, or more homologous to the native sequence from HCV E2 protein.

In some embodiments, full-length HCV E2 proteins, as described herein, may have a sequence that is derived from a wild type HCV polyprotein. In some embodiments, full-length HCV E2 proteins, as described herein, may have a sequence that is derived from a non-wild type HCV polyprotein. Amino acid sequences of a variety of different HCV polyproteins (e.g., from different genotypes, subtypes, isolates, etc.) are known in the art and are available in public databases such as GenBank. Exemplary HCV polyprotein sequences of multiple HCV genotypes, subtypes, and/or isolates are provided in Table 1 below.

TABLE 1

Exemplary HCV Polyprotein Sequences

| GenBank Accession | Genotype & Subtype | HCV Polyprotein Sequence |
|---|---|---|
| AAB67038 (SEQ ID NO: 4) | 1a (H77) | MSTNPKPQRK TKRNTNRRPQ DVKFPGGGQI VGGVYLLPRR GPRLGVRATR KTSERSQPRG RRQPIPKARR PEGRTWAQPG YPWPLYGNEG CGWAGWLLSP RGSRPSWGPT DPRRRSRNLG KVIDTLTCGF ADLMGYIPLV GAPLGGAARA LAHGVRVLED GVNYATGNLP GCSFSIFLLA LLSCLTVPAS AYQVRNSSGL YHVTNDCPNS SIVYEAADAI LHTPGCVPCV REGNASRCWV AVTPTVATRD GKLPTTQLRR HIDLLVGSAT LCSALYVGDL CGSVFLVGQL FTFSPRRHWT TQDCNCSIYP GHITGHRMAW DMMMNWSPTA ALVVAQLLRI PQAIMDMIAG AHWGVLAGIA YFSMVGNWAK VLVVLLLFAG VDAETHVTGG NAGRTTAGLV GLLTPGAKQN IQLINTNGSW HINSTALNCN ESLNTGWLAG LFYQHKFNSS GCPERLTSCR RLTDFAQGWG PISYANGSGL DERPYCWHYP PRPCGIVPAK SVCGPVYCFT PSPVVVGTTD RSGAPTYSWG ANDTDVFVLN NTRPPLGNWF GCTWMNSTGF TKVCGAPPCV IGGVGNNTLL CPTDCFRKHP EATYSRCGSG PWITPRCMVD YPYRLWHYPC TINYTIFKVR MYVGGVEHRL EAACNWTRGE RCDLEDRDRS ELSPLLLSTT QWQVLPCSFT TLPALSTGLI HLHQNIVDVQ YLYGVGSSIA SWAIKWEYVV LLFLLLADAR VCSCLWMMLL ISQAEAALEN LVILNAASLA GTHGLVSFLV FFCFAWYLKG RWVPGAAYAF YGMWPLLLLL LALPQRAYAL DTEVAASCGG VVLVGLMALT LSPYYKRYIS WCMWWLQYFL TRVEAQLHVW VPPLNVRGGR DAVILLMCVV HPTLVFDITK LLLLAIFGPLW ILQASLLKVP YFVRVQGLLR ICALARKIAG GHYVQMAIIK LGALTGTYVY NHLTPLRDWA HNGLRDLAVA VEPVVFSRME TKLITWGADT AACGDIINGL PVSARRGQEI LLGPADGMVS KGWRLQAPIT AYTQQTRGLL GCIITSLTGR DKNQVEGEVQ IVSTATQTFL ATCINGVCWT VYHGAGTRTI ASPKGPVIQM YTNVDQDLVG WPAPQGSRSL APCTCGSSDL YLVTRHADVI PVRRRGDSRG SLLSPRPISY LKGSSGGPLL CPAGHAVGLF RAAVCTRGVA KAVDFIPVEN LGTTMRSPVF TDNSSPPAVP QSFQVAHLHA PTGSGKSTKV PAAYAAQGYK VLVLNPSVAA TLGFGAYMSK AHGVDPNIRT GVRTITTGSP ITYSTYGKPL ADGGCSGGAY DIIICDECHS TDATSILGIG TVLDQAETAG ARLVVLATAT PPGSVTVSHP NIEEVALSTT GEIPFYGKAI PLEVIKGGRH LIFCHSKKKC DELAAKLVAL GINAVAYYRG LDVSVIPTSG DVVVVSTDAL MTGFTGDFDS VIDCNTCVTQ TVDFSLDPTF TIETTTLPQD AVSRTQRRGR TGRGKPGIYR FVAPGERPSG MFDSSVLCEC YDAGCAWYEL TPAETTVRLR AYMNTPGLPV CQDHLEFWEG VFTGLTHIDA HFLSQTKQSG ENFPYLVAYQ ATVCARAQAP PPSWDQMWKC LIRLKPTLHG PTPLLYRLGA VQNEVTLTHP ITKYIMTCMS ADLEVVTSTW VLVGGVLAAL AAYCLSTGCV VIVGRIVLSG KPAIIPDREV LYQEFDEMEE CSQHLPYIEQ GMMLAEQFKQ KALGLLQTAS RHAEVITPAV QTNWQKLEVF WAKHMWNFIS GIQYLAGLST LPGNPAIASL MAFTAAVTSP LTTGQTLLFN ILGGWVAAQL AAPGAATAFV GAGLAGAAIG SVGLGKVLVD ILAGYGAGVA GALVAFKIMS GEVPSTEDLV NLLPAILSPG ALVVGVVCAA ILRRHVGPGE GAVQWMNRLI AFASRGNHVS PTHYVPESDA AARVTAILSS LTVTQLLRRL HQWISSECTT PCSGSWLRDI WDWICEVLSD FKTWLKAKLM PQLPGIPFVS CQRGYRGVWR GDGIMHTRCH CGAEITGHVK NGTMRIVGPR TCRNMWSGTF PINAYTTGPC TPLPAPNYKF ALWRVSAEEY VEIRRVGDFH YVSGMTTDNL KCPCQIPSPE FFTELDGVRL HRFAPPCKPL LREEVSFRVG LHEYPVGSQL PCEPEPDVAV LTSMLTDPSH ITAEAAGRRL ARGSPPSMAS SSASQLSAPS LKATCTANHD SPDAELIEAN LLWRQEMGGN ITRVESENKV VILDSFDPLV AEEDEREVSV PAEILRKSRR FARALPVWAR PDYNPPLVET WKKPDYEPPV VHGCPLPPPR SPPVPPPRKK RTVVLTESTL STALAELATK SFGSSSTSGI TGDNTTTSSE PAPSGCPPDS DVESYSSMPP LEGEPGDPDL SDGSWSTVSS GADTEDVVCC SMSYSWTGAL VTPCAAEEQK LPINALSNSL LRHHNLVYST TSRSACQRQK KVTFDRLQVL DSHYQDVLKE VKAAASKVKA NLLSVEEACS LTPPHSAKSK FGYGAKDVRC HARKAVAHIN SVWKDLLEDS VTPIDTTIMA KNEVFCVQPE KGGRKPARLI VFPDLGVRVC EKMALYDVVS KLPLAVMGSS YGFQYSPGQR VEFLVQAWKS KKTPMGFSYD TRCFDSTVTE SDIRTEEAIY QCCDLDPQAR VAIKSLTERL YVGGPLTNSR GENCGYRRCR ASGVLTTSCG NTLTCYIKAR AACRAAGLQD CTMLVCGDDL VVICESAGVQ EDAANLRAFT EAMTRYSAPP GDPPQPEYDL ELITSCSSNV SVAHDGAGKR VYYLTRDPTT PLARAAWETA RHTPVNSWLG NIIMFAPTLW ARMILMTHFF SVLIARDQLE QALNCEIYGA CYSIEPLDLP PIIQRLHGLS AFSLHSYSPG EINRVAACLR KLGVPPLRAW RHRARSVRAR LLSRGGRAAI CGKYLFNWAV RTKLKLTPIT AAGRLDLSGW FTAGYSGGDI YHSVSHARPR WFWFCLLLLA AGVGIYLLPN R (SEQ ID NO: 4) |
| AAK08509 (SEQ ID NO: 5) | 1b | MSTNPKPQRK TKRNTNRRPQ DVKFPGGGQI VGGVYLLPRR GPRLGVRATR KTSERSQPRG RRQPIPKARR PEGRTWAQPG YPWPLYGNEG MGWAGWLLSP RGSRPSWGPT DPRRRSRNLG KVIDTLTCGF ADLMGYIPLV GAPLGGAARA LAHGVRVLED GVNYATGNLP GCSFSIFLLA LLSCLTIPAS AYEVRNVSGI YHVTNDCSNS SIVYEAADMI MHTPGCVPCV RESNFSRCWV ALTPTLAARN SSIPTTTIRR HVDLLVGAAA LCSAMYVGDL CGSVFLVSQL FTFSPRRYET VQDCNCSIYP GHVSGHRMAW DMMMNWSPTT ALVVSQLLRI PQAVVDMVAG AHWGVLAGLA YYSMVGNWAK VLIVMLLFAG VDGHTHVTGG RVASSTQSLV SWLSQGPSQK IQLVNTNGSW HINRTALNCN DSLQTGFIAA LFYAHRFNAS GCPERMASCR PIDKFAQGWG PITHVPNIS DQRPYCWHYA PQPCGIVPAS QVCGPVYCFT PSPVVVGTTD RSGVPTYSWG ENETDVLLLN NTRPPGNWF GCTWMNSTGF TKTCGGPPCN IGGVGNNTLI CPTDCFRKHP EATYTKCGSG PWLTPRCLVD YPYRLWHYPC TINFTIFKVR MYVGGVEHRL NAACNWTRGE |

TABLE 1-continued

Exemplary HCV Polyprotein Sequences

| GenBank Accession | Genotype & Subtype | HCV Polyprotein Sequence |
|---|---|---|
| | | RCDLEDRDRS ELSPLLLSTT EWQVLPCSFT TLPALSTGLI HLHQNIVDVQ |
| | | YLYGVGSVVV SVVIKWEYVL LLFLLLADAR VCACLWMMLL IAQAEATLEN |
| | | LVVLNAASVA GAHGLLSFLV FFCAAWYIKG RLVPGAAYAL YGVWPLLLLL |
| | | LALPPRAYAM DREMAASCGG AVFVGLVLLT LSPYYKVFLA RLIWWLQYFI |
| | | TRAEAHLQVW VPPLNVRGGR DAIILLTCAV HPELIFDITK LLLAILGPLM |
| | | VLQAGITRVP YFVRAQGLIH ACMLVRKVAG GHYVQMAFMK LGALTGTYIY |
| | | NHLTPLRDWA HAGLRDLAVA VEPVVFSDME TKIITWGADT AACGDIILGL |
| | | PVSARRGKEI LLGPADSLEG RGWRLLAPIT AYSQQTRGLL GCIITSLTGR |
| | | DKNQVEGEVQ VVSTATQSFL ATCVNGVCWT VYHGAGSKTL AGPKGPITQM |
| | | YTNVDQDLVG WQAPPGARSL TPCTCGSSDL YLVTRHADVI PVRRRGDSRG |
| | | SLLSPRPVSY LKGSSGGPLL CPSGHAVGIF RAAVCTRGVA KAVDFVPVES |
| | | METTMRSPVF TDNSSPPAVP QSFQVAHLHA PTGSGKSTKV PAAYAAQGYK |
| | | VLVLNPSVAA TLGFGAYMSK AHGIDPNIRT GVRTITTGAP VTYSTYGKFL |
| | | ADGGCSGGAY DIIICDECHS TDSTTILGIG TVLDQAETAG ARLVVLATAT |
| | | PPGSVTVPHP NIEEVALSNT GEIPFYGKAI PIEAIRGGRH LIFCHSKKKC |
| | | DELAAKLSGL GINAVAYYRG LDVSVIPTIG DVVVVATDAL MTGYTGDFDS |
| | | VIDCNTCVTQ TVDFSLDPTF TIETTTVPQD AVSRSQRRGR TGRGRRGIYR |
| | | FVTPGERPSG MFDSSVLCEC YDAGCAWYEL TPAETSVRLR AYLNTPGLPV |
| | | CQDHLEFWES VFTGLTHIDA HFLSQTKQAG DNFPYLVAYQ ATVCARAQAP |
| | | PPSWDQMWKC LIRLKPTLHG PTPLLYRLGA VQNEVTLTHP ITKYIMACMS |
| | | ADLEVVTSTW VLVGGVLAAL AAYCLTTGSV VIVGRIILSG RPAIVPDREL |
| | | LYQEFDEMEE CATHLPYIEQ GMQLAEQFKQ KALGLLQTAT KQAEAAAPVV |
| | | ESKWRALETF WAKHMWNFIS GIQYLAGLST LPGNPAIASL MAFTASITSP |
| | | LTTQSTLLFN ILGGWVAAQL APPSAASAFV GAGIAGAAVG SIGLGKVLVD |
| | | ILAGYGAGVA GALVAFKVMS GEMPSTEDLV NLLPAILSPG ALVVGVVCAA |
| | | ILRRHVGPGE GAVQWMNRLI AFASRGNHVS PTHYVPESDA AARVTQILSS |
| | | LTITQLLKRL HQWINEDCST PCSGSWLRDV WDWICTVLTD FKTWLQSKLL |
| | | PQLPGVPFFS CQRGYKGVWR GDGIMQTTCP CGAQITGHVK NGSMRIVGPK |
| | | TCSNTWHGTF PINAYTTGPC TPSPAPNYSR ALWRVAAEEY VEVTRVGDFH |
| | | YVTGMTTDNV KCPCQVPAPE FFSEVDGVRL HRYAPACRPL LREEVTFQVG |
| | | LNQYLVGSQL PCEPEPDVAV LTSMLTDPSH ITAETAKRRL ARGSPPSLAS |
| | | SSASQLSAPS LKATCTTHHV SPDADLIEAN LLWRQEMGGN ITRVESENKV |
| | | VVLDSFDPLR AEEDEREVSV PAEILRKSKK FPAAMPIWAR PDYNPPLLES |
| | | WKDPDYVPPV VHGCPLPPIK APPIPPPRRK RTVVLTESSV SSALAELATK |
| | | TFGSSESSAV DSGTATALPD QASDDGDKGS DVESYSSMPP LEGEPGDPDL |
| | | SDGSWSTVSE EASEDVVCCS MSYTWTGALI TPCAAEESKL PINALSNSLL |
| | | RHHNMVYATT SRSAGLRQKK VTFDRLQVLD DHYRDVLKEM KAKASTVKAK |
| | | LLSVEEACKL TPPHSAKSKF GYGAKDVRNL SSKAVNHIHS VWKDLLEDTV |
| | | TPIDTTIMAK NEVFCVQPEK GGRKPARLIV FPDLGVRVCE KMALYDVVST |
| | | LPQVVMGSSY GFQYSPGQRV EFLVNTWKSK KNPMGFSYDT RCFDSTVTEN |
| | | DIRVEESIYQ CCDLAPEARQ AIKSLTERLY IGGPLTNSKG QNCGYRRCRA |
| | | SGVLTTSCGN TLTCYLKASA ACRAAKLQDC TMLVNGDDLV VICESAGTQE |
| | | DAASLRVFTE AMTRYSAPPG DPPQPEYDLE LITSCSSNVS VAHDASGKRV |
| | | YYLTRDPTTP LARAAWETAR HTPVNSWLGN IIMYAPTLWA RMILMTHFFS |
| | | ILLAQEQLEK ALDCQIYGAC YSIEPLDLPQ IIERLHGLSA FSLHSYSPGE |
| | | INRVASCLRK LGVPPLRVWR HRARSVRARL LSQGGRAATC GKYLFNWAVK |
| | | TKLKLTPIPA ASQLDLSGWF VAGYSGGDIY HSLSRARPRW FMLCLLLLSV |
| | | GVGIYLLPNR (SEQ ID NO: 5) |
| BAB32872 (SEQ ID NO: 6) | 2a (JFH-1) | MSTNPKPQRK TKRNTNRRPE DVKFPGGGQI VGGVYLLPRR GPRLGVRTTR |
| | | KTSERSQPRG RRQPIPKDRR STGKAWGKPG RPWPLYGNEG LGWAGWLLSP |
| | | RGSRPSWGPT DPRHRSRNVG KVIDTLTCGF ADLMGYIPVV GAPLSGAARA |
| | | VAHGVRVLED GVNYATGNLP GPPFSIFLLA LLSCITVPVS AAQVKNTSSS |
| | | YMVTNDCSND SITWQLEAAV LHVPGCVPCE RVGNTSRCWV PVSPNMAVRQ |
| | | PGALTQGLRT HIDMVVMSAT FCSALYVGDL CGGVMLAAQV FIVSPQYHWF |
| | | VQECNCSIYP GTITGHRMAW DMMMNWSPTA TMILAYVMRV PEVIIDIVSG |
| | | AHWGVMFGLA YFSMQGAWAK VIVILLLAAG VDAGTTTVGG AVARSTNVIA |
| | | GVFSHGPQQN IQLINTNGSW HINRRTALNCN DSLNTGFLAA LFYTNRFNSS |
| | | GCPGRLSACR NIEAFRIGWG TLQYEDNVTN PEDMRPYCWH YPPKPCGVVP |
| | | ARSVCGPVYC FTPSPVVVGT TDRRGVPTYT WGENETDVFL LNSTRPPQGS |
| | | WFGCTWMNST GFTKTCGAPP CRTRADFNAS TDLLCPTDCF RKHPDATYIK |
| | | CGSGPWLTPK CLVHYPYRLW HYPCTVNFTI FKIRMYVGGV EHRLTAACNF |
| | | TRGDRCDLED RDRSQLSPLL HSTTEWAILP CTYSDLPALS TGLLHLHQNI |
| | | VDVQYMYGLS PAITKYVVRW EWVVLLFLLL ADARVCACLW MLILLGQAEA |
| | | ALEKLVVLHA ASAANCHGLL YFAIFFVAAW HIRGRVVPLT TYCLTGLWPF |
| | | CLLLLMALPRQ AYAYDAPVHG QIGVGLLILI TLFTLTPGYK TLLGQCLWWL |
| | | CYLLTLGEAM IQEWVPPMQV RGGRDGIAWA VTIFCPGVVF DITKWLLALL |
| | | GPAYLLRAAL THVPYFVRAH ALIRVCALVK QLAGGRYVQV ALLALGRWTG |
| | | TYIYDHLTPM SDWAASGLRD LAVAVEPIIF SPMEKKVIVW GAETAACGDI |
| | | LHGLPVSARL GQEILLGPAD GYTSKGWKLL APITAYAQQT RGLLGAIVVS |
| | | MTGRDRTEQA GEVQILSTVS QSFLGTTISG VLWTVYHGAG NKTLAGLRGP |
| | | VTQMYSSAEG DLVGWPSPPG TKSLEPCKCG AVDLYLVTRN ADVIPARRRG |
| | | DKRGALLSPR PISTLKGSSG GPVLCPRGHV VGLFRAAVCS RGVAKSIDFI |
| | | PVETLDVVTR SPTFSDNSTP PAVPQTYQVG YLHAPTGSGK STKVPVAYAA |
| | | QGYKVLVLNP SVAATLGFGA YLSKAHGINP NIRTGVRTVM TGEAITYSTY |

TABLE 1-continued

Exemplary HCV Polyprotein Sequences

| GenBank Accession | Genotype & Subtype | HCV Polyprotein Sequence |
|---|---|---|
| | | GKFLADGGCA SGAYDIIICD ECHAVDATSI LGIGTVLDQA ETAGVRLTVL |
| | | ATATPPGSVT TPHPDIEEVG LGREGEIPFY GRAIPLSCIK GGRHLIFCHS |
| | | KKKCDELAAA LRGMGLNAVA YYRGLDVSII PAQGDVVVVA TDALMTGYTG |
| | | DFDSVIDCNV AVTQAVDFSL DPTFTITTQT VPQDAVSRSQ RRGRTGRGRQ |
| | | GTYRYVSTGE RASGMFDSVV LCECYDAGAA WYDLTPAETT VRLRAYFNTP |
| | | GLPVCQDHLE FWEAVFTGLT HIDAHFLSQT KQAGENFAYL VAYQATVCAR |
| | | AKAPPPSWDA MWKCLARLKP TLAGPTPLLY RLGPITNEVT LTHPGTKYIA |
| | | TCMQADLEVM TSTWVLAGGV LAAVAAYCLA TGCVSIIGRL HVNQRVVVAP |
| | | DKEVLYEAFD EMEECASRAA LIEEGQRIAE MLKSKIQGLL QQASKQAQDI |
| | | QPAMQASWPK VEQFWARHMW NFISGIQYLA GLSTLPGNPA VASMMAFSAA |
| | | LTSPLSTSTT ILLNIMGGWL ASQIAPPAGA TGFVVSGLVG AAVGSIGLGK |
| | | VLVDILAGYG AGISGALVAF KIMSGEKPSM EDVINLLPGI LSPGALVVGV |
| | | ICAAILRRHV GPGEGAVQWM NRLIAFASRG NHVAPTHYVT ESDASQRVTQ |
| | | LLGSLTITSL LRRLHNWITE DCPIPCSGSW LRDVWDWVCT ILTDFKNWLT |
| | | SKLFPKLPGL PFISCQKGYK GVWAGTGIMT TRCPCGANIS GNVRLGSMRI |
| | | TGPKTCMNTW QGTFPINCYT EGQCAPKPPT NYKTAIWRVA ASEYAEVTQH |
| | | GSYSYVTGLT TDNLKIPCQL PSPEFFSWVD GVQIHRFAPT PKPFFRDEVS |
| | | FCVGLNSYAV GSQLPCEPEP DADVLRSMLT DPPHITAETA ARRLARGSPP |
| | | SEASSSVSQL SAPSLRATCT THSNTYDVDM VDANLLMEGG VAQTEPESRV |
| | | PVLDFLEPMA EEESDLEPSI PSECMLPRSG FPRALPAWAR PDYNPPLVES |
| | | WRRPDYQPPT VAGCALPPPK KAPTPPPRRR RTVGLSESTI SEALQQLAIK |
| | | TFGQPPSSGD AGSSTGAGAA ESGGPTSPGE PAPSETGSAS SMPPLEGEPG |
| | | DPDLESDQVE LQPPPQGGGV APGSGSGSWS TCSEEDDTTV CCSMSYSWTG |
| | | ALITPCSPEE EKLPINPLSN SLLRYHNKVY CTTSKSASQR AKKVTFDRTQ |
| | | VLDAHYDSVL KDIKLAASKV SARLLTLEEA CQLTPPHSAR SKYGFGAKEV |
| | | RSLSGRAVNH IKSVWKDLLE DPQTPIPTTI MAKNEVFCVD PAKGGKKPAR |
| | | LIVYPDLGVR VCEKMALYDI TQKLPQAVMG ASYGFQYSPA QRVEYLLKAW |
| | | AEKKDPMGFS YDTRCFDSTV TERDIRTEES IYQACSLPEE ARTAIHSLTE |
| | | RLYVGGPMFN SKGQTCGYRR CRASGVLTTS MGNTITCYVK ALAACKAAGI |
| | | VAPTMLVCGD DLVVISESQG TEEDERNLRA FTEAMTRYSA PPGDPPRPEY |
| | | DLELITSCSS NVSVALGPRG RRRYYLTRDP TTPLARAAWE TVRHSPINSW |
| | | LGNIIQYAPT IWVRMVLMTH FFSILMVQDT LDQNLNFEMY GSVYSVNPLD |
| | | LPAIIERLHG LDAFSMHTYS HHELTRVASA LRKLGAPPLR VWKSRARAVR |
| | | ASLISRGGKA AVCGRYLFNW AVKTKLKLTP LPEARLLDLS SWFTVGAGGG |
| | | DIFHSVSRAR PRSLLFGLLL LFVGVGLFLL PAR (SEQ ID NO: 6) |
| BAB08107 (SEQ ID NO: 7) | 2b (JPUT971017) | MSTNPKPQRK TKRNTNRRPQ DVKFPGGGQI VGGVYLLPRR GPRLGVRATR |
| | | KTSERSQPRG RRQPIPKDRR STGKSWGKPG YPWPLYGNEG CGWAGWLLSP |
| | | RGSRPTWGPS DPRHRSRNLG RVIDTITCGF ADLMGYIPVV GAPVGGVARA |
| | | LAHGVRVLED GINYATRNLP GCSFSIFLLA LLSCVTVPVS SVEIRNISTS |
| | | YYATNDCSNN SITWQLTNAV LHLPGCVPCE NDNGTLRCWI QVTPNVAVKH |
| | | RGALTHNLRA HVDVIVMAAT VCSALYVGDV CGAVMIVSQA LIVSPERHNF |
| | | TQECNCSIYQ GHITGQRMAW DMMLNWSPTL TMILAYAARV PELVLEIVFG |
| | | GHWGVVFGLA YFSMQGAWAK VIAILLLVAG VDATTYSTGA TVGRTVGSFA |
| | | GLFKLGAQQN VQLINTNGSW HINRTALNCN DSLHTGFMAA LFYANKFNSS |
| | | GCPERLSSCR GLDDFRIGWG TLEYETNVTN VEDMRPYCWH YPPKPCGIVP |
| | | AQSVCGPVYC FTPSPVVVGT TDRQGVPTYN WGDNETDVFL LNSTRPPRGA |
| | | WFGCTWMNGT GFTKTCGAPP CRIRKDFNST LDLLCPTDCF RKHPDATYVK |
| | | CGAGPWLTPR CLIDYPYRLW HYPCTVNFTI FKVRMYVGGV EHRFSAACNF |
| | | TRGDRCRLED RDRGQQSPLL HSTTEWAVLP CSFSDLPALS TGLLHLHQNI |
| | | VDVQYLYGLS PAVTKYIVKW EWVVLFLLL ADARICACLW MLIILGQAEA |
| | | ALEKLIILHS ASAASANGPL WFFIFFTAAW YLKGRVVPAA TYSVLGLWSF |
| | | LLLVLALPQQ AYALDAAEQG ELGLVILMII SIFTLTPAYK ILLSRSVWWL |
| | | SYMLVLAEAQ VQQWVPPLEA RGGRDGIIWV AVILHPHLVF EVTKWLLAIL |
| | | GSAYLLKASL LRVPYFVRAH ALLRVCTLVR HLAGARYIQM LLITMGRWTG |
| | | TYIYDHLSPL STWAAQGLRD LAVAVEPVVF SPMEKKVIVW GAETVACGDI |
| | | LHGLPVSARL GREVLLGPAD GYTSKGWKLL APITAYTQQT RGLLGAIVVS |
| | | LTGRDKNEQA GQVQVLSSVT QSFLGTSISG VLWTVYHGAG NKTLASPRGP |
| | | VTQMYTSAEG DLVGWPSPPG TKSLDPCTCG AVDLYLVTRN ADVIPVRRKD |
| | | DRRGALLSPR PLSTLKGSSG GPVLCPRGHA VGLFRAAVCA RGVAKSIDFI |
| | | PVESLDIARR TPSFSDNSTP PAVPQTYQVG YLHAPTGSGK STKVPAAYTS |
| | | QGYKVLVLNP SVAATLGFGA YMSKAHGINP NIRTGVRTVT TGDSITYSTY |
| | | GKFLADGGCS AGAYDIIICD ECHSVDATTI LGIGTVLDQA ETAGVRLVVL |
| | | ATATPPGSVT TPHANIEEVA LGHEGEIPFY GKAIPLASIK GGRHLIFCHS |
| | | KKKCDELAAA LRGMGVNAVA YYRGLDVSVI PTQGDVVVVA TDALMTGYTG |
| | | DFDSVIDCNV AVTQIVDFSL DPTFTITTQT VPQDAVSRSQ RRGRTGRGRL |
| | | GTYRYVSSGE RPSGMFDSVV LCECYDAGAA WYELTPAETT VRLRAYFNTP |
| | | GLPVCQDHLE FWEAVFTGLT HIDAHFLSQT KQGGDNFAYL TAYQATVCAR |
| | | AKAPPPSWDV MWKCLTRLKP TLTGPTPLLY RLGAVTNEIT LTHPVTKYIA |
| | | TCMQADLEVM TSTWVLAGGV LAAVAAYCLA TGCISIIGRI HLNDQVVVAP |
| | | DKEILYEAFD EMEECASKAA LIEEGQRMAE MLKSKILGLL QQATKQAQDI |
| | | QPAMQSSWPK IEQFWARHMW NFISGIQYLA GLSTLPGNPA VASMMAFSAA |
| | | LTSPLPTSTT ILLNIMGGWL ASQIAPPAGA TGFVVSGLVG AAVGSIGLGK |
| | | ILVDVLAGYG AGISGALVAF KIMSGEKPSV EDVINLLPAI LSPGALVVGV |
| | | ICAAILRRHV GQGEGAVQWM NRLIAFASRG NHVAPTHYVA ESDASLRVTQ |

TABLE 1-continued

Exemplary HCV Polyprotein Sequences

| GenBank Accession | Genotype & Subtype | HCV Polyprotein Sequence |
|---|---|---|
| | | VLSSLTITSL LRRLHAWITE DCPVPCSGSW LRDIWEWVCS ILTDFKNWLS |
| | | AKLLPKMPGL PFISCQKGYR GVWAGTGVMT TRCSCGANIS GHVRLGTMKI |
| | | TGPKTCLNMW QGTFPINCYT EGPCVPKPPP NYKTAIWRVA ASEYVEVTQH |
| | | GSFSYVTGLT SDNLKVPCQV PAPEFFSWVD GVQIHRFAPT PGPFFRDEVT |
| | | FTVGLNSLVV GSQLPCDPEP DTEVLASMLT DPSHITAETA ARRLARGSPP |
| | | SQASSSASQL SAPSLKATCT THKTAYDCDM VDANLFMGGD VTRIESDSKV |
| | | IVLDSLDSMT EVEDDREPSV PSEYLTRRRK FPPALPPWAR PDYNPPVIET |
| | | WKRPDYEPPT VLGCALPPTP QAPVPPPRRR RARVLTQDNV EGVLREMADK |
| | | VLSPLQDTND SGHSTGADTG GDSVQQPSGE TAASDAGSLS SMPPLEGEPG |
| | | DPDLEFEPAR SAPPSEGECE VIDSDSKSWS TVSDQEDSVI CCSMSYSWTG |
| | | ALITPCGPEE EKLPISPLSN SLMRFHNKVY STTSRSASLR AKKVTFDRVQ |
| | | VLDAHYDSVL QDVKRAASKV SARLLSVEEA CALTPPHSAK SRYGFGAKEV |
| | | RSLSRGAVNH IRSVWEDLLE DQHTPIDTTA MAKNEVFCID PAKGGKKPAR |
| | | LIVYPDLGVR VCEKMALYDI AQKLPKAIMG PSYGFQYSPA ERVDFLLKAW |
| | | GSKKDPMGFS YDTRCFDSTV TERDIRTEES IYQACSLPQE ARTVIHSITE |
| | | RLYVGGPMTN SKGQSCGYRR CRASGVFTTS MGNTMTCYIK ALAACKAAGI |
| | | VDPTMLVCGD DLVVISESQG NEEDERNLRA FTEAMTRYSA PPGDLPRPEY |
| | | DLELITSCSS NVSVALDSRG RRRYFLTRDP TTPITRAAWE TVRHSPVNSW |
| | | LGNIIQYAPT IWVRMVIMTH FFSILLAQDT LNQNLNFEMY GAVYSVNPLD |
| | | LPAIIERLHG LDAFSLHTYS PHELSRVAAT LRKLGAPPLR AWKSRARAVR |
| | | ASLIIQGGRA ATCGRYLFNW AVKTKLKLTP LPEASRLDLS GWFTVGAGGG |
| | | DIFHSVSHAR PRLLLLCLLL LSVGVGIFLL PAR (SEQ ID NO: 7) |
| CAA72338 (SEQ ID NO: 8) | 4 (ED43) | MSTNPKPQRK TKRNTNRRPM DVKFPGGGQI VGGVYLLPRR GPRLGVRATR |
| | | KTSERSQPRG RRQPIPKARR PEGRSWAQPG YPWPLYGNEG CGWAGWLLSP |
| | | RGSRPSWGPN DPRGRSRNLG KVIDTLTCGF ADLMGYIPLV GAPVGSVARA |
| | | LAHGVRALED GINYATGNLP GCSFSIFLLA LLSCLTVPAS AVNYRNVSGI |
| | | YHVTNDCPNS SIVYEADHHI MHLPGCVPCV REGNQSRCWV ALTPTVAAPY |
| | | IGAPLESLRS HVDLMVGAAT VCSGLYIGDL CGGLFLVGQM FSFRPRRHWT |
| | | TQDCNCSIYT GHITGHRMAW DMMMNWSPTT TLVLAQVMRI PTTLVDLLSG |
| | | GHWGVLVGVA YFSMQANWAK VILVLFLFAG VDAETHVSGA AVGRSTAGLA |
| | | NLFSSGSKQN LQLINSNGSW HINRTALNCN DSLNTGFLAS LFYTHKFNSS |
| | | GCSERLACCK SLDSYGQGWG PLGVANISGS SDDRPYCWHY APRPCGIVPA |
| | | SSVCGPVYCF TPSPVVVGTT DHVGVPTYTW GENETDVFLL NSTRPPHGAW |
| | | FGCVWMNSTG FTKTCGAPPC EVNTNNGTWH CPTDCFRKHP ETTYAKCGSG |
| | | PWITPRCLID YPYRLWHFPC TANFSVFNIR TFVGGIEHRM QAACNWTRGE |
| | | VCGLEHRDRV ELSPLLLTTT AWQILPCSFT TLPALSTGLI HLHQNIVDVQ |
| | | YLYGVGSAVV SWALKWEYVV LAFLLLADAR VSAYLWMMFM VSQVEAALSN |
| | | LININAASAA GAQGFWYAIL FICIVWHVKG RFPAAAAYAA CGLWPCFLLL |
| | | LMLPERAYAY DQEVAGSLGG AIVVMLTILT LSPHYKLWLA RGLWWIQYFI |
| | | ARTEAVLHVY IPSFNVRGPR DSVIVLAVLV CPDLVFDITK YLLAILGPLH |
| | | ILQASLLRIP YFVRAQALVK ICSLLRGVVY GKYFQMVVLK SRGLTGTYIY |
| | | DHLTPMSDWP PYGLRDLAVA LEPVVFTPME KKVIVWGADT AACGDIIRGL |
| | | PVSARLGNEI LLGPADTETS KGWRLLAPIT AYAQQTRGLF STIVTSLTGR |
| | | DTNENCGEVQ VLSTATQSFL GTAVNGVMWT VYHGAGAKTI SGPKGPVNQM |
| | | YTNVDQDLVG WPAPPGVRSL APCTCGSADL YLVTRHADVI PVRRRGDTRG |
| | | ALLSPRPISI LKGSSGGPLL CPMGHRAGIF RAAVCTRGVA KAVDFVPVES |
| | | LETTMRSPVF TDNSTPPAVP QTYQVAHLHA PTGSGKSTKV PAAHAAQGYK |
| | | VLVLNPSVAA TLGFGVYMSK AYGIDPNIRS GVRTITTGAP ITYSTYGKFL |
| | | ADGGCSGGAY DIIICDECYS TDSTTILGIG TVLDQAETAG VRLTVLATAT |
| | | PPGSVTTPHS NIEEVALPTT GEIPFYGKAI PLELIKGGRH LIFCHSKKKC |
| | | DELARQLTSL GLNAVAYYRG LDVSVIPTSG DVVVCATDAL MTGFTGDFDS |
| | | VIDCNTSVIQ TVDFSLDPTF SIEITTVPQD AVSRSQRRGR TGRGRLGTYR |
| | | YVTPGERPSG MFDTAELCEC YDAGCAWYEL TPAETTTRLK AYFDTPGLPV |
| | | CQDHLEFWES VFTGLTHIDG HFLSQTKQSG ENFPYLVAYQ ATVSAKVWLA |
| | | PPSWDTMWKC LIRLKPTLHG PTPLLYRLGS VQNEVVLTHP ITKYIMACMS |
| | | ADLEVVTSTW VLVGGVLAAL AAYCLSVGSV VIVGRVVLSG QPAVIPDREV |
| | | LYQQFDEMEE CSKHLPLVEH GLQLAEQFKQ KALGLLNFAG KQAQEATPVI |
| | | QSNFAKLEQF WANDMWNFIS GIQYLAGLST LPGNPAIASL MSFTAAVTSP |
| | | LTTQQTLLFN ILGGWVASQI RDSDASTAFV VSGLAGAAVG SVGLGKILVD |
| | | ILPGYGAGVR GAVVTFKIMS GEMPSTEDLV NLLPAILSPG ALVVEVVCPA |
| | | ILRRHVGPGE GAVQWMNRLI AFASRGNHVS PTHYVPESDA ARRVTTILSS |
| | | LTVTSLLRRL HKWINEDCST PCAESWLWEV WDWVLHVLSD FKTCLKAKFV |
| | | PLMPGIPLLS WPRGYKGEWR GDGVMHTTCP CGADLAGHIK NGSMRITGPK |
| | | TCSNTWHGTF PINAYTTGPG VPIPAPNYKF ALWRVSAEDY VEVRRVGDFH |
| | | YVTGVTQDNI KPPCQVPAPE LFTEVDGIRI HRHAPKCKPL LRDEVSFSVG |
| | | LNSFVVGSQL PCEPEPDVAV LTSMLTDPSH ITAESARRRL ARGSRPSLAS |
| | | SSASQLSPRL LQATCTAPHD SPGTDLLEAN LLWGSTATRV ETDEKVIILD |
| | | SFESCVAEQN DDREVSVAAE ILRPTKKFPP ALPIWARPDY NPPLTETWKQ |
| | | QDYQAPTVHG CALPPAKQPP VPSPRRKRTV QLTESVVSTA LAELAAKTFG |
| | | QSEPSSDRDT DLTTPTETTD SGPIVVDDAS DDGSYSSMPP LEGEPGDPDL |
| | | TSDSWSTVSG SEDVVCCSMS YSWTGALVTP CAAEESKLPI SPLSNSLLRH |
| | | HNMVYATTTR SAVTRQKKVT FDRLQVVDST YNEVLKEIKA RASRVKPRLL |
| | | TTEEACDLTP PHSARSKFGY GKKDVRSHSR KAINHISSVW KDLLDDNNTP |
| | | IPTTIMAKNE VFAVNPAKGG RKPARLIVYP DLGSRVCEKR ALHDVIKKTA |

TABLE 1-continued

Exemplary HCV Polyprotein Sequences

| GenBank Accession | Genotype & Subtype | HCV Polyprotein Sequence |
|---|---|---|
| | | LAVMGAAYGF QYSPAQRVEF LLTAWKSKND PMGFSYDTRC FDSTVTEKDI<br>RVEEEVYQCC DLEPEARKVI TALTDRLYVG GPMHNSKGDL CGYRRCRATG<br>VYTTSFGNTL TCYLKATAAI RAAALRDCTM LVCGDDLVVI AESDGVEEDN<br>RALRAFTEAM TRYSAPPGDA PQPAYDLELI TSCSSNVSVA HDVTGKKVYY<br>LTRDPETPLA RAVWETVRHT PVNSWLGNII VYAPTIWVRM ILMTHFFSIL<br>QSQEALEKAL DFDMYGVTYS ITPLDLPAII QRLHGLSAFT LHGYSPHELN<br>RVAGALRKLG VPPLRAWRHR ARAVRAKLIA QGGRAKICGI YLFNWAVKTK<br>LKLTPLPAAA KLDLSGWFTV GAGGGDIYHS MSHARPRYLL LCLLILTVGV<br>GIFLLPAR (SEQ ID NO: 8) |
| ABE98159<br>(SEQ ID<br>NO: 9) | 6a | MSTLPKPQRK TKRNTNRRPM DVKFPGGGQI VGGVYLLPRR GPRLGVRATR<br>KTSERSQPRG RRQPIPKARQ PQGRHWAQPG YPWPLYGNEG CGWAGWLLSP<br>RGSRPHWGPN DPRRRSRNLG KVIDTLTCGF ADLMGYIPVV GAPLGGVAAA<br>LAHGVRAIED GINYATGNLP GCSFSIFLLA LLSCLTTPAS ALTYGNSSGL<br>YHLTNDCPNS SIVLEADAMI LHLPGCLPCV RVDNQSTCWH AVSPTLAIPN<br>ASTSATGFRR HVDLLAGAAV VCSSLYIGDL CGSLFLAGQL FTFQPRRHWT<br>VQDCNCSIYT GHVTGHRMAW DMMMNWSPTT TLVLSSILRV PEICASVIFG<br>GHWGILIAVA YFGMAGNWLK VLAVLFLFAG VEATTTIGRE MGSTTAGLVR<br>FLAPGPKQNL QLINTNGSWH INRTALNCND SLQTGFIASL FYAHTFNSSG<br>CPERMAACRP LADFRQGWGQ ITYKDNISGP SDDRPYCWHY APRPCSVVPA<br>STVCGPVYCF TPSPVVVGTT DRRGNPTYTW GENETDVFML GSLRPPTGGW<br>FGCTWMNSTG FTKTCGAPPC QIVPGDYNSS ANELLCPTDC FRKHPEATYQ<br>RCGSGPWLTP RCLVHYPYRL WHYPCTINFT VHKVRMFVGG IEHRFDAACN<br>WTRGERCELH DRDRIEMSPL LFSTTQLSIL PCSFSTMPAL STGLIHLHQN<br>IVDVQYLYGV SSSVTSWVVK WEYIVLMFLV LADARICTCL WLMLLISNVE<br>AAVERLVVLN AASAAGTAGW WWAVLFLCCV WYVKGRLVPA CTYTALGMWP<br>LLLTILALPR RAYAMDNEQA ASLGAVGLLV ITIFTITPMY KKLLTCFIWW<br>NQYFLARAEA MIHEWVPDLR VRGGRDSIIL LTCLLHPQLG FEVTKILLAI<br>LAPLYILQYS LLKVPYFVRA HILLRACLLV RRLAGGKYVQ ACLLRLGAWT<br>GTYVYDHLAP LSDWASDGLR DLAVAVEPVI FSPMEKKIIT WGADTAACGD<br>ILSGLPVSAR LGNLVLLGPA DDMQRGGWKL LAPITAYAQQ TRGLVGTIVT<br>SLTGRDKNEV EGEVQVVSTA TQSFLATSIN GVMWTVYHGA GSKTLAGPKG<br>PVCQMYTNVD QDLVGWPSPP GARSLTPCTC GSNDLYLVTR EADVIPARRR<br>GDSRAALLSP RPISTLKGSS GGPIMCPSGH VVGLFRAAVC TRGVAKSLDF<br>IPVENMETTM RSPSFTDNST PPAVPQTYQV GYLHAPTSGG KSTRVPAAYA<br>SQGYKVLVLN PSVAATLSFG SYMRQAYGVE PNVRTGVRTI TTGGAITYST<br>YGKFLADGGC SGGAYDIIIC DECHSTDPTT VLGIGTVLDQ AETAGVRLTV<br>LATATPPGSV TVPHPNITET ALPTTGEIPF YGKAIPLEYI KGGRHLIFCH<br>SKKKCDELAG KLKSLGLNAV AFYRGVDVSV IPTSGDVVVC ATDALMTGYT<br>GDFDSVIDCN VAVTQVVDFS LDPTFSIETT TVPQDAVSRS QRRGRTGRGK<br>PGVYRFVSQG ERPSGMFDTV VLCEAYDTGC AWYELTPSET TVRLRAYLNT<br>PGLPVCQDHL EFWEGVFTGL THIDAHFLSQ TKQGGENFAY LVAYQATVCA<br>RAKAPPPSWD TMWKCLIRLK PTLTGPTPLL YRLGAVQNEI ITTHPITKYI<br>MTCMSADLEV ITSTWVIVGG VLAALAAYCL SVGCVVICGR ITLTGKPVVV<br>PDREVLYQQF DEMEECSRHI PYLAEGQQIA EQFRQKVLGL LQASAKQAEE<br>LKPAVHSAWP RVEEFWRKHM WNFVSGIQYL AGLSIWPGNP AVASLMSFTA<br>SLTSPLRTSQ TLLLNILGGW IATQVAPPPA STAFVVSGLA GATVGSIGLG<br>RVLVDVLAGY GAGVSGALVA FKIMSGECPS TEDMVNLLPA LLSPGALVVG<br>VVCAAILRRH VGPAEGANQW MNRLIAFASR GNHVSPTHYV PETDASKNVT<br>QILTSLTITS LLRRLHQWVT EDTATPCATS WLRDVWDWVC TVLSDFKVWL<br>KAKLLPRLPG IPPLSCQTGY RGVWAGDGVC HTTCTCGAVI AGHVKNGSMK<br>ITGPKTCSNT WHGTFPINAT TTGPSTPRPA PNYQRALWRV SAEDYVEVRR<br>LGDCHYVVGA TAEGLKCPCQ VPAPEFFTEV DGVRIHRYAP PCKPLLRDEV<br>TFSVGLSTYA IGSQLPCEPE PDVTVVTSML TDPTHITAET AARRLKRGSP<br>PSLASSSASQ LSAPSLKATC TTSKDHPDME LIEANLLWRQ EMGGNITRVE<br>SENKVVILDS FEPLTADYDE REISVSAECH RPPRHKFPPA LPIWARPDYN<br>PPLIQAWQMP GYEPPVVSGC AVAPPKPAPI PPPRRKRLVH LDESTVSHAL<br>AQLADKVFVE SSDPGPGSSD SGLSITSPVP PTPTTPDDAC SEAESYSSMP<br>PLEGEPGDPD LSSGSWSTVS DQDDVVCCSM SYSWTGALIT PCAAEEEKLP<br>INPLSNSLIR HHNMVYSTTS RSASLRQKKV TFDRVQVFDQ HYQEVLKEIK<br>LRASTVQAKL LSIEEACDLT PSHSARSKYG YGAKDVRSHA SKAVDHIRSV<br>WEDLLEDSDT PIPTTIMAKN EVFCVDPSKG GRKPARLIVF PDLGVRVCEK<br>MALYDVTRKL PQAVMGPAYG FQYSPNQRVE YLLKMWRSKK VPMGFSYDTR<br>CFDSTVTERD IRTENEIYQS CQLDPMARKA VSSLTERLYV GGPMVNSKGQ<br>SCGYRRCRAS GVLPTSMGNT LTCYLKAQAA CRAANIKDYD MLVCGDDLVV<br>ICESAGVQED TASLRAFTDA MTRYSAPPGD APQPTYDLEL ITSCSSNVSV<br>AHDGNGKRYY YLTRDCTTPL ARAAWETARH TPVNSWLGNI IMFAPTIWVR<br>MVLMTHFFSI LQSEQLEKA LDFDIYGVTY SVSPLDLPAI IQRLHGMAAF<br>SLHGYSPVEL NRVGACLRKL GAPPLRAWRH RARAVRAKLI AQGGKAAICG<br>KYLFNWAVKT KLKLTPLASA SKDLDLSDWFV AGYDGGDIYH SVSLARPRLL<br>LLGLLLLTVG VGIFLLPAR (SEQ ID NO: 9) |

While sequences of exemplary HCV polyproteins are provided herein, it will be appreciated that any sequence having characteristics of an epitope of E2 protein may be employed. In some embodiments, an HCV polyprotein for use in accordance with the present invention has an amino acid sequence which is about 60% identical, about 70% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to a sequence selected from the group consisting of SEQ ID NOs: 4-9. In some embodiments, such an HCV polyprotein comprises a sequence that retains the ability to bind one or more HCV E2 antibodies.

In some embodiments, a portion of an HCV polyprotein has an amino acid sequence which comprises about 50 contiguous amino acids of a sequence selected from the group consisting of SEQ ID NOs: 4-9. In some embodiments, a portion of an HCV polyprotein has an amino acid sequence which is about 60% identical, about 70% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to a contiguous stretch of about 50 amino acids of a sequence selected from the group consisting of SEQ ID NOs: 4-9.

In some embodiments, a portion of an HCV polyprotein has an amino acid sequence which comprises about 42 contiguous amino acids of a sequence selected from the group consisting of SEQ ID NOs: 4-9. In some embodiments, a portion of an HCV polyprotein has an amino acid sequence which is about 60% identical, about 70% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to a contiguous stretch of about 42 amino acids of a sequence selected from the group consisting of SEQ ID NOs: 4-9.

In some embodiments, a portion of an HCV polyprotein has an amino acid sequence which comprises about 45, about 40, about 35, about 30, about 25, about 20, about 15, about 10, or about 5 contiguous amino acids of a sequence selected from the group consisting of SEQ ID NOs: 4-9. In some embodiments, a portion of an HCV polyprotein has an amino acid sequence which is about 60% identical, about 70% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to a contiguous stretch of about 45, about 40, about 35, about 30, about 25, about 20, about 15, about 10, or about 5 contiguous amino acids of a sequence selected from the group consisting of SEQ ID NOs: 4-9.

One of skill in the art will recognize that the HCV polyproteins listed in Table 1 are merely representative examples of HCV polyproteins. Various genotypes, subtypes, and/or isolates of HCV exist and continue to be identified. It will be understood by one skilled in the art that the methods and compositions provided herein may be adapted to utilize sequences of additional genotypes, subtypes, and/or isolates. Such variation is contemplated and encompassed within the methods and compositions provided herein.

Mimotopes

A mimotope, in its broadest sense, refers to a macromolecule which mimics the structure of an epitope. In some embodiments, a mimotope elicits an antibody response identical or similar to that elicited by its corresponding epitope. In some embodiments, an antibody that recognizes an epitope also recognizes a mimotope which mimics that epitope. In some embodiments, a mimotope is a peptide. In some embodiments, a mimotope is a small molecule, carbohydrate, lipid, or nucleic acid.

Antibodies in accordance with the invention may be used for screening for mimotopes. Mimotopes may be prepared using phage display, and the peptides screened with the subject antibodies (Livnah et al., 1996, *Science*, 273:464; and Prezzi et al., 1996, *J. Immunol.*, 156:4504; both of which are incorporated herein by reference). In some embodiments, mimotopes are peptide or non-peptide mimotopes of conformationally-conserved HCV epitopes. Antibodies that recognize conformationally conserved HCV epitopes may be used as templates for the rational design of peptide or non-peptide structural mimics of the conformational epitope or mimotopes.

In some embodiments, by mimicking the structure of the conformationally defined viral epitope, a mimotope interferes with the ability of HCV virus particles to bind to its natural binding partners (e.g., HCV target receptor), e.g., by binding to the natural binding partner itself. For example, analysis of a solved crystal structure defining the interface between a monoclonal antibody and tumor necrosis factor (TNF) enabled the rational design of a non-peptide mimetic capable of antagonizing the biological function of TNF by binding to the TNF receptor (Takasaki et al., 1997, *Nat. Biotech.*, 15:1266-1270; incorporated herein by reference). Computational techniques that may be employed to rationally deduce protein folding from a primary amino acid sequence for use in designing a peptide structural mimetic are reviewed in Teichmann et al. (1999, *Curr. Opin. Struct. Biol.*, 9:390-399; incorporated herein by reference). The practical application of computer programs for use in structurally modeling conformationally conserved epitopes is described by Schwartz et al. (1999, *J. Mol. Biol.* 287:983; incorporated herein by reference). An alternative method for rationally creating a peptide structural mimic of an antibody epitope involves systematic permutations of synthetic peptides designed to be a linear representation of a discontinuous antibody-binding site (Reineke et al., 1999, *Nat. Biotech.*, 17:271; incorporated herein by reference).

Peptides or other small molecules may have specific affinity for a monoclonal antibody and may be competitive with an epitope of a conformationally intact E2 protein. Alternatively or additionally, peptides or other small molecules may have specific affinity for a monoclonal antibody and may be competitive with an epitope of E2 complexed with E1. Such peptides may be used as vaccines, in diagnostic assays, for immunization for the production of antibodies to a specific HCV epitope, in competitive assays for defining genotype and/or subtype, and the like. See, for example, Puntoriero et al. (1998, *EMBO J.*, 17:3521-3533; incorporated herein by reference), Meola et al. (1995, *J. Immunol.*, 154:3162-3172; incorporated herein by reference), and Tafi et al., (1997, *Biol. Chem.*, 378:495-502; incorporated herein by reference).

Another approach to effectively create structural mimetics of conformationally conserved HCV epitopes is to produce anti-idiotypic antibodies to conformationally dependent HCV antibodies. Anti-idiotypics may effectively block the binding of native virus with its target receptor (Chanh et al., 1987, *Proc. Natl. Acad. Sci., USA*, 84:3891-3895; Kopecky et al., 1999, *Intervirol.*, 42:9-16; and Xue et al., 1993, *J. Gen. Virol.*, 74:73-79; all of which are incorporated herein by reference). Anti-idiotypic antibodies recognizing the conformational binding sites of any one of HCV antibodies HC-1, HC-3, HC-11, and CBH-23 could prevent viral infectivity by interfering with E2 binding to a target cellular protein, or even by interfering with virion attachment to the target cell.

In some embodiments, epitope mimics (e.g., mimotopes) can serve as tools for drug discovery. To give but one example, an epitope mimic (e.g., peptide, small molecule, etc.) that mimics the binding of E2 protein to an HCV antibody could be used to screen for other agents (e.g., peptides, proteins, antibodies, small molecules, etc.) that bind to the epitope. In some embodiments, such identified agents may exhibit similar binding specificity and/or affinity for the E2 epitope than an HCV E2 antibody does. In some embodiments, such identified agents may exhibit increased binding specificity and/or affinity for the E2 epitope than an HCV E2 antibody does.

Applications

In some embodiments, HCV antibodies in accordance with the invention may be used for prophylactic, therapeutic, and/or diagnostic purposes. In some embodiments, HCV antibodies in accordance with the invention may be used to treat (e.g., alleviate, ameliorate, relieve, delay onset of, inhibit progression of, reduce severity of, and/or reduce incidence of one or more symptoms or features of) HCV infection, HCV-mediated liver disease, and/or any other HCV-associated condition. In some embodiments, HCV antibodies may be used for a variety of therapeutic purposes, e.g., immunotherapy. In some embodiments, HCV antibodies may be used for a variety of prophylactic purposes and/or passive immunization, e.g., for development of vaccines for HCV. In some embodiments, HCV antibodies may be used for a variety of diagnostic purposes, e.g., for capturing and/or identifying HCV virions and/or E2 protein. These and other uses for HCV antibodies are described in further detail in the sections below. In some embodiments, therapeutic, diagnostic, and/or prophylactic applications utilize HCV antibodies and/or pharmaceutical compositions thereof, as described herein. It will be appreciated that antibodies can be directed to conformational epitopes, as described herein.

In some embodiments, HCV E2 antibodies can be directed to E2 epitopes of a single HCV genotype, two HCV genotypes, three HCV genotypes, four HCV genotypes, five HCV genotypes, six HCV genotypes, seven HCV genotypes, eight HCV genotypes, nine HCV genotypes, ten HCV genotypes, eleven HCV genotypes, or more than eleven HCV genotypes, should new HCV genotypes be discovered in the future.

In some embodiments, HCV E2 antibodies can be directed to E2 epitopes of a single HCV subtype, two HCV subtypes, three HCV subtypes, four HCV subtypes, five HCV subtypes, six HCV subtypes, seven HCV subtypes, eight HCV subtypes, nine HCV subtypes, ten HCV subtypes, 11 HCV subtypes, 12 HCV subtypes, 13 HCV subtypes, 14 HCV subtypes, 15 HCV subtypes, 16 HCV subtypes, 17 HCV subtypes, 18 HCV subtypes, 19 HCV subtypes, 20 HCV subtypes, 21 HCV subtypes, or more than 21 HCV subtypes, should new HCV subtypes be discovered in the future.

In some embodiments, HCV E2 antibodies can be directed to E2 epitopes of a single HCV strain, two HCV strains, three HCV strains, four HCV strains, five HCV strains, six HCV strains, seven HCV strains, eight HCV strains, nine HCV strains, ten HCV strains, 20 HCV strains, 30 HCV strains, 40 HCV strains, 50 HCV strains, 75 HCV strains, 100 HCV strains, or more than 100 HCV strains, should new HCV strains be discovered in the future.

Therapeutic Applications

The present invention provides systems and methods for treating patients suffering from, susceptible to, and/or displaying symptoms of HCV infection. In some embodiments, the invention provides systems and methods useful for stratifying patients suffering from, susceptible to, and/or displaying symptoms of HCV infection.

In some embodiments, therapeutic applications comprise administering a therapeutically effective amount of at least one HCV antibody in accordance with the invention to a subject in need thereof. In some embodiments, administration of HCV antibodies to a subject may alleviate, ameliorate, relieve, delay onset of, inhibit progression of, reduce severity of, and/or reduce incidence of one or more signs, symptoms, and/or features of HCV infection.

In some embodiments, administration of HCV antibodies reduces the level of HCV virions circulating in a subject (e.g., HCV virions that are capable of infecting new cells). In some embodiments, administration of HCV antibodies reduces the level of HCV virions circulating in a subject by about 10%, about 20%, about 30%, about 40%, about 50%, about 60%, about 70%, about 80%, about 90%, about 95%, about 99%, or about 100% relative to non-treated controls.

In some embodiments, HCV antibodies may be used in vitro to reduce viral load in a subject. For reducing viral load of a body component, particularly a body component of a patient infected with HCV, a patient's blood is passed through a device comprising antibodies bound to a surface or solid support for capturing HCV virions (see, for example, U.S. Pat. Nos. 5,698,390 and 4,692,411; both of which are incorporated herein by reference). Various other devices found in the literature can be used with the subject antibodies to achieve a similar result. A body component can be a biological fluid (e.g., blood, serum, etc.), a tissue, an organ, such as the liver, and the like.

In some embodiments, the "level of HCV virions circulating in a subject" refers to an absolute number of virions circulating in a subject. In some embodiments, the "level of HCV virions circulating in a subject" refers to the number of virions per unit volume (e.g., milliliter, liter, etc.) of the subject's blood. In some embodiments, the "level of HCV virions circulating in a subject" refers to viral load and/or HCV RNA levels.

In some embodiments, administration of HCV antibodies inhibits replication of HCV virions in a subject, for example, by blocking infection of uninfected cells. In some embodiments, administration of HCV antibodies inhibits replication of HCV virions in a subject by about 2-fold, about 3-fold, about 4-fold, about 5-fold, about 10-fold, about 50-fold, about 100-fold, about 500-fold, about 1000-fold, about 10,000-fold, or greater than about 10,000-fold relative to non-treated controls.

In some embodiments, administration of HCV antibodies kills and/or inactivates HCV virions in a subject. In some embodiments, administration of HCV antibodies kills and/or inactivates about 10%, about 20%, about 30%, about 40%, about 50%, about 60%, about 70%, about 80%, about 90%, about 95%, about 99%, or about 100% of HCV virions in a subject relative to non-treated controls.

In some embodiments, administration of HCV antibodies inhibits binding of virus to cellular target proteins. In some embodiments, administration of HCV antibodies inhibits binding of virus to at least one cellular target protein by about 2-fold, about 3-fold, about 4-fold, about 5-fold, about 10-fold, about 50-fold, about 100-fold, about 500-fold, about 1000-fold, about 10,000-fold, or greater than about 10,000-fold relative to non-treated controls. To give but one example, administration of HCV antibodies may inhibit binding of HCV virus to CD81. In some embodiments, administration of HCV antibodies inhibits binding of HCV to CD81 by about 2-fold, about 3-fold, about 4-fold, about 5-fold, about 10-fold, about 50-fold, about 100-fold, about 500-fold, about 1000-fold, about 10,000-fold, or greater than about 10,000-fold relative to non-treated controls.

In some embodiments, administration of HCV antibodies inhibits virus-mediated fusion with a target cell. In some embodiments, administration of HCV antibodies inhibits virus-mediated fusion with a target cell by about 2-fold, about 3-fold, about 4-fold, about 5-fold, about 10-fold, about 50-fold, about 100-fold, about 500-fold, about 1000-fold, about 10,000-fold, or greater than about 10,000-fold relative to non-treated controls.

In some embodiments, administration of HCV antibodies inhibits conformational changes of one or more proteins associated with virus entry. In some embodiments, administration of HCV antibodies inhibits conformational changes of one or more proteins associated with virus entry by about 2-fold, about 3-fold, about 4-fold, about 5-fold, about 10-fold, about 50-fold, about 100-fold, about 500-fold, about 1000-fold, about 10,000-fold, or greater than about 10,000-fold relative to non-treated controls.

In some embodiments, administration of HCV antibodies promotes antibody-mediated complement activation. In some embodiments, administration of HCV antibodies promotes antibody-mediated complement activation by about 2-fold, about 3-fold, about 4-fold, about 5-fold, about 10-fold, about 50-fold, about 100-fold, about 500-fold, about 1000-fold, about 10,000-fold, or greater than about 10,000-fold relative to non-treated controls.

In some embodiments, administration of HCV antibodies promotes antibody-mediated aggregation of virions, which leads to clearance by phagocytic cells. In some embodiments, administration of HCV antibodies promotes antibody-mediated aggregation of virions by about 2-fold, about 3-fold, about 4-fold, about 5-fold, about 10-fold, about 50-fold, about 100-fold, about 500-fold, about 1000-fold, about 10,000-fold, or greater than about 10,000-fold relative to non-treated controls.

The chimpanzee is an accepted animal model for screening HCV vaccines and therapeutics (see, for example, Farci et al., 1996, *Proc. Natl. Acad. Sci., USA*, 93:15394-15399; Farci et al., 1994, *Proc. Natl. Acad. Sci., USA*, 91:7792-7796; Farci et al., 1992, *Science*, 258:135-140; Krawczynski et al., 1996, *J. Infect. Dis.*, 173:822-828; and Bassett et al., 1998, *J. Virol.*, 72:2589-2599; all of which are incorporated herein by reference). Antibody effectiveness can be determined by monitoring for the presence and titer of HCV RNA using quantitative PCR methods. A successful reduction of viral load, or prevention of infection in a test animal or subject is reflected as a reduction or elimination of HCV RNA in serum. Enzymatic tests such as measurement of alanine aminotransferase or other liver enzymes and/or use of sequential punch needle liver biopsies also may also be used to test effectiveness, where improvement in the rating of either would indicate a reduction in viral-induced liver damage.

In some embodiments, administration of HCV antibodies results in interference with conformational changes in the viral envelope proteins necessary for cell infectivity. For example, administered HCV antibodies may bind to such viral envelope proteins, thereby sterically blocking an envelope protein's ability to recognize and/or interact with cellular surfaces (e.g., with proteins, e.g., CD81; lipids; carbohydrates; receptors; etc. on cell surfaces). In some embodiments, administered HCV antibodies may bind to such viral envelope proteins, thereby changing the three-dimensional conformation of the envelope protein in such a way that renders the envelope protein incapable of recognizing and/or interacting with cellular surfaces (e.g., with proteins, lipids, carbohydrates, receptors, etc. on cell surfaces).

In some embodiments, treatment regimens are particularly tailored for the individual being treated. Briefly, a patient to be treated is provided, and a sample of serum is taken from the patient. The serum sample is then analyzed for the presence of particular antibodies, to give but a few examples, neutralizing antibodies, antibodies that bind to a particular region or epitope of a protein of HCV, etc. Any method known in the art, including but not limited to those described in this application, may be used to determine the presence of the antibodies to be detected (e.g., ELISA, competition assay, virus neutralization-of-binding assay, etc.). Based on the level of antibodies in the patient's serum, treatment can be designed for the patient. For example, a patient who does not have antibodies known to interfere with the binding of virions to their natural receptor may be treated with monoclonal antibodies of this type. In some embodiments, serum from a patient (e.g., a patient suffering from, susceptible to, infected with, and/or displaying symptoms of HCV infection, HCV-mediated liver disease, and/or any other HCV-associated condition) is considered positive for the presence of a competing antibody if 50% or greater inhibition of E2 binding is obtained at a dilution of the patient's serum of 1/100 or greater, 1/200 or greater, 1/300 or greater, 1/400 or greater, 1/500 or greater, 1/600 or greater, 1/700 or greater, 1/800 or greater, 1/900 or greater, or 1/1000 or greater.

In some embodiments, methods such as those described above may be advantageous because the treatment is tailored to the particular individual being treated, for example; only those antibodies that are needed and not produced naturally by the patient are administered. This avoids or reduces the risk of adverse reactions from administering therapeutics that are not needed. Such methods eliminate the expense of treating patients who would not benefit from such treatment. For example, if a patient were already producing therapeutic levels of an antibody to a particular epitope of E2, there may be no need to administer a human monoclonal antibody directed against the epitope exogenously.

Treatment of a subject with HCV antibodies may be given alone, during the course of another treatment, and/or after the cessation of treatment of other antiviral compounds. Alternatively or additionally, HCV antibodies may be physically conjugated (e.g., covalently or non-covalently) to known toxins or proteins capable of inducing apoptosis or other cell death processes. Modified HCV antibodies can be administered to individuals suffering from, susceptible to, infected with, and/or displaying symptoms of HCV infection, HCV-mediated liver disease, and/or any other HCV-associated condition as a means of killing HCV infected cells.

Prophylactic Applications

In some embodiments, HCV antibodies in accordance with the invention may be utilized for prophylactic applications. In some embodiments, prophylactic applications involve systems and methods for preventing, inhibiting progression of, and/or delaying the onset of HCV infection, HCV-mediated liver disease, and/or any other HCV-associated condition in individuals susceptible to and/or displaying symptoms of HCV infection, HCV-mediated liver disease, and/or any other HCV-associated condition. In some embodiments, prophylactic applications involve systems and methods for preventing, inhibiting progression of, and/or delaying the onset of chronic liver disease. In some embodiments, prophylactic applications involve systems and methods for preventing, inhibiting progression of, and/or delaying the onset of liver disease. In some embodiments, prophylactic applications involve systems and methods for preventing, inhibiting progression of, and/or delaying the onset of liver failure.

In some embodiments, vaccines to HCV may be utilized for passive immunization (i.e., immunization wherein antibodies are administered to a subject). In some embodiments, vaccines to HCV for passive immunization may comprise HCV antibodies, such as any of the compositions described herein. In some embodiments, passive immunization occurs when antibodies are being transferred from mother to fetus during pregnancy. In some embodiments, antibodies are administered directly to an individual (e.g., by injection, orally, etc.).

In some embodiments, prophylactic applications may include administering vaccines. In some embodiments, vaccination is tailored to the individual patient. For example, as described above, serum may be collected from a patient and tested for presence of HCV antibodies. In some embodiments, a vaccine may be designed to induce production of antibodies that have been found to be lacking in the patient. In some embodiments, it is desirable for vaccine compositions to comprise antigens that have a native conformation, mediate a protective response (e.g., complement activation, virus neutralization, etc.), and/or can induce a strong antibody response. In some embodiments, a vaccine contains an epitope or mimotope thereof to which antibodies are not being produced naturally in the individual. For example, synthetic peptide mimotopes isolated with HCV antibodies (e.g., HCV antibodies recognizing multiple genotypes and/or subtypes) have the potential to induce a potent immune response similar to the antibody used in the original isolation of the mimotope. Administration of such a vaccine might induce a patient's immune system to start producing a set of antibodies directed against the administered epitope. It will be appreciated that the mimotopes (or epitopes) in accordance with the invention can be used alone or in combination with recombinant proteins, inactivated HCV virus, killed HCV virus, and/or as a cocktail of several different mimotopes.

In some embodiments, vaccines to HCV may be utilized for active immunization (i.e., immunization wherein microbes, proteins, peptides, epitopes, mimotopes, etc. are administered to a subject). In some embodiments, vaccines to HCV may comprise any agent that mimics at least one conformational epitope of HCV E2 protein may be used. For example, the agent may be a peptide, protein, glycopeptide, glycoprotein, small molecule, mimotope, organic compound, lipid, saccharide, organometallic compound, inorganic compound, etc. In some embodiments, epitopes represented in a vaccine include those against which antibodies known to prevent infection are directed. In some embodiments, epitopes represented in a vaccine in accordance with the invention include ones that are conserved among different genotypes and/or subtypes of the virus or among different strains of virus. In some embodiments, peptides or proteins that contain conformationally defined epitopes of E2 of HCV are used in formulations of a vaccine to prevent, delay onset of, treat, ameliorate symptoms of, and/or reduce severity of infection by HCV. In some embodiments, HCV E2 epitopes may be linear epitopes. In some embodiments, E2 epitopes may be a mixture of linear and conformational epitopes. In some embodiments, E2 epitopes may be conformational epitopes. In some embodiments, peptide epitopes are less than 100 amino acids in length. In certain embodiments, peptide epitopes are less than 50, less than 40, less than 30, less than 20, or less than 10 amino acids in length. In some embodiments, peptides to be used in formulating a vaccine are peptide fragments of E2 protein of HCV. Typically, a peptide is used that folds in a manner similar to its three-dimensional fold in the native E2 protein, thus preserving the three-dimensional structure of the conformational epitope.

In some embodiments, a vaccine may contain proteins that represent concatenated peptides that have one or more conformational epitopes to which antibodies are desired. Several different peptides making up a multimer may be used so that each peptide contains a different epitope, or the same peptide may be used more than once in the multimer.

Peptides in accordance with the invention may be synthesized using any method known in the art, including Merrifield solid phase chemistry (see, e.g., Atherton and Sheppard, 1989, *Solid Phase Peptide Synthesis: A Practical Approach*, ILR Press, Oxford, England; Stewart and Young, 1984, *Solid Phase Peptide Synthesis*, 2nd ed., Pierce Chemical Company, Rockford; Merrifield, 1963, *J. Am. Chem. Soc.*, 85:2149-2154; all of which are incorporated herein by reference). Alternatively or additionally, peptides may be obtained by cleavage of E2 protein and optional purification of cleavage products. In some embodiments, peptides may be made recombinantly and produced in *E. coli*, yeast (e.g., *S. cerevisiae*), insect cells (e.g., Sf9 cells), and/or mammalian cells (e.g., CHO cells) using any available techniques in the art (e.g., Sambrook et al.; Miller & Calos, eds., *Gene Transfer vectors for Mammalian Cells*, 1987; and Ausubel et al., eds., *Current Protocols in Molecular Biology*, 1987; both of which are incorporated herein by reference). In some embodiments, peptides may be modified to increase their immunogenicity, solubility in aqueous solution, and/or to increase their propensity to fold correctly. For example, peptides may be glycosylated, farnesylated, hydroxylated, reduced, oxidized, methylated, etc.

In certain embodiments, a peptide is or comprises amino acids 523 through 540 of the E2 protein of HCV subtype 1a, 1b, 2a, 2b, 3a, 4, 5, and/or 6. As would be appreciated by one of ordinary skill in this art, analogous, homologous, similar, and/or identical amino acid sequences of E2 proteins from other subtypes of HCV may be used. Analogous sequences may be determined by aligning multiple sequences of the E2 protein from different strains or subtypes of HCV. Homologous, similar, and/or identical sequences that preserve the desired epitope may also be used in the formulation of vaccines.

In some embodiments, the sequences are about 50% homologous to the native sequence from HCV 1a, 1b, 2a, 2b, 3a, 4, 5, and/or 6 E2 protein, about 60% homologous, about 70% homologous, about 80% homologous, about 90% homologous, about 95% homologous, about 99% homologous, or more than about 99% homologous. In some embodiments, the sequences are about 50% similar to the native sequence from HCV 1a, 1b, 2a, 2b, 3a, 4, 5, and/or 6 E2 protein, about 60% similar, about 70% similar, about 80% similar, about 90% similar, about 95% similar, about 99% similar, or more than about 99% similar. In some embodiments, the sequences are about 50% identical to the native sequence from HCV 1a, 1b, 2a, 2b, 3a, 4, 5, and/or 6 E2 protein, about 60% identical, about 70% identical, about 80% identical, about 90% identical, about 95% identical, about 99% identical, or more than about 99% identical.

In some embodiments, the sequences are at least 50% homologous to the native sequence from HCV 1a, 1b, 2a, 2b, 3a, 4, 5, and/or 6 E2 protein, at least 60% homologous, at least 70% homologous, at least 80% homologous, at least 90% homologous, at least 95% homologous, at least 99% homologous, or substantially 100% homologous. In some embodiments, the sequences are at least 50% similar to the native sequence from HCV 1a, 1b, 2a, 2b, 3a, 4, 5, and/or 6 E2 protein, at least 60% similar, at least 70% similar, at least 80% similar, at least 90% similar, at least 95% similar, at least 99% similar, or substantially 100% similar. In some embodiments, the sequences are at least 50% identical to the native sequence from HCV 1a, 1b, 2a, 2b, 3a, 4, 5, and/or 6 E2 protein, at least 60% identical, at least 70% identical, at least 80% identical, at least 90% identical, at least 95% identical, at least 99% identical, or substantially 100% identical.

In some embodiments, a vaccine composition comprises at least one adjuvant. Any adjuvant may be used in accordance with the present invention. A large number of adjuvants are known; a useful compendium of many such compounds is prepared by the National Institutes of Health and can be found on the internet (www.niaid.nih.gov/daids/vaccine/pdf/compendium.pdf). See also Allison (1998, *Dev. Biol. Stand.*, 92:3-11; incorporated herein by reference), Unkeless et al. (1998, *Annu. Rev. Immunol.*, 6:251-281; incorporated herein by reference), and Phillips et al. (1992, *Vaccine*, 10:151-158; incorporated herein by reference). Hundreds of different adjuvants are known in the art and could be employed in the practice of the present invention. Exemplary adjuvants that can be utilized in accordance with the invention include, but are not limited to, cytokines, gel-type adjuvants (e.g., aluminum hydroxide, aluminum phosphate, calcium phosphate, etc.); microbial adjuvants (e.g., immunomodulatory DNA sequences that include CpG motifs; endotoxins such as monophosphoryl lipid A; exotoxins such as cholera toxin, *E. coli* heat labile toxin, and pertussis toxin; muramyl dipeptide, etc.); oil-emulsion and emulsifier-based adjuvants (e.g., Freund's Adjuvant, MF59 [Novartis], SAF, etc.); particulate adjuvants (e.g., liposomes, biodegradable microspheres, saponins, etc.); synthetic adjuvants (e.g., nonionic block copolymers, muramyl peptide analogues, polyphosphazene, synthetic polynucleotides, etc.); and/or combinations thereof. Other exemplary adjuvants include some polymers (e.g., polyphosphazenes; described in U.S. Pat. No. 5,500,161, which is incorporated herein by reference), Q57, QS21, squalene, tetrachlorodecaoxide, etc.

Pharmaceutically acceptable excipients are described in further detail below in the section entitled "Pharmaceutical Compositions."

Diagnostic Applications

In some embodiments, HCV antibodies in accordance with the invention are used for diagnostic applications. For example, by virtue of the variety of binding profiles of HCV antibodies, diagnostic assays may be employed which will detect a plurality of HCV genotypes and/or subtypes, so as to provide a pan-HCV antibody, while at the same time being able to dissect individual genotypes and/or subtypes by subtractive analysis.

For diagnostic purposes, antibodies may be used in a wide variety of formats for detecting E2 protein, discerning HCV genotypes and/or subtypes, detecting virions and antibodies (see, e.g., U.S. Pat. No. 5,695,390; incorporated herein by reference). Antibodies may be used individually or in combination with other antibodies of the subject group or other antibodies or with lectins which bind to the glycosyl groups present on HCV envelope proteins (i.e., E1 or E2) and/or other proteins with which HCV E2 complexes (e.g., a HCV E1:HCV E2 complex). For diagnostic purposes, a wide variety of labels may be employed, which for the most part have been mentioned previously. These include, but are not limited to, fluorophores, chemiluminescent moieties, radioisotopes, enzymes, particles (e.g., colloidal carbon particles, gold particles, latex particles, etc.) ligands for which there are high affinity receptors, and prolabels, which can be activated to provide a detectable signal.

In some embodiments, a surface is coated with a protein, which can bind to HCV antigens as free protein (e.g., circulating proteins) or as part of an intact or partially intact virion. One may use antibodies of the subject invention which bind to multiple HCV genotypes and/or subtypes or to lectins (e.g., *Galanthus nivalis* lectin; "GNA"). One may also use antibodies in accordance with the invention which bind to HCV subtypes 1, 2, 3, 4, 5, and 6. In some embodiments, antibodies in accordance with the invention bind to at least one, two, three, four, five, or more than five different genotypes and/or subtypes.

In some embodiments, assays may involve contacting a surface with a medium, which may contain free or HCV-associated protein(s), where the medium may be the sample or a solution of known E2 of one or more genotypes and/or subtypes. After incubation and washing to remove non-specifically bound protein, the assay may proceed in various manners depending upon what is being assayed. Where a blood sample suspected of being seropositive is being assayed, the sample may be applied to the layer of E2 protein, incubated, and washed, and the presence of human antibodies bound to the protein layer determined. One may use labeled α-human antibodies (other than against the isotype of the subject antibodies, where the subject antibodies have been initially used). In assays for antibodies in seropositive subjects, subject antibodies may be used as controls with the same reagent used to detect any human anti-HCV antibodies in the sera of such subjects. The specificity of the antibodies in the sample can be confirmed by using the subject antibodies, which are differentially labeled from the anti-human antibodies and determine whether they are blocked by the antibodies in the sample.

Where the sample is assayed for HCV E2 protein, detection employs labeled subject antibodies, the selection depending upon whether one is interested in genotyping or detection of E2 protein. After washing away non-specifically bound antibody, the presence of labeled antibodies is determined by detecting the presence of the label in accordance with known techniques. Alternatively or additionally, where the subject antibodies are bound to a surface, a labeled lectin for E2 may be employed to detect the presence of E2 protein.

Antibodies in accordance with the invention can be used to measure the reactivity of other antibodies, including antibodies in sera, monoclonal antibodies, antibodies expressed as a result of genetic engineering, etc. In some embodiments, intact virions are used. In some embodiments, conformationally conserved envelope proteins are used. For virion capture, see, for example, Kimura et al., 1998, *J. Med. Virology*, 56:25-32; Morita et al., 1996, *Hapato-Gastroenterology*, 43:582-585; Sata et al., 1993, *Virology*, 196:354-357; and Hijikata et al., 1993, *J. Virol.*, 67:1953-1958; all of which are incorporated herein by reference. One protocol involves steps of coating a solid support with a lectin (e.g., GNA) and then contacting the surface with a medium (e.g., serum of a seropositive patient) comprising intact HCV virions. Additives which might destroy virions should usually be avoided (e.g., detergents). After incubating the medium and washing to remove non-specifically bound components of the medium, virions may be contacted with antibodies in accordance with the invention and antibodies of the sample. This may be performed concurrently or consecutively, where the sample is added first. An amount of the subject antibody is used which is sensitive to displacement by another antibody. Such amount may be determined empirically, and one may wish to use different amounts of the subject antibody in a series of tests. By knowing the signal, which is obtained in the absence and presence of the sample, one can determine the reactivity or binding affinity of the antibodies in the sample. Various techniques may be used to determine the amount of a subject antibody bound to the virions. Where the subject antibodies are labeled, e.g., with biotin or digoxigenin, streptavidin or anti-digoxigenin labeled with a fluorophore or enzyme whose substrate produces a detectable signal can serve to determine the amount of the subject antibodies.

Labeled subject antibodies may be used in assaying for the presence of HCV from biopsy material. Labeled antibody may be incubated with immobilized biopsy material, such as a liver slice, with a solution of one or more of the subject labeled antibodies. After washing away non-specifically bound antibodies, the presence of the antibodies bound to the cells of the biopsied tissue may be detected in accordance with the nature of the label.

In some embodiments, HCV antibodies in accordance with the invention can be used to identify HCV receptors. Those skilled in the art will appreciate the multitude of ways this can be accomplished (Sambrook J., Fritsch E. and Maniatis T. *Molecular Cloning: A Laboratory Manual. Cold Spring Harbor Press*, Cold Spring Harbor, N.Y., 1989; and Ausubel et al., eds., *Current Protocols in Molecular Biology*, 1987; both of which are incorporated herein by reference). Typically, protein and peptide receptors can be identified by determining whether an antibody to E2 can inhibit attachment of HCV virions to a cell susceptible to HCV infection. Thus, receptors for HCV E2 proteins and peptides can be identified in this manner. A susceptible cell can be incubated in the presence of HCV and anti-HCV E2 antibody, and a cell-binding assay can be utilized to determine whether attachment is decreased in the presence of the antibody.

Cells expressing putative receptors for HCV and/or libraries of putative receptors for HCV may be screened for their abilities to bind HCV. For example, cells expressing a putative HCV receptor (e.g., a receptor for HCV E2) can be contacted with an HCV protein or peptide in the presence of an antibody for a time and under conditions sufficient to allow binding of the HCV protein or peptide to putative receptor on the surface of the cell. Alternatively or additionally, HCV proteins, peptides, or virions can be pre-incubated with antibody prior to contacting the putative receptor on the cell surface. Binding can be detected by any means known in the art, e.g., flow cytometry etc. (see Ausubel et al. or Sambrook et al., supra). A decrease in binding to the surface of the cell in the presence of antibody compared to binding in the absence of the cell in the absence of the antibody indicates the identification of an HCV receptor.

In some embodiments, methods of identifying HCV receptors (e.g., such as E2 receptors) include the use of solid supports, such as beads, columns, and the like. For example, receptors for HCV proteins and peptides (e.g., E2 proteins and/or fragments thereof) and/or HCV virions can be identified by attaching an HCV antibody to a solid support and then contacting the antibody with an HCV protein or peptide for a time sufficient for the HCV protein or peptide to bind to the antibody. This provides an HCV protein ligand for putative HCV receptors that can be contacted with the antibody:ligand complex on the solid support for a time and under conditions sufficient to allow binding of a receptor to the HCV protein or peptide. Proteins can be expressed from a library or provided as a cell extract or purified protein preparation from natural or recombinant cells. Once specific binding complexes between the HCV protein peptide are formed, unbound HCV proteins or peptides, e.g., library proteins or peptide that did not bind specifically to the HCV proteins or peptides, are removed, e.g., by standard washing steps. Bound proteins are then eluted and identified, e.g., by gel electrophoresis.

Administration

HCV antibodies in accordance with the invention and pharmaceutical compositions thereof in accordance with the present invention may be administered using any amount and any route of administration effective for treatment.

The exact amount required will vary from subject to subject, depending on the species, age, and general condition of the subject, the severity of the infection, the particular composition, its mode of administration, its mode of activity, and the like. HCV antibodies are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disorder being treated and the severity of the disorder; the activity of the specific HCV antibody employed; the specific pharmaceutical composition administered; the half-life of the composition after administration; the age, body weight, general health, sex, and diet of the subject; the time of administration, route of administration, and rate of excretion of the specific compound employed; the duration of the treatment; drugs used in combination or coincidental with the specific compound employed; and like factors, well known in the medical arts.

Pharmaceutical compositions of the present invention may be administered by any route. In some embodiments, pharmaceutical compositions of the present invention are administered by a variety of routes, including oral (PO), intravenous (IV), intramuscular (IM), intra-arterial, intramedullary, intrathecal, subcutaneous (SQ), intraventricular, transdermal, interdermal, intradermal, rectal (PR), vaginal, intraperitoneal (IP), intragastric (IG), topical (e.g., by powders, ointments, creams, gels, lotions, and/or drops), mucosal, intranasal, buccal, enteral, vitreal, sublingual; by intratracheal instillation, bronchial instillation, and/or inhalation; as an oral spray, nasal spray, and/or aerosol, and/or through a portal vein catheter.

In general, the most appropriate route of administration will depend upon a variety of factors including the nature of the agent being administered (e.g., its stability in the environment of the gastrointestinal tract), the condition of the subject (e.g., whether the subject is able to tolerate a particular mode of administration), etc. In specific embodiments, HCV antibodies in accordance with the present invention and/or pharmaceutical compositions thereof may be administered intravenously, for example, by intravenous infusion. In specific embodiments, HCV antibodies in accordance with the present invention and/or pharmaceutical compositions thereof may be administered by intramuscular injection. In specific embodiments, HCV antibodies in accordance with the present invention and/or pharmaceutical compositions thereof may be administered by subcutaneous injection. In specific embodiments, HCV antibodies in accordance with the present invention and/or pharmaceutical compositions thereof may be administered via portal vein catheter. However, the invention encompasses the delivery of HCV antibodies in accordance with the present invention and/or pharmaceutical compositions thereof by any appropriate route taking into consideration likely advances in the sciences of drug delivery.

In certain embodiments, HCV antibodies in accordance with the present invention and/or pharmaceutical compositions thereof in accordance with the invention may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg of subject body weight per day to obtain the desired therapeutic effect. The desired dosage may be delivered more than three times per day, three times per day, two times per day, once per day, every other day, every third day, every week, every two weeks, every three weeks, every four weeks, every two months, every six months, or every twelve months. In certain embodiments, the desired dosage may be delivered using multiple administrations (e.g., two, three, four, five, six, seven, eight, nine, ten, eleven, twelve, thirteen, fourteen, or more administrations).

It will be appreciated that HCV antibodies in accordance with the present invention and/or pharmaceutical compositions thereof can be employed in combination therapies. The particular combination of therapies (e.g., therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, HCV antibodies useful for treating, preventing, and/or delaying the onset of HCV infection may be administered concurrently with another agent useful for treating, preventing, and/or delaying the onset of HCV infection), or they may achieve different effects (e.g., control of any adverse effects). The invention encompasses the delivery of pharmaceutical compositions in combination with agents that may improve their bioavailability, reduce and/or modify their metabolism, inhibit their excretion, and/or modify their distribution within the body.

Pharmaceutical compositions in accordance with the present invention may be administered either alone or in combination with one or more other therapeutic agents. By "in combination with," it is not intended to imply that the agents must be administered at the same time and/or formulated for delivery together, although these methods of delivery are within the scope of the invention. Compositions can be administered concurrently with, prior to, or subsequent to, one or more other desired therapeutics or medical procedures. In will be appreciated that therapeutically active agents utilized in combination may be administered together in a single composition or administered separately in different compositions. In general, each agent will be administered at a dose and/or on a time schedule determined for that agent.

In general, it is expected that agents utilized in combination with be utilized at levels that do not exceed the levels at which they are utilized individually. In some embodiments, the levels utilized in combination will be lower than those utilized individually.

In some embodiments, HCV E2 antibodies in accordance with the invention (e.g., HC-1, HC-3, HC-11, and CBH-23) may be administered with interferon, with ribavirin, or with both interferon and ribavirin.

In some embodiments, compositions for combination therapy can comprise a plurality of antibodies directed to a single conformational epitope. In some embodiments, compositions for combination therapy can comprise a plurality of antibodies that recognize distinct conformational epitopes (e.g., on the same viral envelope protein or on different viral envelope proteins), thereby simultaneously interfering with multiple mechanisms in the infectious process.

In certain embodiments, compositions in accordance with the invention comprise exactly one antibody to E2 (e.g., HC-1, HC-3, HC-11, and CBH-23). In certain embodiments, compositions include exactly two, exactly three, exactly four, exactly five, exactly six, or more than six HCV E2 antibodies. In some embodiments, compositions comprise all possible permutations and combinations of HC-1, HC-3, HC-11, and CBH-23. Exemplary compositions comprising 1, 2, 3, or 4 antibodies selected from the group consisting of HC-1, HC-3, HC-11, and CBH-23 are shown in Table 2:

TABLE 2

Exemplary Compositions Comprising HCV Antibodies

| One Antibody | Two Antibodies | Three Antibodies | Four Antibodies |
| --- | --- | --- | --- |
| HC-1 | HC-1 and HC-3 | HC-1, HC-3, and HC-11 | HC-1, HC-3, HC-11, and CBH-23 |
| HC-2 | HC-1 and HC-11 | HC-1, HC-3, and CBH-23 | |
| HC-11 | HC-1 and CBH-23 | HC-1, HC-11, and CBH-23 | |
| CBH-23 | HC-3 and HC-11 | HC-3, HC-11, and CBH-23 | |
| | HC-3 and CBH-23 | | |
| | HC-11 and CBH-23 | | |

In some embodiments, hybridoma cell lines that secrete anti-HCV E2 antibodies have been deposited in the American Type Culture Collection (ATCC) located at 10801 University Boulevard, Manassas, Va. 20110-2209. For example, hybridoma cell lines that secrete human monoclonal antibody HC-1 has been deposited under Accession number PTA-9416; human monoclonal antibody HC-3 secreted by the hybridoma cell line has been deposited in the ATCC under Accession number PTA-9417; human monoclonal antibody HC-11 secreted by the hybridoma cell line has been deposited in the ATCC under Accession number PTA-9418; and human monoclonal antibody CBH-23 secreted by the hybridoma cell line has been deposited in the ATCC under Accession number PTA-9419.

It will be appreciated by one of skill in the art that any permutation or combination of HC-1, HC-3, HC-11, and CBH-23 can be combined with any other antibody (e.g., antibodies that recognize E1, E2, and/or other envelope proteins) to formulate compositions comprising a plurality of different antibodies. In certain embodiments, HC-1, HC-3, HC-11, and/or CBH-23 can be combined with any of the following previously described antibodies against E2: CBH-2, CBH-4G, CBH-5, CBH-7, CBH-8C, CBH-8E, CBH-9, CBH-11, fragments thereof, and/or combinations thereof (see U.S. Pat. No. 6,692,908; and U.S. Patent Publications 2006/0104980 and 2006/0188511; all of which are incorporated herein by reference). In certain embodiments, HC-1, HC-3, HC-11, and/or CBH-23 can be combined with H-111, H-114 (both of which are previously described antibodies against E1), fragments thereof, and/or combinations thereof (see U.S. Patent Publication 2003/180284; incorporated herein by reference). In certain embodiments, HC-1, HC-3, HC-11, and/or CBH-23 can be combined with humanized AP33 (Owsianka et al., 2005, *J. Virol.*, 79:11095-104; incorporated herein by reference); Fab e137 (Perotti et al., 2008, *J. Virol.*, 82:1047-52; incorporated herein by reference, 2008); mAbs 1:7 and A8 (Johansson et al., 2007, *Proc. Natl. Acad. Sci., USA*, 104:16269-74; incorporated herein by reference); AR3 human MAbs (Law et al., 2008, *Nat. Med.*, 14:25-27; incorporated herein by reference); fragments thereof; and/or combinations thereof.

Pharmaceutical Compositions

The present invention provides HCV antibodies and pharmaceutical compositions comprising at least one HCV antibody and at least one pharmaceutically acceptable excipient. Such pharmaceutical compositions may optionally comprise one or more additional therapeutically active substances. In accordance with some embodiments, methods of administering a pharmaceutical composition comprising administering HCV antibodies to a subject in need thereof are provided. In some embodiments, pharmaceutical compositions are administered to humans. For the purposes of the present disclosure, the phrase "active ingredient" generally refers to an HCV antibody in accordance with the invention. In certain embodiments, an HCV antibody is an antibody that recognizes E2 envelope protein. In certain embodiments, an HCV antibody is an antibody that recognizes a conformational epitope of E2 envelope protein.

Pharmaceutical compositions for administration of HCV E2 antibodies may be provided in a sterile injectible form (e.g., a form that is suitable for subcutaneous injection or intravenous infusion). For example, in some embodiments, antibodies are provided in a liquid dosage form that is suitable for injection. In some embodiments, antibodies are provided as lyophilized sterile powders, optionally under vacuum, which are reconstituted with an aqueous diluent (e.g., water, buffer, salt solution, etc.) prior to injection. In some embodiments, antibodies are diluted and/or reconstituted in water, sodium chloride solution, sodium acetate solution, benzyl alcohol solution, phosphate buffered saline, etc. In some embodiments, powder should be mixed gently with the aqueous diluent (e.g., not shaken).

In some embodiments, antibody formulations comprise one or more pharmaceutically acceptable excipients (e.g., preservative, inert diluent, dispersing agent, surface active agent and/or emulsifier, buffering agent, etc.). In some embodiments, antibody formulations comprise one or more preservatives. In some embodiments, antibody formulations comprise no preservative.

In some embodiments, antibodies are provided in a form that can be refrigerated and/or frozen. In some embodiments, antibodies are provided in a form that cannot be refrigerated and/or frozen. In some embodiments, reconstituted antibody solutions and/or antibody liquid dosage forms may be stored for a certain period of time after reconstitution (e.g., 2 hours, 12 hours, 24 hours, 2 days, 5 days, 7 days, 10 days, 2 weeks, a month, two months, or longer). In some embodiments, storage of antibody formulations for longer than the specified time results in antibody degradation.

Liquid dosage forms and/or reconstituted antibody solutions may comprise particulate matter and/or discoloration prior to administration. In general, a solution should not be used if discolored or cloudy and/or if particulate matter remains after filtration.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations of the present invention may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, $21^{st}$ Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutically acceptable excipient is at least 95%, at least 96%, at least 97%, at least 98%, at least 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the formulations. Excipients such as cocoa butter and suppository waxes, coloring agents, coating agents, sweetening, flavoring, and/or perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, etc., and/or combinations thereof.

Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite [aluminum silicate] and VEEGUM® [magnesium aluminum silicate]), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate [TWEEN®20], polyoxyethylene sorbitan [TWEEN®60], polyoxyethylene sorbitan monooleate [TWEEN®80], sorbitan monopalmitate [SPAN®40], sorbitan monostearate [SPAN® 60], sorbitan tristearate [SPAN® 65], glyceryl monooleate, sorbitan monooleate [SPAN®80]), polyoxyethylene esters (e.g., polyoxyethylene monostearate [MYRJ®45], polyoxyethylene hydrogenated castor oil, polyethoxylated castor oil, polyoxymethylene stearate, and SOLUTOL®), sucrose fatty acid esters, polyethylene glycol fatty acid esters (e.g., CREMOPHOR®), polyoxyethylene ethers, (e.g., polyoxyethylene lauryl ether [BRIJ® 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLURONIC® F 68, POLOXAMER® 188, cetrimonium bromide, cetylpyridinium chloride, benzalkonium chloride, docusate sodium, etc. and/or combinations thereof.

Exemplary binding agents include, but are not limited to, starch (e.g., cornstarch, starch paste, etc.); gelatin; sugars (e.g., sucrose, glucose, dextrose, dextrin, molasses, lactose, lactitol, mannitol, etc.); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate [VEEGUM®], larch arabogalactan, etc.); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL® 115, GERMABEN®II, NEOLONE™, KATHON™, and/or EUXYL®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such a CREMOPHOR®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are prepared by entrapping the drug in liposomes or microemulsions which are compatible with body tissues.

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient such as sodium citrate or dicalcium phosphate and/or fillers or extenders (e.g., starches, lactose, sucrose, glucose, mannitol, and silicic acid), binders (e.g., carboxymethylcellulose, alginates, gelatin, polyvinylpyrrolidinone, sucrose, and acacia), humectants (e.g., glycerol), disintegrating agents (e.g., agar, calcium carbonate, potato starch, tapioca starch, alginic acid, certain silicates, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay), and lubricants (e.g., talc, calcium stearate, magnesium stearate, solid polyethylene glycols, sodium lauryl sulfate), and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Dosage forms for topical and/or transdermal administration of a compound in accordance with this invention may include ointments, pastes, creams, lotions, gels, powders, solutions, sprays, inhalants and/or patches. Generally, the active ingredient is admixed under sterile conditions with a pharmaceutically acceptable excipient and/or any needed preservatives and/or buffers as may be required. Additionally, the present invention contemplates the use of transdermal patches, which often have the added advantage of providing controlled delivery of a compound to the body. Such dosage forms may be prepared, for example, by dissolving and/or dispensing the compound in the proper medium. Alternatively or additionally, the rate may be controlled by either providing a rate controlling membrane and/or by dispersing the compound in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable.

Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition in accordance with the invention may be prepared, packaged, and/or sold in a formulation suitable for pulmonary administration via the buccal cavity. Such a formulation may comprise dry particles which comprise the active ingredient and which have a diameter in the range from about 0.5 nm to about 7 nm or from about 1 nm to about 6 nm. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (w/w) of the composition, and the active ingredient may constitute 0.1% to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions in accordance with the invention formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface-active agent, and/or a preservative such as methylhydroxybenzoate. The droplets provided by this route of administration may have an average diameter in the range from about 0.1 nm to about 200 nm.

Formulations described herein as being useful for pulmonary delivery are useful for intranasal delivery of a pharmaceutical composition. Another formulation suitable for intranasal administration is a coarse powder comprising the active ingredient and having an average particle from about 0.2 μm to 500 μm. Such a formulation is administered in the manner in which snuff is taken, i.e., by rapid inhalation through the nasal passage from a container of the powder held close to the nose.

Formulations suitable for nasal administration may, for example, comprise from about as little as 0.1% (w/w) and as much as 100% (w/w) of the active ingredient, and may comprise one or more of the additional ingredients described herein. A pharmaceutical composition in accordance with the invention may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 nm to about 200 nm, and may further comprise one or more of the additional ingredients described herein.

A pharmaceutical composition in accordance with the invention may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* 21$^{st}$ ed., Lippincott Williams & Wilkins, 2005.

Kits

The invention provides a variety of kits for conveniently and/or effectively carrying out methods in accordance with the present invention. Kits typically comprise one or more HCV antibodies in accordance with the invention (e.g., HC-1, HC-3, HC-11, and CBH-23). In some embodiments, kits comprise a collection of different HCV antibodies to be used for different purposes (e.g., diagnostics, treatment, and/or prophylaxis). Typically kits will comprise sufficient amounts of HCV antibodies to allow a user to perform multiple administrations to a subject(s) and/or to perform multiple experiments. In some embodiments, kits are supplied with or include one or more HCV antibodies that have been specified by the purchaser.

In certain embodiments, kits for use in accordance with the present invention may include one or more reference samples; instructions (e.g., for processing samples, for performing tests, for interpreting results, for solubilizing HCV antibodies, for storage of HCV antibodies, etc.); buffers; and/or other reagents necessary for performing tests. In certain embodiments kits can comprise panels of antibodies. Other components of kits may include cells, cell culture media, tissue, and/or tissue culture media.

Kits may comprise instructions for use. For example, instructions may inform the user of the proper procedure by which to prepare a pharmaceutical composition comprising HCV antibodies and/or the proper procedure for administering pharmaceutical compositions to a subject.

In some embodiments, kits include a number of unit dosages of a pharmaceutical composition comprising HCV antibodies. A memory aid may be provided, for example in the form of numbers, letters, and/or other markings and/or with a calendar insert, designating the days/times in the treatment schedule in which dosages can be administered. Placebo dosages, and/or calcium dietary supplements, either in a form similar to or distinct from the dosages of the pharmaceutical compositions, may be included to provide a kit in which a dosage is taken every day.

Kits may comprise one or more vessels or containers so that certain of the individual components or reagents may be separately housed. Kits may comprise a means for enclosing the individual containers in relatively close confinement for commercial sale, e.g., a plastic box, in which instructions, packaging materials such as styrofoam, etc., may be enclosed.

In some embodiments, kits are used in the treatment, diagnosis, and/or prophylaxis of a subject suffering from and/or susceptible to HCV. In some embodiments, such kits comprise (i) at least one HCV antibody; (ii) a syringe, needle, applicator, etc. for administration of the at least one HCV antibody to a subject; and (iii) instructions for use.

In some embodiments, kits are used in the treatment, diagnosis, and/or prophylaxis of a subject suffering from and/or susceptible to HCV. In some embodiments, such kits comprise (i) at least one HCV antibody provided as a lyophilized powder; and (ii) a diluent for reconstituting the lyophilized powder. Such kits may optionally comprise a syringe, needle, applicator, etc. for administration of the at least one HCV antibody to a subject; and/or instructions for use.

The present invention provides kits containing reagents for the generation of vaccines comprising at least one HCV antibody. In some embodiments, such kits may include cells expressing HCV antibodies, characteristic portions thereof, and/or biologically active portions thereof; (ii) media for growing the cells; and (iii) columns, resin, buffers, tubes, and other tools useful for antibody purification. In some embodiments, such kits may include (i) plasmids containing nucleotides encoding HCV antibodies, characteristic portions thereof, and/or biologically active portions thereof; (ii) cells capable of being transformed with the plasmids, such as mammalian cell lines, including but not limited to, Vero and MDCK cell lines; (iii) media for growing the cells; (iv) expression plasmids containing no nucleotides encoding HCV antibodies as negative controls; (v) columns, resin, buffers, tubes, and other tools useful for antibody purification; and (vi) instructions for use.

In some embodiments, kits are used to detect the presence of HCV in one or more samples. Such samples may be pathological samples, including, but not limited to, blood, serum/plasma, peripheral blood mononuclear cells/peripheral blood lymphocytes (PBMC/PBL), sputum, urine, feces, throat swabs, dermal lesion swabs, cerebrospinal fluids, cervical smears, pus samples, food matrices, and tissues from various parts of the body such as brain, spleen, and liver. Such samples may be environmental samples, including, but not limited to, soil, water, and flora. Other samples that have not been listed may also be applicable. In some embodiments, such kits comprise (i) at least one HCV antibody; (ii) a sample known to contain HCV, as a positive control; and (iii) a sample known not to contain HCV, as a negative control; and (iv) instructions for use.

In some embodiments, kits are used to neutralize HCV in one or more samples. Such kits may provide materials needed to treat an HCV-containing sample with at least one HCV antibody and to test the ability of the treated sample to infect cultured cells relative to untreated sample. Such kits may include (i) at least one HCV antibody; (ii) cells capable of being cultured and infected with HCV; (iii) an antibody that is incapable of binding to and neutralizing HCV, as a negative control; (iv) an antibody that is capable of binding to and neutralizing HCV, as a positive control; (v) a sample known not to contain HCV, as a negative control; (vi) a sample known to contain HCV, as a positive control; and (vii) instructions for use.

These and other aspects of the present invention will be further appreciated upon consideration of the following Examples, which are intended to illustrate certain particular embodiments of the invention but are not intended to limit its scope, as defined by the claims.

EXAMPLES

Example 1

Definition of a Conserved Immunodominant Domain on HCV E2 Glycoprotein by Neutralizing Human Monoclonal Antibodies Materials and Methods
Cells and Culture Conditions 293T and CHO-K1 cells were obtained from ATCC. Huh7 cells were obtained from Dr. Michael Lai (University of Southern California) and Huh7.5 cells were obtained from Dr. Charles Rice (Rockefeller University). Cells were grown in Dulbecco's modified minimal essential medium (DMEM, Invitrogen, Carlsbad, Calif.) supplemented with 10% fetal calf serum (FCS, Sigma-Aldrich Co. St. Louis, Mo.) and 2 mM glutamine. CHO-K1 cells were grown in F-12 Kaighn's medium (Invitrogen 21127-022) containing L-glutamine and supplemented with 10% FCS.

Viruses and Virus Models

Production and purification of HCVpp (genotype 1a) have been previously described (Bartosch et al., 2003, *J. Exp. Med.*, 197:633-42; and Keck et al., 2005, *J. Virol.*, 79:13199-208; both of which are incorporated herein by reference). Briefly, 293T cells were transfected with HCVpp plasmids using the calcium-phosphate method. After 48 hours of growth, cell-free supernatant was collected by filtration using a 0.45 µm pore-size filter.

For production of infectious genotype 2a JFH-1 virus, HCVcc (Wakita et al., 2005, *Nat. Med.*, 11:791-96; incorporated herein by reference), XbaI linearized pJFH-1 plasmid was in vitro transcribed (MEGAscript; Ambion, Austin, Tex.) and electroporated into Huh7.5 cells. Briefly, 10 µg of in vitro transcribed JFH-1 RNA was mixed with $0.4 \times 10^6$ Huh7.5 cells in a 4-mm cuvette in calcium-free PBS containing 10 µg calf liver tRNA and pulsed at 0.27 kV and 960 µF using a Bio-Rad Gene Pulser system. Electroporated cells were seeded into 10 cm cell culture dishes with 10 ml complete DMEM containing 10% FCS. Expression of HCV E2 was confirmed by indirect immunofluorescent assay (IFA) at each passage of the cells. For JFH-1 virus production, transfected cells were passaged at 4- to 5-day intervals with a 1:4 to 1:5 split into fresh culture flasks. Virus harvests placed in small aliquots were stored at −80° C. Production of 1a HJ3-5 HCVcc has been described previously (Yi et al., 2006, *Proc. Natl. Acad. Sci., USA*, 103:2310-15; and Yi et al., 2007, *J. Virol.*, 81:629-38; both of which are incorporated herein by reference).

Antibodies and Reagents

CBH-4G, an antibody to HCV E2 has been previously described (Hadlock et al., 2000, *J. Virol.*, 74:10407; and Keck et al., 2005, *J. Virol.*, 79:13199; both of which are incorporated herein by reference). Murine MAb to c-myc was purchased from Santa Cruz Biotechnology (Santa Cruz, Calif.). CD81 LEL was obtained from Dr. Shoshana Levy (Stanford University). FITC-conjugated goat anti-human IgG, Fc γ fragment specific and R-phycoerythrin-conjugated F(ab')2 fragment goat anti-mouse IgG (H+L) were obtained from Jackson Immuno Research (West Grove, Pa.). Alkaline phosphatase conjugated goat anti-human IgG (H+L) and alkaline phosphatase conjugated goat anti-mouse IgG (H+L) were purchased from Promega (Madison, Wis.). *Galanthus nivalis* lectin (GNA) and p-nitrophenyl phosphate disodium hexahydrate (phosphatase substrate) were purchased from Sigma (St. Louis, Mo.).

Monoclonal Antibody Production and Purification

Generation of new HCV antibodies from peripheral blood B cells was performed essentially as described in Hadlock et al. (2000, *J. Virol.*, 74:10407; incorporated herein by reference). Specific HCV antibodies were selected by indirect immunofluorescent assay (IFA) using a subtype 1a or 1b HCVpp infected cell lysates as the target antigen (GenBank accession no AF348705). Monoclonality was achieved by limiting dilution cloning and confirmed by DNA sequencing (Sequetech, Mountain View, Calif.) of the IgG genes. Cloning and analyzing the $V_L$ and $V_H$ domains of the IgG genes were performed as previously described (Keck et al., 2004, *J. Virol.*, 78:7257; incorporated herein by reference). HCV antibody production and purification were performed essentially as described in Hadlock et al. (2000, *J. Virol.*, 74:10407; incorporated herein by reference) and biotinylation of the antibodies was carried out according to the manufacturer's instructions (Pierce Biotechnology, Inc, Rockford, Ill.).

IgG Subclass Typing

IgG subclass typing was conducted using the Human IgG Subclass SD Combi BINDARDID Kit (The Binding Site Inc., San Diego, Calif.) in accordance with the manufacturer's protocol.

Indirect Immunofluorescent Assay 293T cells were transfected with the constructs bearing E1E2 sequences of genotypes 1 to 6, 40-48 hours post-transfection cells were fixed onto HTC Super Cured 24-spot slides (Cel-Line Associates, Newfield, N.J.) with 100% acetone for 10 minutes at room temperature. Fixed cells were incubated with antibodies as indicated for 30 minutes at 37° C. and washed for 5 minutes with PBS, pH 7.4. Slides were then incubated for 30 minutes at 37° C. with a 0.001% solution of Evan's blue counterstain and fluorescein isothiocyanate (FITC)-conjugated goat anti-human IgG (Jackson ImmunoResearch Laboratories, West Grove, Pa.). Bound antibody to fixed cells was revealed by fluorescence microscopy as described (Hadlock et al., 1997, *J. Virol.*, 71:5828-40; incorporated herein by reference).

Antibody Sequencing

Human monoclonal antibodies $V_L$ and $V_H$ domain CDR sequences was performed as described (Keck et al., 2004, *J. Virol.*, 78:7257-63; incorporated herein by reference). Essentially, the entire variable regions of heavy and light chain from H-111 were sequenced to identify the FRs and CDRs, the germline V gene counterparts, and to determine the maturational status of the V domains. $V_L$ and $V_H$ domains of HC-1, HC-3, HC-11 and CBH-23 were amplified by RT-PCR from total cellular RNA isolated from the corresponding hybridoma cells (the RNeasy mini kit, Qiagen, Valencia, Calif.) using 5' family-specific V leader primers and 3' J region primers, as described previously (Campbell et al., 1992, *Mol. Immunol.*, 29:193-203; and Chan et al., 2001, *Blood*, 97:1023-26; both of which are incorporated herein by reference). Sequences were analyzed using Vector NTI (Invitrogen, San Diego, Calif.) and aligned with germline sequences using V-QUEST and VBASE database (Cook and Tomlinson, 1995, *Immuno. Today*, 16:237-42; incorporated herein by reference).

Competition Assay

Antibody cross-competition studies were performed as previously described (Keck et al., 2004, *J. Virol.*, 78:9224; incorporated herein by reference). Briefly, 1b HCVpp cell lysate was captured onto 96-well plates coated with GNA in PBS for 1 hour at 37° C. After washing and blocking, competing antibodies at 20 µg/ml were added to each well and incubated for 30 minutes at room temperature, followed by adding the biotinylated test antibody at 2 µg/ml. After 1.5 hour incubation at room temperature, test antibody was detected using alkaline phosphatase-conjugated streptavidin (R & D Systems, Minneapolis, Minn.), followed by incubation of p-nitrophenyl phosphate for color development. Absorbance was measured with a multiwell plate reader (Molecular Devices, Sunnyvale, Calif.) at 405 nm and subtracting the background reading at 570 nm. Mean OD values, as measured with biotinylated test HCV antibody to E2 in the presence of competing antibody, were divided by signals measured from biotinylated test HCV antibodies to E2 without competing antibody followed by multiplying by 100 to obtain the percent of test antibody bound to E2. Relatedness of the new HCV antibodies to other antibodies was determined by a modified approach of unweighted pair-group method using arithmetic averages, as previously described (Keck et al., 2004, *J. Virol.*, 78:9224; incorporated herein by reference). This method assumes the extent of bidirectional inhibition as the extent of epitope overlap by the competing antibodies. Unidirectional inhibition or enhancement is interpreted as proximal but not overlapping epitopes.

Immunoprecipitation 293T cells producing 1b HCVpp were lysed with a buffer containing 10 mM Tris-HCl, pH 7.5, 150 mM NaCl, 1% NP-40, 20 mM α-Iodoacetamide, and protease inhibitors. This was used as the source of antigen, and approximately 225 ng/ml E2 was used per immunoprecipitation. 2 µg/ml HCV antibodies was incubated with antigen for 1.5 hours at 4° C., followed by incubation with immobilized protein A (Pierce, Rockford, Ill.) for an additional 1.5 hours at 4° C. Between each step, beads were washed once with IP lysis buffer. After the last step, they were washed 3 times with IP lysis buffer and once with distilled water. Precipitates were heated at 70° C. for 5 minutes in SDS-PAGE sample buffer, run on a 10% SDS-polyacrylamide gel, and transferred to a nitrocellulose membrane. The membrane was immunoblotted with murine MAb AP33 (Owsianka et al., 2005, *J. Virol.*, 79:11095; incorporated herein by reference), followed by incubation with HRP-conjugated secondary antibody (Santa Cruz Biotechnology, Santa Cruz, Calif.) and detection using ECL Plus Western blotting detection system from GE Healthcare.

Antibody Affinity Measurement

Antibody affinity measurements were performed with 1a HCVpp cell lysate containing 1 µg/ml E2 glycoproteins. Microtiter plates were prepared by coating each well with 500 ng of GNA followed by blocking of the wells with BLOTTO consisting of 2.5% non-fat dry milk and 2.5% normal goat serum in TBST (20 mM Tris-HCl, pH 7.5, 150 mM NaCl, 0.1% Tween-20). After blocking, E2 in cell lysate was captured by GNA on plate and later bound by a range of 0.01 µg/ml-200 µg/ml of HCV antibodies. Bound HCV antibodies were incubated with alkaline phosphatase-conjugated goat anti-human IgG (Promega, Madison, Wis.), followed by incubation of p-nitrophenyl phosphate for color development. Absorbance was measured at 405 nm and 570 nm. Data were analyzed by nonlinear regression to measure antibody disassociation constant, $K_d$, and maximum binding, $B_{max}$ (OD), using Prism software (GraphPad).

HCV RNA Transfection and Virus Production

XbaI linearized pJFH-1 plasmid was in vitro transcribed (MEGAscript; Ambion, Austin, Tex.) and electroporated into Huh7.5 cells. Briefly, 10 µg of in vitro transcribed JFH-1 RNA was mixed with $0.4 \times 10^6$ Huh7.5 cells in a 4-mm cuvette in calcium-free PBS containing 10 µg calf liver tRNA and pulsed at 0.27 kV and at 960 µF using Bio-Rad Gene Pulser system. Electroporated cells were seeded into 10 cm cell culture dishes with 10 ml complete DMEM containing 10% FCS. Expression of HCV E2 was confirmed by IFA at each passage of the cells. For JFH-1 virus production, transfected cells were passaged at 4- to 5-day intervals with a 1:4 to 1:5 split into fresh culture flasks. Pooled medium virus titer was measured as foci forming units (FFU) as described below, placed in small aliquots and kept at $-80°$ C.

A second infectious HCV virus is an inter-genotypic chimeric virus produced by replacing the core-NS2 segment of the JFH-1 virus genome with the comparable segment of the subtype 1a H77 virus (Yi et al., 2007, *J. Virol.*, 81:629; incorporated herein by reference). This chimeric virus, H-[NS2/NS3]-J/Y361H/Q1251L (hereinafter referred to as "HJ3-5," contains two compensatory mutations that promote its growth in cell culture, one of which is within the E1 sequence (polyprotein residue 361) as shown (Yi et al., 2007, *J. Virol.*, 81:629; incorporated herein by reference). Virus stocks were produced in FT3-7 cells (Blight et al., 2002, *J. Virol.*, 76:13001; incorporated herein by reference).

HCVpp Neutralization Assay

Neutralization of HCVpp was performed as described previously (Keck et al., 2007, *J. Virol.*, 81:1043-47; and Keck et al., 2005, *J. Virol.*, 79:13199-208; both of which are incorporated herein by reference). Briefly, Huh-7 cells were seeded at $8 \times 10^3$ cells per well in a white nontransparent 96 well plate 24 hours before infection. The infection medium was incubated with various concentrations of antibodies for 60 minutes at 37° C. before adding to Huh-7 cells using PBS as a no antibody control. After 15 hours of incubation, HCVpp medium was replaced with fresh complete medium and incubated for an additional 72 hours. Antibody neutralization activity was determined by the percent reduction of luciferase activity compared with the infection medium containing PBS.

HCVcc Infectivity Assay

Neutralization of HCVcc was assessed by NS3 expression reduction in infected cells as monitored by immunoblotting. 350 µl aliquot of 2a JFH-1 virus ($10^5$ FFU/ml) or 1a HJ3-5 HCVcc infected cells culture supernatants were incubated with antibodies at 20 µg/ml for 1 hour at 37° C. prior to inoculation onto naïve Huh 7.5 cells seeded 24 hours previously into 24-well plates at cell density of 32,000 per well. At 3 hours post-infection (hpi), HCV/antibody-containing medium was removed, and cells were washed with PBS and replaced with fresh complete DMEM. Cells were harvested for Western blotting analysis at 72 hpi. Samples were heated at 70° C. for 5 minutes in SDS-PAGE sample buffer and run on a 10% SDS-polyacrylamide gel and transferred to a nitrocellulose membrane. Membranes were immunoblotted with anti-NS3 antibody, followed by incubation with HRP-conjugated secondary antibody (Santa Cruz Biotechnology, Santa Cruz, Calif.) and detection using ECL Plus Western blotting detection system from GE Healthcare. Images were captured with a Bio-Rad gel doc system. Percent neutralization was compared to no antibody control. RO4 is an isotype-matched monoclonal antibody to HCMV and was used as a negative control.

Focus Forming Unit (FFU) Reduction Assay

A 60 µl aliquot of stock HJ3-5 or JFH-1 virus (approximately 100 FFU) was mixed with an equal volume of diluted antibody and incubated at 37° C. for 1 hour prior to inoculation of 100 µl of the virus/antibody mixture onto Huh7.5 cells seeded 24 hours previously into 8-well chamber slides (Nalge Nunc Rochester, N.Y.). Cultures were placed in a 5% $CO_2$ environment at 37° C. for 24 hours, fed with an additional 200 µl of media, and then re-incubated for an additional 48 hours. Supernatant fluids were removed, cells were washed once with PBS, and cells were fixed with 1:1 methanol-acetone prior to labeling with 1:300 MAb C7-50 specific for the core protein (Affinity BioReagents, Golden, Colo.) as described (Yi et al., 2007, *J. Virol.*, 81:629; incorporated herein by reference). Following extensive washing, secondary labeling with FITC-conjugated goat anti-mouse IgG (1010-02, Southern Biotech, Birmingham, Ala.) at a 1:100 dilution, nuclei were counter-stained with Bisbenzimide H (Hoechst, Frankfurt am Main, Germany), and slides were mounted and examined under a Zeiss UV fluorescence microscope. Foci of antigen-positive cells were counted in each individual slide, with each cluster of infected cells staining positively for core antigen considered to constitute a single infectious focus-forming unit (FFU), as described (Yi et al., 2007, *J. Virol.*, 81:629; and Yi et al., 2006, *Proc. Natl. Acad. Sci., USA*, 103:2310; both of which are incorporated herein by reference). Percent neutralization was calculated as the reduction in FFU compared to virus incubated with an irrelevant control antibody, R04.

Blocking E2 Binding to CD81

Genotype 1b E1E2 expressed in 293T containing 1 µg/ml E2 was incubated with each HCV antibody as indicated at 10 µg/ml for 1 hour at room temperature, and the antibody-antigen complex was then added onto CD81 pre-coated wells. Wells were washed and incubated with 5 µg/ml biotinylated CBH-4D for 1 hour. Bound CBH-4D was detected with alkaline phosphatase-conjugated streptavidin (R&D Systems; Minneapolis, Minn.), followed by incubation of p-nitrophenyl phosphate for color development. Absorbance was measured at 405 nm using plate reader Spectra Max 190 from Molecular Devices (Sunnyvale, Calif.). CBH-5 was used as a positive control and RO4 as a negative control.

Epitope Mapping by Site-Directed Mutagenesis

Figure 7:
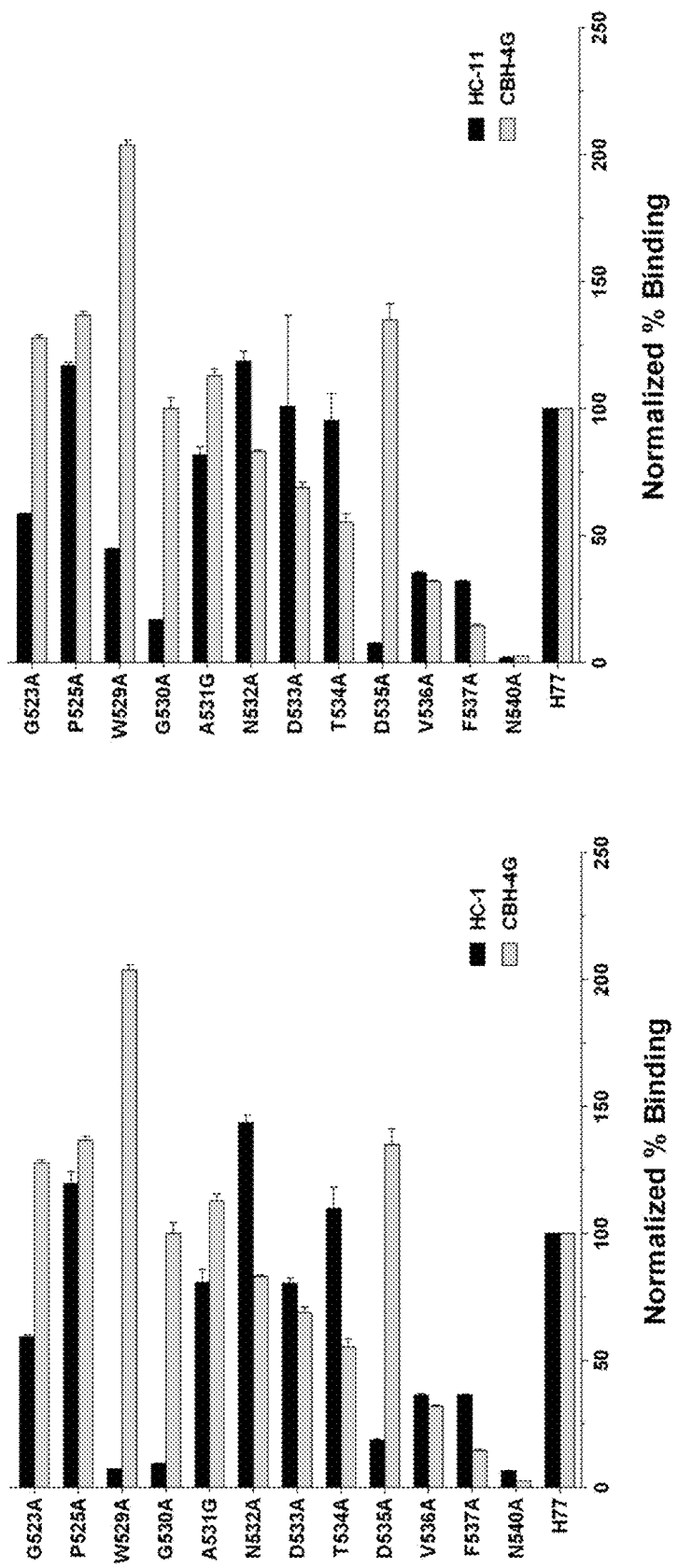
FIG. 7: Epitope mapping of HC-1 and HC-11 by alanine replacement. Mutations were introduced into E2 from genotype 1a H77c strain (GenBank accession no. AF009606) by site-directed mutagenesis (Stratagene, CA). Mutated E2 proteins were expressed in 293T cells and analyzed by ELISA. Mutated amino acids are depicted on the y-axis. The number at the beginning of each peptide corresponds to the position in the polyprotein of reference strain H. (A) HC-1 and (B) HC-11 HCV antibodies binding to each mutant is expressed as the percent of binding value normalized by the binding of CBH-17 and divided by HC antibody binding to the wild-type on the x-axis.

Alanine scanning mutagenesis was conducted using the QuickChange II Site-Directed Mutagenesis Kit (Strategen, La Jolla, Calif.) in accordance with the protocol provided. Mutations were introduced into E2 of genotype 1a H77c strain (GenBank accession number AF009606). All mutants were sequenced (Sequetech, Mountain View, Calif.) to ensure that the clones possessed only the expected mutation. Mutated E2 proteins were expressed in 293T cells and analyzed by ELISA. Briefly, microtiter plates were coated with 500 ng per well of *Galanthus nivalis* lectin (GNA), followed by blocking with BLOTTO, consisting of 2.5% nonfat dry milk and 2.5% normal goat serum in TBST (20 mM Tris-HCl, pH 7.5, 150 mM NaCl, 0.1% Tween-20). After blocking, transfected cell lysates diluted in BLOTTO were added to the plate. Bound mutant E2 proteins were then incubated with HC-1 or HC-11, followed by alkaline phosphatase-conjugated goat anti-human IgG. Samples were then visualized by adding p-nitrophenyl phosphate disodium hexa-hydrate and reading the absorbance at 405 nm. Results are shown in FIG. 7. Derived values for the mutant E2 proteins were then displayed as a percent of that observed for the wt H77c E2. Mutated amino acids are depicted on the y-axis. The number in the between two substituted amino acids correspond to the position in the polyprotein of reference strain H (GenBank accession number AF009606). HC-1 and HC-11 HCV antibodies binding to each mutant is expressed as the percent of binding value normalized by the binding of CBH-17, an antibody to a linear epitope on E2, and divided by HC antibody binding to the wild-type on the x-axis.

Binding of HCV Antibodies to E2 Mutants by ELISA

ELISA was performed to measure antibody binding to the mutant E2 glycoproteins. Microtiter plates were coated with 500 ng GNA per well, followed by blocking with BLOTTO (2.5% nonfat dry milk and 2.5% normal goat serum in TBST [20 mM Tris-HCl, pH 7.5, 150 mM NaCl, 0.1% Tween-20]) for 1 hour. Wild type and mutated E2 glycoproteins expressed in 293T cell lysates were captured onto GNA coated plates. Bound E2 was detected by each antibody with the amount of E2 in each well normalized by using an anti-c-myc mouse MAb. Bound antibodies were incubated with alkaline phosphatase-conjugated goat anti-human IgG and followed by incubation of p-nitrophenyl phosphate for color development. Absorbance was measured at 405 nm and 570 nm. Derived values for the mutant E2 proteins were then displayed as a percent of that observed for the wild-type E2.

HCVpp Neutralization Time Course

Antibody-mediated neutralization of HCVpp infection at different time intervals after attachment was performed essentially as described (Evans et al., 2007, *Nature,* 446:801-5; incorporated herein by reference) with modifications. Culture supernatants collected from 293T cells containing HCVpp was filtered using a 0.45 μm filter and cooled to 4° C. Huh 7.5 cells were seeded at $3.2\times10^4$ per well in poly-L-lysine coated 24 well tissue culture plates 24 hours prior to infection. After pre-cooling of Huh 7.5 cells at 4° C. and at t=−120 minutes, media was replaced with 200 μl of HCVpp supernatant containing 4 μg/ml polybrene and 50 mM Hepes, with or without antibody as indicated. The plates were centrifuged at 2100 rpm for 120 minutes at 4° C. At t=0 minutes, plates were washed twice with 1 ml cold PBS and then fresh 37° C. media containing 4 μg/ml polybrene, with or without antibodies, was added and followed by placing the plates in a 37° C. $CO_2$ incubator. At different time intervals, antibodies were added to media at the indicated concentrations. At 18 hours post infection, culture medium was changed to fresh medium without antibodies. Cells were harvested 3 days post-infection in 100 μl cell culture lysis buffer and the expression of the luciferase reporter was measured with the addition of 100 μl Bright Glo reagent from Promega (Madison, Wis.).

Cushion Pellet Virus Assay

HCV pseudoparticles (HCVpp) were produced as described (Bartosch et al., 2003, *J. Exp. Med.,* 197:633-42; and Keck et al., 2005, *J. Virol.,* 79:13199-208; both of which are incorporated herein by reference) by co-transfection of 293T cells with plasmids containing the env-defective proviral genome and an expression plasmid encoding the HCV glycoproteins (gps). Here, HCVpp carries each of six mutated residues (R657A, D658a, F679A, L692A, I696A, D698A) involved in HC-3 epitope binding. Wild typeH77c and/or E431A (a residue located outside of HC-3 epitope) are positive controls. Cells expressing HCV E1E2 and virus containing extracellular media were collected separately 48 hours post transfection. Cell lysate was prepared by resuspending cells expressing HCV E1E2 using lysis buffer (150 mM NaCl, 20 mM Tris [pH 7.5], 0.5% deoxycholate, 1.0% Nonidet-P40, 1 mM EDTA, 0.5 mg/ml Pefabloc, 2 μg/ml aprotinin, 2 μg/ml leupeptin, 1 μg/ml pepstatin). Nuclei were pelleted by centrifugation at 18,000×g at 4° C. for 10 minutes, and resulting cytoplasmic extracts were collected for the Western blot analysis. Extracellular medium containing virus was first separated from cell debris by passing through a 0.45 μm filter and was further concentrated by processing 30 ml of filtered supernatant through a 20% sucrose cushion by ultracentrifugation using a Beckman Coulter SW 28 rotor (25,000 rpm, 2 hours at 4° C.). Cushion pelletted virus was resuspended in 150 μl of NTE buffer (150 mM NaCl, 1 mM EDTA, 10 mM Tris-HCl, pH 7.4). For Western blotting, equal volumes of 20% sucrose cushion pellet suspension or 293T cell lysates were mixed with an equal volume of 2×SDS sample buffer and denatured by heating at 95° C. for 5 minutes. All samples were resolved by 10% SDS-PAGE using Tris-HCl Ctriterion gels (Bio-Rad Laboratories, Hercules, Calif.). Proteins on the gel were transferred onto a nitrocellulose filter. The filter was blocked with 5% dry-milk in 0.1% T-TBS (20 mM Tris-HCl, pH 7.5, containing 150 mM NaCl and 0.1% Tween-20).

The following pairs of primary and secondary antibodies were used to detect the amount of proteins in the samples: for E1 detection, H111 (Keck et al., 2004, *J. Virol.,* 78:7257-63; incorporated herein by reference) at 2 μg/ml and anti-human IgG HRP (1:5000, GE Healthcare); for E2 detection, AP33 (Owsianka et al., 2005, *J. Virol.,* 79:11095-104; incorporated herein by reference) at 2 μg and goat anti-mouse IgG (1:2000, Santa Cruz Biotechnologies); goat anti-HIV p24 (1:2500, ViroStat, Portland, Oreg.) and bovine anti-goat IgG HRP (1:5000, Santa Cruz Biotechnologies). GAPDH and P24 proteins were used as internal controls for cellular protein and HCV particles production, respectively, and were detected by mouse anti-GAPDH and goat anti-mouse IgG HRP (Santa Cruz Biotechnologies). The filter was incubated with ECL plus and chemiluminescent images were capture using a chemi-doc image system from Bio-Rad.

HCVpp Infectivity Assay

The amount of virus in virus-containing medium was first normalized by p24 expression using QuickTiter lentivirus titer kit (Cell Biolabs Lab, San Diego, Calif.) in accordance with the manufacturer's instructions. Subsequently, equal amount of virus was added to pre-seeded Huh-7.5 cells ($8\times10^3$ cells/well) in a white nontransparent 96-well plate and infections were centrifuged at 730×g for 2 hours at room temperature before placing in a humidified cell culture chamber containing 5% $CO_2$ at 37° C. Unbound virus was replaced with fresh complete medium incubated for a total of 72 hours. After adding 100 μl of reconstituted Bright-Glo (Promega) to each well followed by mixing for 2 minutes at room temperature, luciferase activity was measured by a Veritas microplate luminometer (Turner Biosystems). Virus infectivity is shown as luciferase activity (RLU).

Results

Isolation of New Domain B HCV Antibodies to HCV E2 Glycoprotein

HCV E2 contains at least three immunogenic conformational domains with distinct properties and biological functions (Keck et al., 2007, *J. Virol.,* 81:1043; Keck et al., 2005, *J. Virol.,* 79:13199; and Keck et al., 2004, *J. Virol.,* 78:9224; all of which are incorporated herein by reference). Each domain contains multiple overlapping epitopes having similar properties and function. To expand the panel of neutralizing antibodies, a group of human monoclonal antibodies from peripheral B-cells of three HCV infected individuals having high serum neutralization titers were produced and characterized. Peripheral B cells from individuals with either HCV 1a or 1b infection and high serum antibody neutralization activities were used to produce and characterize a panel of human monoclonal antibodies.

The initial screening made use of a genotype 1b E2 protein for a 1a infected donor, or 1a E2 protein for a 1b infected donor. B cells were activated by Epstein-Barr virus and used to produce human hybridomas as described (Hadlock et al., 2000, *J. Virol.*, 74:10407; incorporated herein by reference). Four hybridomas, labeled as HC-1, HC-3, HC-11, and CBH-23, were selected secreting antibodies that bound to subtype 1a HCVpp and 1b E2 but not 1b E1 glycoproteins by indirect immunofluorescence assay (IFA; FIG. 1). This screening emphasized selecting HCV antibodies to conserved epitopes as previously shown and showed that these antibodies are to E2 (Keck et al., 2004, *J. Virol.*, 78:9224; incorporated herein by reference).

Two rounds of single cell cloning established monoclonality of the hybridomas that was confirmed by sequencing the IgG genes as described (Keck et al., 2004, *J. Virol.*, 78:7257; incorporated herein by reference). In addition, the four antibodies were sequenced, and the complementarity determining regions (CDRs) of each antibody's heavy and light chains were determined (FIG. 2). Heavy chain sequence identifiers are as follows: HC-1 CDR1 (SEQ ID NO: 10), HC-1 CDR2 (SEQ ID NO: 11), HC-1 CDR3 (SEQ ID NO: 12), HC-3 CDR1 (SEQ ID NO: 13), HC-3 CDR2 (SEQ ID NO: 14), HC-3 CDR 3 (SEQ ID NO: 15), HC-11 CDR1 (SEQ ID NO: 16), HC-11 CDR2 (SEQ ID NO: 17), HC-11 CDR3 (SEQ ID NO: 18), CBH-23 CDR1 (SEQ ID NO: 19), CBH-23 CDR2 (SEQ ID NO: 20), and CBH-23 CDR3 (SEQ ID NO: 21). Light chain sequence identifiers are as follows: HC-1 CDR1 (SEQ ID NO: 22), HC-1 CDR3 (SEQ ID NO: 23), HC-3 CDR1 (SEQ ID NO: 24), HC-3 CDR3 (SEQ ID NO: 25), HC-11 CDR1 (SEQ ID NO: 26), HC-11 CDR3 (SEQ ID NO: 27), CBH-23 CDR1 (SEQ ID NO: 28) and CBH-23 CDR3 (SEQ ID NO: 29). In addition, IgG subclasses of each of all four antibodies were determined (FIG. 3).

To find out the extent of epitope conservation among different HCV genotypes and/or subtypes, HC-1, HC-3, HC-11, and CBH-23 were tested by IFA against subtypes 1a, 1b, 2a, 2b, 3a, 4, 5 and 6 HCVpp infected Huh7.5 cells (Owsianka et al., 2008, *J. Gen. Virol.*, 89:653-9; incorporated herein by reference; FIG. 4).

As summarized in FIG. 4, HCV antibodies HC-1 and HC-11 were able to neutralize all HCVpp genotypes except for genotype 4 for HC-1 and genotype 5 for HC-11. Both HC-1 and HC-11 neutralize HCVcc 1a and 2a. CBH-23 was able to neutralize HCVpp 1a and 1b infection, as well as HCVcc 2a infection. HC-3 was able to neutralize HCVpp 1a and HCVcc 2a. In contrast, the isotype-matched control R04, a antibody to a CMV specific protein, was unable to bind to any HCVpp genotypes. All four antibodies were able to immunoprecipitate E2 (FIG. 1) but did not detect E2 under reducing conditions by either ELISA or Western blot analysis, indicating that the HCV antibodies are to conformational epitopes on HCV E2 glycoprotein. HC-3, HC-11 and CBH-23 human hybridomas secrete IgG$_1$ antibodies, and HC-1 secretes IgG$_2$ (FIG. 3). Antibody production was between 20 μg/ml-60 μg/ml in spent supernatant. Sequence analysis of their Ig genes (V$_L$ and V$_H$) showed that HC-1 (SEQ ID NO: 10, SEQ ID NO: 11, SEQ ID NO: 12, SEQ ID NO: 22, and SEQ ID NO: 23), HC-3 (SEQ ID NO: 13, SEQ ID NO: 14, SEQ ID NO: 15, SEQ ID NO: 24, and SEQ ID NO: 25), HC-11 (SEQ ID NO: 16, SEQ ID NO: 17, SEQ ID NO: 18, SEQ ID NO: 26, and SEQ ID NO: 27), and CBH-23 (SEQ ID NO: 19, SEQ ID NO: 20, SEQ ID NO: 21, SEQ ID NO: 28, and SEQ ID NO: 29) were derived from independent B cells expressing unique combinations of heavy and light chain CDR1, 2 and 3 regions (FIG. 2).

Figure 5:
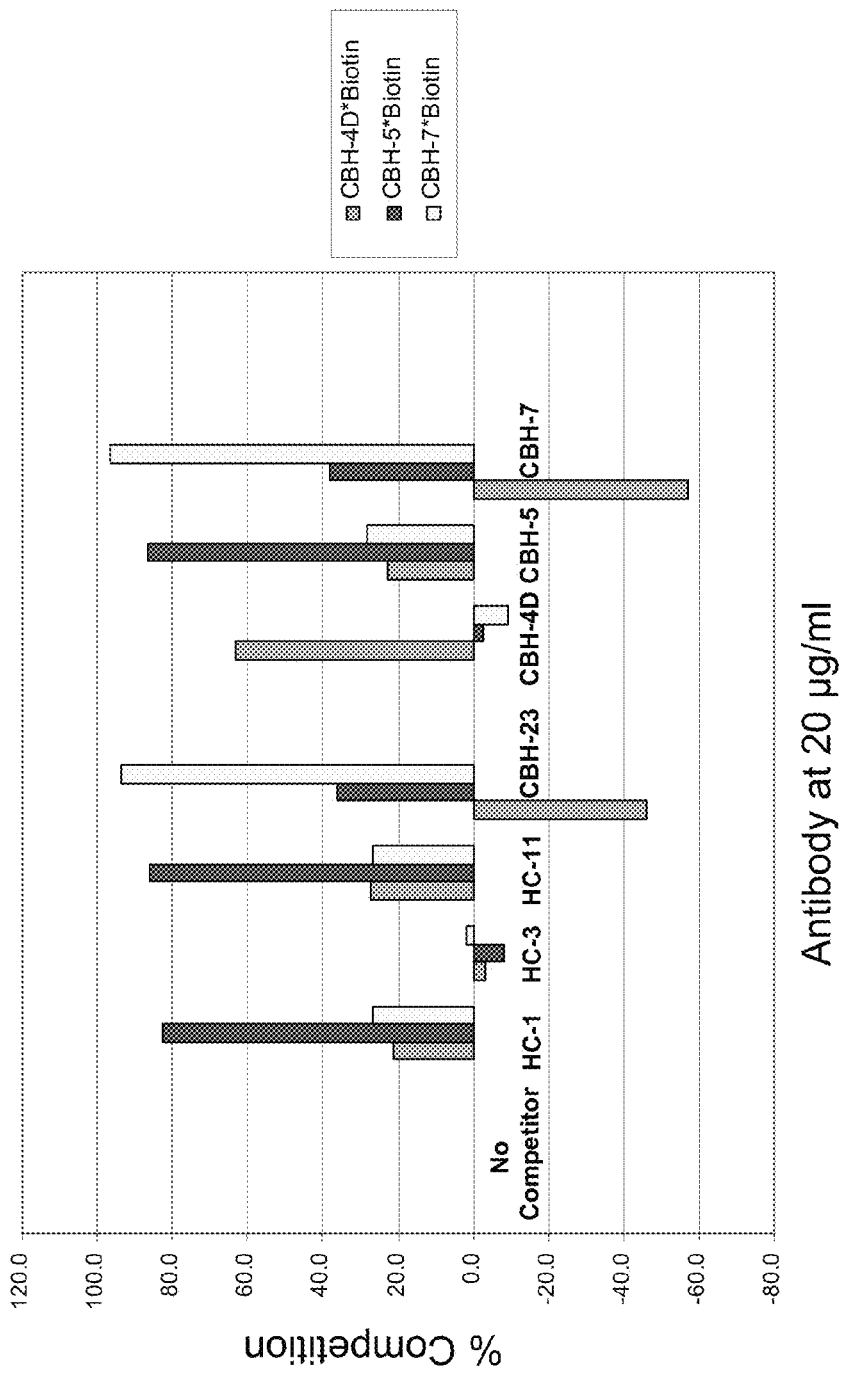
FIG. 5: Antibody competition assay. Competition analysis with representative biotin-labeled domains A (CBH-4D), B (CBH-5), and C (CBH-7) HCV antibodies was performed. HC-1 and HC-11 showed minimum competition with domains A and C antibodies, and 60%-80% competition with CBH-5, suggesting that epitopes recognized by these new antibodies are located within domain B. CBH-23 showed minimum or no competition with domains A and B antibodies, and >90% competition with CBH-7, suggesting that this epitope is located within domain C. HC-3 showed minimum or no competition with domains A, B, and C antibodies, suggesting that this antibody recognizes a new distinct domain. Each control antibody (i.e., CBH-4D, CBH-5 and CBH-7) inhibits itself and minimally inhibits the other two antibodies.

To define the relationship of these new antibodies to the earlier panel, competition analysis with representative biotin-labeled domains A (CBH-4D), B (CBH-5), and C (CBH-7) HCV antibodies was performed (FIG. 5). HC-1 and HC-11 showed minimum or no competition with domains A and C antibodies, and 60%-80% competition with CBH-5 (FIG. 5), suggesting that epitopes recognized by these new antibodies are located within domain B. CBH-23 showed minimum or no competition with domains A and B antibodies, and >90% competition with CBH-7 suggesting that this epitope is located within domain C. HC-3 showed minimum or no competition with domains A, B, and C antibodies, suggesting that this antibody recognizes a new distinct domain.

Domain B Epitopes Elicit Neutralizing Antibodies

If the model of overlapping epitopes within a domain is to have similar properties and functions (Keck et al., 2004, *J. Virol.*, 78:9224; incorporated herein by reference), HC-1, HC-11, and CBH-23 should also neutralize HCV as observed with earlier domains B and C HCV antibodies. Neutralization activities at 20 μg/ml of antibody were first measured using 1a and 1b HCVpp infection with each HCV antibody neutralizing both isolates. Average neutralization of the HCV antibodies against 1b HCVpp was comparable to CBH-5, at 64%. In contrast, an average of 80% neutralization for all HCV antibodies was observed in 1a HCVpp infection, compared with 60% with CBH-5. Indeed, more detailed neutralization analysis with HC-11 showed that this antibody has IC$_{50}$ of 0.9 μg/ml. This value is roughly 5 fold higher in 1a HCVpp neutralization potency than CBH-5 at 4.0 μg/ml. This may reflect differences in their epitopes between subtypes since CBH-5 was isolated from a 1b-infected patient and the new HCV antibodies were isolated from a 1a-infected patient. Neutralization was further tested with infectious subtype 1a and 2a HCVcc (FIG. 4). For 2a HCVcc, neutralizing activity was measured by two assays, inhibition of NS3 protein expression in Huh7.5 infected cells by Western blot analysis and by FFU reduction. The effect of each antibody on 1a HCVcc infectivity was determined by FFU reduction. As shown in FIG. 4, neutralization for 2a HCVcc was complete with HC-1, HC-3, and HC-11 with each HCV antibody at 10 μg/ml as measured by HCV NS3 expression. In contrast, infectivity with 2a HCVcc was unaffected by the negative controls (i.e., RO4 antibody or no antibody (PBS) controls). Levels of β-actin protein used as an internal control were comparable between different samples. These results together are consistent with the model of overlapping conformational epitopes within a distinct immunogenic domain on E2 glycoprotein having similar functions. The successful isolation of HC-1 and HC-11 to domain B provides confirmation that domain B epitopes are highly immunogenic and elicit potent neutralizing antibodies.

Domain B Antibodies Inhibit E2 Binding to CD81

The mechanism of neutralization with earlier domain B and C HCV antibodies is by inhibiting binding E2 to CD81. This was studied with HC-1, HC-3, HC-11, and CBH-23 in a CD81 capture assay. As shown in FIG. 6, preincubation of E2 glycoproteins in the presence of 15 μg/ml of HCV antibodies HC-1, HC-11, CBH-23, or CBH-5 reduced by over 90% E2 binding to CD81 compared to the RO4 negative control. Similar to other domain B or C HCV antibodies, these HCV antibodies neutralize HCV by blocking E2 binding to CD81. In contrast, preincubation of E2 glycoproteins in the presence of HC-3 did not reduce E2 binding to CD81.

Epitope Mapping of HC-1 and HC-12 by Site-Directed Mutagenesis

Alanine scanning mutagenesis was performed to define the residues within the HCV antibody epitopes that engage in E2-CD81 interactions. A series of mutated proteins at amino acid sites ranging between 523 and 540 were obtained by site-directed mutagenesis. This region contains Tyr527, Trp529, Gly530, and Asp535 that are contact point residues for E2 binding to CD81 (Owsianka et al., 2006, *J. Virol.*, 80:8695; incorporated herein by reference). Moreover, residues Gly523, Pro525, Gly530, Asp535 and Asn540 are involved in the CBH-5 epitope (Owsianka et al., 2008, *J. Gen. Virol.*, 89:653-9; incorporated herein by reference). For these mutants, the effect on HC-1 binding was analyzed by using from transfected cells with mutant plasmids encoding E2-c-myc fusion protein. Mutant E2 proteins were assessed for their reactivity to HC-1 by ELISA (FIG. 7). This assessment was confirmed by flow analysis. Since c-myc is a C-terminal tag, the amount of c-myc detected by PE-anti-c-myc was used as an internal control to normalize the level of expression of E2. To evaluate the percentage of HC-1 binding to mutant E2 proteins, E2/c-myc ratio was calculated for each mutant and compared to the ratio obtained with wild-type protein. CBH-4G, a nonneutralizing antibody, was used as a control to identify residues that are specific to HC-1. The lack of binding at substitution sites with both CBH-4G and a HCV antibody suggested either an overall change in E2 conformation or some degree of overlap between a neutralizing and a nonneutralizing epitopes. We previously noted some degree of cross-competition between neutralizing and nonneutralizing HCV antibodies to E2 suggesting spatial proximity of their immunogenic domains on E2 (Keck et al., 2004, *J. Virol.*, 78:9224; incorporated herein by reference).

A significant decrease compared to wild type in HC-1 binding to 10% or less was noted when Trp529 (row 3), Gly530 (row 4), and Asn540 (row 12) were replaced by alanine, as shown in FIG. 7A. Because the Asn540 mutant also affected CBH-4G binding, it is unclear whether this residue participates in the HC-1 epitope. A mutation at position Asp535 (row 9) decreased HC-1 binding by >80%. For HC-11, a significant decrease of binding was observed when Gly530 and Asp535 were replaced by alanine, as shown in FIG. 7B.

A mutation Gly530 (row 4) decreased HC-1 binding by >80%. In contrast to HC-1, a mutation at Trp529 (row 3) reduced HC-11 binding by only 44%, as compared to wild type. For both antibodies (FIGS. 7A and 7B), substitution at Gly523 (row 1) decreased by 60%. Substitutions in Pro525 (row 2), Ala531 (row 5), Asn532 (row 6), Asp533 (row 7), Thr534 (row 8) had no or slight effect with +/−20% on HC-1 and HC-12 binding. Substitutions at Val536 (row 10), Phe537 (row 11) and Asn540 (row 12) reduced HC-1 and HC-11 binding by 75-95%, but also reduced CBH-4G binding by 70-95%. Collectively, these results indicate that Trp529, Gly530 and Asp535 are contact residues for HC-1, and Gly530 and Asp535 are contact residues for HC-11. Thus, the present invention encompasses the recognition that HCV antibodies HC-1 and HC-11 neutralize HCVpp and HCVcc infections by directly blocking residues that are also contact points for E2 binding to CD81. The fact that no single substitution knock down binding by 100% is consistent with HCV antibodies HC-1 and -11 binding to discontinuous epitopes with other contact points to be defined that may or may not be directly involved in E2 binding to CD81.

Figure 8:
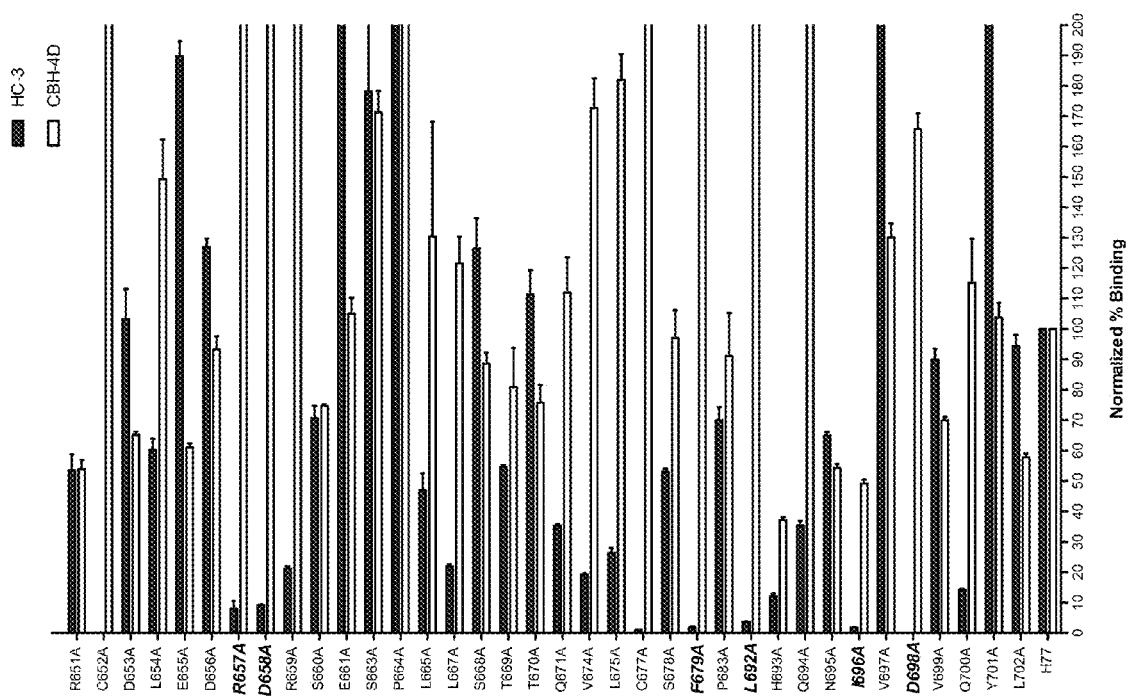
FIG. 8: Epitope mapping of HC-3 by alanine replacement. Alanine replacement was performed as shown in FIG. 7.

Epitope mapping of HC-3 showed no involvement of residues between 530-535, but showed greater than 90% decrease in binding at residues R657, D658, F679, L692, I696, and D698 (FIG. 8).

Figure 9:
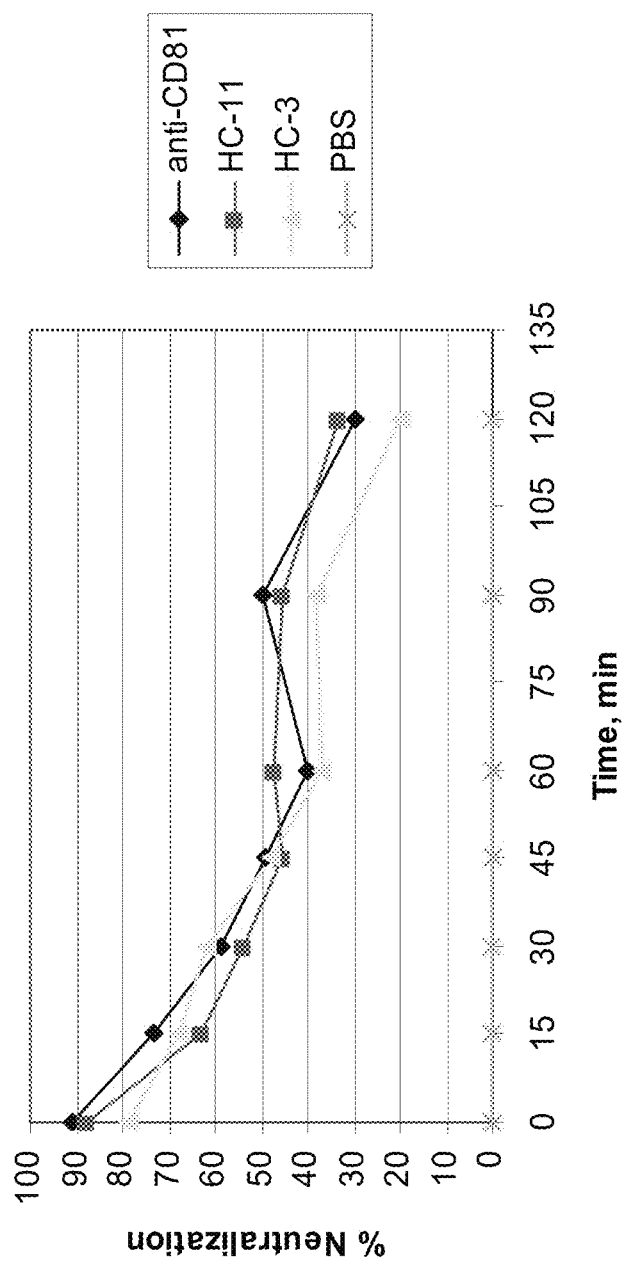
FIG. 9: Time course of antibody-mediated neutralization of HCVpp infection. To approximate the step that HC-3 inhibits during the entry pathway, a time course study was performed compared to domain B and an antibody to CD81. There are similar patterns of progressive lost in blocking virus entry with both anti-CD81 and the domain B HCV antibody, HC-11. This is expected as domain B HCV antibodies inhibit virus entry by blocking E2 binding to CD81. The similarity in patterns with HC-3 with these two antibodies suggests that HC-3 inhibits virus entry at a temporal step near virus interaction with CD81. This includes the possible inhibition of E2 interaction with a different HCV co-receptor, such as SR-B1 or a step immediately following CD81 engagement.

To approximate the step that HC-3 inhibits during the entry pathway, a time course study was performed compared to domain B and an antibody to CD81. Infectious HCVcc were incubated with 4° C. pre-cooled Huh-7.5 cells to permit virus attachment but no entry. Test antibody was then added at 15 minute intervals after placement of the virus-cell complex in a 37° C. incubator. As shown in FIG. 9, there are similar patterns of progressive lost in blocking virus entry with both anti-CD81 and the domain B HCV antibody, HC-11. This is expected as domain B HCV antibodies inhibit virus entry by blocking E2 binding to CD81. The similarity in patterns with HC-3 with these two antibodies suggests that HC-3 inhibits virus entry at a temporal step near virus interaction with CD81. This includes the possible inhibition of E2 interaction with a different HCV co-receptor, such as SR-B1 or a step immediately following CD81 engagement. The identification of contact residues for HC-3 at R657, D658, F679, L692, I696, and D698, and the lack of contact residues between 530-535, are consistent with these findings that HC-3 inhibits virus entry by a different step than blocking E2 binding to CD81.

The amino acids involved in HC-3 binding to E2 were tested in a cushion pellet assay to see if they are also involved in mediating E1E2 dimerization. In this assay, HCVpp carries each of six mutated residues (R657A, D658A and F679A, L692A, I696A, or D698A) that are part of the HC-3 E2 epitope. Alternatively, HCVpp carries wild type H77c or the E431A mutation (a residue located outside of the HC-3 epitope), as a positive control. Cells expressing HCV E1E2 were separated from extracellular medium (containing virus). Cell lysates and cushioned virus pellets were prepared and loaded on a gel for western blotting.

Figure 10:
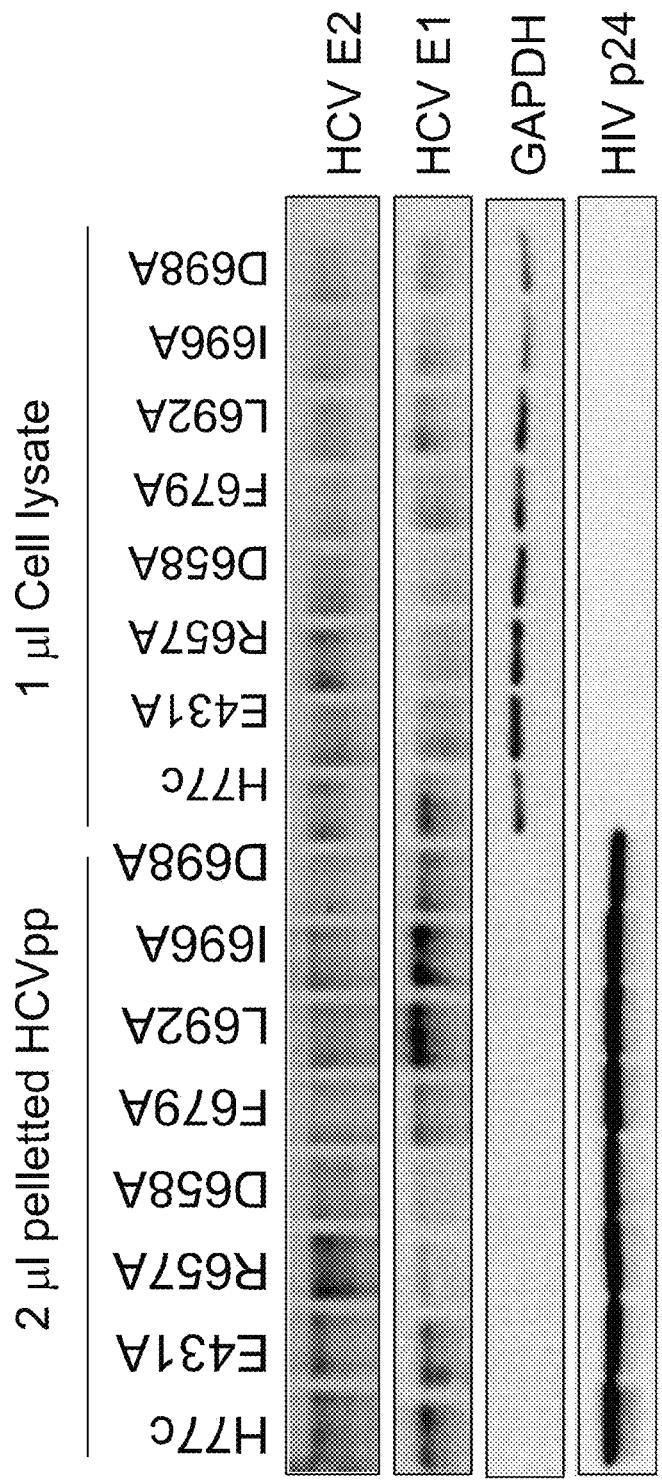
FIG. 10: HC-3 epitope is involved in E1-E2 dimerization. Compared to H77c, HCVpp mutants R657A and D658A (and to a lesser extent, F679A) showed significant reduction in E1 in the cushion pellet HCVpp. This suggests that these residues are involved in heterodimer formation between E1 and E2. These residues have not been previously identified as being involved in E1E2 dimerization. Similar observations were observed with E1E2 from cell lysates. The E431A mutant serves as a control of a mutation not affecting heterodimer formation.

Compared to H77c, HCVpp mutants R657A and D658A (and to a lesser extent, F679A) showed significant reduction in E1 (FIG. 10). This suggests that these residues are involved in heterodimer formation between E1 and E2. These residues have not yet been identified as being involved in E1E2 dimerization. Similar observations were observed with E1E2 from cell lysates (FIG. 10). The E431A mutant serves as a control of a mutation not affecting heterodimer formation.

Figure 11:
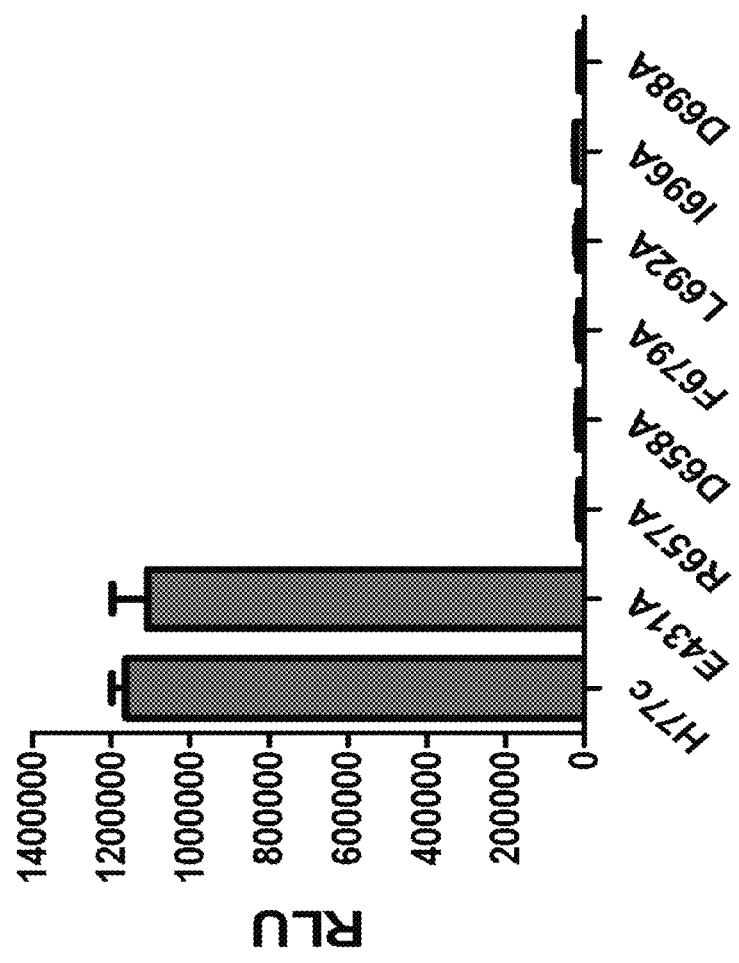
FIG. 11: Effect of HC-3 epitope mutagenesis on the infectivity of HCVpp. Infectivity of virus having R657A, D658A and F679A, L692A, I696A, or D698A mutations was determined. Each mutation is lethal to the virus. A control mutation at E431A showed no change.

Infectivity of virus having mutations at a contact point for HC-3 (i.e., infectivity of virus with a mutation at R657A, D658A and F679A, L692A, I696A, or D698A) was determined. Results of these experiments (FIG. 11) indicate that each mutation is lethal to the virus. The control mutation at E431A showed no change. Together with the findings in FIG. 10, these data suggest that HC-3 mediates neutralization by affecting the transition from a E1E2 heterodimer to a state that is necessary for internalization and subsequent release of the virus into the cytosol. The present invention encompasses the recognition that one or more of these amino acid residues could be a target for small molecules that would mimic the effect of HC-3 to affect this transition step.

Discussion

HCV has an extraordinary capacity to generate quasispecies leading to escape viral mutants that are pathogenic. Despite this ability to evade immune containment, the demonstration of animal protection with passive immunotherapy and findings that broadly neutralizing antibodies are found in infected individuals provide support for a vaccine approach that includes the capability to induce these antibodies. Development of a successful vaccine will require characterization of immunodominant epitopes mediating virus neutralization that is broadly conserved among different genotypes, subtypes, and/or strains. In this example, the HCV antibodies (i.e., HC-1, HC-3, HC-11, and CBH-23) are derived from a B cell donor infected with either subtype 1a or 1b. The antibodies were screened by IFA using subtype 1a or 1b E2 expressed in 293T cells to emphasize selecting HCV antibodies to conserved epitopes. Three of the four HCV antibodies are IgG$_1$, which is consistent with previous findings of the antibody response to HCV infection as mainly of the IgG$_1$ subclass (Chen et al., 1999, *Gastroenterology*, 116:135; and Hadlock et al., 2000, *J. Virol.*, 74:10407; both of which are incorporated herein by reference). The four HCV antibodies bind to epitopes conserved across subtypes 1-6 as detected by IFA and are to conformational epitopes as shown by their ability to immunoprecipitate HCVpp but not to detect E2 by western blot analysis. Elimination of binding to denatured antigens further proved the antibodies are to conformational epitopes. Cross-competition studies placed these antibodies within an earlier group of related HCV antibodies, labeled as domain B containing a cluster of tightly overlapping epitopes. Within the earlier set of domain B HCV antibodies, some as represented by CBH-5 bind and neutralized all subtypes and subtypes HCVpp while others as represented by CBH-8C are more restricted in not binding or neutralizing some subtypes/subtypes (Keck et al., 2004, *J. Virol.*, 78:9224; and Owsianka et al., 2008, *J. Gen. Virol.*, 89:653-9; both of which are incorporated herein by reference). Similar to CBH-5, HC-1 and HC-11 neutralize broadly as tested with 1a and 1b HCVpp, and 1a and 2a HCVcc. While the extent of neutralization achieved was similar to CBH-5 with 1b HCVpp, neutralization potency against 1a with some of the HCV antibodies was far greater than with CBH-5. This suggests some differences in their contact residues and is consistent with the fact that the donor of the B cells was infected with a 1a HCV isolate. Among the expanded panel of domain B HCV antibodies, neutralization potency was correlated with antibody binding affinity. With subtype 1a, CBH-5 has a lower antibody binding affinity of $2.2 \times 10^{-7}$ M $K_d$ (Keck et al., 2004, *J. Virol.*, 78:9224; incorporated herein by reference) compared to the affinities of the HCV antibodies between $2.4-6.6 \times 10^{-9}$ M $K_d$.

In general, the primary mechanism of antibody-mediated virus neutralization is by inhibiting an early step of virus entry and appears to be mostly directed at the E2 glycoprotein. Compelling evidence showed that E2 interactions with glycosaminoglycans, the lipoprotein receptor scavenger receptor class B type 1, SR-B1, and CD81 are involved in HCVpp and HCVcc entry [reviewed in Moradpour et al., 2007, *Nat. Rev. Microbiol.*, 5:453; incorporated herein by reference)]. Whether E2 is also pivotal in later steps remains to be determined, such as interaction with claudin-1, a member in a large family of intercellular adhesion molecules and recently shown to be an essential step in entry that follows E2 binding to CD81 (Evans et al., 2007, *Nature*, 446:801; incorporated herein by reference). Of the HCV antibodies, each inhibits E2 binding to CD81 as shown with other domain B HCV antibodies (Hadlock et al., 2000, *J. Virol.*, 74:10407; incorporated herein by reference). One of ordinary skill in the art will readily recognize that experiments such as those described herein can be carried out to find out whether domain B HCV antibodies inhibit E2 interaction with other HCV receptor molecules.

Specific residues critical for CD81 binding have been localized to mainly two discontinuous sequences on E2 (Drummer et al., 2006, *J. Virol.*, 80:7844; and Owsianka et al., 2006, *J. Virol.*, 80:8695; both of which are incorporated herein by reference). They include a conserved motif located between HVR1 and HVR2 (amino acid 436-443) (Drummer et al., 2006, *J. Virol.*, 80:7844; incorporated herein by reference) and specific residues conserved on all subtypes/subtypes, Trp420, Tyr527, Trp529, Gly530 and Asp535 (Owsianka et al., 2006, *J. Virol.*, 80:8695; incorporated herein by reference). Alanine substitution studies on one of these two regions from 523-540 showed that two of the HCV antibodies representing the entire group revealed critical shared contact residues. HC-1 requires Trp529, Gly530 and Asp535, and HC-12 requires Gly530 and Asp535. These two patterns place HC-12 more similar to the CBH-5 epitope that also involves Gly530 and Asp535 but with at least one different contact point at Gly523 (Owsianka et al., 2008, *J. Gen. Virol.*, 89:653-9; incorporated herein by reference). Indeed, competition studies also showed that the HC-11 epitope is spatially closer to CBH-5 than to either HC-1. Both HC-1 and HC-11 bind to alanine substitution at Gly523 while CBH-5 showed no binding. Recent studies showed that other broadly neutralizing human antibodies from combinatorial libraries isolated from an individual infected with subtype 2b also recognize epitopes containing Gly523, Trp529, Gly530, and Asp535 (Johansson et al., 2007, *Proc. Natl. Acad. Sci., USA*, 104: 16269; incorporated herein by reference). Why HC-1 and HC-12 have greater neutralizing potencies that CBH-5 with subtype 1a can be attributed in part by different antibody affinity to subtype 1a with HC-1, HC-12 and CBH-5 having nearly a two-log drop in $K_d$. This might reflects differences in their epitopes on contact residues outside of 523-540 that could account for the differences in $K_d$ values and neutralizing activities. Also, the location of critical contact residues of all domain B HCV antibodies at Gly530 and Asp535 on HCV E2 provides added proof of specific glycosylation sites on E2 modulating the neutralizing antibody response to HCV. In two independent studies, the glycan at Asn532 has been shown to decrease neutralizing activities of HCV polyclonal sera as well as HCV-specific neutralizing monoclonal antibodies (Falkowska et al., 2007, *J. Virol.*, 81:8072; and Helle et al., 2007, *J. Virol.*, 81:8101; both of which are incorporated herein by reference). When this residue is substituted with alanine, the mutant HCVpp showed greater sensitivity to be neutralized by these antibodies. The location of the glycan at Asn532 could reduce access of all domain B HCV antibodies to two shared contact residues at Gly530 and Asp535. Two other glycans as Asn417 and Asn645 have also been shown to reduce the neutralizing activity of a domain B HCV antibody, CBH-5 (Helle et al., 2007, *J. Virol.*, 81:8101; incorporated herein by reference). Additional studies could provide evidence of other contact points of domain B HCV antibodies near these two glycans.

In summary, three sets of related neutralizing monoclonal antibodies from different laboratories have been isolated from individuals infected with HCV subtype 1a, 1b or 2b isolates (Hadlock et al., 2000, *J. Virol.*, 74:10407; Johansson et al., 2007, *Proc. Natl. Acad. Sci., USA*, 104:16269-74; and Keck et al., 2007, *J. Virol.*, 81:1043; all of which are incorporated herein by reference). Cross-competition studies and epitope mapping to a region on HCV E2 involved in E2 binding to CD81 demonstrate that these antibodies are to overlapping epitopes with varying degrees of conservation among different HCV subtype and subtype isolates. Clearly, domain B is an immunodominant region on HCV E2 containing multiple overlapping epitopes. The fact that an HCVpp alanine substitution mutant at Asn532 having greater sensitivity to be neutralized by a panel of sera obtained from individuals infected with subtype 1a, 1b, 2b, 3, 4 and 5 showed that these sera contain antibodies directed at this region which further confirms that the epitopes in domain B are preferential targets of the immune response (Falkowska et al., 2007, *J. Virol.*, 81:8072; incorporated herein by reference). Although the majority of domain B HCV antibodies are to conserved epitopes, some such as CBH-8C and CBH-11 do not bind to subtype 1a isolates, suggesting that an antibody response to some domain B epitopes could lead to escape virus mutants. An effective vaccine approach may involve eliciting an antibody response to those epitopes as represented by HCV antibodies while eliminating epitopes associated with escape mutants. This can be accomplished through point mutations or through deletions without altering the native structure of the E2 glycoprotein as recently shown for the hypervariable regions (McCaffrey et al., 2007, *J. Virol.*, 81:9584; incorporated herein by reference). Lastly, the biochemical and functional characterizations of the HCV antibodies, the earlier group of domain B HCV antibodies and the described recombinant human antibodies are consistent with the proposed model of antibodies to related epitopes within a domain having similar biophysical and functions properties.

Example 3

Antibody Production

The following Example provides a method that can be utilized to produce HCV monoclonal antibodies.

Expression and Purification of Antibody from a Plasmid Vector

A gene encoding an entire antibody molecule can be amplified from its parent hybridoma by RT-PCT and cloned into a heterologous expression cassette capable of driving expression of the antibody in a constitutive or inducible manner in a eukaryotic cell line. For example, antibody genes can be expressed in an expression plasmid such as pcDNA3.1 Zeo, pIND(SP1), pREP8, (all from Invitrogen, Carlsbad, Calif.), and/or other expression vectors. Alternatively or additionally, antibody genes can be expressed via viral or retroviral vectors such as MLV based vectors, vaccinia virus-based vectors, and/or Adenovirus-based vectors. Similarly, antibody genes can be expressed in insect virus vectors such as baculovirus vectors. Other vectors, such as the pCOMB series of vectors allow for expression of an antibody heavy and light chain pair or a single chain antibody on the surface of M13 phage or bacteria.

Once expressed, antibodies can be purified using, e.g., protein-A or protein-G sepharose, and purified antibody can be chemically or enzymatically modified in any of the following ways: biotinylation (e.g., biotin-C11-hydroxysuccinimide ester, etc.); coupling to beads of various formats (e.g., sepharose, agarose, magnetic, polystyrene, through the use of cyanogen bromide, etc.); and/or bridging the antibody to a useful chemical moiety (e.g., by modifying lysine residues, by modifying basic residues, and/or through the use of reagents specific for free sulfhydryl groups, etc.).

Equivalents and Scope

Those skilled in the art will recognize, or be able to ascertain using no more than routine experimentation, many equivalents to the specific embodiments of the invention, described herein. The scope of the present invention is not intended to be limited to the above Description, but rather is as set forth in the appended claims.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Thus, for example, reference to "an antibody" includes a plurality of such antibodies, and reference to "the cell" includes reference to one or more cells known to those skilled in the art, and so forth. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any HCV genotype/subtype, any HCV antibody, any epitope, any pharmaceutical composition, any method of administration, any therapeutic application, etc.) can be excluded from any one or more claims, for any reason, whether or not related to the existence of prior art.

The publications discussed above and throughout the text are provided solely for their disclosure prior to the filing date of the present application. Nothing herein is to be construed as an admission that the inventors are not entitled to antedate such disclosure by virtue of prior disclosure.

Other Embodiments

Those of ordinary skill in the art will readily appreciate that the foregoing represents merely certain preferred embodiments of the invention. Various changes and modifications to the procedures and compositions described above can be made without departing from the spirit or scope of the present invention, as set forth in the following claims.

What is claimed is:

1. An antibody or fragment thereof directed to a conformational epitope of hepatitis C virus (HCV) envelope glycoprotein 2 (E2), wherein the antibody or fragment thereof comprises a heavy chain CDR1 region comprising sequence GATFSSFI (SEQ ID NO: 16), a heavy chain CDR2 region comprising sequence IIPMFGTA (SEQ ID NO: 17), a heavy chain CDR3 region comprising sequence AMEVPGFCRGGSCSGYMDV (SEQ ID NO: 18), a light chain CDR1 region comprising sequence HSVSSSN (SEQ ID NO: 26), a light chain CDR2 region comprising sequence GAS and a light chain CDR3 region comprising sequence QQYGSSPIT (SEQ ID NO: 27).

2. A monoclonal antibody HC-11 which is secreted by the hybridoma cell line deposited in the ATCC under Accession Number PTA-9418, which is directed to a conformational epitope of hepatitis C virus (HCV) envelope glycoprotein 2 (E2), or a fragment of such monoclonal antibody that retains one or more of the monoclonal antibody's CDRs such that the fragment also binds the epitope.

3. The antibody or fragment thereof of claim 1, wherein the antibody is a monoclonal antibody.

4. The antibody or fragment thereof of claim 1, wherein the antibody is a humanized antibody.

5. The antibody or fragment thereof of claim 1, wherein the antibody is a mammalian antibody.

6. A cell line expressing the antibody or fragment thereof directed to a conformational epitope of hepatitis C virus (HCV) envelope glycoprotein 2 (E2) selected from the group consisting of:

a) an antibody or fragment thereof comprising
    a heavy chain CDR1 region comprising sequence GATFSSFI (SEQ ID NO: 16), a heavy chain CDR2 region comprising sequence IIPMFGTA (SEQ ID NO: 17), a heavy chain CDR3 region comprising sequence AMEVPGFCRGGSCSGYMDV (SEQ ID NO: 18), a light chain CDR1 region comprising sequence HSVSSSN (SEQ ID NO: 26), a light chain CDR2 region comprising sequence GAS and a light chain CDR3 region comprising sequence QQYGSSPIT (SEQ ID NO: 27);
  b) an antibody or fragment thereof comprising
    a heavy chain CDR1 region comprising sequence GGTYNSEV (SEQ ID NO: 10), a heavy chain CDR2 region comprising sequence FIPMFGTA (SEQ ID NO: 11), a heavy chain CDR3 region comprising sequence AKVLQVGGNLVVRPL (SEQ ID NO: 12), a light chain CDR1 region comprising sequence QTISSTH (SEQ ID NO: 22), a light chain CDR2 region comprising sequence GVS and a light chain CDR3 region comprising sequence HQYGNSPQT (SEQ ID NO: 23);

c) an antibody or fragment thereof comprising
a heavy chain CDR1 region comprising sequence GFSLSTTGVG (SEQ ID NO: 13), a heavy chain CDR2 region comprising sequence IYWDDDK (SEQ ID NO: 14), a heavy chain CDR3 region comprising sequence ALNSYRSGTILYRELELRGLFYI (SEQ ID NO:15), a light chain CDR1 region comprising sequence QSISSW (SEQ ID NO: 24), a light chain CDR2 region comprising sequence ESS and a light chain CDR3 region comprising sequence QQYESSSWT (SEQ ID NO: 25); and d) an antibody or fragment thereof comprising
a heavy chain CDR1 region comprising sequence GGTFSSYA (SEQ ID NO: 19), a heavy chain CDR2 region comprising sequence IVPMFGTE (SEQ ID NO: 20), a heavy chain CDR3 region comprising sequence ARHENIYGTPFDY (SEQ ID NO: 21), a light chain CDR1 region comprising sequence HSITRY (SEQ ID NO: 28), a light chain CDR2 region comprising sequence AAS and a light chain CDR3 region comprising sequence QQSYSTLLT (SEQ ID NO: 29).

7. The cell line of claim 6, wherein the cell line is selected from the group consisting of a B cell line, a human cell line, a mammalian cell line, a eukaryotic cell line or a hybridoma.

8. A composition comprising:
an antibody directed to a conformational epitope of hepatitis C virus (HCV) envelope glycoprotein 2 (E2), wherein the antibody is selected from the group consisting of:
(a) the monoclonal antibody HC-11 which is secreted by the hybridoma cell line deposited in the ATCC under Accession Number PTA-9418;
(b) the monoclonal antibody HC-1 which is secreted by the hybridoma cell line deposited in the ATCC under Accession Number PTA-9416;
(c) the monoclonal antibody HC-3 which is secreted by the hybridoma cell line deposited in the ATCC under Accession Number PTA-9417; and
(d) the monoclonal antibody CBH-23 which is secreted by the hybridoma cell line deposited in the ATCC under Accession Number PTA-9419; or
a fragment of such antibody that retains one or more of the antibody's CDRs such that the fragment also binds the epitope; and
a pharmaceutically acceptable excipient.

9. A composition comprising:
an antibody directed to a conformational epitope of hepatitis C virus (HCV) envelope glycoprotein 2 (E2), wherein the antibody is selected from the group consisting of: a) an antibody comprising a heavy chain CDR1 region comprising sequence GATFSSFI (SEQ ID NO: 16), a heavy chain CDR2 region comprising sequence IIPMFGTA (SEQ ID NO: 17), a heavy chain CDR3 region comprising sequence AMEVPGFCRGGSCSGYMDV (SEQ ID NO: 18), a light chain CDR1 region comprising sequence HSVSSSN (SEQ ID NO: 26), a light chain CDR2 region comprising sequence GAS and a light chain CDR3 region comprising sequence QQYGSSPIT (SEQ ID NO: 27);

b) an antibody comprising a heavy chain CDR1 region comprising sequence GGTYNSEV (SEQ ID NO: 10), a heavy chain CDR2 region comprising sequence FIPMFGTA (SEQ ID NO: 11), a heavy chain CDR3 region comprising sequence AKVLQVGGNLVVRPL (SEQ ID NO: 12), a light chain CDR1 region comprising sequence QTISSTH (SEQ ID NO: 22), a light chain CDR2 region comprising sequence GVS and a light chain CDR3 region comprising sequence HQYGNSPQT (SEQ ID NO: 23);

c) an antibody comprising a heavy chain CDR1 region comprising sequence GFSLSTTGVG (SEQ ID NO: 13), a heavy chain CDR2 region comprising sequence IYWDDDK~ID NO: 14), a heavy chain CDR3 region comprising sequence ALNSYRSGTILYRELELRGLFYI (SEQ ID NO: 15), a light chain CDR1 region comprising sequence QSISSW (SEQ ID NO: 24), a light chain CDR2 region comprising sequence ESS and a light chain CDR3 region comprising sequence QQYESSSWT (SEQ ID NO: 25); and d) an antibody comprising a heavy chain CDR1 region comprising sequence GGTFSSYA (SEQ ID NO: 19), a heavy chain CDR2 region comprising sequence IVPMFGTE (SEQ ID NO: 20), a heavy chain CDR3 region comprising sequence ARHENIYGTPFDY (SEQ ID NO: 21), a light chain CDR1 region comprising sequence HSITRY (SEQ ID NO: 28), a light chain CDR2 region comprising sequence AAS and a light chain CDR3 region comprising sequence QQSYSTLLT (SEQ ID NO: 29); or
a fragment of such antibody that retains one or more of the antibody's CDRs such that the fragment also binds the epitope; and
a pharmaceutically acceptable excipient.

10. The composition of claim 8, further comprising at least one additional antiviral agent.

11. The composition of claim 10, wherein the at least one additional antiviral agent is selected from the group consisting of interferons, anti-HCV monoclonal antibodies, anti-HCV polyclonal antibodies, RNA polymerase inhibitors, ribavirin, protease inhibitors, IRES inhibitors, helicase inhibitors, antisense compounds, short interfering RNAs, short hairpin RNAs, micro RNAs, RNA aptamers, and ribozymes.

12. The composition of claim 10, wherein the at least one additional antiviral agent is an anti-HCV monoclonal antibody.

13. The composition of claim 12, wherein the anti-HCV monoclonal antibody recognizes envelope glycoprotein 2 (E2).

14. The composition of claim 12, wherein the antibodies are directed to proteins of identical HCV genotypes.

15. The composition of claim 12, wherein the antibodies are directed to proteins of two or more HCV genotypes.

16. A kit comprising:
at least one HCV antibody or fragment thereof directed to a conformational epitope of hepatitis C virus (HCV) envelope glycoprotein 2 (E2), wherein the antibody or fragment is selected from the group consisting of:
a) an antibody or fragment thereof comprising: a heavy chain CDR1 region comprising sequence GATFSSFI (SEQ ID NO: 16), a heavy chain CDR2 region comprising sequence IIPMFGTA (SEQ ID NO: 17), a heavy chain CDR3 region comprising sequence AMEVPGFCRGGSCSGYMDV (SEQ ID NO: 18), a light chain CDR1 region comprising sequence HSVSSSN (SEQ ID NO: 26), a light chain CDR2 region comprising sequence GAS and a light chain CDR3 region comprising sequence QQYGSSPIT (SEQ ID NO: 27);

b) an antibody or fragment thereof comprising: a heavy chain CDR1 region comprising sequence GGTYNSEV (SEQ ID NO: 10), a heavy chain CDR2 region comprising sequence FIPMFGTA (SEQ ID NO: 11), a heavy chain CDR3 region comprising sequence AKVLQVGGNLVVRPL (SEQ ID NO: 12), a light chain CDR1 region comprising sequence QTISSTH (SEQ ID NO: 22), a light chain CDR2 region comprising sequence GVS and a light chain CDR3 region comprising sequence HQYGNSPQT (SEQ ID NO: 23);

c) an antibody or fragment thereof comprising: a heavy chain CDR1 region comprising sequence GFSLSTTGVG~ID NO: 13), a heavy chain CDR2 region comprising sequence IYWDDDK (SEQ ID NO: 14), a heavy chain CDR3 region comprising sequence ALNSYRSGTILYRELELRGLFYI (SEQ ID NO: 15), a light chain CDR1 region comprising sequence QSISSW (SEQ ID NO: 24), a light chain CDR2 region comprising sequence ESS and a light chain CDR3 region comprising sequence QQYESSSWT (SEQ ID NO: 25); and d) an antibody or fragment thereof comprising: a heavy chain CDR1 region comprising sequence GGTFSSYA (SEQ ID NO: 19), a heavy chain CDR2 region comprising sequence IVPMFGTE (SEQ ID NO: 20), a heavy chain CDR3 region comprising sequence ARHENIYGTPFDY (SEQ ID NO: 21), a light chain CDR1 region comprising sequence HSITRY (SEQ ID NO: 28), a light chain CDR2 region comprising sequence AAS and a light chain CDR3 region comprising sequence QQSYSTLLT (SEQ ID NO: 29);

a syringe, needle, or applicator for administration of the at least one HCV antibody to a subject; and instructions for use.

17. The antibody or fragment thereof of claim 1, wherein the antibody is the monoclonal antibody HC-11 which is secreted by the hybridoma cell line deposited in the ATCC under Accession Number PTA-9418.

18. An antibody or fragment thereof directed to a conformational epitope of hepatitis C virus (HCV) envelope glycoprotein 2 (E2), wherein the antibody or fragment thereof comprises a heavy chain CDR1 region comprising sequence GGTYNSEV (SEQ ID NO: 10), a heavy chain CDR2 region comprising sequence FIPMFGTA (SEQ ID NO: 11), a heavy chain CDR3 region comprising sequence AKVLQVGGNLVVRPL (SEQ ID NO: 12), a light chain CDR1 region comprising sequence QTISSTH (SEQ ID NO: 22), a light chain CDR2 region comprising sequence GVS and a light chain CDR3 region comprising sequence HQYGNSPQT (SEQ ID NO: 23).

19. The antibody or fragment thereof of claim 18, wherein the antibody is the monoclonal antibody HC-1 which is secreted by the hybridoma cell line deposited in the ATCC under Accession Number PTA-9416.

20. An antibody or fragment thereof directed to a conformational epitope of hepatitis C virus (HCV) envelope glycoprotein 2 (E2), wherein the antibody or fragment thereof comprises a heavy chain CDR1 region comprising sequence GFSLSTTGVG (SEQ ID NO: 13), a heavy chain CDR2 region comprising sequence IYWDDDK (SEQ ID NO: 14), a heavy chain CDR3 region comprising sequence ALNSYRSGTILYRELELRGLFYI (SEQ ID NO: 15), a light chain CDR1 region comprising sequence QSISSW (SEQ ID NO: 24), a light chain CDR2 region comprising sequence ESS and a light chain CDR3 region comprising sequence QQYESSSWT (SEQ ID NO: 25).

21. The antibody or fragment thereof of claim 20, wherein the antibody is the monoclonal antibody HC-3 which is secreted by the hybridoma cell line deposited in the ATCC under Accession Number PTA-9417.

22. An antibody or fragment thereof directed to a conformational epitope of hepatitis C virus (HCV) envelope glycoprotein 2 (E2), wherein the antibody or fragment thereof comprises a heavy chain CDR1 region comprising sequence GGTFSSYA (SEQ ID NO: 19), a heavy chain CDR2 region comprising sequence IVPMFGTE (SEQ ID NO: 20), a heavy chain CDR3 region comprising sequence ARHENIYGTPFDY (SEQ ID NO: 21), a light chain CDR1 region comprising sequence HSITRY (SEQ ID NO: 28), a light chain CDR2 region comprising sequence AAS and a light chain CDR3 region comprising sequence QQSYSTLLT (SEQ ID NO: 29).

23. The antibody or fragment thereof of claim 22, wherein the antibody is the monoclonal antibody CBH-23 which is secreted by the hybridoma cell line deposited in the ATCC under Accession Number PTA-9419.

24. An antibody or fragment thereof directed to a conformational epitope of hepatitis C virus (HCV) envelope glycoprotein 2 (E2) wherein the antibody is the monoclonal antibody HC-1 which is secreted by the hybridoma cell line deposited in the ATCC under Accession Number PTA-9416.

25. An antibody or fragment thereof directed to a conformational epitope of hepatitis C virus (HCV) envelope glycoprotein 2 (E2) wherein the antibody is the monoclonal antibody HC-3 which is secreted by the hybridoma cell line deposited in the ATCC under Accession Number PTA-9417.

26. An antibody or fragment thereof directed to a conformational epitope of hepatitis C virus (HCV) envelope glycoprotein 2 (E2) wherein the antibody is the monoclonal antibody CBH-23 which is secreted by the hybridoma cell line deposited in the ATCC under Accession Number PTA-9419.

* * * * *

```
                           SEQUENCE LISTING

<160> NUMBER OF SEQ ID NOS: 29

<210> SEQ ID NO 1
<211> LENGTH: 8
<212> TYPE: PRT
<213> ORGANISM: Artificial sequence
<220> FEATURE:
<223> OTHER INFORMATION: FLAG epitope

<400> SEQUENCE: 1

Asp Tyr Lys Asp Asp Asp Asp Lys
1               5

<210> SEQ ID NO 2
<211> LENGTH: 10
<212> TYPE: PRT
<213> ORGANISM: Artificial sequence
<220> FEATURE:
<223> OTHER INFORMATION: T7 tag sequence

<400> SEQUENCE: 2

Met Ala Ser Met Thr Gly Gly Gln Met Gly
1               5                   10

<210> SEQ ID NO 3
<211> LENGTH: 15
<212> TYPE: PRT
<213> ORGANISM: Artificial sequence
<220> FEATURE:
<223> OTHER INFORMATION: S-tag sequence

<400> SEQUENCE: 3

Lys Glu Thr Ala Ala Ala Lys Phe Glu Arg Gln His Met Asp Ser
1               5                   10                  15

<210> SEQ ID NO 4
<211> LENGTH: 3011
<212> TYPE: PRT
<213> ORGANISM: Artificial sequence
<220> FEATURE:
<223> OTHER INFORMATION: GenBank AAB67038 HCV 1a (H77)

<400> SEQUENCE: 4

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
```

-continued

```
            130                 135                 140
Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
                180                 185                 190

Gln Val Arg Asn Ser Ser Gly Leu Tyr His Val Thr Asn Asp Cys Pro
                195                 200                 205

Asn Ser Ser Ile Val Tyr Glu Ala Ala Asp Ala Ile Leu His Thr Pro
            210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
                260                 265                 270

Ser Ala Leu Tyr Val Gly Asp Leu Cys Gly Ser Val Phe Leu Val Gly
            275                 280                 285

Gln Leu Phe Thr Phe Ser Pro Arg Arg His Trp Thr Thr Gln Asp Cys
            290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
                340                 345                 350

Trp Gly Val Leu Ala Gly Ile Ala Tyr Phe Ser Met Val Gly Asn Trp
            355                 360                 365

Ala Lys Val Leu Val Val Leu Leu Phe Ala Gly Val Asp Ala Glu
            370                 375                 380

Thr His Val Thr Gly Gly Asn Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
                420                 425                 430

Leu Asn Thr Gly Trp Leu Ala Gly Leu Phe Tyr Gln His Lys Phe Asn
            435                 440                 445

Ser Ser Gly Cys Pro Glu Arg Leu Thr Ser Cys Arg Arg Leu Thr Asp
450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Arg Pro Cys Gly Ile
                485                 490                 495

Val Pro Ala Lys Ser Val Cys Gly Pro Val Tyr Cys Phe Thr Pro Ser
                500                 505                 510

Pro Val Val Val Gly Thr Thr Asp Arg Ser Gly Ala Pro Thr Tyr Ser
            515                 520                 525

Trp Gly Ala Asn Asp Thr Asp Val Phe Val Leu Asn Asn Thr Arg Pro
            530                 535                 540

Pro Leu Gly Asn Trp Phe Gly Cys Thr Trp Met Asn Ser Thr Gly Phe
545                 550                 555                 560
```

```
Thr Lys Val Cys Gly Ala Pro Pro Cys Val Ile Gly Val Gly Asn
            565                 570                 575

Asn Thr Leu Leu Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Met
            595                 600                 605

Val Asp Tyr Pro Tyr Arg Leu Trp His Tyr Pro Cys Thr Ile Asn Tyr
            610                 615                 620

Thr Ile Phe Lys Val Arg Met Tyr Val Gly Val Glu His Arg Leu
625             630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
            690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
                740                 745                 750

Ile Leu Asn Ala Ala Ser Leu Ala Gly Thr His Gly Leu Val Ser Phe
            755                 760                 765

Leu Val Phe Phe Cys Phe Ala Trp Tyr Leu Lys Gly Arg Trp Val Pro
            770                 775                 780

Gly Ala Ala Tyr Ala Phe Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Met Trp Trp Leu Gln Tyr
            835                 840                 845

Phe Leu Thr Arg Val Glu Ala Gln Leu His Val Trp Val Pro Pro Leu
850                 855                 860

Asn Val Arg Gly Gly Arg Asp Ala Val Ile Leu Leu Met Cys Val Val
865                 870                 875                 880

His Pro Thr Leu Val Phe Asp Ile Thr Lys Leu Leu Leu Ala Ile Phe
                885                 890                 895

Gly Pro Leu Trp Ile Leu Gln Ala Ser Leu Leu Lys Val Pro Tyr Phe
                900                 905                 910

Val Arg Val Gln Gly Leu Leu Arg Ile Cys Ala Leu Ala Arg Lys Ile
            915                 920                 925

Ala Gly Gly His Tyr Val Gln Met Ala Ile Ile Lys Leu Gly Ala Leu
            930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975
```

```
Ser Arg Met Glu Thr Lys Leu Ile Thr Trp Gly Ala Asp Thr Ala Ala
            980                 985                 990

Cys Gly Asp Ile Ile Asn Gly Leu  Pro Val Ser Ala Arg  Arg Gly Gln
        995                 1000                 1005

Glu Ile  Leu Leu Gly Pro Ala  Asp Gly Met Val Ser  Lys Gly Trp
    1010                 1015                 1020

Arg Leu  Gln Ala Pro Ile Thr  Ala Tyr Thr Gln Gln  Thr Arg Gly
    1025                 1030                 1035

Leu Leu  Gly Cys Ile Ile Thr  Ser Leu Thr Gly Arg  Asp Lys Asn
    1040                 1045                 1050

Gln Val  Glu Gly Glu Val Gln  Ile Val Ser Thr Ala  Thr Gln Thr
    1055                 1060                 1065

Phe Leu  Ala Thr Cys Ile Asn  Gly Val Cys Trp Thr  Val Tyr His
    1070                 1075                 1080

Gly Ala  Gly Thr Arg Thr Ile  Ala Ser Pro Lys Gly  Pro Val Ile
    1085                 1090                 1095

Gln Met  Tyr Thr Asn Val Asp  Gln Asp Leu Val Gly  Trp Pro Ala
    1100                 1105                 1110

Pro Gln  Gly Ser Arg Ser Leu  Ala Pro Cys Thr Cys  Gly Ser Ser
    1115                 1120                 1125

Asp Leu  Tyr Leu Val Thr Arg  His Ala Asp Val Ile  Pro Val Arg
    1130                 1135                 1140

Arg Arg  Gly Asp Ser Arg Gly  Ser Leu Leu Ser Pro  Arg Pro Ile
    1145                 1150                 1155

Ser Tyr  Leu Lys Gly Ser Ser  Gly Gly Pro Leu Leu  Cys Pro Ala
    1160                 1165                 1170

Gly His  Ala Val Gly Leu Phe  Arg Ala Ala Val Cys  Thr Arg Gly
    1175                 1180                 1185

Val Ala  Lys Ala Val Asp Phe  Ile Pro Val Glu Asn  Leu Gly Thr
    1190                 1195                 1200

Thr Met  Arg Ser Pro Val Phe  Thr Asp Asn Ser Ser  Pro Pro Ala
    1205                 1210                 1215

Val Pro  Gln Ser Phe Gln Val  Ala His Leu His Ala  Pro Thr Gly
    1220                 1225                 1230

Ser Gly  Lys Ser Thr Lys Val  Pro Ala Ala Tyr Ala  Ala Gln Gly
    1235                 1240                 1245

Tyr Lys  Val Leu Val Leu Asn  Pro Ser Val Ala Ala  Thr Leu Gly
    1250                 1255                 1260

Phe Gly  Ala Tyr Met Ser Lys  Ala His Gly Val Asp  Pro Asn Ile
    1265                 1270                 1275

Arg Thr  Gly Val Arg Thr Ile  Thr Thr Gly Ser Pro  Ile Thr Tyr
    1280                 1285                 1290

Ser Thr  Tyr Gly Lys Phe Leu  Ala Asp Gly Gly Cys  Ser Gly Gly
    1295                 1300                 1305

Ala Tyr  Asp Ile Ile Ile Cys  Asp Glu Cys His Ser  Thr Asp Ala
    1310                 1315                 1320

Thr Ser  Ile Leu Gly Ile Gly  Thr Val Leu Asp Gln  Ala Glu Thr
    1325                 1330                 1335

Ala Gly  Ala Arg Leu Val Val  Leu Ala Thr Ala Thr  Pro Pro Gly
    1340                 1345                 1350

Ser Val  Thr Val Ser His Pro  Asn Ile Glu Glu Val  Ala Leu Ser
    1355                 1360                 1365

Thr Thr  Gly Glu Ile Pro Phe  Tyr Gly Lys Ala Ile  Pro Leu Glu
```

-continued

```
                1370                1375                1380
Val Ile Lys Gly Gly Arg His Leu Ile Phe Cys His Ser Lys Lys
        1385                1390                1395

Lys Cys Asp Glu Leu Ala Ala Lys Leu Val Ala Leu Gly Ile Asn
        1400                1405                1410

Ala Val Ala Tyr Tyr Arg Gly Leu Asp Val Ser Val Ile Pro Thr
        1415                1420                1425

Ser Gly Asp Val Val Val Ser Thr Asp Ala Leu Met Thr Gly
        1430                1435                1440

Phe Thr Gly Asp Phe Asp Ser Val Ile Asp Cys Asn Thr Cys Val
        1445                1450                1455

Thr Gln Thr Val Asp Phe Ser Leu Asp Pro Thr Phe Thr Ile Glu
        1460                1465                1470

Thr Thr Thr Leu Pro Gln Asp Ala Val Ser Arg Thr Gln Arg Arg
        1475                1480                1485

Gly Arg Thr Gly Arg Gly Lys Pro Gly Ile Tyr Arg Phe Val Ala
        1490                1495                1500

Pro Gly Glu Arg Pro Ser Gly Met Phe Asp Ser Ser Val Leu Cys
        1505                1510                1515

Glu Cys Tyr Asp Ala Gly Cys Ala Trp Tyr Glu Leu Thr Pro Ala
        1520                1525                1530

Glu Thr Thr Val Arg Leu Arg Ala Tyr Met Asn Thr Pro Gly Leu
        1535                1540                1545

Pro Val Cys Gln Asp His Leu Glu Phe Trp Glu Gly Val Phe Thr
        1550                1555                1560

Gly Leu Thr His Ile Asp Ala His Phe Leu Ser Gln Thr Lys Gln
        1565                1570                1575

Ser Gly Glu Asn Phe Pro Tyr Leu Val Ala Tyr Gln Ala Thr Val
        1580                1585                1590

Cys Ala Arg Ala Gln Ala Pro Pro Pro Ser Trp Asp Gln Met Trp
        1595                1600                1605

Lys Cys Leu Ile Arg Leu Lys Pro Thr Leu His Gly Pro Thr Pro
        1610                1615                1620

Leu Leu Tyr Arg Leu Gly Ala Val Gln Asn Glu Val Thr Leu Thr
        1625                1630                1635

His Pro Ile Thr Lys Tyr Ile Met Thr Cys Met Ser Ala Asp Leu
        1640                1645                1650

Glu Val Val Thr Ser Thr Trp Val Leu Val Gly Gly Val Leu Ala
        1655                1660                1665

Ala Leu Ala Ala Tyr Cys Leu Ser Thr Gly Cys Val Val Ile Val
        1670                1675                1680

Gly Arg Ile Val Leu Ser Gly Lys Pro Ala Ile Ile Pro Asp Arg
        1685                1690                1695

Glu Val Leu Tyr Gln Glu Phe Asp Glu Met Glu Glu Cys Ser Gln
        1700                1705                1710

His Leu Pro Tyr Ile Glu Gln Gly Met Met Leu Ala Glu Gln Phe
        1715                1720                1725

Lys Gln Lys Ala Leu Gly Leu Leu Gln Thr Ala Ser Arg His Ala
        1730                1735                1740

Glu Val Ile Thr Pro Ala Val Gln Thr Asn Trp Gln Lys Leu Glu
        1745                1750                1755

Val Phe Trp Ala Lys His Met Trp Asn Phe Ile Ser Gly Ile Gln
        1760                1765                1770
```

```
Tyr Leu Ala Gly Leu Ser Thr Leu Pro Gly Asn Pro Ala Ile Ala
    1775                1780            1785

Ser Leu Met Ala Phe Thr Ala Ala Val Thr Ser Pro Leu Thr Thr
    1790                1795            1800

Gly Gln Thr Leu Leu Phe Asn Ile Leu Gly Gly Trp Val Ala Ala
    1805                1810            1815

Gln Leu Ala Ala Pro Gly Ala Ala Thr Ala Phe Val Gly Ala Gly
    1820                1825            1830

Leu Ala Gly Ala Ala Ile Gly Ser Val Gly Leu Gly Lys Val Leu
    1835                1840            1845

Val Asp Ile Leu Ala Gly Tyr Gly Ala Gly Val Ala Gly Ala Leu
    1850                1855            1860

Val Ala Phe Lys Ile Met Ser Gly Glu Val Pro Ser Thr Glu Asp
    1865                1870            1875

Leu Val Asn Leu Leu Pro Ala Ile Leu Ser Pro Gly Ala Leu Val
    1880                1885            1890

Val Gly Val Val Cys Ala Ala Ile Leu Arg Arg His Val Gly Pro
    1895                1900            1905

Gly Glu Gly Ala Val Gln Trp Met Asn Arg Leu Ile Ala Phe Ala
    1910                1915            1920

Ser Arg Gly Asn His Val Ser Pro Thr His Tyr Val Pro Glu Ser
    1925                1930            1935

Asp Ala Ala Ala Arg Val Thr Ala Ile Leu Ser Ser Leu Thr Val
    1940                1945            1950

Thr Gln Leu Leu Arg Arg Leu His Gln Trp Ile Ser Ser Glu Cys
    1955                1960            1965

Thr Thr Pro Cys Ser Gly Ser Trp Leu Arg Asp Ile Trp Asp Trp
    1970                1975            1980

Ile Cys Glu Val Leu Ser Asp Phe Lys Thr Trp Leu Lys Ala Lys
    1985                1990            1995

Leu Met Pro Gln Leu Pro Gly Ile Pro Phe Val Ser Cys Gln Arg
    2000                2005            2010

Gly Tyr Arg Gly Val Trp Arg Gly Asp Gly Ile Met His Thr Arg
    2015                2020            2025

Cys His Cys Gly Ala Glu Ile Thr Gly His Val Lys Asn Gly Thr
    2030                2035            2040

Met Arg Ile Val Gly Pro Arg Thr Cys Arg Asn Met Trp Ser Gly
    2045                2050            2055

Thr Phe Pro Ile Asn Ala Tyr Thr Thr Gly Pro Cys Thr Pro Leu
    2060                2065            2070

Pro Ala Pro Asn Tyr Lys Phe Ala Leu Trp Arg Val Ser Ala Glu
    2075                2080            2085

Glu Tyr Val Glu Ile Arg Arg Val Gly Asp Phe His Tyr Val Ser
    2090                2095            2100

Gly Met Thr Thr Asp Asn Leu Lys Cys Pro Cys Gln Ile Pro Ser
    2105                2110            2115

Pro Glu Phe Phe Thr Glu Leu Asp Gly Val Arg Leu His Arg Phe
    2120                2125            2130

Ala Pro Pro Cys Lys Pro Leu Leu Arg Glu Glu Val Ser Phe Arg
    2135                2140            2145

Val Gly Leu His Glu Tyr Pro Val Gly Ser Gln Leu Pro Cys Glu
    2150                2155            2160
```

-continued

```
Pro Glu Pro Asp Val Ala Val Leu Thr Ser Met Leu Thr Asp Pro
    2165            2170                2175

Ser His Ile Thr Ala Glu Ala Ala Gly Arg Arg Leu Ala Arg Gly
    2180            2185                2190

Ser Pro Pro Ser Met Ala Ser Ser Ser Ala Ser Gln Leu Ser Ala
    2195            2200                2205

Pro Ser Leu Lys Ala Thr Cys Thr Ala Asn His Asp Ser Pro Asp
    2210            2215                2220

Ala Glu Leu Ile Glu Ala Asn Leu Leu Trp Arg Gln Glu Met Gly
    2225            2230                2235

Gly Asn Ile Thr Arg Val Glu Ser Glu Asn Lys Val Val Ile Leu
    2240            2245                2250

Asp Ser Phe Asp Pro Leu Val Ala Glu Glu Asp Glu Arg Glu Val
    2255            2260                2265

Ser Val Pro Ala Glu Ile Leu Arg Lys Ser Arg Arg Phe Ala Arg
    2270            2275                2280

Ala Leu Pro Val Trp Ala Arg Pro Asp Tyr Asn Pro Pro Leu Val
    2285            2290                2295

Glu Thr Trp Lys Lys Pro Asp Tyr Glu Pro Pro Val Val His Gly
    2300            2305                2310

Cys Pro Leu Pro Pro Pro Arg Ser Pro Pro Val Pro Pro Pro Arg
    2315            2320                2325

Lys Lys Arg Thr Val Val Leu Thr Glu Ser Thr Leu Ser Thr Ala
    2330            2335                2340

Leu Ala Glu Leu Ala Thr Lys Ser Phe Gly Ser Ser Ser Thr Ser
    2345            2350                2355

Gly Ile Thr Gly Asp Asn Thr Thr Thr Ser Ser Glu Pro Ala Pro
    2360            2365                2370

Ser Gly Cys Pro Pro Asp Ser Asp Val Glu Ser Tyr Ser Ser Met
    2375            2380                2385

Pro Pro Leu Glu Gly Glu Pro Gly Asp Pro Asp Leu Ser Asp Gly
    2390            2395                2400

Ser Trp Ser Thr Val Ser Ser Gly Ala Asp Thr Glu Asp Val Val
    2405            2410                2415

Cys Cys Ser Met Ser Tyr Ser Trp Thr Gly Ala Leu Val Thr Pro
    2420            2425                2430

Cys Ala Ala Glu Glu Gln Lys Leu Pro Ile Asn Ala Leu Ser Asn
    2435            2440                2445

Ser Leu Leu Arg His His Asn Leu Val Tyr Ser Thr Thr Ser Arg
    2450            2455                2460

Ser Ala Cys Gln Arg Gln Lys Lys Val Thr Phe Asp Arg Leu Gln
    2465            2470                2475

Val Leu Asp Ser His Tyr Gln Asp Val Leu Lys Glu Val Lys Ala
    2480            2485                2490

Ala Ala Ser Lys Val Lys Ala Asn Leu Leu Ser Val Glu Glu Ala
    2495            2500                2505

Cys Ser Leu Thr Pro Pro His Ser Ala Lys Ser Lys Phe Gly Tyr
    2510            2515                2520

Gly Ala Lys Asp Val Arg Cys His Ala Arg Lys Ala Val Ala His
    2525            2530                2535

Ile Asn Ser Val Trp Lys Asp Leu Leu Glu Asp Ser Val Thr Pro
    2540            2545                2550

Ile Asp Thr Thr Ile Met Ala Lys Asn Glu Val Phe Cys Val Gln
```

```
            2555                2560                2565

Pro Glu Lys Gly Gly Arg Lys Pro Ala Arg Leu Ile Val Phe Pro
    2570                2575                2580

Asp Leu Gly Val Arg Val Cys Glu Lys Met Ala Leu Tyr Asp Val
    2585                2590                2595

Val Ser Lys Leu Pro Leu Ala Val Met Gly Ser Ser Tyr Gly Phe
    2600                2605                2610

Gln Tyr Ser Pro Gly Gln Arg Val Glu Phe Leu Val Gln Ala Trp
    2615                2620                2625

Lys Ser Lys Lys Thr Pro Met Gly Phe Ser Tyr Asp Thr Arg Cys
    2630                2635                2640

Phe Asp Ser Thr Val Thr Glu Ser Asp Ile Arg Thr Glu Glu Ala
    2645                2650                2655

Ile Tyr Gln Cys Cys Asp Leu Asp Pro Gln Ala Arg Val Ala Ile
    2660                2665                2670

Lys Ser Leu Thr Glu Arg Leu Tyr Val Gly Gly Pro Leu Thr Asn
    2675                2680                2685

Ser Arg Gly Glu Asn Cys Gly Tyr Arg Arg Cys Arg Ala Ser Gly
    2690                2695                2700

Val Leu Thr Thr Ser Cys Gly Asn Thr Leu Thr Cys Tyr Ile Lys
    2705                2710                2715

Ala Arg Ala Ala Cys Arg Ala Ala Gly Leu Gln Asp Cys Thr Met
    2720                2725                2730

Leu Val Cys Gly Asp Asp Leu Val Val Ile Cys Glu Ser Ala Gly
    2735                2740                2745

Val Gln Glu Asp Ala Ala Asn Leu Arg Ala Phe Thr Glu Ala Met
    2750                2755                2760

Thr Arg Tyr Ser Ala Pro Pro Gly Asp Pro Pro Gln Pro Glu Tyr
    2765                2770                2775

Asp Leu Glu Leu Ile Thr Ser Cys Ser Ser Asn Val Ser Val Ala
    2780                2785                2790

His Asp Gly Ala Gly Lys Arg Val Tyr Tyr Leu Thr Arg Asp Pro
    2795                2800                2805

Thr Thr Pro Leu Ala Arg Ala Ala Trp Glu Thr Ala Arg His Thr
    2810                2815                2820

Pro Val Asn Ser Trp Leu Gly Asn Ile Ile Met Phe Ala Pro Thr
    2825                2830                2835

Leu Trp Ala Arg Met Ile Leu Met Thr His Phe Phe Ser Val Leu
    2840                2845                2850

Ile Ala Arg Asp Gln Leu Glu Gln Ala Leu Asn Cys Glu Ile Tyr
    2855                2860                2865

Gly Ala Cys Tyr Ser Ile Glu Pro Leu Asp Leu Pro Pro Ile Ile
    2870                2875                2880

Gln Arg Leu His Gly Leu Ser Ala Phe Ser Leu His Ser Tyr Ser
    2885                2890                2895

Pro Gly Glu Ile Asn Arg Val Ala Ala Cys Leu Arg Lys Leu Gly
    2900                2905                2910

Val Pro Pro Leu Arg Ala Trp Arg His Arg Ala Arg Ser Val Arg
    2915                2920                2925

Ala Arg Leu Leu Ser Arg Gly Gly Arg Ala Ala Ile Cys Gly Lys
    2930                2935                2940

Tyr Leu Phe Asn Trp Ala Val Arg Thr Lys Leu Lys Leu Thr Pro
    2945                2950                2955
```

Ile Thr Ala Ala Gly Arg Leu Asp Leu Ser Gly Trp Phe Thr Ala
    2960            2965                2970

Gly Tyr Ser Gly Gly Asp Ile Tyr His Ser Val Ser His Ala Arg
    2975            2980                2985

Pro Arg Trp Phe Trp Phe Cys Leu Leu Leu Leu Ala Ala Gly Val
    2990            2995                3000

Gly Ile Tyr Leu Leu Pro Asn Arg
    3005            3010

<210> SEQ ID NO 5
<211> LENGTH: 3010
<212> TYPE: PRT
<213> ORGANISM: Artificial sequence
<220> FEATURE:
<223> OTHER INFORMATION: GenBank AAK08509 HCV 1b

<400> SEQUENCE: 5

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Ile Tyr His Val Thr Asn Asp Cys Ser
        195                 200                 205

Asn Ser Ser Ile Val Tyr Glu Ala Ala Asp Met Ile Met His Thr Pro
    210                 215                 220

Gly Cys Val Pro Cys Val Arg Glu Ser Asn Phe Ser Arg Cys Trp Val
225                 230                 235                 240

Ala Leu Thr Pro Thr Leu Ala Ala Arg Asn Ser Ser Ile Pro Thr Thr
                245                 250                 255

Thr Ile Arg Arg His Val Asp Leu Leu Val Gly Ala Ala Ala Leu Cys
            260                 265                 270

Ser Ala Met Tyr Val Gly Asp Leu Cys Gly Ser Val Phe Leu Val Ser
        275                 280                 285

Gln Leu Phe Thr Phe Ser Pro Arg Arg Tyr Glu Thr Val Gln Asp Cys
    290                 295                 300

```
Asn Cys Ser Ile Tyr Pro Gly His Val Ser Gly His Arg Met Ala Trp
305                 310                 315                 320

Asp Met Met Met Asn Trp Ser Pro Thr Thr Ala Leu Val Val Ser Gln
            325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Val Gly Asn Trp
            355                 360                 365

Ala Lys Val Leu Ile Val Met Leu Leu Phe Ala Gly Val Asp Gly His
370                 375                 380

Thr His Val Thr Gly Gly Arg Val Ala Ser Ser Thr Gln Ser Leu Val
385                 390                 395                 400

Ser Trp Leu Ser Gln Gly Pro Ser Gln Lys Ile Gln Leu Val Asn Thr
            405                 410                 415

Asn Gly Ser Trp His Ile Asn Arg Thr Ala Leu Asn Cys Asn Asp Ser
            420                 425                 430

Leu Gln Thr Gly Phe Ile Ala Ala Leu Phe Tyr Ala His Arg Phe Asn
            435                 440                 445

Ala Ser Gly Cys Pro Glu Arg Met Ala Ser Cys Arg Pro Ile Asp Lys
450                 455                 460

Phe Ala Gln Gly Trp Gly Pro Ile Thr His Val Val Pro Asn Ile Ser
465                 470                 475                 480

Asp Gln Arg Pro Tyr Cys Trp His Tyr Ala Pro Gln Pro Cys Gly Ile
            485                 490                 495

Val Pro Ala Ser Gln Val Cys Gly Pro Val Tyr Cys Phe Thr Pro Ser
            500                 505                 510

Pro Val Val Val Gly Thr Thr Asp Arg Ser Gly Val Pro Thr Tyr Ser
            515                 520                 525

Trp Gly Glu Asn Glu Thr Asp Val Leu Leu Leu Asn Asn Thr Arg Pro
            530                 535                 540

Pro Gln Gly Asn Trp Phe Gly Cys Thr Trp Met Asn Ser Thr Gly Phe
545                 550                 555                 560

Thr Lys Thr Cys Gly Gly Pro Pro Cys Asn Ile Gly Val Gly Asn
                565                 570                 575

Asn Thr Leu Ile Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Leu
            595                 600                 605

Val Asp Tyr Pro Tyr Arg Leu Trp His Tyr Pro Cys Thr Ile Asn Phe
            610                 615                 620

Thr Ile Phe Lys Val Arg Met Tyr Val Gly Gly Val Glu His Arg Leu
625                 630                 635                 640

Asn Ala Ala Cys Asn Trp Thr Arg Gly Glu Arg Cys Asp Leu Glu Asp
            645                 650                 655

Arg Asp Arg Ser Glu Leu Ser Pro Leu Leu Leu Ser Thr Thr Glu Trp
            660                 665                 670

Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
            690                 695                 700

Val Gly Ser Val Val Val Ser Val Val Ile Lys Trp Glu Tyr Val Leu
705                 710                 715                 720
```

```
Leu Leu Phe Leu Leu Leu Ala Asp Ala Arg Val Cys Ala Cys Leu Trp
                725                 730                 735

Met Met Leu Leu Ile Ala Gln Ala Glu Ala Thr Leu Glu Asn Leu Val
        740                 745                 750

Val Leu Asn Ala Ala Ser Val Ala Gly Ala His Gly Leu Leu Ser Phe
            755                 760                 765

Leu Val Phe Phe Cys Ala Ala Trp Tyr Ile Lys Gly Arg Leu Val Pro
770                 775                 780

Gly Ala Ala Tyr Ala Leu Tyr Gly Val Trp Pro Leu Leu Leu Leu Leu
785                 790                 795                 800

Leu Ala Leu Pro Pro Arg Ala Tyr Ala Met Asp Arg Glu Met Ala Ala
                805                 810                 815

Ser Cys Gly Gly Ala Val Phe Val Gly Leu Val Leu Leu Thr Leu Ser
            820                 825                 830

Pro Tyr Tyr Lys Val Phe Leu Ala Arg Leu Ile Trp Trp Leu Gln Tyr
                835                 840                 845

Phe Ile Thr Arg Ala Glu Ala His Leu Gln Val Trp Val Pro Pro Leu
850                 855                 860

Asn Val Arg Gly Gly Arg Asp Ala Ile Ile Leu Leu Thr Cys Ala Val
865                 870                 875                 880

His Pro Glu Leu Ile Phe Asp Ile Thr Lys Leu Leu Leu Ala Ile Leu
                885                 890                 895

Gly Pro Leu Met Val Leu Gln Ala Gly Ile Thr Arg Val Pro Tyr Phe
                900                 905                 910

Val Arg Ala Gln Gly Leu Ile His Ala Cys Met Leu Val Arg Lys Val
                915                 920                 925

Ala Gly Gly His Tyr Val Gln Met Ala Phe Met Lys Leu Gly Ala Leu
        930                 935                 940

Thr Gly Thr Tyr Ile Tyr Asn His Leu Thr Pro Leu Arg Asp Trp Ala
945                 950                 955                 960

His Ala Gly Leu Arg Asp Leu Ala Val Ala Val Glu Pro Val Val Phe
                965                 970                 975

Ser Asp Met Glu Thr Lys Ile Ile Thr Trp Gly Ala Asp Thr Ala Ala
                980                 985                 990

Cys Gly Asp Ile Ile Leu Gly Leu  Pro Val Ser Ala Arg  Arg Gly Lys
        995                 1000                1005

Glu Ile  Leu Leu Gly Pro Ala  Asp Ser Leu Glu Gly  Arg Gly Trp
1010                1015                1020

Arg Leu Leu Ala Pro Ile Thr  Ala Tyr Ser Gln Gln  Thr Arg Gly
        1025                1030                1035

Leu Leu Gly Cys Ile Ile Thr  Ser Leu Thr Gly Arg  Asp Lys Asn
        1040                1045                1050

Gln Val Glu Gly Glu Val Gln  Val Val Ser Thr Ala  Thr Gln Ser
        1055                1060                1065

Phe Leu Ala Thr Cys Val Asn  Gly Val Cys Trp Thr  Val Tyr His
        1070                1075                1080

Gly Ala Gly Ser Lys Thr Leu  Ala Gly Pro Lys Gly  Pro Ile Thr
        1085                1090                1095

Gln Met Tyr Thr Asn Val Asp  Gln Asp Leu Val Gly  Trp Gln Ala
        1100                1105                1110

Pro Pro Gly Ala Arg Ser Leu  Thr Pro Cys Thr Cys  Gly Ser Ser
        1115                1120                1125

Asp Leu Tyr Leu Val Thr Arg  His Ala Asp Val Ile  Pro Val Arg
```

```
                    1130                1135                1140
Arg Arg Gly Asp Ser Arg Gly Ser Leu Leu Ser Pro Arg Pro Val
    1145                1150                1155
Ser Tyr Leu Lys Gly Ser Ser Gly Gly Pro Leu Leu Cys Pro Ser
    1160                1165                1170
Gly His Ala Val Gly Ile Phe Arg Ala Ala Val Cys Thr Arg Gly
    1175                1180                1185
Val Ala Lys Ala Val Asp Phe Val Pro Val Glu Ser Met Glu Thr
    1190                1195                1200
Thr Met Arg Ser Pro Val Phe Thr Asp Asn Ser Ser Pro Pro Ala
    1205                1210                1215
Val Pro Gln Ser Phe Gln Val Ala His Leu His Ala Pro Thr Gly
    1220                1225                1230
Ser Gly Lys Ser Thr Lys Val Pro Ala Ala Tyr Ala Ala Gln Gly
    1235                1240                1245
Tyr Lys Val Leu Val Leu Asn Pro Ser Val Ala Ala Thr Leu Gly
    1250                1255                1260
Phe Gly Ala Tyr Met Ser Lys Ala His Gly Ile Asp Pro Asn Ile
    1265                1270                1275
Arg Thr Gly Val Arg Thr Ile Thr Thr Gly Ala Pro Val Thr Tyr
    1280                1285                1290
Ser Thr Tyr Gly Lys Phe Leu Ala Asp Gly Gly Cys Ser Gly Gly
    1295                1300                1305
Ala Tyr Asp Ile Ile Ile Cys Asp Glu Cys His Ser Thr Asp Ser
    1310                1315                1320
Thr Thr Ile Leu Gly Ile Gly Thr Val Leu Asp Gln Ala Glu Thr
    1325                1330                1335
Ala Gly Ala Arg Leu Val Val Leu Ala Thr Ala Thr Pro Pro Gly
    1340                1345                1350
Ser Val Thr Val Pro His Pro Asn Ile Glu Glu Val Ala Leu Ser
    1355                1360                1365
Asn Thr Gly Glu Ile Pro Phe Tyr Gly Lys Ala Ile Pro Ile Glu
    1370                1375                1380
Ala Ile Arg Gly Gly Arg His Leu Ile Phe Cys His Ser Lys Lys
    1385                1390                1395
Lys Cys Asp Glu Leu Ala Ala Lys Leu Ser Gly Leu Gly Ile Asn
    1400                1405                1410
Ala Val Ala Tyr Tyr Arg Gly Leu Asp Val Ser Val Ile Pro Thr
    1415                1420                1425
Ile Gly Asp Val Val Val Val Ala Thr Asp Ala Leu Met Thr Gly
    1430                1435                1440
Tyr Thr Gly Asp Phe Asp Ser Val Ile Asp Cys Asn Thr Cys Val
    1445                1450                1455
Thr Gln Thr Val Asp Phe Ser Leu Asp Pro Thr Phe Thr Ile Glu
    1460                1465                1470
Thr Thr Thr Val Pro Gln Asp Ala Val Ser Arg Ser Gln Arg Arg
    1475                1480                1485
Gly Arg Thr Gly Arg Gly Arg Arg Gly Ile Tyr Arg Phe Val Thr
    1490                1495                1500
Pro Gly Glu Arg Pro Ser Gly Met Phe Asp Ser Ser Val Leu Cys
    1505                1510                1515
Glu Cys Tyr Asp Ala Gly Cys Ala Trp Tyr Glu Leu Thr Pro Ala
    1520                1525                1530
```

```
Glu Thr Ser Val Arg Leu Arg Ala Tyr Leu Asn Thr Pro Gly Leu
1535                1540                    1545

Pro Val Cys Gln Asp His Leu Glu Phe Trp Glu Ser Val Phe Thr
1550                1555                    1560

Gly Leu Thr His Ile Asp Ala His Phe Leu Ser Gln Thr Lys Gln
1565                1570                    1575

Ala Gly Asp Asn Phe Pro Tyr Leu Val Ala Tyr Gln Ala Thr Val
1580                1585                    1590

Cys Ala Arg Ala Gln Ala Pro Pro Ser Trp Asp Gln Met Trp
1595                1600                    1605

Lys Cys Leu Ile Arg Leu Lys Pro Thr Leu His Gly Pro Thr Pro
1610                1615                    1620

Leu Leu Tyr Arg Leu Gly Ala Val Gln Asn Glu Val Thr Leu Thr
1625                1630                    1635

His Pro Ile Thr Lys Tyr Ile Met Ala Cys Met Ser Ala Asp Leu
1640                1645                    1650

Glu Val Val Thr Ser Thr Trp Val Leu Val Gly Gly Val Leu Ala
1655                1660                    1665

Ala Leu Ala Ala Tyr Cys Leu Thr Thr Gly Ser Val Val Ile Val
1670                1675                    1680

Gly Arg Ile Ile Leu Ser Gly Arg Pro Ala Ile Val Pro Asp Arg
1685                1690                    1695

Glu Leu Leu Tyr Gln Glu Phe Asp Glu Met Glu Glu Cys Ala Thr
1700                1705                    1710

His Leu Pro Tyr Ile Glu Gln Gly Met Gln Leu Ala Glu Gln Phe
1715                1720                    1725

Lys Gln Lys Ala Leu Gly Leu Leu Gln Thr Ala Thr Lys Gln Ala
1730                1735                    1740

Glu Ala Ala Ala Pro Val Val Glu Ser Lys Trp Arg Ala Leu Glu
1745                1750                    1755

Thr Phe Trp Ala Lys His Met Trp Asn Phe Ile Ser Gly Ile Gln
1760                1765                    1770

Tyr Leu Ala Gly Leu Ser Thr Leu Pro Gly Asn Pro Ala Ile Ala
1775                1780                    1785

Ser Leu Met Ala Phe Thr Ala Ser Ile Thr Ser Pro Leu Thr Thr
1790                1795                    1800

Gln Ser Thr Leu Leu Phe Asn Ile Leu Gly Gly Trp Val Ala Ala
1805                1810                    1815

Gln Leu Ala Pro Pro Ser Ala Ala Ser Ala Phe Val Gly Ala Gly
1820                1825                    1830

Ile Ala Gly Ala Ala Val Gly Ser Ile Gly Leu Gly Lys Val Leu
1835                1840                    1845

Val Asp Ile Leu Ala Gly Tyr Gly Ala Gly Val Ala Gly Ala Leu
1850                1855                    1860

Val Ala Phe Lys Val Met Ser Gly Glu Met Pro Ser Thr Glu Asp
1865                1870                    1875

Leu Val Asn Leu Leu Pro Ala Ile Leu Ser Pro Gly Ala Leu Val
1880                1885                    1890

Val Gly Val Val Cys Ala Ala Ile Leu Arg Arg His Val Gly Pro
1895                1900                    1905

Gly Glu Gly Ala Val Gln Trp Met Asn Arg Leu Ile Ala Phe Ala
1910                1915                    1920
```

```
Ser Arg Gly Asn His Val Ser Pro Thr His Tyr Val Pro Glu Ser
1925                1930                1935

Asp Ala Ala Ala Arg Val Thr Gln Ile Leu Ser Ser Leu Thr Ile
1940                1945                1950

Thr Gln Leu Leu Lys Arg Leu His Gln Trp Ile Asn Glu Asp Cys
1955                1960                1965

Ser Thr Pro Cys Ser Gly Ser Trp Leu Arg Asp Val Trp Asp Trp
1970                1975                1980

Ile Cys Thr Val Leu Thr Asp Phe Lys Thr Trp Leu Gln Ser Lys
1985                1990                1995

Leu Leu Pro Gln Leu Pro Gly Val Pro Phe Phe Ser Cys Gln Arg
2000                2005                2010

Gly Tyr Lys Gly Val Trp Arg Gly Asp Gly Ile Met Gln Thr Thr
2015                2020                2025

Cys Pro Cys Gly Ala Gln Ile Thr Gly His Val Lys Asn Gly Ser
2030                2035                2040

Met Arg Ile Val Gly Pro Lys Thr Cys Ser Asn Thr Trp His Gly
2045                2050                2055

Thr Phe Pro Ile Asn Ala Tyr Thr Thr Gly Pro Cys Thr Pro Ser
2060                2065                2070

Pro Ala Pro Asn Tyr Ser Arg Ala Leu Trp Arg Val Ala Ala Glu
2075                2080                2085

Glu Tyr Val Glu Val Thr Arg Val Gly Asp Phe His Tyr Val Thr
2090                2095                2100

Gly Met Thr Thr Asp Asn Val Lys Cys Pro Cys Gln Val Pro Ala
2105                2110                2115

Pro Glu Phe Phe Ser Glu Val Asp Gly Val Arg Leu His Arg Tyr
2120                2125                2130

Ala Pro Ala Cys Arg Pro Leu Leu Arg Glu Glu Val Thr Phe Gln
2135                2140                2145

Val Gly Leu Asn Gln Tyr Leu Val Gly Ser Gln Leu Pro Cys Glu
2150                2155                2160

Pro Glu Pro Asp Val Ala Val Leu Thr Ser Met Leu Thr Asp Pro
2165                2170                2175

Ser His Ile Thr Ala Glu Thr Ala Lys Arg Arg Leu Ala Arg Gly
2180                2185                2190

Ser Pro Pro Ser Leu Ala Ser Ser Ser Ala Ser Gln Leu Ser Ala
2195                2200                2205

Pro Ser Leu Lys Ala Thr Cys Thr Thr His His Val Ser Pro Asp
2210                2215                2220

Ala Asp Leu Ile Glu Ala Asn Leu Leu Trp Arg Gln Glu Met Gly
2225                2230                2235

Gly Asn Ile Thr Arg Val Glu Ser Glu Asn Lys Val Val Val Leu
2240                2245                2250

Asp Ser Phe Asp Pro Leu Arg Ala Glu Glu Asp Glu Arg Glu Val
2255                2260                2265

Ser Val Pro Ala Glu Ile Leu Arg Lys Ser Lys Lys Phe Pro Ala
2270                2275                2280

Ala Met Pro Ile Trp Ala Arg Pro Asp Tyr Asn Pro Pro Leu Leu
2285                2290                2295

Glu Ser Trp Lys Asp Pro Asp Tyr Val Pro Pro Val Val His Gly
2300                2305                2310

Cys Pro Leu Pro Pro Ile Lys Ala Pro Pro Ile Pro Pro Pro Arg
```

-continued

```
            2315                2320                2325

Arg Lys Arg Thr Val Val Leu Thr Glu Ser Ser Val Ser Ser Ala
        2330                2335                2340

Leu Ala Glu Leu Ala Thr Lys Thr Phe Gly Ser Ser Glu Ser Ser
        2345                2350                2355

Ala Val Asp Ser Gly Thr Ala Thr Ala Leu Pro Asp Gln Ala Ser
        2360                2365                2370

Asp Asp Gly Asp Lys Gly Ser Asp Val Glu Ser Tyr Ser Ser Met
        2375                2380                2385

Pro Pro Leu Glu Gly Glu Pro Gly Asp Pro Asp Leu Ser Asp Gly
        2390                2395                2400

Ser Trp Ser Thr Val Ser Glu Glu Ala Ser Glu Asp Val Val Cys
        2405                2410                2415

Cys Ser Met Ser Tyr Thr Trp Thr Gly Ala Leu Ile Thr Pro Cys
        2420                2425                2430

Ala Ala Glu Glu Ser Lys Leu Pro Ile Asn Ala Leu Ser Asn Ser
        2435                2440                2445

Leu Leu Arg His His Asn Met Val Tyr Ala Thr Thr Ser Arg Ser
        2450                2455                2460

Ala Gly Leu Arg Gln Lys Lys Val Thr Phe Asp Arg Leu Gln Val
        2465                2470                2475

Leu Asp Asp His Tyr Arg Asp Val Leu Lys Glu Met Lys Ala Lys
        2480                2485                2490

Ala Ser Thr Val Lys Ala Lys Leu Leu Ser Val Glu Glu Ala Cys
        2495                2500                2505

Lys Leu Thr Pro Pro His Ser Ala Lys Ser Lys Phe Gly Tyr Gly
        2510                2515                2520

Ala Lys Asp Val Arg Asn Leu Ser Ser Lys Ala Val Asn His Ile
        2525                2530                2535

His Ser Val Trp Lys Asp Leu Leu Glu Asp Thr Val Thr Pro Ile
        2540                2545                2550

Asp Thr Thr Ile Met Ala Lys Asn Glu Val Phe Cys Val Gln Pro
        2555                2560                2565

Glu Lys Gly Gly Arg Lys Pro Ala Arg Leu Ile Val Phe Pro Asp
        2570                2575                2580

Leu Gly Val Arg Val Cys Glu Lys Met Ala Leu Tyr Asp Val Val
        2585                2590                2595

Ser Thr Leu Pro Gln Val Val Met Gly Ser Ser Tyr Gly Phe Gln
        2600                2605                2610

Tyr Ser Pro Gly Gln Arg Val Glu Phe Leu Val Asn Thr Trp Lys
        2615                2620                2625

Ser Lys Lys Asn Pro Met Gly Phe Ser Tyr Asp Thr Arg Cys Phe
        2630                2635                2640

Asp Ser Thr Val Thr Glu Asn Asp Ile Arg Val Glu Glu Ser Ile
        2645                2650                2655

Tyr Gln Cys Cys Asp Leu Ala Pro Glu Ala Arg Gln Ala Ile Lys
        2660                2665                2670

Ser Leu Thr Glu Arg Leu Tyr Ile Gly Gly Pro Leu Thr Asn Ser
        2675                2680                2685

Lys Gly Gln Asn Cys Gly Tyr Arg Arg Cys Arg Ala Ser Gly Val
        2690                2695                2700

Leu Thr Thr Ser Cys Gly Asn Thr Leu Thr Cys Tyr Leu Lys Ala
        2705                2710                2715
```

```
Ser Ala Ala Cys Arg Ala Ala Lys Leu Gln Asp Cys Thr Met Leu
    2720            2725                2730

Val Asn Gly Asp Asp Leu Val Val Ile Cys Glu Ser Ala Gly Thr
    2735            2740                2745

Gln Glu Asp Ala Ala Ser Leu Arg Val Phe Thr Glu Ala Met Thr
    2750            2755                2760

Arg Tyr Ser Ala Pro Pro Gly Asp Pro Pro Gln Pro Glu Tyr Asp
    2765            2770                2775

Leu Glu Leu Ile Thr Ser Cys Ser Ser Asn Val Ser Val Ala His
    2780            2785                2790

Asp Ala Ser Gly Lys Arg Val Tyr Tyr Leu Thr Arg Asp Pro Thr
    2795            2800                2805

Thr Pro Leu Ala Arg Ala Ala Trp Glu Thr Ala Arg His Thr Pro
    2810            2815                2820

Val Asn Ser Trp Leu Gly Asn Ile Ile Met Tyr Ala Pro Thr Leu
    2825            2830                2835

Trp Ala Arg Met Ile Leu Met Thr His Phe Phe Ser Ile Leu Leu
    2840            2845                2850

Ala Gln Glu Gln Leu Glu Lys Ala Leu Asp Cys Gln Ile Tyr Gly
    2855            2860                2865

Ala Cys Tyr Ser Ile Glu Pro Leu Asp Leu Pro Gln Ile Ile Glu
    2870            2875                2880

Arg Leu His Gly Leu Ser Ala Phe Ser Leu His Ser Tyr Ser Pro
    2885            2890                2895

Gly Glu Ile Asn Arg Val Ala Ser Cys Leu Arg Lys Leu Gly Val
    2900            2905                2910

Pro Pro Leu Arg Val Trp Arg His Arg Ala Arg Ser Val Arg Ala
    2915            2920                2925

Arg Leu Leu Ser Gln Gly Gly Arg Ala Ala Thr Cys Gly Lys Tyr
    2930            2935                2940

Leu Phe Asn Trp Ala Val Lys Thr Lys Leu Lys Leu Thr Pro Ile
    2945            2950                2955

Pro Ala Ala Ser Gln Leu Asp Leu Ser Gly Trp Phe Val Ala Gly
    2960            2965                2970

Tyr Ser Gly Gly Asp Ile Tyr His Ser Leu Ser Arg Ala Arg Pro
    2975            2980                2985

Arg Trp Phe Met Leu Cys Leu Leu Leu Ser Val Gly Val Gly
    2990            2995                3000

Ile Tyr Leu Leu Pro Asn Arg
    3005            3010

<210> SEQ ID NO 6
<211> LENGTH: 3033
<212> TYPE: PRT
<213> ORGANISM: Artificial sequence
<220> FEATURE:
<223> OTHER INFORMATION: GenBank BAB32872 HCV 2a (JFH-1)

<400> SEQUENCE: 6

Met Ser Thr Asn Pro Lys Pro Gln Arg Lys Thr Lys Arg Asn Thr
1               5                   10                  15

Arg Arg Pro Glu Asp Val Lys Phe Pro Gly Gly Gly Gln Ile Val Gly
                20                  25                  30

Gly Val Tyr Leu Leu Pro Arg Arg Gly Pro Arg Leu Gly Val Arg Thr
        35                  40                  45
```

-continued

```
Thr Arg Lys Thr Ser Glu Arg Ser Gln Pro Arg Gly Arg Gln Pro
     50                  55                  60

Ile Pro Lys Asp Arg Ser Thr Gly Lys Ala Trp Gly Lys Pro Gly
 65                  70                  75                  80

Arg Pro Trp Pro Leu Tyr Gly Asn Glu Gly Leu Gly Trp Ala Gly Trp
                 85                  90                  95

Leu Leu Ser Pro Arg Gly Ser Arg Pro Ser Trp Gly Pro Thr Asp Pro
                100                 105                 110

Arg His Arg Ser Arg Asn Val Gly Lys Val Ile Asp Thr Leu Thr Cys
                115                 120                 125

Gly Phe Ala Asp Leu Met Gly Tyr Ile Pro Val Val Gly Ala Pro Leu
    130                 135                 140

Ser Gly Ala Ala Arg Ala Val Ala His Gly Val Arg Val Leu Glu Asp
145                 150                 155                 160

Gly Val Asn Tyr Ala Thr Gly Asn Leu Pro Gly Phe Pro Phe Ser Ile
                165                 170                 175

Phe Leu Leu Ala Leu Leu Ser Cys Ile Thr Val Pro Val Ser Ala Ala
                180                 185                 190

Gln Val Lys Asn Thr Ser Ser Tyr Met Val Thr Asn Asp Cys Ser
    195                 200                 205

Asn Asp Ser Ile Thr Trp Gln Leu Glu Ala Ala Val Leu His Val Pro
210                 215                 220

Gly Cys Val Pro Cys Glu Arg Val Gly Asn Thr Ser Arg Cys Trp Val
225                 230                 235                 240

Pro Val Ser Pro Asn Met Ala Val Arg Gln Pro Gly Ala Leu Thr Gln
                245                 250                 255

Gly Leu Arg Thr His Ile Asp Met Val Val Met Ser Ala Thr Phe Cys
                260                 265                 270

Ser Ala Leu Tyr Val Gly Asp Leu Cys Gly Gly Val Met Leu Ala Ala
    275                 280                 285

Gln Val Phe Ile Val Ser Pro Gln Tyr His Trp Phe Val Gln Glu Cys
    290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335

Val Met Arg Val Pro Glu Val Ile Ile Asp Ile Val Ser Gly Ala His
                340                 345                 350

Trp Gly Val Met Phe Gly Leu Ala Tyr Phe Ser Met Gln Gly Ala Trp
    355                 360                 365

Ala Lys Val Ile Val Ile Leu Leu Leu Ala Ala Gly Val Asp Ala Gly
    370                 375                 380

Thr Thr Thr Val Gly Gly Ala Val Ala Arg Ser Thr Asn Val Ile Ala
385                 390                 395                 400

Gly Val Phe Ser His Gly Pro Gln Gln Asn Ile Gln Leu Ile Asn Thr
                405                 410                 415

Asn Gly Ser Trp His Ile Asn Arg Thr Ala Leu Asn Cys Asn Asp Ser
                420                 425                 430

Leu Asn Thr Gly Phe Leu Ala Ala Leu Phe Tyr Thr Asn Arg Phe Asn
    435                 440                 445

Ser Ser Gly Cys Pro Gly Arg Leu Ser Ala Cys Arg Asn Ile Glu Ala
    450                 455                 460
```

Phe Arg Ile Gly Trp Gly Thr Leu Gln Tyr Glu Asp Asn Val Thr Asn
465                 470                 475                 480

Pro Glu Asp Met Arg Pro Tyr Cys Trp His Tyr Pro Pro Lys Pro Cys
            485                 490                 495

Gly Val Val Pro Ala Arg Ser Val Cys Gly Pro Val Tyr Cys Phe Thr
        500                 505                 510

Pro Ser Pro Val Val Val Gly Thr Thr Asp Arg Arg Gly Val Pro Thr
    515                 520                 525

Tyr Thr Trp Gly Glu Asn Glu Thr Asp Val Phe Leu Leu Asn Ser Thr
    530                 535                 540

Arg Pro Pro Gln Gly Ser Trp Phe Gly Cys Thr Trp Met Asn Ser Thr
545                 550                 555                 560

Gly Phe Thr Lys Thr Cys Gly Ala Pro Pro Cys Arg Thr Arg Ala Asp
            565                 570                 575

Phe Asn Ala Ser Thr Asp Leu Leu Cys Pro Thr Asp Cys Phe Arg Lys
            580                 585                 590

His Pro Asp Ala Thr Tyr Ile Lys Cys Gly Ser Gly Pro Trp Leu Thr
    595                 600                 605

Pro Lys Cys Leu Val His Tyr Pro Tyr Arg Leu Trp His Tyr Pro Cys
    610                 615                 620

Thr Val Asn Phe Thr Ile Phe Lys Ile Arg Met Tyr Val Gly Gly Val
625                 630                 635                 640

Glu His Arg Leu Thr Ala Ala Cys Asn Phe Thr Arg Gly Asp Arg Cys
            645                 650                 655

Asp Leu Glu Asp Arg Asp Arg Ser Gln Leu Ser Pro Leu Leu His Ser
            660                 665                 670

Thr Thr Glu Trp Ala Ile Leu Pro Cys Thr Tyr Ser Asp Leu Pro Ala
            675                 680                 685

Leu Ser Thr Gly Leu Leu His Leu His Gln Asn Ile Val Asp Val Gln
    690                 695                 700

Tyr Met Tyr Gly Leu Ser Pro Ala Ile Thr Lys Tyr Val Val Arg Trp
705                 710                 715                 720

Glu Trp Val Val Leu Leu Phe Leu Leu Leu Ala Asp Ala Arg Val Cys
            725                 730                 735

Ala Cys Leu Trp Met Leu Ile Leu Leu Gly Gln Ala Glu Ala Ala Leu
            740                 745                 750

Glu Lys Leu Val Val Leu His Ala Ala Ser Ala Ala Asn Cys His Gly
    755                 760                 765

Leu Leu Tyr Phe Ala Ile Phe Phe Val Ala Ala Trp His Ile Arg Gly
    770                 775                 780

Arg Val Val Pro Leu Thr Thr Tyr Cys Leu Thr Gly Leu Trp Pro Phe
785                 790                 795                 800

Cys Leu Leu Leu Met Ala Leu Pro Arg Gln Ala Tyr Ala Tyr Asp Ala
            805                 810                 815

Pro Val His Gly Gln Ile Gly Val Gly Leu Leu Ile Leu Ile Thr Leu
    820                 825                 830

Phe Thr Leu Thr Pro Gly Tyr Lys Thr Leu Leu Gly Gln Cys Leu Trp
    835                 840                 845

Trp Leu Cys Tyr Leu Leu Thr Leu Gly Glu Ala Met Ile Gln Glu Trp
    850                 855                 860

Val Pro Pro Met Gln Val Arg Gly Gly Arg Asp Gly Ile Ala Trp Ala
865                 870                 875                 880

Val Thr Ile Phe Cys Pro Gly Val Val Phe Asp Ile Thr Lys Trp Leu

```
                      885              890                895
Leu Ala Leu Leu Gly Pro Ala Tyr Leu Leu Arg Ala Ala Leu Thr His
                900                905                910
Val Pro Tyr Phe Val Arg Ala His Ala Leu Ile Arg Val Cys Ala Leu
                915                920                925
Val Lys Gln Leu Ala Gly Gly Arg Tyr Val Gln Val Ala Leu Leu Ala
                930                935                940
Leu Gly Arg Trp Thr Gly Thr Tyr Ile Tyr Asp His Leu Thr Pro Met
945                950                955                960
Ser Asp Trp Ala Ala Ser Gly Leu Arg Asp Leu Ala Val Ala Val Glu
                965                970                975
Pro Ile Ile Phe Ser Pro Met Glu Lys Lys Val Ile Val Trp Gly Ala
                980                985                990
Glu Thr Ala Ala Cys Gly Asp Ile Leu His Gly Leu Pro Val Ser Ala
                995                1000               1005
Arg Leu Gly Gln Glu Ile Leu Leu Gly Pro Ala Asp Gly Tyr Thr
     1010               1015               1020
Ser Lys Gly Trp Lys Leu Leu Ala Pro Ile Thr Ala Tyr Ala Gln
     1025               1030               1035
Gln Thr Arg Gly Leu Leu Gly Ala Ile Val Val Ser Met Thr Gly
     1040               1045               1050
Arg Asp Arg Thr Glu Gln Ala Gly Glu Val Gln Ile Leu Ser Thr
     1055               1060               1065
Val Ser Gln Ser Phe Leu Gly Thr Thr Ile Ser Gly Val Leu Trp
     1070               1075               1080
Thr Val Tyr His Gly Ala Gly Asn Lys Thr Leu Ala Gly Leu Arg
     1085               1090               1095
Gly Pro Val Thr Gln Met Tyr Ser Ser Ala Glu Gly Asp Leu Val
     1100               1105               1110
Gly Trp Pro Ser Pro Pro Gly Thr Lys Ser Leu Glu Pro Cys Lys
     1115               1120               1125
Cys Gly Ala Val Asp Leu Tyr Leu Val Thr Arg Asn Ala Asp Val
     1130               1135               1140
Ile Pro Ala Arg Arg Arg Gly Asp Lys Arg Gly Ala Leu Leu Ser
     1145               1150               1155
Pro Arg Pro Ile Ser Thr Leu Lys Gly Ser Ser Gly Gly Pro Val
     1160               1165               1170
Leu Cys Pro Arg Gly His Val Val Gly Leu Phe Arg Ala Ala Val
     1175               1180               1185
Cys Ser Arg Gly Val Ala Lys Ser Ile Asp Phe Ile Pro Val Glu
     1190               1195               1200
Thr Leu Asp Val Val Thr Arg Ser Pro Thr Phe Ser Asp Asn Ser
     1205               1210               1215
Thr Pro Pro Ala Val Pro Gln Thr Tyr Gln Val Gly Tyr Leu His
     1220               1225               1230
Ala Pro Thr Gly Ser Gly Lys Ser Thr Lys Val Pro Val Ala Tyr
     1235               1240               1245
Ala Ala Gln Gly Tyr Lys Val Leu Val Leu Asn Pro Ser Val Ala
     1250               1255               1260
Ala Thr Leu Gly Phe Gly Ala Tyr Leu Ser Lys Ala His Gly Ile
     1265               1270               1275
Asn Pro Asn Ile Arg Thr Gly Val Arg Thr Val Met Thr Gly Glu
     1280               1285               1290
```

```
Ala Ile Thr Tyr Ser Thr Tyr Gly Lys Phe Leu Ala Asp Gly Gly
    1295                1300                1305

Cys Ala Ser Gly Ala Tyr Asp Ile Ile Ile Cys Asp Glu Cys His
    1310                1315                1320

Ala Val Asp Ala Thr Ser Ile Leu Gly Ile Gly Thr Val Leu Asp
    1325                1330                1335

Gln Ala Glu Thr Ala Gly Val Arg Leu Thr Val Leu Ala Thr Ala
    1340                1345                1350

Thr Pro Pro Gly Ser Val Thr Thr Pro His Pro Asp Ile Glu Glu
    1355                1360                1365

Val Gly Leu Gly Arg Glu Gly Glu Ile Pro Phe Tyr Gly Arg Ala
    1370                1375                1380

Ile Pro Leu Ser Cys Ile Lys Gly Gly Arg His Leu Ile Phe Cys
    1385                1390                1395

His Ser Lys Lys Lys Cys Asp Glu Leu Ala Ala Ala Leu Arg Gly
    1400                1405                1410

Met Gly Leu Asn Ala Val Ala Tyr Tyr Arg Gly Leu Asp Val Ser
    1415                1420                1425

Ile Ile Pro Ala Gln Gly Asp Val Val Val Ala Thr Asp Ala
    1430                1435                1440

Leu Met Thr Gly Tyr Thr Gly Asp Phe Asp Ser Val Ile Asp Cys
    1445                1450                1455

Asn Val Ala Val Thr Gln Ala Val Asp Phe Ser Leu Asp Pro Thr
    1460                1465                1470

Phe Thr Ile Thr Thr Gln Thr Val Pro Gln Asp Ala Val Ser Arg
    1475                1480                1485

Ser Gln Arg Arg Gly Arg Thr Gly Arg Gly Arg Gln Gly Thr Tyr
    1490                1495                1500

Arg Tyr Val Ser Thr Gly Glu Arg Ala Ser Gly Met Phe Asp Ser
    1505                1510                1515

Val Val Leu Cys Glu Cys Tyr Asp Ala Gly Ala Ala Trp Tyr Asp
    1520                1525                1530

Leu Thr Pro Ala Glu Thr Thr Val Arg Leu Arg Ala Tyr Phe Asn
    1535                1540                1545

Thr Pro Gly Leu Pro Val Cys Gln Asp His Leu Glu Phe Trp Glu
    1550                1555                1560

Ala Val Phe Thr Gly Leu Thr His Ile Asp Ala His Phe Leu Ser
    1565                1570                1575

Gln Thr Lys Gln Ala Gly Glu Asn Phe Ala Tyr Leu Val Ala Tyr
    1580                1585                1590

Gln Ala Thr Val Cys Ala Arg Ala Lys Ala Pro Pro Pro Ser Trp
    1595                1600                1605

Asp Ala Met Trp Lys Cys Leu Ala Arg Leu Lys Pro Thr Leu Ala
    1610                1615                1620

Gly Pro Thr Pro Leu Leu Tyr Arg Leu Gly Pro Ile Thr Asn Glu
    1625                1630                1635

Val Thr Leu Thr His Pro Gly Thr Lys Tyr Ile Ala Thr Cys Met
    1640                1645                1650

Gln Ala Asp Leu Glu Val Met Thr Ser Thr Trp Val Leu Ala Gly
    1655                1660                1665

Gly Val Leu Ala Ala Val Ala Ala Tyr Cys Leu Ala Thr Gly Cys
    1670                1675                1680
```

-continued

```
Val Ser Ile Ile Gly Arg Leu His Val Asn Gln Arg Val Val Val
    1685                1690                1695

Ala Pro Asp Lys Glu Val Leu Tyr Glu Ala Phe Asp Glu Met Glu
    1700                1705                1710

Glu Cys Ala Ser Arg Ala Ala Leu Ile Glu Glu Gly Gln Arg Ile
    1715                1720                1725

Ala Glu Met Leu Lys Ser Lys Ile Gln Gly Leu Leu Gln Gln Ala
    1730                1735                1740

Ser Lys Gln Ala Gln Asp Ile Gln Pro Ala Met Gln Ala Ser Trp
    1745                1750                1755

Pro Lys Val Glu Gln Phe Trp Ala Arg His Met Trp Asn Phe Ile
    1760                1765                1770

Ser Gly Ile Gln Tyr Leu Ala Gly Leu Ser Thr Leu Pro Gly Asn
    1775                1780                1785

Pro Ala Val Ala Ser Met Met Ala Phe Ser Ala Ala Leu Thr Ser
    1790                1795                1800

Pro Leu Ser Thr Ser Thr Thr Ile Leu Leu Asn Ile Met Gly Gly
    1805                1810                1815

Trp Leu Ala Ser Gln Ile Ala Pro Pro Ala Gly Ala Thr Gly Phe
    1820                1825                1830

Val Val Ser Gly Leu Val Gly Ala Ala Val Gly Ser Ile Gly Leu
    1835                1840                1845

Gly Lys Val Leu Val Asp Ile Leu Ala Gly Tyr Gly Ala Gly Ile
    1850                1855                1860

Ser Gly Ala Leu Val Ala Phe Lys Ile Met Ser Gly Glu Lys Pro
    1865                1870                1875

Ser Met Glu Asp Val Ile Asn Leu Leu Pro Gly Ile Leu Ser Pro
    1880                1885                1890

Gly Ala Leu Val Val Gly Val Ile Cys Ala Ala Ile Leu Arg Arg
    1895                1900                1905

His Val Gly Pro Gly Glu Gly Ala Val Gln Trp Met Asn Arg Leu
    1910                1915                1920

Ile Ala Phe Ala Ser Arg Gly Asn His Val Ala Pro Thr His Tyr
    1925                1930                1935

Val Thr Glu Ser Asp Ala Ser Gln Arg Val Thr Gln Leu Leu Gly
    1940                1945                1950

Ser Leu Thr Ile Thr Ser Leu Leu Arg Arg Leu His Asn Trp Ile
    1955                1960                1965

Thr Glu Asp Cys Pro Ile Pro Cys Ser Gly Ser Trp Leu Arg Asp
    1970                1975                1980

Val Trp Asp Trp Val Cys Thr Ile Leu Thr Asp Phe Lys Asn Trp
    1985                1990                1995

Leu Thr Ser Lys Leu Phe Pro Lys Leu Pro Gly Leu Pro Phe Ile
    2000                2005                2010

Ser Cys Gln Lys Gly Tyr Lys Gly Val Trp Ala Gly Thr Gly Ile
    2015                2020                2025

Met Thr Thr Arg Cys Pro Cys Gly Ala Asn Ile Ser Gly Asn Val
    2030                2035                2040

Arg Leu Gly Ser Met Arg Ile Thr Gly Pro Lys Thr Cys Met Asn
    2045                2050                2055

Thr Trp Gln Gly Thr Phe Pro Ile Asn Cys Tyr Thr Glu Gly Gln
    2060                2065                2070

Cys Ala Pro Lys Pro Pro Thr Asn Tyr Lys Thr Ala Ile Trp Arg
```

```
            2075                2080                2085
Val Ala Ala Ser Glu Tyr Ala Glu Val Thr Gln His Gly Ser Tyr
            2090                2095                2100

Ser Tyr Val Thr Gly Leu Thr Thr Asp Asn Leu Lys Ile Pro Cys
            2105                2110                2115

Gln Leu Pro Ser Pro Glu Phe Phe Ser Trp Val Asp Gly Val Gln
            2120                2125                2130

Ile His Arg Phe Ala Pro Thr Pro Lys Pro Phe Phe Arg Asp Glu
            2135                2140                2145

Val Ser Phe Cys Val Gly Leu Asn Ser Tyr Ala Val Gly Ser Gln
            2150                2155                2160

Leu Pro Cys Glu Pro Glu Pro Asp Ala Asp Val Leu Arg Ser Met
            2165                2170                2175

Leu Thr Asp Pro Pro His Ile Thr Ala Glu Thr Ala Ala Arg Arg
            2180                2185                2190

Leu Ala Arg Gly Ser Pro Pro Ser Glu Ala Ser Ser Ser Val Ser
            2195                2200                2205

Gln Leu Ser Ala Pro Ser Leu Arg Ala Thr Cys Thr Thr His Ser
            2210                2215                2220

Asn Thr Tyr Asp Val Asp Met Val Asp Ala Asn Leu Leu Met Glu
            2225                2230                2235

Gly Gly Val Ala Gln Thr Glu Pro Glu Ser Arg Val Pro Val Leu
            2240                2245                2250

Asp Phe Leu Glu Pro Met Ala Glu Glu Glu Ser Asp Leu Glu Pro
            2255                2260                2265

Ser Ile Pro Ser Glu Cys Met Leu Pro Arg Ser Gly Phe Pro Arg
            2270                2275                2280

Ala Leu Pro Ala Trp Ala Arg Pro Asp Tyr Asn Pro Pro Leu Val
            2285                2290                2295

Glu Ser Trp Arg Arg Pro Asp Tyr Gln Pro Pro Thr Val Ala Gly
            2300                2305                2310

Cys Ala Leu Pro Pro Pro Lys Lys Ala Pro Thr Pro Pro Pro Arg
            2315                2320                2325

Arg Arg Arg Thr Val Gly Leu Ser Glu Ser Thr Ile Ser Glu Ala
            2330                2335                2340

Leu Gln Gln Leu Ala Ile Lys Thr Phe Gly Gln Pro Pro Ser Ser
            2345                2350                2355

Gly Asp Ala Gly Ser Ser Thr Gly Ala Gly Ala Ala Glu Ser Gly
            2360                2365                2370

Gly Pro Thr Ser Pro Gly Glu Pro Ala Pro Ser Glu Thr Gly Ser
            2375                2380                2385

Ala Ser Ser Met Pro Pro Leu Glu Gly Glu Pro Gly Asp Pro Asp
            2390                2395                2400

Leu Glu Ser Asp Gln Val Glu Leu Gln Pro Pro Gln Gly Gly
            2405                2410                2415

Gly Val Ala Pro Gly Ser Gly Ser Gly Ser Trp Ser Thr Cys Ser
            2420                2425                2430

Glu Glu Asp Asp Thr Thr Val Cys Cys Ser Met Ser Tyr Ser Trp
            2435                2440                2445

Thr Gly Ala Leu Ile Thr Pro Cys Ser Pro Glu Glu Glu Lys Leu
            2450                2455                2460

Pro Ile Asn Pro Leu Ser Asn Ser Leu Leu Arg Tyr His Asn Lys
            2465                2470                2475
```

```
Val Tyr Cys Thr Thr Ser Lys Ser Ala Ser Gln Arg Ala Lys Lys
2480                2485                2490

Val Thr Phe Asp Arg Thr Gln Val Leu Asp Ala His Tyr Asp Ser
2495                2500                2505

Val Leu Lys Asp Ile Lys Leu Ala Ala Ser Lys Val Ser Ala Arg
2510                2515                2520

Leu Leu Thr Leu Glu Glu Ala Cys Gln Leu Thr Pro Pro His Ser
2525                2530                2535

Ala Arg Ser Lys Tyr Gly Phe Gly Ala Lys Glu Val Arg Ser Leu
2540                2545                2550

Ser Gly Arg Ala Val Asn His Ile Lys Ser Val Trp Lys Asp Leu
2555                2560                2565

Leu Glu Asp Pro Gln Thr Pro Ile Pro Thr Thr Ile Met Ala Lys
2570                2575                2580

Asn Glu Val Phe Cys Val Asp Pro Ala Lys Gly Gly Lys Lys Pro
2585                2590                2595

Ala Arg Leu Ile Val Tyr Pro Asp Leu Gly Val Arg Val Cys Glu
2600                2605                2610

Lys Met Ala Leu Tyr Asp Ile Thr Gln Lys Leu Pro Gln Ala Val
2615                2620                2625

Met Gly Ala Ser Tyr Gly Phe Gln Tyr Ser Pro Ala Gln Arg Val
2630                2635                2640

Glu Tyr Leu Leu Lys Ala Trp Ala Glu Lys Lys Asp Pro Met Gly
2645                2650                2655

Phe Ser Tyr Asp Thr Arg Cys Phe Asp Ser Thr Val Thr Glu Arg
2660                2665                2670

Asp Ile Arg Thr Glu Glu Ser Ile Tyr Gln Ala Cys Ser Leu Pro
2675                2680                2685

Glu Glu Ala Arg Thr Ala Ile His Ser Leu Thr Glu Arg Leu Tyr
2690                2695                2700

Val Gly Gly Pro Met Phe Asn Ser Lys Gly Gln Thr Cys Gly Tyr
2705                2710                2715

Arg Arg Cys Arg Ala Ser Gly Val Leu Thr Thr Ser Met Gly Asn
2720                2725                2730

Thr Ile Thr Cys Tyr Val Lys Ala Leu Ala Ala Cys Lys Ala Ala
2735                2740                2745

Gly Ile Val Ala Pro Thr Met Leu Val Cys Gly Asp Asp Leu Val
2750                2755                2760

Val Ile Ser Glu Ser Gln Gly Thr Glu Glu Asp Glu Arg Asn Leu
2765                2770                2775

Arg Ala Phe Thr Glu Ala Met Thr Arg Tyr Ser Ala Pro Pro Gly
2780                2785                2790

Asp Pro Pro Arg Pro Glu Tyr Asp Leu Glu Leu Ile Thr Ser Cys
2795                2800                2805

Ser Ser Asn Val Ser Val Ala Leu Gly Pro Arg Gly Arg Arg Arg
2810                2815                2820

Tyr Tyr Leu Thr Arg Asp Pro Thr Thr Pro Leu Ala Arg Ala Ala
2825                2830                2835

Trp Glu Thr Val Arg His Ser Pro Ile Asn Ser Trp Leu Gly Asn
2840                2845                2850

Ile Ile Gln Tyr Ala Pro Thr Ile Trp Val Arg Met Val Leu Met
2855                2860                2865
```

Thr His Phe Phe Ser Ile Leu Met Val Gln Asp Thr Leu Asp Gln
2870                 2875                 2880

Asn Leu Asn Phe Glu Met Tyr Gly Ser Val Tyr Ser Val Asn Pro
2885                 2890                 2895

Leu Asp Leu Pro Ala Ile Ile Glu Arg Leu His Gly Leu Asp Ala
2900                 2905                 2910

Phe Ser Met His Thr Tyr Ser His His Glu Leu Thr Arg Val Ala
2915                 2920                 2925

Ser Ala Leu Arg Lys Leu Gly Ala Pro Pro Leu Arg Val Trp Lys
2930                 2935                 2940

Ser Arg Ala Arg Ala Val Arg Ala Ser Leu Ile Ser Arg Gly Gly
2945                 2950                 2955

Lys Ala Ala Val Cys Gly Arg Tyr Leu Phe Asn Trp Ala Val Lys
2960                 2965                 2970

Thr Lys Leu Lys Leu Thr Pro Leu Pro Glu Ala Arg Leu Leu Asp
2975                 2980                 2985

Leu Ser Ser Trp Phe Thr Val Gly Ala Gly Gly Gly Asp Ile Phe
2990                 2995                 3000

His Ser Val Ser Arg Ala Arg Pro Arg Ser Leu Leu Phe Gly Leu
3005                 3010                 3015

Leu Leu Leu Phe Val Gly Val Gly Leu Phe Leu Leu Pro Ala Arg
3020                 3025                 3030

<210> SEQ ID NO 7
<211> LENGTH: 3033
<212> TYPE: PRT
<213> ORGANISM: Artificial sequence
<220> FEATURE:
<223> OTHER INFORMATION: GenBank BAB08107 HCV 2b (JPUT971017)

<400> SEQUENCE: 7

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Thr Trp Gly Pro Ser Asp Pro
            100                 105                 110

Arg His Arg Ser Arg Asn Leu Gly Arg Val Ile Asp Thr Ile Thr Cys
        115                 120                 125

Gly Phe Ala Asp Leu Met Gly Tyr Ile Pro Val Val Gly Ala Pro Val
    130                 135                 140

Gly Gly Val Ala Arg Ala Leu Ala His Gly Val Arg Val Leu Glu Asp
145                 150                 155                 160

Gly Ile Asn Tyr Ala Thr Arg Asn Leu Pro Gly Cys Ser Phe Ser Ile
                165                 170                 175

Phe Leu Leu Ala Leu Leu Ser Cys Val Thr Val Pro Val Ser Ser Val
            180                 185                 190

-continued

```
Glu Ile Arg Asn Ile Ser Thr Ser Tyr Tyr Ala Thr Asn Asp Cys Ser
            195                 200                 205

Asn Asn Ser Ile Thr Trp Gln Leu Thr Asn Ala Val Leu His Leu Pro
        210                 215                 220

Gly Cys Val Pro Cys Glu Asn Asp Asn Gly Thr Leu Arg Cys Trp Ile
225                 230                 235                 240

Gln Val Thr Pro Asn Val Ala Val Lys His Arg Gly Ala Leu Thr His
                245                 250                 255

Asn Leu Arg Ala His Val Asp Val Ile Val Met Ala Ala Thr Val Cys
            260                 265                 270

Ser Ala Leu Tyr Val Gly Asp Val Cys Gly Ala Val Met Ile Val Ser
        275                 280                 285

Gln Ala Leu Ile Val Ser Pro Glu Arg His Asn Phe Thr Gln Glu Cys
    290                 295                 300

Asn Cys Ser Ile Tyr Gln Gly His Ile Thr Gly Gln Arg Met Ala Trp
305                 310                 315                 320

Asp Met Met Leu Asn Trp Ser Pro Thr Leu Thr Met Ile Leu Ala Tyr
                325                 330                 335

Ala Ala Arg Val Pro Glu Leu Val Leu Glu Ile Val Phe Gly Gly His
            340                 345                 350

Trp Gly Val Val Phe Gly Leu Ala Tyr Phe Ser Met Gln Gly Ala Trp
        355                 360                 365

Ala Lys Val Ile Ala Ile Leu Leu Leu Val Ala Gly Val Asp Ala Thr
    370                 375                 380

Thr Tyr Ser Thr Gly Ala Thr Val Gly Arg Thr Val Gly Ser Phe Ala
385                 390                 395                 400

Gly Leu Phe Lys Leu Gly Ala Gln Gln Asn Val Gln Leu Ile Asn Thr
                405                 410                 415

Asn Gly Ser Trp His Ile Asn Arg Thr Ala Leu Asn Cys Asn Asp Ser
            420                 425                 430

Leu His Thr Gly Phe Met Ala Ala Leu Phe Tyr Ala Asn Lys Phe Asn
        435                 440                 445

Ser Ser Gly Cys Pro Glu Arg Leu Ser Ser Cys Arg Gly Leu Asp Asp
    450                 455                 460

Phe Arg Ile Gly Trp Gly Thr Leu Glu Tyr Glu Thr Asn Val Thr Asn
465                 470                 475                 480

Val Glu Asp Met Arg Pro Tyr Cys Trp His Tyr Pro Lys Pro Cys
                485                 490                 495

Gly Ile Val Pro Ala Gln Ser Val Cys Gly Pro Val Tyr Cys Phe Thr
            500                 505                 510

Pro Ser Pro Val Val Val Gly Thr Thr Asp Arg Gln Gly Val Pro Thr
        515                 520                 525

Tyr Asn Trp Gly Asp Asn Glu Thr Asp Val Phe Leu Leu Asn Ser Thr
    530                 535                 540

Arg Pro Pro Arg Gly Ala Trp Phe Gly Cys Thr Trp Met Asn Gly Thr
545                 550                 555                 560

Gly Phe Thr Lys Thr Cys Gly Ala Pro Pro Cys Arg Ile Arg Lys Asp
                565                 570                 575

Phe Asn Ser Thr Leu Asp Leu Leu Cys Pro Thr Asp Cys Phe Arg Lys
            580                 585                 590

His Pro Asp Ala Thr Tyr Val Lys Cys Gly Ala Gly Pro Trp Leu Thr
        595                 600                 605

Pro Arg Cys Leu Ile Asp Tyr Pro Tyr Arg Leu Trp His Tyr Pro Cys
```

-continued

```
                610                 615                 620
Thr Val Asn Phe Thr Ile Phe Lys Val Arg Met Tyr Val Gly Gly Val
625                 630                 635                 640

Glu His Arg Phe Ser Ala Ala Cys Asn Phe Thr Arg Gly Asp Arg Cys
                645                 650                 655

Arg Leu Glu Asp Arg Asp Arg Gly Gln Ser Pro Leu Leu His Ser
            660                 665                 670

Thr Thr Glu Trp Ala Val Leu Pro Cys Ser Phe Ser Asp Leu Pro Ala
            675                 680                 685

Leu Ser Thr Gly Leu Leu His Leu His Gln Asn Ile Val Asp Val Gln
            690                 695                 700

Tyr Leu Tyr Gly Leu Ser Pro Ala Val Thr Lys Tyr Ile Val Lys Trp
705                 710                 715                 720

Glu Trp Val Val Leu Leu Phe Leu Leu Leu Ala Asp Ala Arg Ile Cys
                725                 730                 735

Ala Cys Leu Trp Met Leu Ile Ile Leu Gly Gln Ala Glu Ala Ala Leu
            740                 745                 750

Glu Lys Leu Ile Ile Leu His Ser Ala Ser Ala Ala Ser Ala Asn Gly
            755                 760                 765

Pro Leu Trp Phe Phe Ile Phe Phe Thr Ala Ala Trp Tyr Leu Lys Gly
770                 775                 780

Arg Val Val Pro Ala Ala Thr Tyr Ser Val Leu Gly Leu Trp Ser Phe
785                 790                 795                 800

Leu Leu Leu Val Leu Ala Leu Pro Gln Gln Ala Tyr Ala Leu Asp Ala
                805                 810                 815

Ala Glu Gln Gly Glu Leu Gly Leu Val Ile Leu Met Ile Ile Ser Ile
            820                 825                 830

Phe Thr Leu Thr Pro Ala Tyr Lys Ile Leu Leu Ser Arg Ser Val Trp
            835                 840                 845

Trp Leu Ser Tyr Met Leu Val Leu Ala Glu Ala Gln Val Gln Gln Trp
            850                 855                 860

Val Pro Pro Leu Glu Ala Arg Gly Gly Arg Asp Gly Ile Ile Trp Val
865                 870                 875                 880

Ala Val Ile Leu His Pro His Leu Val Phe Glu Val Thr Lys Trp Leu
                885                 890                 895

Leu Ala Ile Leu Gly Ser Ala Tyr Leu Leu Lys Ala Ser Leu Leu Arg
            900                 905                 910

Val Pro Tyr Phe Val Arg Ala His Ala Leu Leu Arg Val Cys Thr Leu
            915                 920                 925

Val Arg His Leu Ala Gly Ala Arg Tyr Ile Gln Met Leu Leu Ile Thr
930                 935                 940

Met Gly Arg Trp Thr Gly Thr Tyr Ile Tyr Asp His Leu Ser Pro Leu
945                 950                 955                 960

Ser Thr Trp Ala Ala Gln Gly Leu Arg Asp Leu Ala Val Ala Val Glu
                965                 970                 975

Pro Val Val Phe Ser Pro Met Glu Lys Lys Val Ile Val Trp Gly Ala
            980                 985                 990

Glu Thr Val Ala Cys Gly Asp Ile  Leu His Gly Leu Pro Val Ser Ala
            995                 1000                1005

Arg Leu  Gly Arg Glu Val Leu  Leu Gly Pro Ala Asp  Gly Tyr Thr
        1010                1015                1020

Ser Lys  Gly Trp Lys Leu Leu  Ala Pro Ile Thr Ala  Tyr Thr Gln
        1025                1030                1035
```

-continued

```
Gln Thr Arg Gly Leu Leu Gly Ala Ile Val Val Ser Leu Thr Gly
    1040                1045                1050
Arg Asp Lys Asn Glu Gln Ala Gly Gln Val Gln Val Leu Ser Ser
    1055                1060                1065
Val Thr Gln Ser Phe Leu Gly Thr Ser Ile Ser Gly Val Leu Trp
    1070                1075                1080
Thr Val Tyr His Gly Ala Gly Asn Lys Thr Leu Ala Ser Pro Arg
    1085                1090                1095
Gly Pro Val Thr Gln Met Tyr Thr Ser Ala Glu Gly Asp Leu Val
    1100                1105                1110
Gly Trp Pro Ser Pro Gly Thr Lys Ser Leu Asp Pro Cys Thr
    1115                1120                1125
Cys Gly Ala Val Asp Leu Tyr Leu Val Thr Arg Asn Ala Asp Val
    1130                1135                1140
Ile Pro Val Arg Arg Lys Asp Asp Arg Gly Ala Leu Leu Ser
    1145                1150                1155
Pro Arg Pro Leu Ser Thr Leu Lys Gly Ser Ser Gly Gly Pro Val
    1160                1165                1170
Leu Cys Pro Arg Gly His Ala Val Gly Leu Phe Arg Ala Ala Val
    1175                1180                1185
Cys Ala Arg Gly Val Ala Lys Ser Ile Asp Phe Ile Pro Val Glu
    1190                1195                1200
Ser Leu Asp Ile Ala Arg Arg Thr Pro Ser Phe Ser Asp Asn Ser
    1205                1210                1215
Thr Pro Pro Ala Val Pro Gln Thr Tyr Gln Val Gly Tyr Leu His
    1220                1225                1230
Ala Pro Thr Gly Ser Gly Lys Ser Thr Lys Val Pro Ala Ala Tyr
    1235                1240                1245
Thr Ser Gln Gly Tyr Lys Val Leu Val Leu Asn Pro Ser Val Ala
    1250                1255                1260
Ala Thr Leu Gly Phe Gly Ala Tyr Met Ser Lys Ala His Gly Ile
    1265                1270                1275
Asn Pro Asn Ile Arg Thr Gly Val Arg Thr Val Thr Thr Gly Asp
    1280                1285                1290
Ser Ile Thr Tyr Ser Thr Tyr Gly Lys Phe Leu Ala Asp Gly Gly
    1295                1300                1305
Cys Ser Ala Gly Ala Tyr Asp Ile Ile Ile Cys Asp Glu Cys His
    1310                1315                1320
Ser Val Asp Ala Thr Thr Ile Leu Gly Ile Gly Thr Val Leu Asp
    1325                1330                1335
Gln Ala Glu Thr Ala Gly Val Arg Leu Val Val Leu Ala Thr Ala
    1340                1345                1350
Thr Pro Pro Gly Thr Val Thr Thr Pro His Ala Asn Ile Glu Glu
    1355                1360                1365
Val Ala Leu Gly His Glu Gly Glu Ile Pro Phe Tyr Gly Lys Ala
    1370                1375                1380
Ile Pro Leu Ala Ser Ile Lys Gly Gly Arg His Leu Ile Phe Cys
    1385                1390                1395
His Ser Lys Lys Lys Cys Asp Glu Leu Ala Ala Ala Leu Arg Gly
    1400                1405                1410
Met Gly Val Asn Ala Val Ala Tyr Tyr Arg Gly Leu Asp Val Ser
    1415                1420                1425
```

```
Val Ile Pro Thr Gln Gly Asp Val Val Val Ala Thr Asp Ala
1430                1435                1440

Leu Met Thr Gly Tyr Thr Gly Asp Phe Asp Ser Val Ile Asp Cys
1445                1450                1455

Asn Val Ala Val Thr Gln Ile Val Asp Phe Ser Leu Asp Pro Thr
1460                1465                1470

Phe Thr Ile Thr Thr Gln Thr Val Pro Gln Asp Ala Val Ser Arg
1475                1480                1485

Ser Gln Arg Arg Gly Arg Thr Gly Arg Gly Arg Leu Gly Thr Tyr
1490                1495                1500

Arg Tyr Val Ser Ser Gly Glu Arg Pro Ser Gly Met Phe Asp Ser
1505                1510                1515

Val Val Leu Cys Glu Cys Tyr Asp Ala Gly Ala Ala Trp Tyr Glu
1520                1525                1530

Leu Thr Pro Ala Glu Thr Thr Val Arg Leu Arg Ala Tyr Phe Asn
1535                1540                1545

Thr Pro Gly Leu Pro Val Cys Gln Asp His Leu Glu Phe Trp Glu
1550                1555                1560

Ala Val Phe Thr Gly Leu Thr His Ile Asp Ala His Phe Leu Ser
1565                1570                1575

Gln Thr Lys Gln Gly Gly Asp Asn Phe Ala Tyr Leu Thr Ala Tyr
1580                1585                1590

Gln Ala Thr Val Cys Ala Arg Ala Lys Ala Pro Pro Pro Ser Trp
1595                1600                1605

Asp Val Met Trp Lys Cys Leu Thr Arg Leu Lys Pro Thr Leu Thr
1610                1615                1620

Gly Pro Thr Pro Leu Leu Tyr Arg Leu Gly Ala Val Thr Asn Glu
1625                1630                1635

Ile Thr Leu Thr His Pro Val Thr Lys Tyr Ile Ala Thr Cys Met
1640                1645                1650

Gln Ala Asp Leu Glu Val Met Thr Ser Thr Trp Val Leu Ala Gly
1655                1660                1665

Gly Val Leu Ala Ala Val Ala Ala Tyr Cys Leu Ala Thr Gly Cys
1670                1675                1680

Ile Ser Ile Ile Gly Arg Ile His Leu Asn Asp Gln Val Val Val
1685                1690                1695

Ala Pro Asp Lys Glu Ile Leu Tyr Glu Ala Phe Asp Glu Met Glu
1700                1705                1710

Glu Cys Ala Ser Lys Ala Ala Leu Ile Glu Glu Gly Gln Arg Met
1715                1720                1725

Ala Glu Met Leu Lys Ser Lys Ile Leu Gly Leu Leu Gln Gln Ala
1730                1735                1740

Thr Lys Gln Ala Gln Asp Ile Gln Pro Ala Met Gln Ser Ser Trp
1745                1750                1755

Pro Lys Ile Glu Gln Phe Trp Ala Arg His Met Trp Asn Phe Ile
1760                1765                1770

Ser Gly Ile Gln Tyr Leu Ala Gly Leu Ser Thr Leu Pro Gly Asn
1775                1780                1785

Pro Ala Val Ala Ser Met Met Ala Phe Ser Ala Ala Leu Thr Ser
1790                1795                1800

Pro Leu Pro Thr Ser Thr Thr Ile Leu Leu Asn Ile Met Gly Gly
1805                1810                1815

Trp Leu Ala Ser Gln Ile Ala Pro Pro Ala Gly Ala Thr Gly Phe
```

```
                1820                1825                1830
Val Val Ser Gly Leu Val Gly Ala Ala Val Gly Ser Ile Gly Leu
                1835                1840                1845
Gly Lys Ile Leu Val Asp Val Leu Ala Gly Tyr Gly Ala Gly Ile
                1850                1855                1860
Ser Gly Ala Leu Val Ala Phe Lys Ile Met Ser Gly Glu Lys Pro
                1865                1870                1875
Ser Val Glu Asp Val Val Asn Leu Leu Pro Ala Ile Leu Ser Pro
                1880                1885                1890
Gly Ala Leu Val Val Gly Val Ile Cys Ala Ala Ile Leu Arg Arg
                1895                1900                1905
His Val Gly Gln Gly Glu Gly Ala Val Gln Trp Met Asn Arg Leu
                1910                1915                1920
Ile Ala Phe Ala Ser Arg Gly Asn His Val Ala Pro Thr His Tyr
                1925                1930                1935
Val Ala Glu Ser Asp Ala Ser Leu Arg Val Thr Gln Val Leu Ser
                1940                1945                1950
Ser Leu Thr Ile Thr Ser Leu Leu Arg Arg Leu His Ala Trp Ile
                1955                1960                1965
Thr Glu Asp Cys Pro Val Pro Cys Ser Gly Ser Trp Leu Arg Asp
                1970                1975                1980
Ile Trp Glu Trp Val Cys Ser Ile Leu Thr Asp Phe Lys Asn Trp
                1985                1990                1995
Leu Ser Ala Lys Leu Leu Pro Lys Met Pro Gly Leu Pro Phe Ile
                2000                2005                2010
Ser Cys Gln Lys Gly Tyr Arg Gly Val Trp Ala Gly Thr Gly Val
                2015                2020                2025
Met Thr Thr Arg Cys Ser Cys Gly Ala Asn Ile Ser Gly His Val
                2030                2035                2040
Arg Leu Gly Thr Met Lys Ile Thr Gly Pro Lys Thr Cys Leu Asn
                2045                2050                2055
Met Trp Gln Gly Thr Phe Pro Ile Asn Cys Tyr Thr Glu Gly Pro
                2060                2065                2070
Cys Val Pro Lys Pro Pro Asn Tyr Lys Thr Ala Ile Trp Arg
                2075                2080                2085
Val Ala Ala Ser Glu Tyr Val Glu Val Thr Gln His Gly Ser Phe
                2090                2095                2100
Ser Tyr Val Thr Gly Leu Thr Ser Asp Asn Leu Lys Val Pro Cys
                2105                2110                2115
Gln Val Pro Ala Pro Glu Phe Phe Ser Trp Val Asp Gly Val Gln
                2120                2125                2130
Ile His Arg Phe Ala Pro Thr Pro Gly Pro Phe Phe Arg Asp Glu
                2135                2140                2145
Val Thr Phe Thr Val Gly Leu Asn Ser Leu Val Val Gly Ser Gln
                2150                2155                2160
Leu Pro Cys Asp Pro Glu Pro Asp Thr Glu Val Leu Ala Ser Met
                2165                2170                2175
Leu Thr Asp Pro Ser His Ile Thr Ala Glu Thr Ala Ala Arg Arg
                2180                2185                2190
Leu Ala Arg Gly Ser Pro Pro Ser Gln Ala Ser Ser Ser Ala Ser
                2195                2200                2205
Gln Leu Ser Ala Pro Ser Leu Lys Ala Thr Cys Thr Thr His Lys
                2210                2215                2220
```

```
Thr Ala Tyr Asp Cys Asp Met Val Asp Ala Asn Leu Phe Met Gly
    2225                2230                2235

Gly Asp Val Thr Arg Ile Glu Ser Asp Ser Lys Val Ile Val Leu
    2240                2245                2250

Asp Ser Leu Asp Ser Met Thr Glu Val Glu Asp Arg Glu Pro
    2255                2260                2265

Ser Val Pro Ser Glu Tyr Leu Thr Arg Arg Lys Phe Pro Pro
    2270                2275                2280

Ala Leu Pro Pro Trp Ala Arg Pro Asp Tyr Asn Pro Pro Val Ile
    2285                2290                2295

Glu Thr Trp Lys Arg Pro Asp Tyr Glu Pro Pro Thr Val Leu Gly
    2300                2305                2310

Cys Ala Leu Pro Pro Thr Pro Gln Ala Pro Val Pro Pro Pro Arg
    2315                2320                2325

Arg Arg Arg Ala Arg Val Leu Thr Gln Asp Asn Val Glu Gly Val
    2330                2335                2340

Leu Arg Glu Met Ala Asp Lys Val Leu Ser Pro Leu Gln Asp Thr
    2345                2350                2355

Asn Asp Ser Gly His Ser Thr Gly Ala Asp Thr Gly Gly Asp Ser
    2360                2365                2370

Val Gln Gln Pro Ser Gly Glu Thr Ala Ala Ser Asp Ala Gly Ser
    2375                2380                2385

Leu Ser Ser Met Pro Pro Leu Glu Gly Glu Pro Gly Asp Pro Asp
    2390                2395                2400

Leu Glu Phe Glu Pro Ala Arg Ser Ala Pro Pro Ser Glu Gly Glu
    2405                2410                2415

Cys Glu Val Ile Asp Ser Asp Ser Lys Ser Trp Ser Thr Val Ser
    2420                2425                2430

Asp Gln Glu Asp Ser Val Ile Cys Cys Ser Met Ser Tyr Ser Trp
    2435                2440                2445

Thr Gly Ala Leu Ile Thr Pro Cys Gly Pro Glu Glu Glu Lys Leu
    2450                2455                2460

Pro Ile Ser Pro Leu Ser Asn Ser Leu Met Arg Phe His Asn Lys
    2465                2470                2475

Val Tyr Ser Thr Thr Ser Arg Ser Ala Ser Leu Arg Ala Lys Lys
    2480                2485                2490

Val Thr Phe Asp Arg Val Gln Val Leu Asp Ala His Tyr Asp Ser
    2495                2500                2505

Val Leu Gln Asp Val Lys Arg Ala Ala Ser Lys Val Ser Ala Arg
    2510                2515                2520

Leu Leu Ser Val Glu Glu Ala Cys Ala Leu Thr Pro Pro His Ser
    2525                2530                2535

Ala Lys Ser Arg Tyr Gly Phe Gly Ala Lys Glu Val Arg Ser Leu
    2540                2545                2550

Ser Arg Gly Ala Val Asn His Ile Arg Ser Val Trp Glu Asp Leu
    2555                2560                2565

Leu Glu Asp Gln His Thr Pro Ile Asp Thr Thr Ala Met Ala Lys
    2570                2575                2580

Asn Glu Val Phe Cys Ile Asp Pro Ala Lys Gly Gly Lys Lys Pro
    2585                2590                2595

Ala Arg Leu Ile Val Tyr Pro Asp Leu Gly Val Arg Val Cys Glu
    2600                2605                2610
```

-continued

```
Lys Met Ala Leu Tyr Asp Ile Ala Gln Lys Leu Pro Lys Ala Ile
2615                2620                2625

Met Gly Pro Ser Tyr Gly Phe Gln Tyr Ser Pro Ala Glu Arg Val
2630                2635                2640

Asp Phe Leu Leu Lys Ala Trp Gly Ser Lys Lys Asp Pro Met Gly
2645                2650                2655

Phe Ser Tyr Asp Thr Arg Cys Phe Asp Ser Thr Val Thr Glu Arg
2660                2665                2670

Asp Ile Arg Thr Glu Glu Ser Ile Tyr Gln Ala Cys Ser Leu Pro
2675                2680                2685

Gln Glu Ala Arg Thr Val Ile His Ser Ile Thr Glu Arg Leu Tyr
2690                2695                2700

Val Gly Gly Pro Met Thr Asn Ser Lys Gly Gln Ser Cys Gly Tyr
2705                2710                2715

Arg Arg Cys Arg Ala Ser Gly Val Phe Thr Thr Ser Met Gly Asn
2720                2725                2730

Thr Met Thr Cys Tyr Ile Lys Ala Leu Ala Ala Cys Lys Ala Ala
2735                2740                2745

Gly Ile Val Asp Pro Thr Met Leu Val Cys Gly Asp Asp Leu Val
2750                2755                2760

Val Ile Ser Glu Ser Gln Gly Asn Glu Glu Asp Glu Arg Asn Leu
2765                2770                2775

Arg Ala Phe Thr Glu Ala Met Thr Arg Tyr Ser Ala Pro Pro Gly
2780                2785                2790

Asp Leu Pro Arg Pro Glu Tyr Asp Leu Glu Leu Ile Thr Ser Cys
2795                2800                2805

Ser Ser Asn Val Ser Val Ala Leu Asp Ser Arg Gly Arg Arg Arg
2810                2815                2820

Tyr Phe Leu Thr Arg Asp Pro Thr Thr Pro Ile Thr Arg Ala Ala
2825                2830                2835

Trp Glu Thr Val Arg His Ser Pro Val Asn Ser Trp Leu Gly Asn
2840                2845                2850

Ile Ile Gln Tyr Ala Pro Thr Ile Trp Val Arg Met Val Ile Met
2855                2860                2865

Thr His Phe Phe Ser Ile Leu Leu Ala Gln Asp Thr Leu Asn Gln
2870                2875                2880

Asn Leu Asn Phe Glu Met Tyr Gly Ala Val Tyr Ser Val Asn Pro
2885                2890                2895

Leu Asp Leu Pro Ala Ile Ile Glu Arg Leu His Gly Leu Asp Ala
2900                2905                2910

Phe Ser Leu His Thr Tyr Ser Pro His Glu Leu Ser Arg Val Ala
2915                2920                2925

Ala Thr Leu Arg Lys Leu Gly Ala Pro Pro Leu Arg Ala Trp Lys
2930                2935                2940

Ser Arg Ala Arg Ala Val Arg Ala Ser Leu Ile Ile Gln Gly Gly
2945                2950                2955

Arg Ala Ala Thr Cys Gly Arg Tyr Leu Phe Asn Trp Ala Val Lys
2960                2965                2970

Thr Lys Leu Lys Leu Thr Pro Leu Pro Glu Ala Ser Arg Leu Asp
2975                2980                2985

Leu Ser Gly Trp Phe Thr Val Gly Ala Gly Gly Gly Asp Ile Phe
2990                2995                3000

His Ser Val Ser His Ala Arg Pro Arg Leu Leu Leu Leu Cys Leu
```

-continued

```
           3005              3010              3015
Leu Leu  Leu Ser Val Gly Val  Gly Ile Phe Leu Leu  Pro Ala Arg
           3020              3025              3030

<210> SEQ ID NO 8
<211> LENGTH: 3008
<212> TYPE: PRT
<213> ORGANISM: Artificial sequence
<220> FEATURE:
<223> OTHER INFORMATION: GenBank CAA72338 HCV 4 (ED43)

<400> SEQUENCE: 8

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Gly Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Ser Val Ala Arg Ala Leu Ala His Gly Val Arg Ala Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
            180                 185                 190

Asn Tyr Arg Asn Val Ser Gly Ile Tyr His Val Thr Asn Asp Cys Pro
        195                 200                 205

Asn Ser Ser Ile Val Tyr Glu Ala Asp His His Ile Met His Leu Pro
    210                 215                 220

Gly Cys Val Pro Cys Val Arg Glu Gly Asn Gln Ser Arg Cys Trp Val
225                 230                 235                 240

Ala Leu Thr Pro Thr Val Ala Ala Pro Tyr Ile Gly Ala Pro Leu Glu
                245                 250                 255

Ser Leu Arg Ser His Val Asp Leu Met Val Gly Ala Ala Thr Val Cys
            260                 265                 270

Ser Gly Leu Tyr Ile Gly Asp Leu Cys Gly Gly Leu Phe Leu Val Gly
        275                 280                 285

Gln Met Phe Ser Phe Arg Pro Arg Arg His Trp Thr Thr Gln Asp Cys
    290                 295                 300

Asn Cys Ser Ile Tyr Thr Gly His Ile Thr Gly His Arg Met Ala Trp
305                 310                 315                 320

Asp Met Met Met Asn Trp Ser Pro Thr Thr Thr Leu Val Leu Ala Gln
                325                 330                 335

Val Met Arg Ile Pro Thr Thr Leu Val Asp Leu Leu Ser Gly Gly His
```

```
                340             345             350
Trp Gly Val Leu Val Gly Val Ala Tyr Phe Ser Met Gln Ala Asn Trp
            355                 360                 365

Ala Lys Val Ile Leu Val Leu Phe Leu Phe Ala Gly Val Asp Ala Glu
        370                 375                 380

Thr His Val Ser Gly Ala Ala Val Gly Arg Ser Thr Ala Gly Leu Ala
385                 390                 395                 400

Asn Leu Phe Ser Ser Gly Ser Lys Gln Asn Leu Gln Leu Ile Asn Ser
                405                 410                 415

Asn Gly Ser Trp His Ile Asn Arg Thr Ala Leu Asn Cys Asn Asp Ser
            420                 425                 430

Leu Asn Thr Gly Phe Leu Ala Ser Leu Phe Tyr Thr His Lys Phe Asn
        435                 440                 445

Ser Ser Gly Cys Ser Glu Arg Leu Ala Cys Cys Lys Ser Leu Asp Ser
    450                 455                 460

Tyr Gly Gln Gly Trp Gly Pro Leu Gly Val Ala Asn Ile Ser Gly Ser
465                 470                 475                 480

Ser Asp Asp Arg Pro Tyr Cys Trp His Tyr Ala Pro Arg Pro Cys Gly
                485                 490                 495

Ile Val Pro Ala Ser Ser Val Cys Gly Pro Val Tyr Cys Phe Thr Pro
            500                 505                 510

Ser Pro Val Val Val Gly Thr Thr Asp His Val Gly Val Pro Thr Tyr
        515                 520                 525

Thr Trp Gly Glu Asn Glu Thr Asp Val Phe Leu Leu Asn Ser Thr Arg
    530                 535                 540

Pro Pro His Gly Ala Trp Phe Gly Cys Val Trp Met Asn Ser Thr Gly
545                 550                 555                 560

Phe Thr Lys Thr Cys Gly Ala Pro Pro Cys Glu Val Asn Thr Asn Asn
                565                 570                 575

Gly Thr Trp His Cys Pro Thr Asp Cys Phe Arg Lys His Pro Glu Thr
            580                 585                 590

Thr Tyr Ala Lys Cys Gly Ser Gly Pro Trp Ile Thr Pro Arg Cys Leu
        595                 600                 605

Ile Asp Tyr Pro Tyr Arg Leu Trp His Phe Pro Cys Thr Ala Asn Phe
    610                 615                 620

Ser Val Phe Asn Ile Arg Thr Phe Val Gly Gly Ile Glu His Arg Met
625                 630                 635                 640

Gln Ala Ala Cys Asn Trp Thr Arg Gly Glu Val Cys Gly Leu Glu His
                645                 650                 655

Arg Asp Arg Val Glu Leu Ser Pro Leu Leu Leu Thr Thr Thr Ala Trp
            660                 665                 670

Gln Ile Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Val Gly Ser Ala Val Val Ser Trp Ala Leu Lys Trp Glu Tyr Val Val
705                 710                 715                 720

Leu Ala Phe Leu Leu Leu Ala Asp Ala Arg Val Ser Ala Tyr Leu Trp
                725                 730                 735

Met Met Phe Met Val Ser Gln Val Glu Ala Ala Leu Ser Asn Leu Ile
            740                 745                 750

Asn Ile Asn Ala Ala Ser Ala Ala Gly Ala Gln Gly Phe Trp Tyr Ala
        755                 760                 765
```

```
Ile Leu Phe Ile Cys Ile Val Trp His Val Lys Gly Arg Phe Pro Ala
    770             775             780

Ala Ala Ala Tyr Ala Ala Cys Gly Leu Trp Pro Cys Phe Leu Leu Leu
785             790             795                         800

Leu Met Leu Pro Glu Arg Ala Tyr Ala Tyr Asp Gln Glu Val Ala Gly
                805             810             815

Ser Leu Gly Gly Ala Ile Val Val Met Leu Thr Ile Leu Thr Leu Ser
                820             825             830

Pro His Tyr Lys Leu Trp Leu Ala Arg Gly Leu Trp Trp Ile Gln Tyr
            835             840             845

Phe Ile Ala Arg Thr Glu Ala Val Leu His Val Tyr Ile Pro Ser Phe
    850             855             860

Asn Val Arg Gly Pro Arg Asp Ser Val Ile Val Leu Ala Val Leu Val
865             870             875             880

Cys Pro Asp Leu Val Phe Asp Ile Thr Lys Tyr Leu Leu Ala Ile Leu
                885             890             895

Gly Pro Leu His Ile Leu Gln Ala Ser Leu Leu Arg Ile Pro Tyr Phe
            900             905             910

Val Arg Ala Gln Ala Leu Val Lys Ile Cys Ser Leu Leu Arg Gly Val
            915             920             925

Val Tyr Gly Lys Tyr Phe Gln Met Val Val Leu Lys Ser Arg Gly Leu
    930             935             940

Thr Gly Thr Tyr Ile Tyr Asp His Leu Thr Pro Met Ser Asp Trp Pro
945             950             955             960

Pro Tyr Gly Leu Arg Asp Leu Ala Val Ala Leu Glu Pro Val Val Phe
            965             970             975

Thr Pro Met Glu Lys Lys Val Ile Val Trp Gly Ala Asp Thr Ala Ala
            980             985             990

Cys Gly Asp Ile Ile Arg Gly Leu Pro Val Ser Ala Arg Leu Gly Asn
            995             1000            1005

Glu Ile Leu Leu Gly Pro Ala Asp Thr Glu Thr Ser Lys Gly Trp
    1010            1015            1020

Arg Leu Leu Ala Pro Ile Thr Ala Tyr Ala Gln Gln Thr Arg Gly
    1025            1030            1035

Leu Phe Ser Thr Ile Val Thr Ser Leu Thr Gly Arg Asp Thr Asn
    1040            1045            1050

Glu Asn Cys Gly Glu Val Gln Val Leu Ser Thr Ala Thr Gln Ser
    1055            1060            1065

Phe Leu Gly Thr Ala Val Asn Gly Val Met Trp Thr Val Tyr His
    1070            1075            1080

Gly Ala Gly Ala Lys Thr Ile Ser Gly Pro Lys Gly Pro Val Asn
    1085            1090            1095

Gln Met Tyr Thr Asn Val Asp Gln Asp Leu Val Gly Trp Pro Ala
    1100            1105            1110

Pro Pro Gly Val Arg Ser Leu Ala Pro Cys Thr Cys Gly Ser Ala
    1115            1120            1125

Asp Leu Tyr Leu Val Thr Arg His Ala Asp Val Ile Pro Val Arg
    1130            1135            1140

Arg Arg Gly Asp Thr Arg Gly Ala Leu Leu Ser Pro Arg Pro Ile
    1145            1150            1155

Ser Ile Leu Lys Gly Ser Ser Gly Gly Pro Leu Leu Cys Pro Met
    1160            1165            1170
```

```
Gly His Arg Ala Gly Ile Phe Arg Ala Ala Val Cys Thr Arg Gly
1175                1180                1185

Val Ala Lys Ala Val Asp Phe Val Pro Val Glu Ser Leu Glu Thr
1190                1195                1200

Thr Met Arg Ser Pro Val Phe Thr Asp Asn Ser Thr Pro Pro Ala
1205                1210                1215

Val Pro Gln Thr Tyr Gln Val Ala His Leu His Ala Pro Thr Gly
1220                1225                1230

Ser Gly Lys Ser Thr Lys Val Pro Ala Ala His Ala Ala Gln Gly
1235                1240                1245

Tyr Lys Val Leu Val Leu Asn Pro Ser Val Ala Ala Thr Leu Gly
1250                1255                1260

Phe Gly Val Tyr Met Ser Lys Ala Tyr Gly Ile Asp Pro Asn Ile
1265                1270                1275

Arg Ser Gly Val Arg Thr Ile Thr Thr Gly Ala Pro Ile Thr Tyr
1280                1285                1290

Ser Thr Tyr Gly Lys Phe Leu Ala Asp Gly Gly Cys Ser Gly Gly
1295                1300                1305

Ala Tyr Asp Ile Ile Ile Cys Asp Glu Cys Tyr Ser Thr Asp Ser
1310                1315                1320

Thr Thr Ile Leu Gly Ile Gly Thr Val Leu Asp Gln Ala Glu Thr
1325                1330                1335

Ala Gly Val Arg Leu Thr Val Leu Ala Thr Ala Thr Pro Pro Gly
1340                1345                1350

Ser Val Thr Thr Pro His Ser Asn Ile Glu Glu Val Ala Leu Pro
1355                1360                1365

Thr Thr Gly Glu Ile Pro Phe Tyr Gly Lys Ala Ile Pro Leu Glu
1370                1375                1380

Leu Ile Lys Gly Gly Arg His Leu Ile Phe Cys His Ser Lys Lys
1385                1390                1395

Lys Cys Asp Glu Leu Ala Arg Gln Leu Thr Ser Leu Gly Leu Asn
1400                1405                1410

Ala Val Ala Tyr Tyr Arg Gly Leu Asp Val Ser Val Ile Pro Thr
1415                1420                1425

Ser Gly Asp Val Val Val Cys Ala Thr Asp Ala Leu Met Thr Gly
1430                1435                1440

Phe Thr Gly Asp Phe Asp Ser Val Ile Asp Cys Asn Thr Ser Val
1445                1450                1455

Ile Gln Thr Val Asp Phe Ser Leu Asp Pro Thr Phe Ser Ile Glu
1460                1465                1470

Ile Thr Thr Val Pro Gln Asp Ala Val Ser Arg Ser Gln Arg Arg
1475                1480                1485

Gly Arg Thr Gly Arg Gly Arg Leu Gly Thr Tyr Arg Tyr Val Thr
1490                1495                1500

Pro Gly Glu Arg Pro Ser Gly Met Phe Asp Thr Ala Glu Leu Cys
1505                1510                1515

Glu Cys Tyr Asp Ala Gly Cys Ala Trp Tyr Glu Leu Thr Pro Ala
1520                1525                1530

Glu Thr Thr Thr Arg Leu Lys Ala Tyr Phe Asp Thr Pro Gly Leu
1535                1540                1545

Pro Val Cys Gln Asp His Leu Glu Phe Trp Glu Ser Val Phe Thr
1550                1555                1560

Gly Leu Thr His Ile Asp Gly His Phe Leu Ser Gln Thr Lys Gln
```

```
                 1565                1570                1575

Ser Gly Glu Asn Phe Pro Tyr Leu Val Ala Tyr Gln Ala Thr Val
    1580                1585                1590

Ser Ala Lys Val Trp Leu Ala Pro Pro Ser Trp Asp Thr Met Trp
    1595                1600                1605

Lys Cys Leu Ile Arg Leu Lys Pro Thr Leu His Gly Pro Thr Pro
    1610                1615                1620

Leu Leu Tyr Arg Leu Gly Ser Val Gln Asn Glu Val Val Leu Thr
    1625                1630                1635

His Pro Ile Thr Lys Tyr Ile Met Ala Cys Met Ser Ala Asp Leu
    1640                1645                1650

Glu Val Val Thr Ser Thr Trp Val Leu Val Gly Gly Val Leu Ala
    1655                1660                1665

Ala Leu Ala Ala Tyr Cys Leu Ser Val Gly Ser Val Val Ile Val
    1670                1675                1680

Gly Arg Val Val Leu Ser Gly Gln Pro Ala Val Ile Pro Asp Arg
    1685                1690                1695

Glu Val Leu Tyr Gln Gln Phe Asp Glu Met Glu Glu Cys Ser Lys
    1700                1705                1710

His Leu Pro Leu Val Glu His Gly Leu Gln Leu Ala Glu Gln Phe
    1715                1720                1725

Lys Gln Lys Ala Leu Gly Leu Leu Asn Phe Ala Gly Lys Gln Ala
    1730                1735                1740

Gln Glu Ala Thr Pro Val Ile Gln Ser Asn Phe Ala Lys Leu Glu
    1745                1750                1755

Gln Phe Trp Ala Asn Asp Met Trp Asn Phe Ile Ser Gly Ile Gln
    1760                1765                1770

Tyr Leu Ala Gly Leu Ser Thr Leu Pro Gly Asn Pro Ala Ile Ala
    1775                1780                1785

Ser Leu Met Ser Phe Thr Ala Ala Val Thr Ser Pro Leu Thr Thr
    1790                1795                1800

Gln Gln Thr Leu Leu Phe Asn Ile Leu Gly Gly Trp Val Ala Ser
    1805                1810                1815

Gln Ile Arg Asp Ser Asp Ala Ser Thr Ala Phe Val Val Ser Gly
    1820                1825                1830

Leu Ala Gly Ala Ala Val Gly Ser Val Gly Leu Gly Lys Ile Leu
    1835                1840                1845

Val Asp Ile Leu Pro Gly Tyr Gly Ala Gly Val Arg Gly Ala Val
    1850                1855                1860

Val Thr Phe Lys Ile Met Ser Gly Glu Met Pro Ser Thr Glu Asp
    1865                1870                1875

Leu Val Asn Leu Leu Pro Ala Ile Leu Ser Pro Gly Ala Leu Val
    1880                1885                1890

Val Glu Val Val Cys Pro Ala Ile Leu Arg Arg His Val Gly Pro
    1895                1900                1905

Gly Glu Gly Ala Val Gln Trp Met Asn Arg Leu Ile Ala Phe Ala
    1910                1915                1920

Ser Arg Gly Asn His Val Ser Pro Thr His Tyr Val Pro Glu Ser
    1925                1930                1935

Asp Ala Ala Arg Arg Val Thr Thr Ile Leu Ser Ser Leu Thr Val
    1940                1945                1950

Thr Ser Leu Leu Arg Arg Leu His Lys Trp Ile Asn Glu Asp Cys
    1955                1960                1965
```

-continued

Ser Thr Pro Cys Ala Glu Ser Trp Leu Trp Glu Val Trp Asp Trp
    1970            1975            1980

Val Leu His Val Leu Ser Asp Phe Lys Thr Cys Leu Lys Ala Lys
    1985            1990            1995

Phe Val Pro Leu Met Pro Gly Ile Pro Leu Leu Ser Trp Pro Arg
    2000            2005            2010

Gly Tyr Lys Gly Glu Trp Arg Gly Asp Gly Val Met His Thr Thr
    2015            2020            2025

Cys Pro Cys Gly Ala Asp Leu Ala Gly His Ile Lys Asn Gly Ser
    2030            2035            2040

Met Arg Ile Thr Gly Pro Lys Thr Cys Ser Asn Thr Trp His Gly
    2045            2050            2055

Thr Phe Pro Ile Asn Ala Tyr Thr Thr Gly Pro Gly Val Pro Ile
    2060            2065            2070

Pro Ala Pro Asn Tyr Lys Phe Ala Leu Trp Arg Val Ser Ala Glu
    2075            2080            2085

Asp Tyr Val Glu Val Arg Arg Val Gly Asp Phe His Tyr Val Thr
    2090            2095            2100

Gly Val Thr Gln Asp Asn Ile Lys Phe Pro Cys Gln Val Pro Ala
    2105            2110            2115

Pro Glu Leu Phe Thr Glu Val Asp Gly Ile Arg Ile His Arg His
    2120            2125            2130

Ala Pro Lys Cys Lys Pro Leu Leu Arg Asp Glu Val Ser Phe Ser
    2135            2140            2145

Val Gly Leu Asn Ser Phe Val Val Gly Ser Gln Leu Pro Cys Glu
    2150            2155            2160

Pro Glu Pro Asp Val Ala Val Leu Thr Ser Met Leu Thr Asp Pro
    2165            2170            2175

Ser His Ile Thr Ala Glu Ser Ala Arg Arg Leu Ala Arg Gly
    2180            2185            2190

Ser Arg Pro Ser Leu Ala Ser Ser Ser Ala Ser Gln Leu Ser Pro
    2195            2200            2205

Arg Leu Leu Gln Ala Thr Cys Thr Ala Pro His Asp Ser Pro Gly
    2210            2215            2220

Thr Asp Leu Leu Glu Ala Asn Leu Leu Trp Gly Ser Thr Ala Thr
    2225            2230            2235

Arg Val Glu Thr Asp Glu Lys Val Ile Ile Leu Asp Ser Phe Glu
    2240            2245            2250

Ser Cys Val Ala Glu Gln Asn Asp Asp Arg Glu Val Ser Val Ala
    2255            2260            2265

Ala Glu Ile Leu Arg Pro Thr Lys Lys Phe Pro Pro Ala Leu Pro
    2270            2275            2280

Ile Trp Ala Arg Pro Asp Tyr Asn Pro Pro Leu Thr Glu Thr Trp
    2285            2290            2295

Lys Gln Gln Asp Tyr Gln Ala Pro Thr Val His Gly Cys Ala Leu
    2300            2305            2310

Pro Pro Ala Lys Gln Pro Pro Val Pro Ser Pro Arg Arg Lys Arg
    2315            2320            2325

Thr Val Gln Leu Thr Glu Ser Val Val Ser Thr Ala Leu Ala Glu
    2330            2335            2340

Leu Ala Ala Lys Thr Phe Gly Gln Ser Glu Pro Ser Ser Asp Arg
    2345            2350            2355

```
Asp Thr Asp Leu Thr Thr Pro Thr Glu Thr Thr Asp Ser Gly Pro
    2360            2365            2370

Ile Val Val Asp Asp Ala Ser Asp Asp Gly Ser Tyr Ser Ser Met
    2375            2380            2385

Pro Pro Leu Glu Gly Glu Pro Gly Asp Pro Asp Leu Thr Ser Asp
    2390            2395            2400

Ser Trp Ser Thr Val Ser Gly Ser Glu Asp Val Val Cys Cys Ser
    2405            2410            2415

Met Ser Tyr Ser Trp Thr Gly Ala Leu Val Thr Pro Cys Ala Ala
    2420            2425            2430

Glu Glu Ser Lys Leu Pro Ile Ser Pro Leu Ser Asn Ser Leu Leu
    2435            2440            2445

Arg His His Asn Met Val Tyr Ala Thr Thr Thr Arg Ser Ala Val
    2450            2455            2460

Thr Arg Gln Lys Lys Val Thr Phe Asp Arg Leu Gln Val Val Asp
    2465            2470            2475

Ser Thr Tyr Asn Glu Val Leu Lys Glu Ile Lys Ala Arg Ala Ser
    2480            2485            2490

Arg Val Lys Pro Arg Leu Leu Thr Thr Glu Glu Ala Cys Asp Leu
    2495            2500            2505

Thr Pro Pro His Ser Ala Arg Ser Lys Phe Gly Tyr Gly Lys Lys
    2510            2515            2520

Asp Val Arg Ser His Ser Arg Lys Ala Ile Asn His Ile Ser Ser
    2525            2530            2535

Val Trp Lys Asp Leu Leu Asp Asp Asn Asn Thr Pro Ile Pro Thr
    2540            2545            2550

Thr Ile Met Ala Lys Asn Glu Val Phe Ala Val Asn Pro Ala Lys
    2555            2560            2565

Gly Gly Arg Lys Pro Ala Arg Leu Ile Val Tyr Pro Asp Leu Gly
    2570            2575            2580

Ser Arg Val Cys Glu Lys Arg Ala Leu His Asp Val Ile Lys Lys
    2585            2590            2595

Thr Ala Leu Ala Val Met Gly Ala Ala Tyr Gly Phe Gln Tyr Ser
    2600            2605            2610

Pro Ala Gln Arg Val Glu Phe Leu Leu Thr Ala Trp Lys Ser Lys
    2615            2620            2625

Asn Asp Pro Met Gly Phe Ser Tyr Asp Thr Arg Cys Phe Asp Ser
    2630            2635            2640

Thr Val Thr Glu Lys Asp Ile Arg Val Glu Glu Val Tyr Gln
    2645            2650            2655

Cys Cys Asp Leu Glu Pro Glu Ala Arg Lys Val Ile Thr Ala Leu
    2660            2665            2670

Thr Asp Arg Leu Tyr Val Gly Gly Pro Met His Asn Ser Lys Gly
    2675            2680            2685

Asp Leu Cys Gly Tyr Arg Arg Cys Arg Ala Thr Gly Val Tyr Thr
    2690            2695            2700

Thr Ser Phe Gly Asn Thr Leu Thr Cys Tyr Leu Lys Ala Thr Ala
    2705            2710            2715

Ala Ile Arg Ala Ala Ala Leu Arg Asp Cys Thr Met Leu Val Cys
    2720            2725            2730

Gly Asp Asp Leu Val Val Ile Ala Glu Ser Asp Gly Val Glu Glu
    2735            2740            2745

Asp Asn Arg Ala Leu Arg Ala Phe Thr Glu Ala Met Thr Arg Tyr
```

```
                    2750                2755                 2760
Ser Ala Pro Pro Gly Asp Ala Pro Gln Pro Ala Tyr Asp Leu Glu
    2765                2770                2775
Leu Ile Thr Ser Cys Ser Ser Asn Val Ser Val Ala His Asp Val
        2780                2785                2790
Thr Gly Lys Lys Val Tyr Tyr Leu Thr Arg Asp Pro Glu Thr Pro
    2795                2800                2805
Leu Ala Arg Ala Val Trp Glu Thr Val Arg His Thr Pro Val Asn
    2810                2815                2820
Ser Trp Leu Gly Asn Ile Ile Val Tyr Ala Pro Thr Ile Trp Val
    2825                2830                2835
Arg Met Ile Leu Met Thr His Phe Phe Ser Ile Leu Gln Ser Gln
    2840                2845                2850
Glu Ala Leu Glu Lys Ala Leu Asp Phe Asp Met Tyr Gly Val Thr
    2855                2860                2865
Tyr Ser Ile Thr Pro Leu Asp Leu Pro Ala Ile Ile Gln Arg Leu
    2870                2875                2880
His Gly Leu Ser Ala Phe Thr Leu His Gly Tyr Ser Pro His Glu
    2885                2890                2895
Leu Asn Arg Val Ala Gly Ala Leu Arg Lys Leu Gly Val Pro Pro
    2900                2905                2910
Leu Arg Ala Trp Arg His Arg Ala Arg Ala Val Arg Ala Lys Leu
    2915                2920                2925
Ile Ala Gln Gly Gly Arg Ala Lys Ile Cys Gly Ile Tyr Leu Phe
    2930                2935                2940
Asn Trp Ala Val Lys Thr Lys Leu Lys Leu Thr Pro Leu Pro Ala
    2945                2950                2955
Ala Ala Lys Leu Asp Leu Ser Gly Trp Phe Thr Val Gly Ala Gly
    2960                2965                2970
Gly Gly Asp Ile Tyr His Ser Met Ser His Ala Arg Pro Arg Tyr
    2975                2980                2985
Leu Leu Leu Cys Leu Leu Ile Leu Thr Val Gly Val Gly Ile Phe
    2990                2995                3000
Leu Leu Pro Ala Arg
    3005

<210> SEQ ID NO 9
<211> LENGTH: 3019
<212> TYPE: PRT
<213> ORGANISM: Artificial sequence
<220> FEATURE:
<223> OTHER INFORMATION: GenBank ABE98159 HCV 6a

<400> SEQUENCE: 9

Met Ser Thr Leu Pro Lys Pro Gln Arg Lys Thr Lys Arg Asn Thr Asn
1               5                   10                  15
Arg Arg Pro Met Asp Val Lys Phe Pro Gly Gly Gly Gln Ile Val Gly
            20                  25                  30
Gly Val Tyr Leu Leu Pro Arg Arg Gly Pro Arg Leu Gly Val Arg Ala
        35                  40                  45
Thr Arg Lys Thr Ser Glu Arg Ser Gln Pro Arg Gly Arg Arg Gln Pro
    50                  55                  60
Ile Pro Lys Ala Arg Gln Pro Gln Gly Arg His Trp Ala Gln Pro Gly
65                  70                  75                  80
Tyr Pro Trp Pro Leu Tyr Gly Asn Glu Gly Cys Gly Trp Ala Gly Trp
```

```
            85                  90                  95
Leu Leu Ser Pro Arg Gly Ser Arg Pro His Trp Gly Pro Asn Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Val Val Gly Ala Pro Leu
            130                 135                 140

Gly Gly Val Ala Ala Leu Ala His Gly Val Arg Ala Ile Glu Asp
145                 150                 155                 160

Gly Ile Asn Tyr Ala Thr Gly Asn Leu Pro Gly Cys Ser Phe Ser Ile
            165                 170                 175

Phe Leu Leu Ala Leu Leu Ser Cys Leu Thr Thr Pro Ala Ser Ala Leu
            180                 185                 190

Thr Tyr Gly Asn Ser Ser Gly Leu Tyr His Leu Thr Asn Asp Cys Pro
            195                 200                 205

Asn Ser Ser Ile Val Leu Glu Ala Asp Ala Met Ile Leu His Leu Pro
            210                 215                 220

Gly Cys Leu Pro Cys Val Arg Val Asp Asn Gln Ser Thr Cys Trp His
225                 230                 235                 240

Ala Val Ser Pro Thr Leu Ala Ile Pro Asn Ala Ser Thr Ser Ala Thr
            245                 250                 255

Gly Phe Arg Arg His Val Asp Leu Leu Ala Gly Ala Val Val Cys
            260                 265                 270

Ser Ser Leu Tyr Ile Gly Asp Leu Cys Gly Ser Leu Phe Leu Ala Gly
            275                 280                 285

Gln Leu Phe Thr Phe Gln Pro Arg Arg His Trp Thr Val Gln Asp Cys
            290                 295                 300

Asn Cys Ser Ile Tyr Thr Gly His Val Thr Gly His Arg Met Ala Trp
305                 310                 315                 320

Asp Met Met Met Asn Trp Ser Pro Thr Thr Thr Leu Val Leu Ser Ser
            325                 330                 335

Ile Leu Arg Val Pro Glu Ile Cys Ala Ser Val Ile Phe Gly Gly His
            340                 345                 350

Trp Gly Ile Leu Ile Ala Val Ala Tyr Phe Gly Met Ala Gly Asn Trp
            355                 360                 365

Leu Lys Val Leu Ala Val Leu Phe Leu Phe Ala Gly Val Glu Ala Thr
            370                 375                 380

Thr Thr Ile Gly Arg Glu Met Gly Ser Thr Thr Ala Gly Leu Val Arg
385                 390                 395                 400

Phe Leu Ala Pro Gly Pro Lys Gln Asn Leu Gln Leu Ile Asn Thr Asn
            405                 410                 415

Gly Ser Trp His Ile Asn Arg Thr Ala Leu Asn Cys Asn Asp Ser Leu
            420                 425                 430

Gln Thr Gly Phe Ile Ala Ser Leu Phe Tyr Ala His Thr Phe Asn Ser
            435                 440                 445

Ser Gly Cys Pro Glu Arg Met Ala Ala Cys Arg Pro Leu Ala Asp Phe
            450                 455                 460

Arg Gln Gly Trp Gly Gln Ile Thr Tyr Lys Asp Asn Ile Ser Gly Pro
465                 470                 475                 480

Ser Asp Asp Arg Pro Tyr Cys Trp His Tyr Ala Pro Arg Pro Cys Ser
            485                 490                 495

Val Val Pro Ala Ser Thr Val Cys Gly Pro Val Tyr Cys Phe Thr Pro
            500                 505                 510
```

```
Ser Pro Val Val Gly Thr Thr Asp Arg Arg Gly Asn Pro Thr Tyr
        515                 520                 525

Thr Trp Gly Glu Asn Glu Thr Asp Val Phe Met Leu Gly Ser Leu Arg
    530                 535                 540

Pro Pro Thr Gly Gly Trp Phe Gly Cys Thr Trp Met Asn Ser Thr Gly
545                 550                 555                 560

Phe Thr Lys Thr Cys Gly Ala Pro Pro Cys Gln Ile Val Pro Gly Asp
                565                 570                 575

Tyr Asn Ser Ser Ala Asn Glu Leu Leu Cys Pro Thr Asp Cys Phe Arg
                580                 585                 590

Lys His Pro Glu Ala Thr Tyr Gln Arg Cys Gly Ser Gly Pro Trp Leu
            595                 600                 605

Thr Pro Arg Cys Leu Val His Tyr Pro Tyr Arg Leu Trp His Tyr Pro
            610                 615                 620

Cys Thr Ile Asn Phe Thr Val His Lys Val Arg Met Phe Val Gly Gly
625                 630                 635                 640

Ile Glu His Arg Phe Asp Ala Ala Cys Asn Trp Thr Arg Gly Glu Arg
                645                 650                 655

Cys Glu Leu His Asp Arg Asp Arg Ile Glu Met Ser Pro Leu Leu Phe
            660                 665                 670

Ser Thr Thr Gln Leu Ser Ile Leu Pro Cys Ser Phe Ser Thr Met Pro
            675                 680                 685

Ala Leu Ser Thr Gly Leu Ile His Leu His Gln Asn Ile Val Asp Val
690                 695                 700

Gln Tyr Leu Tyr Gly Val Ser Ser Ser Val Thr Ser Trp Val Val Lys
705                 710                 715                 720

Trp Glu Tyr Ile Val Leu Met Phe Leu Val Leu Ala Asp Ala Arg Ile
                725                 730                 735

Cys Thr Cys Leu Trp Leu Met Leu Leu Ile Ser Asn Val Glu Ala Ala
            740                 745                 750

Val Glu Arg Leu Val Val Leu Asn Ala Ala Ser Ala Ala Gly Thr Ala
            755                 760                 765

Gly Trp Trp Trp Ala Val Leu Phe Leu Cys Cys Val Trp Tyr Val Lys
    770                 775                 780

Gly Arg Leu Val Pro Ala Cys Thr Tyr Thr Ala Leu Gly Met Trp Pro
785                 790                 795                 800

Leu Leu Leu Thr Ile Leu Ala Leu Pro Arg Arg Ala Tyr Ala Met Asp
                805                 810                 815

Asn Glu Gln Ala Ala Ser Leu Gly Ala Val Gly Leu Leu Val Ile Thr
            820                 825                 830

Ile Phe Thr Ile Thr Pro Met Tyr Lys Lys Leu Leu Thr Cys Phe Ile
            835                 840                 845

Trp Trp Asn Gln Tyr Phe Leu Ala Arg Ala Glu Ala Met Ile His Glu
    850                 855                 860

Trp Val Pro Asp Leu Arg Val Arg Gly Gly Arg Asp Ser Ile Ile Leu
865                 870                 875                 880

Leu Thr Cys Leu Leu His Pro Gln Leu Gly Phe Glu Val Thr Lys Ile
                885                 890                 895

Leu Leu Ala Ile Leu Ala Pro Leu Tyr Ile Leu Gln Tyr Ser Leu Leu
            900                 905                 910

Lys Val Pro Tyr Phe Val Arg Ala His Ile Leu Leu Arg Ala Cys Leu
            915                 920                 925
```

-continued

```
Leu Val Arg Arg Leu Ala Gly Gly Lys Tyr Val Gln Ala Cys Leu Leu
    930                 935                 940
Arg Leu Gly Ala Trp Thr Gly Thr Tyr Val Tyr Asp His Leu Ala Pro
945                 950                 955                 960
Leu Ser Asp Trp Ala Ser Asp Gly Leu Arg Asp Leu Ala Val Ala Val
                965                 970                 975
Glu Pro Val Ile Phe Ser Pro Met Glu Lys Ile Ile Thr Trp Gly
            980                 985                 990
Ala Asp Thr Ala Ala Cys Gly Asp Ile Leu Ser Gly Leu Pro Val Ser
        995                 1000                1005
Ala Arg Leu Gly Asn Leu Val Leu Leu Gly Pro Ala Asp Asp Met
    1010                1015                1020
Gln Arg Gly Gly Trp Lys Leu Leu Ala Pro Ile Thr Ala Tyr Ala
    1025                1030                1035
Gln Gln Thr Arg Gly Leu Val Gly Thr Ile Val Thr Ser Leu Thr
    1040                1045                1050
Gly Arg Asp Lys Asn Glu Val Glu Gly Glu Val Gln Val Val Ser
    1055                1060                1065
Thr Ala Thr Gln Ser Phe Leu Ala Thr Ser Ile Asn Gly Val Met
    1070                1075                1080
Trp Thr Val Tyr His Gly Ala Gly Ser Lys Thr Leu Ala Gly Pro
    1085                1090                1095
Lys Gly Pro Val Cys Gln Met Tyr Thr Asn Val Asp Gln Asp Leu
    1100                1105                1110
Val Gly Trp Pro Ser Pro Pro Gly Ala Arg Ser Leu Thr Pro Cys
    1115                1120                1125
Thr Cys Gly Ser Asn Asp Leu Tyr Leu Val Thr Arg Glu Ala Asp
    1130                1135                1140
Val Ile Pro Ala Arg Arg Arg Gly Asp Ser Arg Ala Ala Leu Leu
    1145                1150                1155
Ser Pro Arg Pro Ile Ser Thr Leu Lys Gly Ser Ser Gly Gly Pro
    1160                1165                1170
Ile Met Cys Pro Ser Gly His Val Val Gly Leu Phe Arg Ala Ala
    1175                1180                1185
Val Cys Thr Arg Gly Val Ala Lys Ser Leu Asp Phe Ile Pro Val
    1190                1195                1200
Glu Asn Met Glu Thr Thr Met Arg Ser Pro Ser Phe Thr Asp Asn
    1205                1210                1215
Ser Thr Pro Pro Ala Val Pro Gln Thr Tyr Gln Val Gly Tyr Leu
    1220                1225                1230
His Ala Pro Thr Gly Ser Gly Lys Ser Thr Arg Val Pro Ala Ala
    1235                1240                1245
Tyr Ala Ser Gln Gly Tyr Lys Val Leu Val Leu Asn Pro Ser Val
    1250                1255                1260
Ala Ala Thr Leu Ser Phe Gly Ser Tyr Met Arg Gln Ala Tyr Gly
    1265                1270                1275
Val Glu Pro Asn Val Arg Thr Gly Val Arg Thr Ile Thr Thr Gly
    1280                1285                1290
Gly Ala Ile Thr Tyr Ser Thr Tyr Gly Lys Phe Leu Ala Asp Gly
    1295                1300                1305
Gly Cys Ser Gly Gly Ala Tyr Asp Ile Ile Ile Cys Asp Glu Cys
    1310                1315                1320
His Ser Thr Asp Pro Thr Thr Val Leu Gly Ile Gly Thr Val Leu
```

```
            1325                1330                1335
Asp Gln Ala Glu Thr Ala Gly Val Arg Leu Thr Val Leu Ala Thr
    1340                1345                1350
Ala Thr Pro Pro Gly Ser Val Thr Val Pro His Pro Asn Ile Thr
    1355                1360                1365
Glu Thr Ala Leu Pro Thr Thr Gly Glu Ile Pro Phe Tyr Gly Lys
    1370                1375                1380
Ala Ile Pro Leu Glu Tyr Ile Lys Gly Gly Arg His Leu Ile Phe
    1385                1390                1395
Cys His Ser Lys Lys Cys Asp Glu Leu Ala Gly Lys Leu Lys
    1400                1405                1410
Ser Leu Gly Leu Asn Ala Val Ala Phe Tyr Arg Gly Val Asp Val
    1415                1420                1425
Ser Val Ile Pro Thr Ser Gly Asp Val Val Cys Ala Thr Asp
    1430                1435                1440
Ala Leu Met Thr Gly Tyr Thr Gly Asp Phe Asp Ser Val Ile Asp
    1445                1450                1455
Cys Asn Val Ala Val Thr Gln Val Val Asp Phe Ser Leu Asp Pro
    1460                1465                1470
Thr Phe Ser Ile Glu Thr Thr Thr Val Pro Gln Asp Ala Val Ser
    1475                1480                1485
Arg Ser Gln Arg Arg Gly Arg Thr Gly Arg Gly Lys Pro Gly Val
    1490                1495                1500
Tyr Arg Phe Val Ser Gln Gly Glu Arg Pro Ser Gly Met Phe Asp
    1505                1510                1515
Thr Val Val Leu Cys Glu Ala Tyr Asp Thr Gly Cys Ala Trp Tyr
    1520                1525                1530
Glu Leu Thr Pro Ser Glu Thr Thr Val Arg Leu Arg Ala Tyr Leu
    1535                1540                1545
Asn Thr Pro Gly Leu Pro Val Cys Gln Asp His Leu Glu Phe Trp
    1550                1555                1560
Glu Gly Val Phe Thr Gly Leu Thr His Ile Asp Ala His Phe Leu
    1565                1570                1575
Ser Gln Thr Lys Gln Gly Gly Glu Asn Phe Ala Tyr Leu Val Ala
    1580                1585                1590
Tyr Gln Ala Thr Val Cys Ala Arg Ala Lys Ala Pro Pro Pro Ser
    1595                1600                1605
Trp Asp Thr Met Trp Lys Cys Leu Ile Arg Leu Lys Pro Thr Leu
    1610                1615                1620
Thr Gly Pro Thr Pro Leu Leu Tyr Arg Leu Gly Ala Val Gln Asn
    1625                1630                1635
Glu Ile Ile Thr Thr His Pro Ile Thr Lys Tyr Ile Met Thr Cys
    1640                1645                1650
Met Ser Ala Asp Leu Glu Val Ile Thr Ser Thr Trp Val Ile Val
    1655                1660                1665
Gly Gly Val Leu Ala Ala Leu Ala Ala Tyr Cys Leu Ser Val Gly
    1670                1675                1680
Cys Val Val Ile Cys Gly Arg Ile Thr Leu Thr Gly Lys Pro Val
    1685                1690                1695
Val Val Pro Asp Arg Glu Val Leu Tyr Gln Gln Phe Asp Glu Met
    1700                1705                1710
Glu Glu Cys Ser Arg His Ile Pro Tyr Leu Ala Glu Gly Gln Gln
    1715                1720                1725
```

-continued

```
Ile Ala Glu Gln Phe Arg Gln Lys Val Leu Gly Leu Leu Gln Ala
    1730                1735                1740

Ser Ala Lys Gln Ala Glu Glu Leu Lys Pro Ala Val His Ser Ala
    1745                1750                1755

Trp Pro Arg Val Glu Glu Phe Trp Arg Lys His Met Trp Asn Phe
    1760                1765                1770

Val Ser Gly Ile Gln Tyr Leu Ala Gly Leu Ser Ile Trp Pro Gly
    1775                1780                1785

Asn Pro Ala Val Ala Ser Leu Met Ser Phe Thr Ala Ser Leu Thr
    1790                1795                1800

Ser Pro Leu Arg Thr Ser Gln Thr Leu Leu Asn Ile Leu Gly
    1805                1810                1815

Gly Trp Ile Ala Thr Gln Val Ala Pro Pro Ala Ser Thr Ala
    1820                1825                1830

Phe Val Val Ser Gly Leu Ala Gly Ala Thr Val Gly Ser Ile Gly
    1835                1840                1845

Leu Gly Arg Val Leu Val Asp Val Leu Ala Gly Tyr Gly Ala Gly
    1850                1855                1860

Val Ser Gly Ala Leu Val Ala Phe Lys Ile Met Ser Gly Glu Cys
    1865                1870                1875

Pro Ser Thr Glu Asp Met Val Asn Leu Leu Pro Ala Leu Leu Ser
    1880                1885                1890

Pro Gly Ala Leu Val Val Gly Val Val Cys Ala Ala Ile Leu Arg
    1895                1900                1905

Arg His Val Gly Pro Ala Glu Gly Ala Asn Gln Trp Met Asn Arg
    1910                1915                1920

Leu Ile Ala Phe Ala Ser Arg Gly Asn His Val Ser Pro Thr His
    1925                1930                1935

Tyr Val Pro Glu Thr Asp Ala Ser Lys Asn Val Thr Gln Ile Leu
    1940                1945                1950

Thr Ser Leu Thr Ile Thr Ser Leu Leu Arg Arg Leu His Gln Trp
    1955                1960                1965

Val Thr Glu Asp Thr Ala Thr Pro Cys Ala Thr Ser Trp Leu Arg
    1970                1975                1980

Asp Val Trp Asp Trp Val Cys Thr Val Leu Ser Asp Phe Lys Val
    1985                1990                1995

Trp Leu Lys Ala Lys Leu Leu Pro Arg Leu Pro Gly Ile Pro Phe
    2000                2005                2010

Leu Ser Cys Gln Thr Gly Tyr Arg Gly Val Trp Ala Gly Asp Gly
    2015                2020                2025

Val Cys His Thr Thr Cys Thr Cys Gly Ala Val Ile Ala Gly His
    2030                2035                2040

Val Lys Asn Gly Ser Met Lys Ile Thr Gly Pro Lys Thr Cys Ser
    2045                2050                2055

Asn Thr Trp His Gly Thr Phe Pro Ile Asn Ala Thr Thr Thr Gly
    2060                2065                2070

Pro Ser Thr Pro Arg Pro Ala Pro Asn Tyr Gln Arg Ala Leu Trp
    2075                2080                2085

Arg Val Ser Ala Glu Asp Tyr Val Glu Val Arg Arg Leu Gly Asp
    2090                2095                2100

Cys His Tyr Val Val Gly Ala Thr Ala Glu Gly Leu Lys Cys Pro
    2105                2110                2115
```

```
Cys Gln Val Pro Ala Pro Glu Phe Phe Thr Glu Val Asp Gly Val
2120                2125                2130

Arg Ile His Arg Tyr Ala Pro Pro Cys Lys Pro Leu Leu Arg Asp
2135                2140                2145

Glu Val Thr Phe Ser Val Gly Leu Ser Thr Tyr Ala Ile Gly Ser
2150                2155                2160

Gln Leu Pro Cys Glu Pro Glu Pro Asp Val Thr Val Val Thr Ser
2165                2170                2175

Met Leu Thr Asp Pro Thr His Ile Thr Ala Glu Thr Ala Ala Arg
2180                2185                2190

Arg Leu Lys Arg Gly Ser Pro Pro Ser Leu Ala Ser Ser Ser Ala
2195                2200                2205

Ser Gln Leu Ser Ala Pro Ser Leu Lys Ala Thr Cys Thr Thr Ser
2210                2215                2220

Lys Asp His Pro Asp Met Glu Leu Ile Glu Ala Asn Leu Leu Trp
2225                2230                2235

Arg Gln Glu Met Gly Gly Asn Ile Thr Arg Val Glu Ser Glu Asn
2240                2245                2250

Lys Val Val Ile Leu Asp Ser Phe Glu Pro Leu Thr Ala Asp Tyr
2255                2260                2265

Asp Glu Arg Glu Ile Ser Val Ser Ala Glu Cys His Arg Pro Pro
2270                2275                2280

Arg His Lys Phe Pro Pro Ala Leu Pro Ile Trp Ala Arg Pro Asp
2285                2290                2295

Tyr Asn Pro Pro Leu Ile Gln Ala Trp Gln Met Pro Gly Tyr Glu
2300                2305                2310

Pro Pro Val Val Ser Gly Cys Ala Val Ala Pro Lys Pro Ala
2315                2320                2325

Pro Ile Pro Pro Pro Arg Arg Lys Arg Leu Val His Leu Asp Glu
2330                2335                2340

Ser Thr Val Ser His Ala Leu Ala Gln Leu Ala Asp Lys Val Phe
2345                2350                2355

Val Glu Ser Ser Asp Gly Pro Gly Pro Ser Ser Asp Ser Gly Leu
2360                2365                2370

Ser Ile Thr Ser Pro Val Pro Pro Thr Pro Thr Pro Asp Asp
2375                2380                2385

Ala Cys Ser Glu Ala Glu Ser Tyr Ser Ser Met Pro Pro Leu Glu
2390                2395                2400

Gly Glu Pro Gly Asp Pro Asp Leu Ser Ser Gly Ser Trp Ser Thr
2405                2410                2415

Val Ser Asp Gln Asp Asp Val Val Cys Cys Ser Met Ser Tyr Ser
2420                2425                2430

Trp Thr Gly Ala Leu Ile Thr Pro Cys Ala Ala Glu Glu Glu Lys
2435                2440                2445

Leu Pro Ile Asn Pro Leu Ser Asn Ser Leu Ile Arg His His Asn
2450                2455                2460

Met Val Tyr Ser Thr Thr Ser Arg Ser Ala Ser Leu Arg Gln Lys
2465                2470                2475

Lys Val Thr Phe Asp Arg Val Gln Val Phe Asp Gln His Tyr Gln
2480                2485                2490

Glu Val Leu Lys Glu Ile Lys Leu Arg Ala Ser Thr Val Gln Ala
2495                2500                2505

Lys Leu Leu Ser Ile Glu Glu Ala Cys Asp Leu Thr Pro Ser His
```

-continued

|      |      |      |      | 2510 |      |      |      | 2515 |      |      |      | 2520 |      |      |

| Ser | Ala | Arg | Ser | Lys | Tyr | Gly | Tyr | Gly | Ala | Lys | Asp | Val | Arg | Ser |
| 2525 | | | | | 2530 | | | | | 2535 | | | | |

| His | Ala | Ser | Lys | Ala | Val | Asp | His | Ile | Arg | Ser | Val | Trp | Glu | Asp |
| 2540 | | | | | 2545 | | | | | 2550 | | | | |

| Leu | Leu | Glu | Asp | Ser | Asp | Thr | Pro | Ile | Pro | Thr | Thr | Ile | Met | Ala |
| 2555 | | | | | 2560 | | | | | 2565 | | | | |

| Lys | Asn | Glu | Val | Phe | Cys | Val | Asp | Pro | Ser | Lys | Gly | Gly | Arg | Lys |
| 2570 | | | | | 2575 | | | | | 2580 | | | | |

| Pro | Ala | Arg | Leu | Ile | Val | Phe | Pro | Asp | Leu | Gly | Val | Arg | Val | Cys |
| 2585 | | | | | 2590 | | | | | 2595 | | | | |

| Glu | Lys | Met | Ala | Leu | Tyr | Asp | Val | Thr | Arg | Lys | Leu | Pro | Gln | Ala |
| 2600 | | | | | 2605 | | | | | 2610 | | | | |

| Val | Met | Gly | Pro | Ala | Tyr | Gly | Phe | Gln | Tyr | Ser | Pro | Asn | Gln | Arg |
| 2615 | | | | | 2620 | | | | | 2625 | | | | |

| Val | Glu | Tyr | Leu | Leu | Lys | Met | Trp | Arg | Ser | Lys | Lys | Val | Pro | Met |
| 2630 | | | | | 2635 | | | | | 2640 | | | | |

| Gly | Phe | Ser | Tyr | Asp | Thr | Arg | Cys | Phe | Asp | Ser | Thr | Val | Thr | Glu |
| 2645 | | | | | 2650 | | | | | 2655 | | | | |

| Arg | Asp | Ile | Arg | Thr | Glu | Asn | Glu | Ile | Tyr | Gln | Ser | Cys | Gln | Leu |
| 2660 | | | | | 2665 | | | | | 2670 | | | | |

| Asp | Pro | Met | Ala | Arg | Lys | Ala | Val | Ser | Ser | Leu | Thr | Glu | Arg | Leu |
| 2675 | | | | | 2680 | | | | | 2685 | | | | |

| Tyr | Val | Gly | Gly | Pro | Met | Val | Asn | Ser | Lys | Gly | Gln | Ser | Cys | Gly |
| 2690 | | | | | 2695 | | | | | 2700 | | | | |

| Tyr | Arg | Arg | Cys | Arg | Ala | Ser | Gly | Val | Leu | Pro | Thr | Ser | Met | Gly |
| 2705 | | | | | 2710 | | | | | 2715 | | | | |

| Asn | Thr | Leu | Thr | Cys | Tyr | Leu | Lys | Ala | Gln | Ala | Ala | Cys | Arg | Ala |
| 2720 | | | | | 2725 | | | | | 2730 | | | | |

| Ala | Asn | Ile | Lys | Asp | Tyr | Asp | Met | Leu | Val | Cys | Gly | Asp | Asp | Leu |
| 2735 | | | | | 2740 | | | | | 2745 | | | | |

| Val | Val | Ile | Cys | Glu | Ser | Ala | Gly | Val | Gln | Glu | Asp | Thr | Ala | Ser |
| 2750 | | | | | 2755 | | | | | 2760 | | | | |

| Leu | Arg | Ala | Phe | Thr | Asp | Ala | Met | Thr | Arg | Tyr | Ser | Ala | Pro | Pro |
| 2765 | | | | | 2770 | | | | | 2775 | | | | |

| Gly | Asp | Ala | Pro | Gln | Pro | Thr | Tyr | Asp | Leu | Glu | Leu | Ile | Thr | Ser |
| 2780 | | | | | 2785 | | | | | 2790 | | | | |

| Cys | Ser | Ser | Asn | Val | Ser | Val | Ala | His | Asp | Gly | Asn | Gly | Lys | Arg |
| 2795 | | | | | 2800 | | | | | 2805 | | | | |

| Tyr | Tyr | Tyr | Leu | Thr | Arg | Asp | Cys | Thr | Thr | Pro | Leu | Ala | Arg | Ala |
| 2810 | | | | | 2815 | | | | | 2820 | | | | |

| Ala | Trp | Glu | Thr | Ala | Arg | His | Thr | Pro | Val | Asn | Ser | Trp | Leu | Gly |
| 2825 | | | | | 2830 | | | | | 2835 | | | | |

| Asn | Ile | Ile | Met | Phe | Ala | Pro | Thr | Ile | Trp | Val | Arg | Met | Val | Leu |
| 2840 | | | | | 2845 | | | | | 2850 | | | | |

| Met | Thr | His | Phe | Phe | Ser | Ile | Leu | Gln | Ser | Gln | Glu | Gln | Leu | Glu |
| 2855 | | | | | 2860 | | | | | 2865 | | | | |

| Lys | Ala | Leu | Asp | Phe | Asp | Ile | Tyr | Gly | Val | Thr | Tyr | Ser | Val | Ser |
| 2870 | | | | | 2875 | | | | | 2880 | | | | |

| Pro | Leu | Asp | Leu | Pro | Ala | Ile | Ile | Gln | Arg | Leu | His | Gly | Met | Ala |
| 2885 | | | | | 2890 | | | | | 2895 | | | | |

| Ala | Phe | Ser | Leu | His | Gly | Tyr | Ser | Pro | Val | Glu | Leu | Asn | Arg | Val |
| 2900 | | | | | 2905 | | | | | 2910 | | | | |

```
Gly Ala Cys Leu Arg Lys Leu Gly Ala Pro Pro Leu Arg Ala Trp
        2915                2920                2925

Arg His Arg Ala Arg Ala Val Arg Ala Lys Leu Ile Ala Gln Gly
    2930                2935                2940

Gly Lys Ala Ala Ile Cys Gly Lys Tyr Leu Phe Asn Trp Ala Val
    2945                2950                2955

Lys Thr Lys Leu Lys Leu Thr Pro Leu Ala Ser Ala Ser Lys Leu
    2960                2965                2970

Asp Leu Ser Asp Trp Phe Val Ala Gly Tyr Asp Gly Gly Asp Ile
    2975                2980                2985

Tyr His Ser Val Ser Leu Ala Arg Pro Arg Leu Leu Leu Leu Gly
    2990                2995                3000

Leu Leu Leu Leu Thr Val Gly Val Gly Ile Phe Leu Leu Pro Ala
    3005                3010                3015

Arg
```

```
<210> SEQ ID NO 10
<211> LENGTH: 8
<212> TYPE: PRT
<213> ORGANISM: Artificial sequence
<220> FEATURE:
<223> OTHER INFORMATION: HC-1 Heavy Chain CDR1

<400> SEQUENCE: 10

Gly Gly Thr Tyr Asn Ser Glu Val
1               5

<210> SEQ ID NO 11
<211> LENGTH: 8
<212> TYPE: PRT
<213> ORGANISM: Artificial sequence
<220> FEATURE:
<223> OTHER INFORMATION: HC-1 Heavy Chain CDR2

<400> SEQUENCE: 11

Phe Ile Pro Met Phe Gly Thr Ala
1               5

<210> SEQ ID NO 12
<211> LENGTH: 15
<212> TYPE: PRT
<213> ORGANISM: Artificial sequence
<220> FEATURE:
<223> OTHER INFORMATION: HC-1 Heavy Chain CDR3

<400> SEQUENCE: 12

Ala Lys Val Leu Gln Val Gly Gly Asn Leu Val Val Arg Pro Leu
1               5                   10                  15

<210> SEQ ID NO 13
<211> LENGTH: 10
<212> TYPE: PRT
<213> ORGANISM: Artificial sequence
<220> FEATURE:
<223> OTHER INFORMATION: HC-3 Heavy Chain CDR1

<400> SEQUENCE: 13

Gly Phe Ser Leu Ser Thr Thr Gly Val Gly
1               5                   10

<210> SEQ ID NO 14
<211> LENGTH: 7
```

```
<212> TYPE: PRT
<213> ORGANISM: Artificial sequence
<220> FEATURE:
<223> OTHER INFORMATION: HC-3 Heavy Chain CDR2

<400> SEQUENCE: 14

Ile Tyr Trp Asp Asp Lys
1               5

<210> SEQ ID NO 15
<211> LENGTH: 23
<212> TYPE: PRT
<213> ORGANISM: Artificial sequence
<220> FEATURE:
<223> OTHER INFORMATION: HC-3 Heavy Chain CDR3

<400> SEQUENCE: 15

Ala Leu Asn Ser Tyr Arg Ser Gly Thr Ile Leu Tyr Arg Glu Leu Glu
1               5                   10                  15

Leu Arg Gly Leu Phe Tyr Ile
            20

<210> SEQ ID NO 16
<211> LENGTH: 8
<212> TYPE: PRT
<213> ORGANISM: Artificial sequence
<220> FEATURE:
<223> OTHER INFORMATION: HC-11 Heavy Chain CDR1

<400> SEQUENCE: 16

Gly Ala Thr Phe Ser Ser Phe Ile
1               5

<210> SEQ ID NO 17
<211> LENGTH: 8
<212> TYPE: PRT
<213> ORGANISM: Artificial sequence
<220> FEATURE:
<223> OTHER INFORMATION: HC-11 Heavy Chain CDR2

<400> SEQUENCE: 17

Ile Ile Pro Met Phe Gly Thr Ala
1               5

<210> SEQ ID NO 18
<211> LENGTH: 19
<212> TYPE: PRT
<213> ORGANISM: Artificial sequence
<220> FEATURE:
<223> OTHER INFORMATION: HC-11 Heavy Chain CDR3

<400> SEQUENCE: 18

Ala Met Glu Val Pro Phe Gly Cys Arg Gly Gly Ser Cys Ser Gly Tyr
1               5                   10                  15

Met Asp Val

<210> SEQ ID NO 19
<211> LENGTH: 8
<212> TYPE: PRT
<213> ORGANISM: Artificial sequence
<220> FEATURE:
<223> OTHER INFORMATION: CBH-23 Heavy Chain CDR1

<400> SEQUENCE: 19

Gly Gly Thr Phe Ser Ser Tyr Ala
1               5
```

```
<210> SEQ ID NO 20
<211> LENGTH: 8
<212> TYPE: PRT
<213> ORGANISM: Artificial sequence
<220> FEATURE:
<223> OTHER INFORMATION: CBH-23 Heavy Chain CDR2

<400> SEQUENCE: 20

Ile Val Pro Met Phe Gly Thr Glu
1               5

<210> SEQ ID NO 21
<211> LENGTH: 13
<212> TYPE: PRT
<213> ORGANISM: Artificial sequence
<220> FEATURE:
<223> OTHER INFORMATION: CBH-23 Heavy Chain CDR3

<400> SEQUENCE: 21

Ala Arg His Glu Asn Ile Tyr Gly Thr Pro Phe Asp Tyr
1               5                   10

<210> SEQ ID NO 22
<211> LENGTH: 7
<212> TYPE: PRT
<213> ORGANISM: Artificial sequence
<220> FEATURE:
<223> OTHER INFORMATION: HC-1 Light Chain CDR1

<400> SEQUENCE: 22

Gln Thr Ile Ser Ser Thr His
1               5

<210> SEQ ID NO 23
<211> LENGTH: 9
<212> TYPE: PRT
<213> ORGANISM: Artificial sequence
<220> FEATURE:
<223> OTHER INFORMATION: HC-1 Light Chain CDR3

<400> SEQUENCE: 23

His Gln Tyr Gly Asn Ser Pro Gln Thr
1               5

<210> SEQ ID NO 24
<211> LENGTH: 6
<212> TYPE: PRT
<213> ORGANISM: Artificial sequence
<220> FEATURE:
<223> OTHER INFORMATION: HC-3 Light Chain CDR1

<400> SEQUENCE: 24

Gln Ser Ile Ser Ser Trp
1               5

<210> SEQ ID NO 25
<211> LENGTH: 9
<212> TYPE: PRT
<213> ORGANISM: Artificial sequence
<220> FEATURE:
<223> OTHER INFORMATION: HC-3 Light Chain CDR3

<400> SEQUENCE: 25

Gln Gln Tyr Glu Ser Ser Ser Trp Thr
1               5
```

```
<210> SEQ ID NO 26
<211> LENGTH: 7
<212> TYPE: PRT
<213> ORGANISM: Artificial sequence
<220> FEATURE:
<223> OTHER INFORMATION: HC-11 Light Chain CDR1

<400> SEQUENCE: 26

His Ser Val Ser Ser Ser Asn
1               5

<210> SEQ ID NO 27
<211> LENGTH: 9
<212> TYPE: PRT
<213> ORGANISM: Artificial sequence
<220> FEATURE:
<223> OTHER INFORMATION: HC-11 Light Chain CDR3

<400> SEQUENCE: 27

Gln Gln Tyr Gly Ser Ser Pro Ile Thr
1               5

<210> SEQ ID NO 28
<211> LENGTH: 6
<212> TYPE: PRT
<213> ORGANISM: Artificial sequence
<220> FEATURE:
<223> OTHER INFORMATION: CBH-23 Light Chain CDR1

<400> SEQUENCE: 28

His Ser Ile Thr Arg Tyr
1               5

<210> SEQ ID NO 29
<211> LENGTH: 9
<212> TYPE: PRT
<213> ORGANISM: Artificial sequence
<220> FEATURE:
<223> OTHER INFORMATION: CBH-23 Light Chain CDR3

<400> SEQUENCE: 29

Gln Gln Ser Tyr Ser Thr Leu Leu Thr
1               5
```